US010900974B2

(12) United States Patent
Quinodoz et al.

(10) Patent No.: US 10,900,974 B2
(45) Date of Patent: Jan. 26, 2021

(54) METHODS FOR IDENTIFYING MACROMOLECULE INTERACTIONS

(71) Applicant: California Institute of Technology, Pasadena, CA (US)

(72) Inventors: Sofia A. Quinodoz, Pasadena, CA (US); Mitchell Guttman, West Hollywood, CA (US)

(73) Assignee: California Institute of Technology, Pasadena, CA (US)

( * ) Notice: Subject to any disclaimer, the term of this patent is extended or adjusted under 35 U.S.C. 154(b) by 555 days.

(21) Appl. No.: 15/466,861

(22) Filed: Mar. 22, 2017

(65) Prior Publication Data

US 2019/0187156 A1     Jun. 20, 2019

Related U.S. Application Data

(60) Provisional application No. 62/311,813, filed on Mar. 22, 2016.

(51) Int. Cl.
| | |
|---|---|
| *G01N 33/68* | (2006.01) |
| *C12N 15/10* | (2006.01) |
| *C12Q 1/6806* | (2018.01) |
| *G01N 33/58* | (2006.01) |

(52) U.S. Cl.
CPC ..... *G01N 33/6875* (2013.01); *C12N 15/1065* (2013.01); *C12N 15/1093* (2013.01); *C12Q 1/6806* (2013.01); *G01N 33/58* (2013.01)

(58) Field of Classification Search
CPC ............... G01N 33/6875; G01N 33/58; C12N 15/1065; C12N 15/1093; C12Q 1/6806
See application file for complete search history.

(56) References Cited

U.S. PATENT DOCUMENTS

| | | | | |
|---|---|---|---|---|
| 2015/0225786 A1* | 8/2015 | Litterst | ................ | C12Q 1/6809 506/2 |
| 2016/0194699 A1* | 7/2016 | Borodina | ............. | C12Q 1/6806 506/4 |

FOREIGN PATENT DOCUMENTS

WO    WO-2012106385 A2 *   8/2012  .......... C12Q 1/6816

OTHER PUBLICATIONS

Blackstock, D. et al., Halo-tag mediated self-labeling of fluorescent proteins to molecular beacons for nucleic acid detection, ChemCommun. 2014, vol. 50, pp. 13735-13738.

Chen, C.K. et al., Xist recruits the X chromosome to the nuclear lamina to enable chromosome-wide silencing, Science, vol. 354, Issue 6311, Oct. 28, 2016, pp. 468-472.

Engreitz, Jesse M. et al.; "The Xist lncRNA exploits three-dimensional genome architecture to spread across the X-chromosome"; Science; Aug. 16, 2013; 341(6147); 18pp.; doi:10.1126/science.1237973.

Kozlov, I.A. et al., Efficient Strategies for the Conjugation of Oligonucleotides to Antibodies Enabling Highly Sensitive Protein Detection, Wiley InterScience (www.interscience.wiley.com) Mar. 8, 2004, pp. 621-630.

Los, G.V. et al., HaloTag: A Novel Protein Labeling Technology for Cell Imaging and Protein Analysis, ACS Chemical Biology, vol. 3, No. 6, Jun. 6, 2008, pp. 373-382.

McHugh, Colleen A. et al.; "The Xist lncRNA interacts directly with Sharp to silence transcription through HDAC3"; Nature; vol. 521; May 14, 2015; 24pp.

Singh, V. et al., Genetically Encoded Multispectral Labeling of Proteins with Polyfluorophores on a DNA Backbone, NIH Public Access Author Manuscript, J. Am. Chem. Soc. 2013, 135(16) 19 pages.

\* cited by examiner

*Primary Examiner* — Robert H Havlin
(74) *Attorney, Agent, or Firm* — Knobbe, Martens, Olson & Bear, LLP

(57) ABSTRACT

A method for identifying interactions of DNA, RNA, and/or protein molecules in a cell includes distributing a cell lysate or fraction thereof into a plurality of lysate suspensions, adding a unique nucleotide tag to each lysate suspension to tag each DNA, RNA, and/or protein, pooling the tagged suspensions, and repeating the tagging, pooling, and sorting (distributing) as desired to decrease the probability that non-interacting molecules will receive all of the same nucleotide tags.

12 Claims, 32 Drawing Sheets
(29 of 32 Drawing Sheet(s) Filed in Color)
Specification includes a Sequence Listing.

DNA Phosphate Modified (DPM) Adaptor

Odd and Even Tags

Terminal Tag

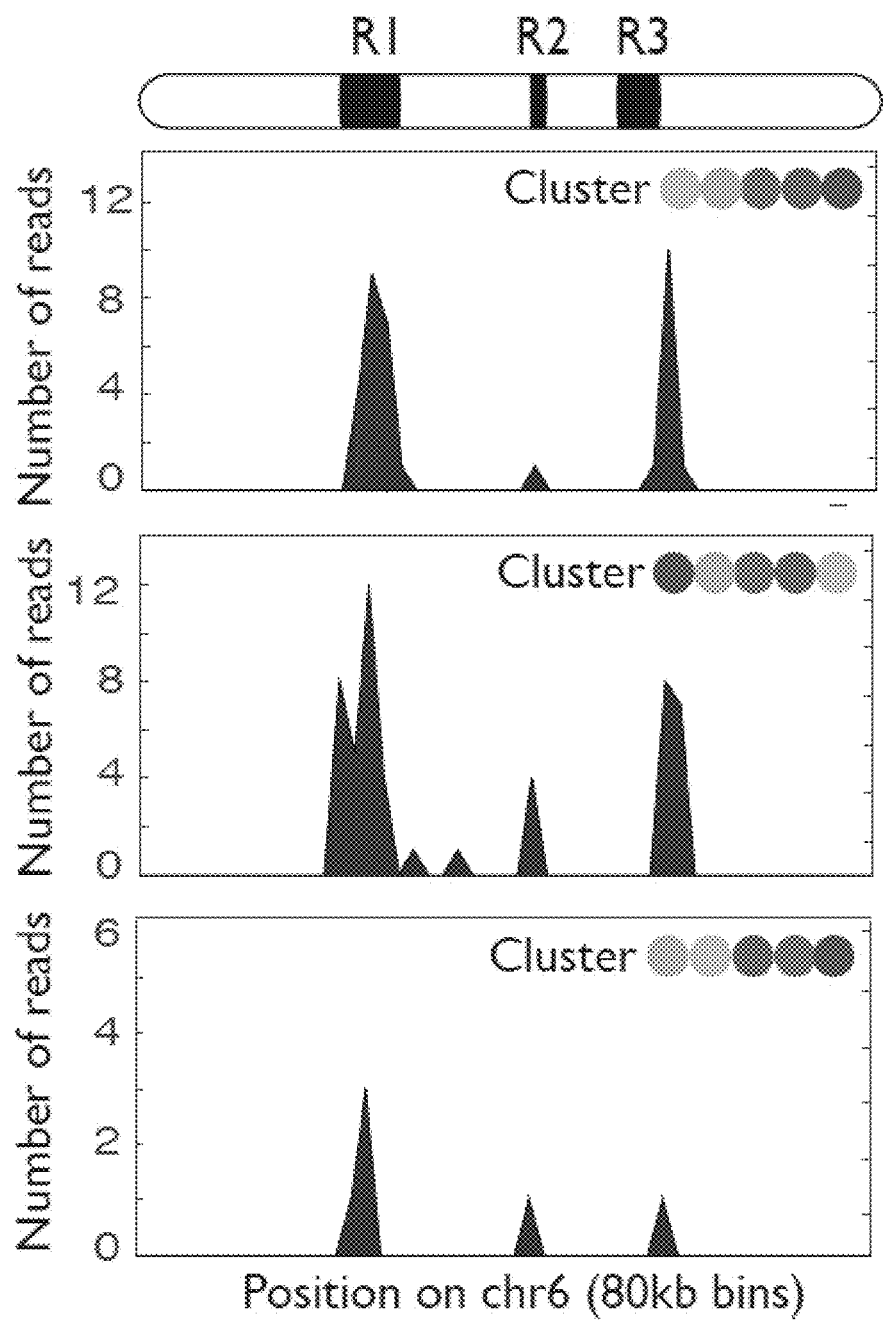

```
                          SEQUENCE LISTING

<160> NUMBER OF SEQ ID NOS: 1243

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
gcgagggagt caggcaag                                                    18

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
aucagcaccc ggatgtagat aggatggact tagcgtcag                             39

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
gcgagggagt caggcaag                                                    18

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uacacgacgc ucuuccgauc u                                                21

<210> SEQ ID NO 5
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
```

```
aatgatacgg cgaccaccga gatctacact ctttccctac acgacgctct tccgatctgc    60
gagggagtca ggcaag                                                    76
```

<210> SEQ ID NO 6
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
aatgatacgg cgaccaccga gatctacact ctttccctac acgacgctct tccgatct     58
```

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
caagcagaag acggcatacg agatgcctag ccgtgactgg agttcagacg tgtgctcttc    60
cgatct                                                               66
```

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
tacacgacgc tcttccgatc t                                              21
```

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
tgacttgtca tgtcttccga tct                                            23
```

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
gcgagggagt caggcaag                                                  18
```

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 11
tgacttgcgc taagtccatc ctatctacat ccg                                  33

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agttgtcacc ataataagat cggaaga                                         27

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agttgtcaag gtagctaaga tcggaaga                                        28

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agttgtcatg aacaatagat cggaaga                                         27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agttgtcatt cggtggagat cggaaga                                         27

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agttgtcaca actgatgaga tcggaaga                                        28

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 17
agttgtcctc tcaaggagat cggaaga                                              27

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agttgtcact tcctgataga tcggaaga                                             28

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agttgtcgct acttcgagat cggaaga                                              27

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
agttgtcagt cggttaaaga tcggaaga                                             28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agttgtcatg tatgaacaga tcggaaga                                             28

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agttgtcttc ttcgtcagat cggaaga                                              27

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
```
agttgtccac agaggcaaga tcggaaga                                              28

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agttgtcatc catctcagat cggaaga                                               27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agttgtccac tatggtagat cggaaga                                               27

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agttgtccca ttcgtacaga tcggaaga                                              28

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agttgtccgt ctccttagat cggaaga                                               27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
agttgtcggt taatggagat cggaaga                                               27

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agttgtccgt aaggagaaga tcggaaga                                              28

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 30
agttgtctgg tgagatagat cggaaga                                               27

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 31
agttgtcctt agttacgaga tcggaaga                                              28

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 32
agttgtcgag ccagtctaga tcggaaga                                              28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 33
agttgtcgag tggtattaga tcggaaga                                              28

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 34
agttgtcata atgcagagat cggaaga                                               27

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 35
agttgtccag ctacaaagat cggaaga                                               27

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
agttgtcgat aacggcagat cggaaga                                          27

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agttgtcggt tgtattcaga tcggaaga                                         28

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agttgtcgta ttctcctaga tcggaaga                                         28

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agttgtcgtc ttagatgaga tcggaaga                                         28

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agttgtcttg tattgaagat cggaaga                                          27

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
agttgtctaa cttatcgaga tcggaaga                                         28

```
<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
agttgtcact tgtcaaagat cggaaga                                            27

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agttgtctag aactacaaga tcggaaga                                           28

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
agttgtcagg ataggcagat cggaaga                                            27

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agttgtctat tgccgccaga tcggaaga                                           28

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agttgtcttg gccgtaaaga tcggaaga                                           28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
agttgtctga ggattccaga tcggaaga                                           28
```

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agttgtctta acatgagaga tcggaaga                                          28

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agttgtctaa tcaatcagat cggaaga                                           27

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
agttgtctca gtatatagat cggaaga                                           27

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agttgtcgaa ggagcgagat cggaaga                                           27

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
agttgtcatc gcgtactaga tcggaaga                                          28

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
agttgtccag atccgtgaga tcggaaga                                          28

<210> SEQ ID NO 54

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agttgtcgat accaggaaga tcggaaga                                          28

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
agttgtccga agacctagat cggaaga                                           27

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agttgtcggc cttggaaaga tcggaaga                                          28

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
agttgtcgga tgctacagat cggaaga                                           27

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
agttgtcggc cgtaggagat cggaaga                                           27

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
agttgtctca agcgtaagat cggaaga                                           27

<210> SEQ ID NO 60
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
agttgtcatg gtcgccaaga gatcggaaga                                    30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
agttgtctgc cggtttaaga gatcggaaga                                    30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agttgtcgca acaacagaga gatcggaaga                                    30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
agttgtccaa acaacagaga gatcggaaga                                    30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
agttgtcata tgtgaaacga gatcggaaga                                    30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
agttgtctgc ttagaagcga gatcggaaga                                    30

<210> SEQ ID NO 66
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 66
agttgtcgct agcagtcgga gatcggaaga                                          30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
agttgtccat gactggatga gatcggaaga                                          30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
agttgtcact tcggagctga gatcggaaga                                          30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
agttgtctta acgttgttga gatcggaaga                                          30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
agttgtcgct agtctaatga gatcggaaga                                          30

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
agttgtccgc aagtgctgga gatcggaaga                                          30

<210> SEQ ID NO 72
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 72
agttgtcaac gtacatcaca gatcggaaga                                          30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agttgtctgg gacgactaca gatcggaaga                                          30

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
agttgtcgcg agttggacca gatcggaaga                                          30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
agttgtcctg tatggcgcca gatcggaaga                                          30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
agttgtcagg gtgctctcca gatcggaaga                                          30

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
agttgtctca ttgcagagca gatcggaaga                                          30

<210> SEQ ID NO 78
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 78
agttgtcgga aacgttcgca gatcggaaga                                          30

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
agttgtcccg actcgatgca gatcggaaga                                          30

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
agttgtcatc tacgtcatca gatcggaaga                                          30

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
agttgtctat gttctgctca gatcggaaga                                          30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
agttgtcgca cggggtgtca gatcggaaga                                          30

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
agttgtccgg tcgaacaaca gatcggaaga                                          30

<210> SEQ ID NO 84
<211> LENGTH: 29
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 84
agttgtcaca catataaaag atcggaaga                29

<210> SEQ ID NO 85
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agttgtctgt gatgtcaaag atcggaaga                29

<210> SEQ ID NO 86
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
agttgtcgtg ggggataaag atcggaaga                29

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
agttgtccac tggtcacaag atcggaaga                29

<210> SEQ ID NO 88
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
agttgtcagg agcatccaag atcggaaga                29

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
agttgtctta attactcaag atcggaaga                29

<210> SEQ ID NO 90
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 90
agttgtccca atatgagaag atcggaaga                                        29

<210> SEQ ID NO 91
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
agttgtccat atgttcgaag atcggaaga                                        29

<210> SEQ ID NO 92
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
agttgtcatg tagtatgaag atcggaaga                                        29

<210> SEQ ID NO 93
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
agttgtctga cgtcgataag atcggaaga                                        29

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
agttgtcgcc ctggtctaag atcggaaga                                        29

<210> SEQ ID NO 95
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
agttgtccat ccacattaag atcggaaga                                        29

<210> SEQ ID NO 96
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 96
agttgtcaac atactaatag atcggaaga                                        29

<210> SEQ ID NO 97
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
agttgtcttg gataggatag atcggaaga                                        29

<210> SEQ ID NO 98
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
agttgtcggg cgtgtaatag atcggaaga                                        29

<210> SEQ ID NO 99
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
agttgtccta tttcaactag atcggaaga                                        29

<210> SEQ ID NO 100
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
agttgtcaca aagggcctag atcggaaga                                        29

<210> SEQ ID NO 101
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
agttgtctac gctcatctag atcggaaga                                        29

<210> SEQ ID NO 102
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
agttgtcgga agaagagtag atcggaaga            29

<210> SEQ ID NO 103
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
agttgtccca ataatggtag atcggaaga            29

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
agttgtcact gagtctgtag atcggaaga            29

<210> SEQ ID NO 105
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
agttgtctac agacaattag atcggaaga            29

<210> SEQ ID NO 106
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
agttgtcggt gaggccttag atcggaaga            29

<210> SEQ ID NO 107
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
agttgtcctc tgttcgttag atcggaaga            29

<210> SEQ ID NO 108
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cagacgtgtg ctcttccgat cttattatgg t					31

<210> SEQ ID NO 109
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cagacgtgtg ctcttccgat cttagctacc tt					32

<210> SEQ ID NO 110
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cagacgtgtg ctcttccgat ctattgttca t					31

<210> SEQ ID NO 111
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cagacgtgtg ctcttccgat ctccaccgaa t					31

<210> SEQ ID NO 112
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cagacgtgtg ctcttccgat ctcatcagtt gt					32

<210> SEQ ID NO 113
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
cagacgtgtg ctcttccgat ctccttgaga g					31

<210> SEQ ID NO 114
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cagacgtgtg ctcttccgat ctatcaggaa gt					32

<210> SEQ ID NO 115
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cagacgtgtg ctcttccgat ctcgaagtag c                                    31

<210> SEQ ID NO 116
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
cagacgtgtg ctcttccgat ctttaaccga ct                                   32

<210> SEQ ID NO 117
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cagacgtgtg ctcttccgat ctgttcatac at                                   32

<210> SEQ ID NO 118
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
cagacgtgtg ctcttccgat ctgacgaaga a                                    31

<210> SEQ ID NO 119
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
cagacgtgtg ctcttccgat cttgcctctg tg                                   32

<210> SEQ ID NO 120
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cagacgtgtg ctcttccgat ctgagatgga t                                    31

<210> SEQ ID NO 121
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cagacgtgtg ctcttccgat ctaccatagt g                          31

<210> SEQ ID NO 122
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cagacgtgtg ctcttccgat ctgtacgaat gg                         32

<210> SEQ ID NO 123
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cagacgtgtg ctcttccgat ctaaggagac g                          31

<210> SEQ ID NO 124
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
cagacgtgtg ctcttccgat ctccattaac c                          31

<210> SEQ ID NO 125
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
cagacgtgtg ctcttccgat cttctcctta cg                         32

<210> SEQ ID NO 126
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
cagacgtgtg ctcttccgat ctatctcacc a                          31

```
<210> SEQ ID NO 127
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cagacgtgtg ctcttccgat ctcgtaacta ag                                       32

<210> SEQ ID NO 128
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
cagacgtgtg ctcttccgat ctagactggc tc                                       32

<210> SEQ ID NO 129
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cagacgtgtg ctcttccgat ctaataccac tc                                       32

<210> SEQ ID NO 130
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
cagacgtgtg ctcttccgat ctctgcatta t                                        31

<210> SEQ ID NO 131
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
cagacgtgtg ctcttccgat ctttgtagct g                                        31

<210> SEQ ID NO 132
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
cagacgtgtg ctcttccgat ctgccgttat c                                        31

<210> SEQ ID NO 133
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cagacgtgtg ctcttccgat ctgaatacaa cc                                        32

<210> SEQ ID NO 134
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
cagacgtgtg ctcttccgat ctaggagaat ac                                        32

<210> SEQ ID NO 135
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cagacgtgtg ctcttccgat ctcatctaag ac                                        32

<210> SEQ ID NO 136
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cagacgtgtg ctcttccgat cttcaataca a                                         31

<210> SEQ ID NO 137
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
cagacgtgtg ctcttccgat ctcgataagt ta                                        32

<210> SEQ ID NO 138
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
cagacgtgtg ctcttccgat ctttgacaag t                                         31

<210> SEQ ID NO 139
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cagacgtgtg ctcttccgat cttgtagttc ta                                    32

<210> SEQ ID NO 140
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
cagacgtgtg ctcttccgat ctgcctatcc t                                     31

<210> SEQ ID NO 141
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cagacgtgtg ctcttccgat ctggcggcaa ta                                    32

<210> SEQ ID NO 142
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cagacgtgtg ctcttccgat ctttacggcc aa                                    32

<210> SEQ ID NO 143
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
cagacgtgtg ctcttccgat ctggaatcct ca                                    32

<210> SEQ ID NO 144
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
cagacgtgtg ctcttccgat ctctcatgtt aa                                    32

<210> SEQ ID NO 145
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 145
cagacgtgtg ctcttccgat ctgattgatt a                                      31

<210> SEQ ID NO 146
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
cagacgtgtg ctcttccgat ctatatactg a                                      31

<210> SEQ ID NO 147
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
cagacgtgtg ctcttccgat ctcgctcctt c                                      31

<210> SEQ ID NO 148
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
cagacgtgtg ctcttccgat ctagtacgcg at                                     32

<210> SEQ ID NO 149
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
cagacgtgtg ctcttccgat ctcacggatc tg                                     32

<210> SEQ ID NO 150
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cagacgtgtg ctcttccgat cttcctggta tc                                     32

<210> SEQ ID NO 151
<211> LENGTH: 31
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 151
cagacgtgtg ctcttccgat ctaggtcttc g                                  31

<210> SEQ ID NO 152
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
cagacgtgtg ctcttccgat ctttccaagg cc                                 32

<210> SEQ ID NO 153
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
cagacgtgtg ctcttccgat ctgtagcatc c                                  31

<210> SEQ ID NO 154
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
cagacgtgtg ctcttccgat ctcctacggc c                                  31

<210> SEQ ID NO 155
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cagacgtgtg ctcttccgat cttacgcttg a                                  31

<210> SEQ ID NO 156
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cagacgtgtg ctcttccgat ctcttggcga ccat                               34

<210> SEQ ID NO 157
<211> LENGTH: 34
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 157
cagacgtgtg ctcttccgat ctcttaaacc ggca                                 34

<210> SEQ ID NO 158
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cagacgtgtg ctcttccgat ctctctgttg ttgc                                 34

<210> SEQ ID NO 159
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cagacgtgtg ctcttccgat ctctctgttg tttg                                 34

<210> SEQ ID NO 160
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cagacgtgtg ctcttccgat ctcgtttcac atat                                 34

<210> SEQ ID NO 161
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
cagacgtgtg ctcttccgat ctcgcttcta agca                                 34

<210> SEQ ID NO 162
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
cagacgtgtg ctcttccgat ctccgactgc tagc                                 34

<210> SEQ ID NO 163
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
cagacgtgtg ctcttccgat ctcatccagt catg        34

<210> SEQ ID NO 164
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
cagacgtgtg ctcttccgat ctcagctccg aagt        34

<210> SEQ ID NO 165
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
cagacgtgtg ctcttccgat ctcaacaacg ttaa        34

<210> SEQ ID NO 166
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cagacgtgtg ctcttccgat ctcattagac tagc        34

<210> SEQ ID NO 167
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cagacgtgtg ctcttccgat ctccagcact tgcg        34

<210> SEQ ID NO 168
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
cagacgtgtg ctcttccgat ctgtgatgta cgtt        34

<210> SEQ ID NO 169
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
cagacgtgtg ctcttccgat ctgtagtcgt ccca    34

<210> SEQ ID NO 170
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
cagacgtgtg ctcttccgat ctggtccaac tcgc    34

<210> SEQ ID NO 171
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
cagacgtgtg ctcttccgat ctggcgccat acag    34

<210> SEQ ID NO 172
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
cagacgtgtg ctcttccgat ctggagagca ccct    34

<210> SEQ ID NO 173
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cagacgtgtg ctcttccgat ctgctctgca atga    34

<210> SEQ ID NO 174
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
cagacgtgtg ctcttccgat ctgcgaacgt ttcc    34

<210> SEQ ID NO 175
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 175
cagacgtgtg ctcttccgat ctgcatcgag tcgg                    34

<210> SEQ ID NO 176
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
cagacgtgtg ctcttccgat ctgatgacgt agat                    34

<210> SEQ ID NO 177
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
cagacgtgtg ctcttccgat ctgagcagaa cata                    34

<210> SEQ ID NO 178
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
cagacgtgtg ctcttccgat ctgacacccc gtgc                    34

<210> SEQ ID NO 179
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
cagacgtgtg ctcttccgat ctgttgttcg accg                    34

<210> SEQ ID NO 180
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cagacgtgtg ctcttccgat cttttatatg tgt                     33

<210> SEQ ID NO 181
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
```
cagacgtgtg ctcttccgat ctttgacatc aca                                33

<210> SEQ ID NO 182
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
cagacgtgtg ctcttccgat ctttatcccc cac                                33

<210> SEQ ID NO 183
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
cagacgtgtg ctcttccgat cttgtgacca gtg                                33

<210> SEQ ID NO 184
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cagacgtgtg ctcttccgat cttggatgct cct                                33

<210> SEQ ID NO 185
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cagacgtgtg ctcttccgat cttgagtaat taa                                33

<210> SEQ ID NO 186
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cagacgtgtg ctcttccgat cttctcatat tgg                                33

<210> SEQ ID NO 187
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cagacgtgtg ctcttccgat cttcgaacat atg                                33

<210> SEQ ID NO 188
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cagacgtgtg ctcttccgat cttcatacta cat                                33

<210> SEQ ID NO 189
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cagacgtgtg ctcttccgat cttatcgacg tca                                33

<210> SEQ ID NO 190
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
cagacgtgtg ctcttccgat cttagaccag ggc                                33

<210> SEQ ID NO 191
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
cagacgtgtg ctcttccgat cttaatgtgg atg                                33

<210> SEQ ID NO 192
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
cagacgtgtg ctcttccgat ctattagtat gtt                                33

<210> SEQ ID NO 193
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
cagacgtgtg ctcttccgat ctatcctatc caa                                33

<210> SEQ ID NO 194
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 194
cagacgtgtg ctcttccgat ctattacacg ccc                                33

<210> SEQ ID NO 195
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 195
cagacgtgtg ctcttccgat ctagttgaaa tag                                33

<210> SEQ ID NO 196
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 196
cagacgtgtg ctcttccgat ctaggccctt tgt                                33

<210> SEQ ID NO 197
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 197
cagacgtgtg ctcttccgat ctagatgagc gta                                33

<210> SEQ ID NO 198
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 198
cagacgtgtg ctcttccgat ctactcttct tcc                                33

<210> SEQ ID NO 199
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
cagacgtgtg ctcttccgat ctaccattat tgg                                33

```
<210> SEQ ID NO 200
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
cagacgtgtg ctcttccgat ctacagactc agt                                33

<210> SEQ ID NO 201
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
cagacgtgtg ctcttccgat ctaattgtct gta                                33

<210> SEQ ID NO 202
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
cagacgtgtg ctcttccgat ctaaggcctc acc                                33

<210> SEQ ID NO 203
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
cagacgtgtg ctcttccgat ctaacgaaca gag                                33

<210> SEQ ID NO 204
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tagctacctt                                                          10

<210> SEQ ID NO 205
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
catcagttgt                                                          10
```

<210> SEQ ID NO 206
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
atcaggaagt                                                          10

<210> SEQ ID NO 207
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ttaaccgact                                                          10

<210> SEQ ID NO 208
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gttcatacat                                                          10

<210> SEQ ID NO 209
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
tgcctctgtg                                                          10

<210> SEQ ID NO 210
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gtacgaatgg                                                          10

<210> SEQ ID NO 211
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tctccttacg                                                          10

<210> SEQ ID NO 212

<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 212
cgtaactaag                                                          10

<210> SEQ ID NO 213
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 213
agactggctc                                                          10

<210> SEQ ID NO 214
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 214
aataccactc                                                          10

<210> SEQ ID NO 215
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 215
gaatacaacc                                                          10

<210> SEQ ID NO 216
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 216
aggagaatac                                                          10

<210> SEQ ID NO 217
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 217
catctaagac                                                          10

<210> SEQ ID NO 218
<211> LENGTH: 10

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
cgataagtta                                                            10

<210> SEQ ID NO 219
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tgtagttcta                                                            10

<210> SEQ ID NO 220
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ggcggcaata                                                            10

<210> SEQ ID NO 221
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ttacggccaa                                                            10

<210> SEQ ID NO 222
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ggaatcctca                                                            10

<210> SEQ ID NO 223
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ctcatgttaa                                                            10

<210> SEQ ID NO 224
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 224
agtacgcgat                                                              10

<210> SEQ ID NO 225
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
cacggatctg                                                              10

<210> SEQ ID NO 226
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tcctggtatc                                                              10

<210> SEQ ID NO 227
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ttccaaggcc                                                              10

<210> SEQ ID NO 228
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
cttggcgacc at                                                           12

<210> SEQ ID NO 229
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
cttaaaccgg ca                                                           12

<210> SEQ ID NO 230
<211> LENGTH: 12
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 230
ctctgttgtt gc                                                            12

<210> SEQ ID NO 231
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ctctgttgtt tg                                                            12

<210> SEQ ID NO 232
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
cgtttcacat at                                                            12

<210> SEQ ID NO 233
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
cgcttctaag ca                                                            12

<210> SEQ ID NO 234
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ccgactgcta gc                                                            12

<210> SEQ ID NO 235
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
catccagtca tg                                                            12

<210> SEQ ID NO 236
<211> LENGTH: 12
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 236
cagctccgaa gt                                                            12

<210> SEQ ID NO 237
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
caacaacgtt aa                                                            12

<210> SEQ ID NO 238
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
cattagacta gc                                                            12

<210> SEQ ID NO 239
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ccagcacttg cg                                                            12

<210> SEQ ID NO 240
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
gtgatgtacg tt                                                            12

<210> SEQ ID NO 241
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
gtagtcgtcc ca                                                            12

<210> SEQ ID NO 242
<211> LENGTH: 12
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 242
ggtccaactc gc                                                          12

<210> SEQ ID NO 243
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ggcgccatac ag                                                          12

<210> SEQ ID NO 244
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ggagagcacc ct                                                          12

<210> SEQ ID NO 245
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
gctctgcaat ga                                                          12

<210> SEQ ID NO 246
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
gcgaacgttt cc                                                          12

<210> SEQ ID NO 247
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gcatcgagtc gg                                                          12

<210> SEQ ID NO 248
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gatgacgtag at                                                          12

<210> SEQ ID NO 249
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gagcagaaca ta                                                          12

<210> SEQ ID NO 250
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
gacaccccgt gc                                                          12

<210> SEQ ID NO 251
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gttgttcgac cg                                                          12

<210> SEQ ID NO 252
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
tttatatgtg t                                                           11

<210> SEQ ID NO 253
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ttgacatcac a                                                           11

<210> SEQ ID NO 254
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 254
ttatccccca c					11

<210> SEQ ID NO 255
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tgtgaccagt g					11

<210> SEQ ID NO 256
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tggatgctcc t					11

<210> SEQ ID NO 257
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tgagtaatta a					11

<210> SEQ ID NO 258
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
tctcatattg g					11

<210> SEQ ID NO 259
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tcgaacatat g					11

<210> SEQ ID NO 260
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
tcatactaca t                                                           11

<210> SEQ ID NO 261
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tatcgacgtc a                                                           11

<210> SEQ ID NO 262
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tagaccaggg c                                                           11

<210> SEQ ID NO 263
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
taatgtggat g                                                           11

<210> SEQ ID NO 264
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
attagtatgt t                                                           11

<210> SEQ ID NO 265
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
atcctatcca a                                                           11

<210> SEQ ID NO 266
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
attacacgcc c                                                            11

<210> SEQ ID NO 267
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
agttgaaata g                                                            11

<210> SEQ ID NO 268
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
aggccctttg t                                                            11

<210> SEQ ID NO 269
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
agatgagcgt a                                                            11

<210> SEQ ID NO 270
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
actcttcttc c                                                            11

<210> SEQ ID NO 271
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
accattattg g                                                            11

<210> SEQ ID NO 272
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
acagactcag t                                                            11

```
<210> SEQ ID NO 273
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
aattgtctgt a                                                              11

<210> SEQ ID NO 274
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
aaggcctcac c                                                              11

<210> SEQ ID NO 275
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
aacgaacaga g                                                              11

<210> SEQ ID NO 276
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tgacttgtca tgtcttccga tcttgggtgt ttt                                      33

<210> SEQ ID NO 277
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
tgacttgtca tgtcttccga tcttcgagtc ttt                                      33

<210> SEQ ID NO 278
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
tgacttgtca tgtcttccga tctgcagatt gtt                                      33
```

<210> SEQ ID NO 279
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
tgacttgtca tgtcttccga tcttctatgc gtt                                    33

<210> SEQ ID NO 280
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tgacttgtca tgtcttccga tctggacttt ctt                                    33

<210> SEQ ID NO 281
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
tgacttgtca tgtcttccga tctgccgtgc ctt                                    33

<210> SEQ ID NO 282
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
tgacttgtca tgtcttccga tctagtgttt att                                    33

<210> SEQ ID NO 283
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
tgacttgtca tgtcttccga tctgactggc att                                    33

<210> SEQ ID NO 284
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
tgacttgtca tgtcttccga tcttgacatg ttt                                    33

```
<210> SEQ ID NO 285
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
tgacttgtca tgtcttccga tctcccttta ttt                                33

<210> SEQ ID NO 286
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
tgacttgtca tgtcttccga tctttggttg gtt                                33

<210> SEQ ID NO 287
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
tgacttgtca tgtcttccga tctataagta gtt                                33

<210> SEQ ID NO 288
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tgacttgtca tgtcttccga tctcctcttg ctt                                33

<210> SEQ ID NO 289
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
tgacttgtca tgtcttccga tctaagctta ctt                                33

<210> SEQ ID NO 290
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
tgacttgtca tgtcttccga tctggcattg att                                33

<210> SEQ ID NO 291
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
tgacttgtca tgtcttccga tcttgcctga att                                    33

<210> SEQ ID NO 292
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
tgacttgtca tgtcttccga tctgcgcggt ttt                                    33

<210> SEQ ID NO 293
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
tgacttgtca tgtcttccga tctcagcatc ttt                                    33

<210> SEQ ID NO 294
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
tgacttgtca tgtcttccga tcttgcaatt gtt                                    33

<210> SEQ ID NO 295
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tgacttgtca tgtcttccga tctggccagc gtt                                    33

<210> SEQ ID NO 296
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
tgacttgtca tgtcttccga tctatccatt ctt                                    33

<210> SEQ ID NO 297
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
tgacttgtca tgtcttccga tctaatctgc ctt                                     33

<210> SEQ ID NO 298
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
tgacttgtca tgtcttccga tctccgattt att                                     33

<210> SEQ ID NO 299
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
tgacttgtca tgtcttccga tctcgggggc att                                     33

<210> SEQ ID NO 300
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
tgacttgtca tgtcttccga tctcgccggg ttt                                     33

<210> SEQ ID NO 301
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
tgacttgtca tgtcttccga tctaggtcta ttt                                     33

<210> SEQ ID NO 302
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
tgacttgtca tgtcttccga tctgacgctg gtt                                     33

<210> SEQ ID NO 303
<211> LENGTH: 33
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 303
tgacttgtca tgtcttccga tctcataata gtt                                    33

<210> SEQ ID NO 304
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
tgacttgtca tgtcttccga tctatgtggg ctt                                    33

<210> SEQ ID NO 305
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
tgacttgtca tgtcttccga tctgcgacta ctt                                    33

<210> SEQ ID NO 306
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
tgacttgtca tgtcttccga tctgtactgg att                                    33

<210> SEQ ID NO 307
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
tgacttgtca tgtcttccga tctaaagcga att                                    33

<210> SEQ ID NO 308
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
tgacttgtca tgtcttccga tctctgtcgt ttt                                    33

<210> SEQ ID NO 309
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
tgacttgtca tgtcttccga tctagaaggc ttt                                33

<210> SEQ ID NO 310
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
tgacttgtca tgtcttccga tctttacagt gtt                                33

<210> SEQ ID NO 311
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
tgacttgtca tgtcttccga tctctgatcc gtt                                33

<210> SEQ ID NO 312
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
tgacttgtca tgtcttccga tctcctaggt ctt                                33

<210> SEQ ID NO 313
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tgacttgtca tgtcttccga tctctaccgc ctt                                33

<210> SEQ ID NO 314
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tgacttgtca tgtcttccga tcttacggtt att                                33

<210> SEQ ID NO 315
<211> LENGTH: 33
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 315
tgacttgtca tgtcttccga tcttttgcgc att                                    33

<210> SEQ ID NO 316
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tgacttgtca tgtcttccga tctgaagagg ttt                                    33

<210> SEQ ID NO 317
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
tgacttgtca tgtcttccga tctggtttga ttt                                    33

<210> SEQ ID NO 318
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
tgacttgtca tgtcttccga tctacgaatg gtt                                    33

<210> SEQ ID NO 319
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
tgacttgtca tgtcttccga tctgttggga gtt                                    33

<210> SEQ ID NO 320
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
tgacttgtca tgtcttccga tcttcgccgg ctt                                    33

<210> SEQ ID NO 321
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 321
tgacttgtca tgtcttccga tctccttcca ctt                                    33

<210> SEQ ID NO 322
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
tgacttgtca tgtcttccga tctcccgcgg att                                    33

<210> SEQ ID NO 323
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
tgacttgtca tgtcttccga tctgctaaga att                                    33

<210> SEQ ID NO 324
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
tgacttgtca tgtcttccga tctaagaagt ttt                                    33

<210> SEQ ID NO 325
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
tgacttgtca tgtcttccga tctgaactcc ttt                                    33

<210> SEQ ID NO 326
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
tgacttgtca tgtcttccga tctgtcttct gtt                                    33

<210> SEQ ID NO 327
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
tgacttgtca tgtcttccga tcttggcccc gtt                     33

<210> SEQ ID NO 328
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
tgacttgtca tgtcttccga tctttgagct ctt                     33

<210> SEQ ID NO 329
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
tgacttgtca tgtcttccga tcttgttagc ctt                     33

<210> SEQ ID NO 330
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tgacttgtca tgtcttccga tctaaacgct att                     33

<210> SEQ ID NO 331
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
tgacttgtca tgtcttccga tctccccgcc att                     33

<210> SEQ ID NO 332
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
tgacttgtca tgtcttccga tctttcaagg ttt                     33

<210> SEQ ID NO 333
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
tgacttgtca tgtcttccga tctcttctca ttt    33

<210> SEQ ID NO 334
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
tgacttgtca tgtcttccga tctgcatcgg gtt    33

<210> SEQ ID NO 335
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
tgacttgtca tgtcttccga tcttactcga gtt    33

<210> SEQ ID NO 336
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
tgacttgtca tgtcttccga tctcactagg ctt    33

<210> SEQ ID NO 337
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
tgacttgtca tgtcttccga tcttaacaca ctt    33

<210> SEQ ID NO 338
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
tgacttgtca tgtcttccga tctcgattcg att    33

<210> SEQ ID NO 339
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
tgacttgtca tgtcttccga tctgggcgca att                33

<210> SEQ ID NO 340
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
tgacttgtca tgtcttccga tcttccctct ttt                33

<210> SEQ ID NO 341
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
tgacttgtca tgtcttccga tctacttgcc ttt                33

<210> SEQ ID NO 342
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
tgacttgtca tgtcttccga tctagcgcct gtt                33

<210> SEQ ID NO 343
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
tgacttgtca tgtcttccga tctacgttac gtt                33

<210> SEQ ID NO 344
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
tgacttgtca tgtcttccga tctgacaact ctt                33

<210> SEQ ID NO 345
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
tgacttgtca tgtcttccga tctatagtcc ctt                                    33

<210> SEQ ID NO 346
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
tgacttgtca tgtcttccga tctaccagat att                                    33

<210> SEQ ID NO 347
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
tgacttgtca tgtcttccga tctagtaccc att                                    33

<210> SEQ ID NO 348
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
tgacttgtca tgtcttccga tcttatgccg ttt                                    33

<210> SEQ ID NO 349
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
tgacttgtca tgtcttccga tcttgatgca ttt                                    33

<210> SEQ ID NO 350
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
tgacttgtca tgtcttccga tcttaaagag gtt                                    33

<210> SEQ ID NO 351
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
tgacttgtca tgtcttccga tctacgggca gtt                                    33

```
<210> SEQ ID NO 352
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
tgacttgtca tgtcttccga tcttgtatcg ctt                                33

<210> SEQ ID NO 353
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
tgacttgtca tgtcttccga tctcaaataa ctt                                33

<210> SEQ ID NO 354
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
tgacttgtca tgtcttccga tcttttcgcg att                                33

<210> SEQ ID NO 355
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
tgacttgtca tgtcttccga tcttcaacca att                                33

<210> SEQ ID NO 356
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
tgacttgtca tgtcttccga tctgtatgat ttt                                33

<210> SEQ ID NO 357
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
tgacttgtca tgtcttccga tctaacccac ttt                                33
```

<210> SEQ ID NO 358
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 358
tgacttgtca tgtcttccga tctcatttat gtt                                    33

<210> SEQ ID NO 359
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 359
tgacttgtca tgtcttccga tctcgctcac gtt                                    33

<210> SEQ ID NO 360
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 360
tgacttgtca tgtcttccga tcttgtcgat ctt                                    33

<210> SEQ ID NO 361
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 361
tgacttgtca tgtcttccga tctggatccc ctt                                    33

<210> SEQ ID NO 362
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 362
tgacttgtca tgtcttccga tctgaaacat att                                    33

<210> SEQ ID NO 363
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 363
tgacttgtca tgtcttccga tcttcacaac att                                    33

<210> SEQ ID NO 364
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
tgacttgtca tgtcttccga tctattatag ttt                                33

<210> SEQ ID NO 365
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
tgacttgtca tgtcttccga tctcgagcaa ttt                                33

<210> SEQ ID NO 366
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
tgacttgtca tgtcttccga tctgtgccag gtt                                33

<210> SEQ ID NO 367
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
tgacttgtca tgtcttccga tctgagtaca gtt                                33

<210> SEQ ID NO 368
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
tgacttgtca tgtcttccga tctgagggag ctt                                33

<210> SEQ ID NO 369
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
tgacttgtca tgtcttccga tcttccaaaa ctt                                33

<210> SEQ ID NO 370

```
<210> SEQ ID NO 370
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
tgacttgtca tgtcttccga tctaattaag att                                      33

<210> SEQ ID NO 371
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
tgacttgtca tgtcttccga tctatgaaca att                                      33

<210> SEQ ID NO 372
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
tgggtgtttt                                                                10

<210> SEQ ID NO 373
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
tcgagtcttt                                                                10

<210> SEQ ID NO 374
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gcagattgtt                                                                10

<210> SEQ ID NO 375
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
tctatgcgtt                                                                10

<210> SEQ ID NO 376
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
ggactttctt                                                                10

<210> SEQ ID NO 377
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
gccgtgcctt                                                                10

<210> SEQ ID NO 378
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
agtgtttatt                                                                10

<210> SEQ ID NO 379
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
gactggcatt                                                                10

<210> SEQ ID NO 380
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
tgacatgttt                                                                10

<210> SEQ ID NO 381
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
ccctttattt                                                                10

<210> SEQ ID NO 382
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 382
ttggttggtt                                                          10

<210> SEQ ID NO 383
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
ataagtagtt                                                          10

<210> SEQ ID NO 384
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
cctcttgctt                                                          10

<210> SEQ ID NO 385
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
aagcttactt                                                          10

<210> SEQ ID NO 386
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
ggcattgatt                                                          10

<210> SEQ ID NO 387
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
tgcctgaatt                                                          10

<210> SEQ ID NO 388
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 388
gcgcggtttt                                                           10

<210> SEQ ID NO 389
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
cagcatcttt                                                           10

<210> SEQ ID NO 390
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
tgcaattgtt                                                           10

<210> SEQ ID NO 391
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
ggccagcgtt                                                           10

<210> SEQ ID NO 392
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
atccattctt                                                           10

<210> SEQ ID NO 393
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
aatctgcctt                                                           10

<210> SEQ ID NO 394
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 394
ccgatttatt                                                          10

<210> SEQ ID NO 395
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
cgggggcatt                                                          10

<210> SEQ ID NO 396
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
cgccgggttt                                                          10

<210> SEQ ID NO 397
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
aggtctattt                                                          10

<210> SEQ ID NO 398
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
gacgctggtt                                                          10

<210> SEQ ID NO 399
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
cataatagtt                                                          10

<210> SEQ ID NO 400
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 400
atgtgggctt                                                                10

<210> SEQ ID NO 401
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
gcgactactt                                                                10

<210> SEQ ID NO 402
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
gtactggatt                                                                10

<210> SEQ ID NO 403
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
aaagcgaatt                                                                10

<210> SEQ ID NO 404
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
ctgtcgtttt                                                                10

<210> SEQ ID NO 405
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
agaaggcttt                                                                10

<210> SEQ ID NO 406
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 406
ttacagtgtt                                                              10

<210> SEQ ID NO 407
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
ctgatccgtt                                                              10

<210> SEQ ID NO 408
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
cctaggtctt                                                              10

<210> SEQ ID NO 409
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
ctaccgcctt                                                              10

<210> SEQ ID NO 410
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
tacggttatt                                                              10

<210> SEQ ID NO 411
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
tttgcgcatt                                                              10

<210> SEQ ID NO 412
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 412
gaagaggttt                                                              10

<210> SEQ ID NO 413
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ggtttgattt                                                              10

<210> SEQ ID NO 414
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
acgaatggtt                                                              10

<210> SEQ ID NO 415
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
gttgggagtt                                                              10

<210> SEQ ID NO 416
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
tcgccggctt                                                              10

<210> SEQ ID NO 417
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
ccttccactt                                                              10

<210> SEQ ID NO 418
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
```
cccgcggatt                                                                 10

<210> SEQ ID NO 419
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
gctaagaatt                                                                 10

<210> SEQ ID NO 420
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
aagaagtttt                                                                 10

<210> SEQ ID NO 421
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
gaactccttt                                                                 10

<210> SEQ ID NO 422
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
gtcttctgtt                                                                 10

<210> SEQ ID NO 423
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
tggccccgtt                                                                 10

<210> SEQ ID NO 424
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
ttgagctctt                                                                10

<210> SEQ ID NO 425
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
tgttagcctt                                                                10

<210> SEQ ID NO 426
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
aaacgctatt                                                                10

<210> SEQ ID NO 427
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
ccccgccatt                                                                10

<210> SEQ ID NO 428
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
ttcaaggttt                                                                10

<210> SEQ ID NO 429
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
cttctcattt                                                                10

<210> SEQ ID NO 430
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
gcatcgggtt                                                                10

<210> SEQ ID NO 431
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
tactcgagtt                                                          10

<210> SEQ ID NO 432
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
cactaggctt                                                          10

<210> SEQ ID NO 433
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
taacacactt                                                          10

<210> SEQ ID NO 434
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
cgattcgatt                                                          10

<210> SEQ ID NO 435
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
gggcgcaatt                                                          10

<210> SEQ ID NO 436
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
tccctctttt                                                          10

<210> SEQ ID NO 437
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
acttgccttt                                                                10

<210> SEQ ID NO 438
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
agcgcctgtt                                                                10

<210> SEQ ID NO 439
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
acgttacgtt                                                                10

<210> SEQ ID NO 440
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
gacaactctt                                                                10

<210> SEQ ID NO 441
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
atagtccctt                                                                10

<210> SEQ ID NO 442
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
accagatatt                                                                10

```
<210> SEQ ID NO 443
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
agtacccatt                                                             10

<210> SEQ ID NO 444
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
tatgccgttt                                                             10

<210> SEQ ID NO 445
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
tgatgcattt                                                             10

<210> SEQ ID NO 446
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
taaagaggtt                                                             10

<210> SEQ ID NO 447
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
acgggcagtt                                                             10

<210> SEQ ID NO 448
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
tgtatcgctt                                                             10

<210> SEQ ID NO 449
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
caaataactt                                                          10

<210> SEQ ID NO 450
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
tttcgcgatt                                                          10

<210> SEQ ID NO 451
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
tcaaccaatt                                                          10

<210> SEQ ID NO 452
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
gtatgatttt                                                          10

<210> SEQ ID NO 453
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
aacccacttt                                                          10

<210> SEQ ID NO 454
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
catttatgtt                                                          10

<210> SEQ ID NO 455
<211> LENGTH: 10
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
cgctcacgtt                                                          10

<210> SEQ ID NO 456
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
tgtcgatctt                                                          10

<210> SEQ ID NO 457
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
ggatcccctt                                                          10

<210> SEQ ID NO 458
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
gaaacatatt                                                          10

<210> SEQ ID NO 459
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
tcacaacatt                                                          10

<210> SEQ ID NO 460
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
attatagttt                                                          10

<210> SEQ ID NO 461
<211> LENGTH: 10
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 461
cgagcaattt                                                          10

<210> SEQ ID NO 462
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
gtgccaggtt                                                          10

<210> SEQ ID NO 463
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
gagtacagtt                                                          10

<210> SEQ ID NO 464
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
gagggagctt                                                          10

<210> SEQ ID NO 465
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
tccaaaactt                                                          10

<210> SEQ ID NO 466
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
aattaagatt                                                          10

<210> SEQ ID NO 467
<211> LENGTH: 10
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 467
atgaacaatt                                                                10

<210> SEQ ID NO 468
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
tgacttgtca tgtcttccga tcttgggtgt ttt                                       33

<210> SEQ ID NO 469
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
tgacttgtca tgtcttccga tcttcgagtc ttt                                       33

<210> SEQ ID NO 470
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
tgacttgtca tgtcttccga tctgcagatt gtt                                       33

<210> SEQ ID NO 471
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
tgacttgtca tgtcttccga tcttctatgc gtt                                       33

<210> SEQ ID NO 472
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
tgacttgtca tgtcttccga tctggacttt ctt                                       33

<210> SEQ ID NO 473
<211> LENGTH: 33
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 473
tgacttgtca tgtcttccga tctgccgtgc ctt                                    33

<210> SEQ ID NO 474
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
tgacttgtca tgtcttccga tctagtgttt att                                    33

<210> SEQ ID NO 475
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
tgacttgtca tgtcttccga tctgactggc att                                    33

<210> SEQ ID NO 476
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
tgacttgtca tgtcttccga tcttgacatg ttt                                    33

<210> SEQ ID NO 477
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
tgacttgtca tgtcttccga tctcccttta ttt                                    33

<210> SEQ ID NO 478
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
tgacttgtca tgtcttccga tctttggttg gtt                                    33

<210> SEQ ID NO 479
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 479
tgacttgtca tgtcttccga tctataagta gtt                                  33

<210> SEQ ID NO 480
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
tgacttgtca tgtcttccga tctcctcttg ctt                                  33

<210> SEQ ID NO 481
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
tgacttgtca tgtcttccga tctaagctta ctt                                  33

<210> SEQ ID NO 482
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
tgacttgtca tgtcttccga tctggcattg att                                  33

<210> SEQ ID NO 483
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
tgacttgtca tgtcttccga tcttgcctga att                                  33

<210> SEQ ID NO 484
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
tgacttgtca tgtcttccga tctgcgcggt ttt                                  33

<210> SEQ ID NO 485
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
tgacttgtca tgtcttccga tctcagcatc ttt                                33

<210> SEQ ID NO 486
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
tgacttgtca tgtcttccga tcttgcaatt gtt                                33

<210> SEQ ID NO 487
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
tgacttgtca tgtcttccga tctggccagc gtt                                33

<210> SEQ ID NO 488
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
tgacttgtca tgtcttccga tctatccatt ctt                                33

<210> SEQ ID NO 489
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
tgacttgtca tgtcttccga tctaatctgc ctt                                33

<210> SEQ ID NO 490
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
tgacttgtca tgtcttccga tctccgattt att                                33

<210> SEQ ID NO 491
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
tgacttgtca tgtcttccga tctcgggggc att                33

<210> SEQ ID NO 492
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
tgacttgtca tgtcttccga tctcgccggg ttt                33

<210> SEQ ID NO 493
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
tgacttgtca tgtcttccga tctaggtcta ttt                33

<210> SEQ ID NO 494
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
tgacttgtca tgtcttccga tctgacgctg gtt                33

<210> SEQ ID NO 495
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
tgacttgtca tgtcttccga tctcataata gtt                33

<210> SEQ ID NO 496
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
tgacttgtca tgtcttccga tctatgtggg ctt                33

<210> SEQ ID NO 497
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
tgacttgtca tgtcttccga tctgcgacta ctt                            33

<210> SEQ ID NO 498
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
tgacttgtca tgtcttccga tctgtactgg att                            33

<210> SEQ ID NO 499
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
tgacttgtca tgtcttccga tctaaagcga att                            33

<210> SEQ ID NO 500
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
tgacttgtca tgtcttccga tctctgtcgt ttt                            33

<210> SEQ ID NO 501
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
tgacttgtca tgtcttccga tctagaaggc ttt                            33

<210> SEQ ID NO 502
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
tgacttgtca tgtcttccga tctttacagt gtt                            33

<210> SEQ ID NO 503
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503

```
tgacttgtca tgtcttccga tctctgatcc gtt                                33
```

<210> SEQ ID NO 504
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504

```
tgacttgtca tgtcttccga tctcctaggt ctt                                33
```

<210> SEQ ID NO 505
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505

```
tgacttgtca tgtcttccga tctctaccgc ctt                                33
```

<210> SEQ ID NO 506
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506

```
tgacttgtca tgtcttccga tcttacggtt att                                33
```

<210> SEQ ID NO 507
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507

```
tgacttgtca tgtcttccga tcttttgcgc att                                33
```

<210> SEQ ID NO 508
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508

```
tgacttgtca tgtcttccga tctgaagagg ttt                                33
```

<210> SEQ ID NO 509
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509

```
tgacttgtca tgtcttccga tctggtttga ttt                                33
```

<210> SEQ ID NO 510
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
tgacttgtca tgtcttccga tctacgaatg gtt                          33

<210> SEQ ID NO 511
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
tgacttgtca tgtcttccga tctgttggga gtt                          33

<210> SEQ ID NO 512
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
tgacttgtca tgtcttccga tcttcgccgg ctt                          33

<210> SEQ ID NO 513
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
tgacttgtca tgtcttccga tctccttcca ctt                          33

<210> SEQ ID NO 514
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
tgacttgtca tgtcttccga tctcccgcgg att                          33

<210> SEQ ID NO 515
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
tgacttgtca tgtcttccga tctgctaaga att                          33

<210> SEQ ID NO 516
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
tgacttgtca tgtcttccga tctaagaagt ttt                                33

<210> SEQ ID NO 517
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
tgacttgtca tgtcttccga tctgaactcc ttt                                33

<210> SEQ ID NO 518
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
tgacttgtca tgtcttccga tctgtcttct gtt                                33

<210> SEQ ID NO 519
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
tgacttgtca tgtcttccga tcttggcccc gtt                                33

<210> SEQ ID NO 520
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
tgacttgtca tgtcttccga tctttgagct ctt                                33

<210> SEQ ID NO 521
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
tgacttgtca tgtcttccga tcttgttagc ctt                                33

```
<210> SEQ ID NO 522
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
tgacttgtca tgtcttccga tctaaacgct att                                    33

<210> SEQ ID NO 523
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
tgacttgtca tgtcttccga tctccccgcc att                                    33

<210> SEQ ID NO 524
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
tgacttgtca tgtcttccga tctttcaagg ttt                                    33

<210> SEQ ID NO 525
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
tgacttgtca tgtcttccga tctcttctca ttt                                    33

<210> SEQ ID NO 526
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
tgacttgtca tgtcttccga tctgcatcgg gtt                                    33

<210> SEQ ID NO 527
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tgacttgtca tgtcttccga tcttactcga gtt                                    33

<210> SEQ ID NO 528
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
tgacttgtca tgtcttccga tctcactagg ctt                                    33

<210> SEQ ID NO 529
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
tgacttgtca tgtcttccga tcttaacaca ctt                                    33

<210> SEQ ID NO 530
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
tgacttgtca tgtcttccga tctcgattcg att                                    33

<210> SEQ ID NO 531
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
tgacttgtca tgtcttccga tctgggcgca att                                    33

<210> SEQ ID NO 532
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
tgacttgtca tgtcttccga tcttccctct ttt                                    33

<210> SEQ ID NO 533
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
tgacttgtca tgtcttccga tctacttgcc ttt                                    33

<210> SEQ ID NO 534
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
tgacttgtca tgtcttccga tctagcgcct gtt                                   33

<210> SEQ ID NO 535
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
tgacttgtca tgtcttccga tctacgttac gtt                                   33

<210> SEQ ID NO 536
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
tgacttgtca tgtcttccga tctgacaact ctt                                   33

<210> SEQ ID NO 537
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
tgacttgtca tgtcttccga tctatagtcc ctt                                   33

<210> SEQ ID NO 538
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
tgacttgtca tgtcttccga tctaccagat att                                   33

<210> SEQ ID NO 539
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
tgacttgtca tgtcttccga tctagtaccc att                                   33

<210> SEQ ID NO 540
<211> LENGTH: 33
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 540
tgacttgtca tgtcttccga tcttatgccg ttt                33

<210> SEQ ID NO 541
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 541
tgacttgtca tgtcttccga tcttgatgca ttt                33

<210> SEQ ID NO 542
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 542
tgacttgtca tgtcttccga tcttaaagag gtt                33

<210> SEQ ID NO 543
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 543
tgacttgtca tgtcttccga tctacgggca gtt                33

<210> SEQ ID NO 544
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 544
tgacttgtca tgtcttccga tcttgtatcg ctt                33

<210> SEQ ID NO 545
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 545
tgacttgtca tgtcttccga tctcaaataa ctt                33

<210> SEQ ID NO 546
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
tgacttgtca tgtcttccga tcttttcgcg att                                    33

<210> SEQ ID NO 547
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
tgacttgtca tgtcttccga tcttcaacca att                                    33

<210> SEQ ID NO 548
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
tgacttgtca tgtcttccga tctgtatgat ttt                                    33

<210> SEQ ID NO 549
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
tgacttgtca tgtcttccga tctaacccac ttt                                    33

<210> SEQ ID NO 550
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
tgacttgtca tgtcttccga tctcatttat gtt                                    33

<210> SEQ ID NO 551
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
tgacttgtca tgtcttccga tctcgctcac gtt                                    33

<210> SEQ ID NO 552
<211> LENGTH: 33
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 552
tgacttgtca tgtcttccga tcttgtcgat ctt                                    33

<210> SEQ ID NO 553
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
tgacttgtca tgtcttccga tctggatccc ctt                                    33

<210> SEQ ID NO 554
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
tgacttgtca tgtcttccga tctgaaacat att                                    33

<210> SEQ ID NO 555
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
tgacttgtca tgtcttccga tcttcacaac att                                    33

<210> SEQ ID NO 556
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
tgacttgtca tgtcttccga tctattatag ttt                                    33

<210> SEQ ID NO 557
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
tgacttgtca tgtcttccga tctcgagcaa ttt                                    33

<210> SEQ ID NO 558
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 558
tgacttgtca tgtcttccga tctgtgccag gtt                                    33

<210> SEQ ID NO 559
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
tgacttgtca tgtcttccga tctgagtaca gtt                                    33

<210> SEQ ID NO 560
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
tgacttgtca tgtcttccga tctgagggag ctt                                    33

<210> SEQ ID NO 561
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
tgacttgtca tgtcttccga tcttccaaaa ctt                                    33

<210> SEQ ID NO 562
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
tgacttgtca tgtcttccga tctaattaag att                                    33

<210> SEQ ID NO 563
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
tgacttgtca tgtcttccga tctatgaaca att                                    33

<210> SEQ ID NO 564
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 564
tgggtgtttt                                                         10

<210> SEQ ID NO 565
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
tcgagtcttt                                                         10

<210> SEQ ID NO 566
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
gcagattgtt                                                         10

<210> SEQ ID NO 567
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
tctatgcgtt                                                         10

<210> SEQ ID NO 568
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
ggactttctt                                                         10

<210> SEQ ID NO 569
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
gccgtgcctt                                                         10

<210> SEQ ID NO 570
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 570 agtgtttatt					10

<210> SEQ ID NO 571
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571 gactggcatt					10

<210> SEQ ID NO 572
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572 tgacatgttt					10

<210> SEQ ID NO 573
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573 ccctttattt					10

<210> SEQ ID NO 574
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574 ttggttggtt					10

<210> SEQ ID NO 575
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575 ataagtagtt					10

<210> SEQ ID NO 576
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
cctcttgctt                                                            10

<210> SEQ ID NO 577
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
aagcttactt                                                            10

<210> SEQ ID NO 578
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
ggcattgatt                                                            10

<210> SEQ ID NO 579
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
tgcctgaatt                                                            10

<210> SEQ ID NO 580
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
gcgcggtttt                                                            10

<210> SEQ ID NO 581
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
cagcatcttt                                                            10

<210> SEQ ID NO 582
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
tgcaattgtt                                                          10

<210> SEQ ID NO 583
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
ggccagcgtt                                                          10

<210> SEQ ID NO 584
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
atccattctt                                                          10

<210> SEQ ID NO 585
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
aatctgcctt                                                          10

<210> SEQ ID NO 586
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
ccgatttatt                                                          10

<210> SEQ ID NO 587
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
cgggggcatt                                                          10

<210> SEQ ID NO 588
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
cgccgggttt                                                          10

<210> SEQ ID NO 589
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
aggtctattt                                                          10

<210> SEQ ID NO 590
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
gacgctggtt                                                          10

<210> SEQ ID NO 591
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
cataatagtt                                                          10

<210> SEQ ID NO 592
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
atgtgggctt                                                          10

<210> SEQ ID NO 593
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
gcgactactt                                                          10

<210> SEQ ID NO 594
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
gtactggatt                                                          10

<210> SEQ ID NO 595
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
aaagcgaatt                                                                10

<210> SEQ ID NO 596
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
ctgtcgtttt                                                                10

<210> SEQ ID NO 597
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
agaaggcttt                                                                10

<210> SEQ ID NO 598
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
ttacagtgtt                                                                10

<210> SEQ ID NO 599
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
ctgatccgtt                                                                10

<210> SEQ ID NO 600
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
cctaggtctt                                                                10

```
<210> SEQ ID NO 601
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
ctaccgcctt                                                              10

<210> SEQ ID NO 602
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
tacggttatt                                                              10

<210> SEQ ID NO 603
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
tttgcgcatt                                                              10

<210> SEQ ID NO 604
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
gaagaggttt                                                              10

<210> SEQ ID NO 605
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
ggtttgattt                                                              10

<210> SEQ ID NO 606
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
acgaatggtt                                                              10

<210> SEQ ID NO 607
```

-continued

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
gttgggagtt                                                            10

<210> SEQ ID NO 608
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
tcgccggctt                                                            10

<210> SEQ ID NO 609
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
ccttccactt                                                            10

<210> SEQ ID NO 610
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
cccgcggatt                                                            10

<210> SEQ ID NO 611
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
gctaagaatt                                                            10

<210> SEQ ID NO 612
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
aagaagtttt                                                            10

<210> SEQ ID NO 613
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
gaactccttt                                                              10

<210> SEQ ID NO 614
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
gtcttctgtt                                                              10

<210> SEQ ID NO 615
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
tggccccgtt                                                              10

<210> SEQ ID NO 616
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
ttgagctctt                                                              10

<210> SEQ ID NO 617
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
tgttagcctt                                                              10

<210> SEQ ID NO 618
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
aaacgctatt                                                              10

<210> SEQ ID NO 619
<211> LENGTH: 10
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 619
ccccgccatt                                                          10

<210> SEQ ID NO 620
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
ttcaaggttt                                                          10

<210> SEQ ID NO 621
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
cttctcattt                                                          10

<210> SEQ ID NO 622
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
gcatcgggtt                                                          10

<210> SEQ ID NO 623
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
tactcgagtt                                                          10

<210> SEQ ID NO 624
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
cactaggctt                                                          10

<210> SEQ ID NO 625
<211> LENGTH: 10
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 625
taacacactt                                                                10

<210> SEQ ID NO 626
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
cgattcgatt                                                                10

<210> SEQ ID NO 627
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
gggcgcaatt                                                                10

<210> SEQ ID NO 628
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
tccctctttt                                                                10

<210> SEQ ID NO 629
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
acttgccttt                                                                10

<210> SEQ ID NO 630
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
agcgcctgtt                                                                10

<210> SEQ ID NO 631
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 631
acgttacgtt                                                                10

<210> SEQ ID NO 632
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
gacaactctt                                                                10

<210> SEQ ID NO 633
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
atagtccctt                                                                10

<210> SEQ ID NO 634
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
accagatatt                                                                10

<210> SEQ ID NO 635
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
agtacccatt                                                                10

<210> SEQ ID NO 636
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
tatgccgttt                                                                10

<210> SEQ ID NO 637
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 637
tgatgcattt                                                          10

<210> SEQ ID NO 638
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
taaagaggtt                                                          10

<210> SEQ ID NO 639
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
acgggcagtt                                                          10

<210> SEQ ID NO 640
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
tgtatcgctt                                                          10

<210> SEQ ID NO 641
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
caaataactt                                                          10

<210> SEQ ID NO 642
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
tttcgcgatt                                                          10

<210> SEQ ID NO 643
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 643
tcaaccaatt                                                          10

<210> SEQ ID NO 644
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
gtatgatttt                                                          10

<210> SEQ ID NO 645
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
aacccacttt                                                          10

<210> SEQ ID NO 646
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
catttatgtt                                                          10

<210> SEQ ID NO 647
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
cgctcacgtt                                                          10

<210> SEQ ID NO 648
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
tgtcgatctt                                                          10

<210> SEQ ID NO 649
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 649
ggatcccctt                                                            10

<210> SEQ ID NO 650
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
gaaacatatt                                                            10

<210> SEQ ID NO 651
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
tcacaacatt                                                            10

<210> SEQ ID NO 652
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
attatagttt                                                            10

<210> SEQ ID NO 653
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
cgagcaattt                                                            10

<210> SEQ ID NO 654
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
gtgccaggtt                                                            10

<210> SEQ ID NO 655
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
```

```
gagtacagtt                                                          10

<210> SEQ ID NO 656
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656
gagggagctt                                                          10

<210> SEQ ID NO 657
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
tccaaaactt                                                          10

<210> SEQ ID NO 658
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
aattaagatt                                                          10

<210> SEQ ID NO 659
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659
atgaacaatt                                                          10

<210> SEQ ID NO 660
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
aaacacccaa gatcggaaga gcgtcgtgta                                    30

<210> SEQ ID NO 661
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
```
aagactcgaa gatcggaaga gcgtcgtgta                                              30

<210> SEQ ID NO 662
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
acaatctgca gatcggaaga gcgtcgtgta                                              30

<210> SEQ ID NO 663
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
acgcatagaa gatcggaaga gcgtcgtgta                                              30

<210> SEQ ID NO 664
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
agaaagtcca gatcggaaga gcgtcgtgta                                              30

<210> SEQ ID NO 665
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
aggcacggca gatcggaaga gcgtcgtgta                                              30

<210> SEQ ID NO 666
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
ataaacacta gatcggaaga gcgtcgtgta                                              30

<210> SEQ ID NO 667
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
atgccagtca gatcggaaga gcgtcgtgta                                              30

<210> SEQ ID NO 668
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
aacatgtcaa gatcggaaga gcgtcgtgta                                      30

<210> SEQ ID NO 669
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
aataaaggga gatcggaaga gcgtcgtgta                                      30

<210> SEQ ID NO 670
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
accaaccaaa gatcggaaga gcgtcgtgta                                      30

<210> SEQ ID NO 671
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
actacttata gatcggaaga gcgtcgtgta                                      30

<210> SEQ ID NO 672
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
agcaagagga gatcggaaga gcgtcgtgta                                      30

<210> SEQ ID NO 673
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
agtaagctta gatcggaaga gcgtcgtgta                                      30

<210> SEQ ID NO 674
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
atcaatgcca gatcggaaga gcgtcgtgta                                              30

<210> SEQ ID NO 675
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 675
attcaggcaa gatcggaaga gcgtcgtgta                                              30

<210> SEQ ID NO 676
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
aaaccgcgca gatcggaaga gcgtcgtgta                                              30

<210> SEQ ID NO 677
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
aagatgctga gatcggaaga gcgtcgtgta                                              30

<210> SEQ ID NO 678
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
acaattgcaa gatcggaaga gcgtcgtgta                                              30

<210> SEQ ID NO 679
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
acgctggcca gatcggaaga gcgtcgtgta                                              30

<210> SEQ ID NO 680
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
agaatggata gatcggaaga gcgtcgtgta                                    30

<210> SEQ ID NO 681
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
aggcagatta gatcggaaga gcgtcgtgta                                    30

<210> SEQ ID NO 682
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
ataaatcgga gatcggaaga gcgtcgtgta                                    30

<210> SEQ ID NO 683
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683 atgccccga gatcggaaga gcgtcgtgta                                     30

<210> SEQ ID NO 684
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
aacccggcga gatcggaaga gcgtcgtgta                                    30

<210> SEQ ID NO 685
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
aatagaccta gatcggaaga gcgtcgtgta                                    30

<210> SEQ ID NO 686

<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
accagcgtca gatcggaaga gcgtcgtgta                                    30

<210> SEQ ID NO 687
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
actattatga gatcggaaga gcgtcgtgta                                    30

<210> SEQ ID NO 688
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
agcccacata gatcggaaga gcgtcgtgta                                    30

<210> SEQ ID NO 689
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
agtagtcgca gatcggaaga gcgtcgtgta                                    30

<210> SEQ ID NO 690
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
atccagtaca gatcggaaga gcgtcgtgta                                    30

<210> SEQ ID NO 691
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
attcgcttta gatcggaaga gcgtcgtgta                                    30

<210> SEQ ID NO 692
<211> LENGTH: 30

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
aaacgacaga gatcggaaga gcgtcgtgta                                      30

<210> SEQ ID NO 693
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
aagccttcta gatcggaaga gcgtcgtgta                                      30

<210> SEQ ID NO 694
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
acactgtaaa gatcggaaga gcgtcgtgta                                      30

<210> SEQ ID NO 695
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
acggatcaga gatcggaaga gcgtcgtgta                                      30

<210> SEQ ID NO 696
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
agacctagga gatcggaaga gcgtcgtgta                                      30

<210> SEQ ID NO 697
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
aggcggtaga gatcggaaga gcgtcgtgta                                      30

<210> SEQ ID NO 698
<211> LENGTH: 30
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 698
ataaccgtaa gatcggaaga gcgtcgtgta                                    30

<210> SEQ ID NO 699
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
atgcgcaaaa gatcggaaga gcgtcgtgta                                    30

<210> SEQ ID NO 700
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
aacctcttca gatcggaaga gcgtcgtgta                                    30

<210> SEQ ID NO 701
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
aatcaaacca gatcggaaga gcgtcgtgta                                    30

<210> SEQ ID NO 702
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
accattcgta gatcggaaga gcgtcgtgta                                    30

<210> SEQ ID NO 703
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
actcccaaca gatcggaaga gcgtcgtgta                                    30

<210> SEQ ID NO 704
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 704
agccggcgaa gatcggaaga gcgtcgtgta                                          30

<210> SEQ ID NO 705
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
agtggaagga gatcggaaga gcgtcgtgta                                          30

<210> SEQ ID NO 706
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
atccgcggga gatcggaaga gcgtcgtgta                                          30

<210> SEQ ID NO 707
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
attcttagca gatcggaaga gcgtcgtgta                                          30

<210> SEQ ID NO 708
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
aaacttctta gatcggaaga gcgtcgtgta                                          30

<210> SEQ ID NO 709
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
aaggagttca gatcggaaga gcgtcgtgta                                          30

<210> SEQ ID NO 710
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 710
acagaagaca gatcggaaga gcgtcgtgta                                      30

<210> SEQ ID NO 711
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
acggggccaa gatcggaaga gcgtcgtgta                                      30

<210> SEQ ID NO 712
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
agagctcaaa gatcggaaga gcgtcgtgta                                      30

<210> SEQ ID NO 713
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
aggctaacaa gatcggaaga gcgtcgtgta                                      30

<210> SEQ ID NO 714
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
atagcgttta gatcggaaga gcgtcgtgta                                      30

<210> SEQ ID NO 715
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
atggcgggga gatcggaaga gcgtcgtgta                                      30

<210> SEQ ID NO 716
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 716
aaccttgaaa gatcggaaga gcgtcgtgta          30

<210> SEQ ID NO 717
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
aatgagaaga gatcggaaga gcgtcgtgta          30

<210> SEQ ID NO 718
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 718
acccgatgca gatcggaaga gcgtcgtgta          30

<210> SEQ ID NO 719
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
actcgagtaa gatcggaaga gcgtcgtgta          30

<210> SEQ ID NO 720
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
agcctagtga gatcggaaga gcgtcgtgta          30

<210> SEQ ID NO 721
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
agtgtgttaa gatcggaaga gcgtcgtgta          30

<210> SEQ ID NO 722
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 722
atcgaatcga gatcggaaga gcgtcgtgta                                              30

<210> SEQ ID NO 723
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
attgcgccca gatcggaaga gcgtcgtgta                                              30

<210> SEQ ID NO 724
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
aaagagggaa gatcggaaga gcgtcgtgta                                              30

<210> SEQ ID NO 725
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
aaggcaagta gatcggaaga gcgtcgtgta                                              30

<210> SEQ ID NO 726
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
acaggcgcta gatcggaaga gcgtcgtgta                                              30

<210> SEQ ID NO 727
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727
acgtaacgta gatcggaaga gcgtcgtgta                                              30

<210> SEQ ID NO 728
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 728
agagttgtca gatcggaaga gcgtcgtgta    30

<210> SEQ ID NO 729
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
agggactata gatcggaaga gcgtcgtgta    30

<210> SEQ ID NO 730
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
atatctggta gatcggaaga gcgtcgtgta    30

<210> SEQ ID NO 731
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
atgggtacta gatcggaaga gcgtcgtgta    30

<210> SEQ ID NO 732
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
aacggcataa gatcggaaga gcgtcgtgta    30

<210> SEQ ID NO 733
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
aatgcatcaa gatcggaaga gcgtcgtgta    30

<210> SEQ ID NO 734
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734

```
acctctttaa gatcggaaga gcgtcgtgta                                              30
```

<210> SEQ ID NO 735
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735

```
actgcccgta gatcggaaga gcgtcgtgta                                              30
```

<210> SEQ ID NO 736
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736

```
agcgatacaa gatcggaaga gcgtcgtgta                                              30
```

<210> SEQ ID NO 737
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737

```
agttatttga gatcggaaga gcgtcgtgta                                              30
```

<210> SEQ ID NO 738
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738

```
atcgcgaaaa gatcggaaga gcgtcgtgta                                              30
```

<210> SEQ ID NO 739
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739

```
attggttgaa gatcggaaga gcgtcgtgta                                              30
```

<210> SEQ ID NO 740
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
aaatcataca gatcggaaga gcgtcgtgta                              30

<210> SEQ ID NO 741
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
aagtgggtta gatcggaaga gcgtcgtgta                              30

<210> SEQ ID NO 742
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
acataaatga gatcggaaga gcgtcgtgta                              30

<210> SEQ ID NO 743
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
acgtgagcga gatcggaaga gcgtcgtgta                              30

<210> SEQ ID NO 744
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
agatcgacaa gatcggaaga gcgtcgtgta                              30

<210> SEQ ID NO 745
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
aggggatcca gatcggaaga gcgtcgtgta                              30

<210> SEQ ID NO 746
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
atatgtttca gatcggaaga gcgtcgtgta                              30

<210> SEQ ID NO 747
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
atgttgtgaa gatcggaaga gcgtcgtgta                                    30

<210> SEQ ID NO 748
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
aactataata gatcggaaga gcgtcgtgta                                    30

<210> SEQ ID NO 749
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
aattgctcga gatcggaaga gcgtcgtgta                                    30

<210> SEQ ID NO 750
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
acctggcaca gatcggaaga gcgtcgtgta                                    30

<210> SEQ ID NO 751
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
actgtactca gatcggaaga gcgtcgtgta                                    30

<210> SEQ ID NO 752
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
agctccctca gatcggaaga gcgtcgtgta                                    30

<210> SEQ ID NO 753
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 753
agttttggaa gatcggaaga gcgtcgtgta        30

<210> SEQ ID NO 754
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 754
atcttaatta gatcggaaga gcgtcgtgta        30

<210> SEQ ID NO 755
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 755
attgttcata gatcggaaga gcgtcgtgta        30

<210> SEQ ID NO 756
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 756
tgacttggat actgcggctg acgt        24

<210> SEQ ID NO 757
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 757
tgacttgcgt gacattaagg ttgt        24

<210> SEQ ID NO 758
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 758
tgacttgacc tcacgtctag gcgt        24

```
<210> SEQ ID NO 759
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
tgacttgtga ttacgttcca cggt                                              24

<210> SEQ ID NO 760
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
tgacttgact aggtggcggt ctgt                                              24

<210> SEQ ID NO 761
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
tgacttgata tcaatgatgg tgct                                              24

<210> SEQ ID NO 762
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
tgacttggat tcctctgcga tgct                                              24

<210> SEQ ID NO 763
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
tgacttgggt agcttacgtc atct                                              24

<210> SEQ ID NO 764
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 764
tgacttgtgt aggttctgga atct                                              24

<210> SEQ ID NO 765
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 765
tgacttgtca agctagacgg ttct                                           24

<210> SEQ ID NO 766
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
tgacttgaag tcctgccact acgt                                           24

<210> SEQ ID NO 767
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
tgacttgacc aacaagatag tgct                                           24

<210> SEQ ID NO 768
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
tgacttggaa tcacgagttc gtct                                           24

<210> SEQ ID NO 769
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
tgacttggta accatattgc cgtt                                           24

<210> SEQ ID NO 770
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770
tgacttgaga ggattggaga atct                                           24

<210> SEQ ID NO 771
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 771
tgacttgcaa tgcgtgtgtt cggt                                          24

<210> SEQ ID NO 772
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 772
tgacttggtg ccgtgactcc atct                                          24

<210> SEQ ID NO 773
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
tgacttgtag aagtgctcca ggtt                                          24

<210> SEQ ID NO 774
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
tgacttgggc tgagctggtc tagt                                          24

<210> SEQ ID NO 775
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
tgacttgcga ttagtgcgag aggt                                          24

<210> SEQ ID NO 776
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
tgacttgtcc ttcgttaagg ctgt                                          24

<210> SEQ ID NO 777
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 777
tgacttgtcg gaggatctag tggt                                              24

<210> SEQ ID NO 778
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
tgacttgggc ttcattaact aggt                                              24

<210> SEQ ID NO 779
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779
tgacttggac gctctataca ccgt                                              24

<210> SEQ ID NO 780
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
tgacttgcgt agtccaggtc gtct                                              24

<210> SEQ ID NO 781
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
tgacttgtgc ataggacagg cagt                                              24

<210> SEQ ID NO 782
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 782
tgacttgaac tcaagcacct ctct                                              24

<210> SEQ ID NO 783
<211> LENGTH: 24
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 783
tgacttgggt atcgtatagg tcgt                                              24

<210> SEQ ID NO 784
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
tgacttgcga cgactgacta ggtt                                              24

<210> SEQ ID NO 785
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
tgacttggtc gcaccacaac catt                                              24

<210> SEQ ID NO 786
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
tgacttgtgg tcgcatgata aggt                                              24

<210> SEQ ID NO 787
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
tgacttgacg cttggctaat aggt                                              24

<210> SEQ ID NO 788
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
tgacttgaga agatcgcaat tagt                                              24

<210> SEQ ID NO 789
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 789
tgacttgacg ctcctagatg ttct                                          24

<210> SEQ ID NO 790
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 790
tgacttgcga ctactgctca ccgt                                          24

<210> SEQ ID NO 791
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 791
tgacttgata gattgttgcg tgct                                          24

<210> SEQ ID NO 792
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 792
tgacttgctc tacaccgctg aagt                                          24

<210> SEQ ID NO 793
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
tgacttgttc cgtggcttac tggt                                          24

<210> SEQ ID NO 794
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
tgacttgcgt gaagtgactg aggt                                          24

<210> SEQ ID NO 795
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 795
tgacttgacc gacatccgct gtgt                                              24

<210> SEQ ID NO 796
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
tgacttgttc aagccttgcg gagt                                              24

<210> SEQ ID NO 797
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
tgacttggtt attgccacca gtgt                                              24

<210> SEQ ID NO 798
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
tgacttggcc agttagcaag acgt                                              24

<210> SEQ ID NO 799
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799
tgacttgttg ctcgttggtc cagt                                              24

<210> SEQ ID NO 800
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800
tgacttgacc tgcttccgtg atgt                                              24

<210> SEQ ID NO 801
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
tgacttgcca cgttcaactg gcgt                                          24

<210> SEQ ID NO 802
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
tgacttgcgc tggaactcat aagt                                          24

<210> SEQ ID NO 803
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803
tgacttggag tcttcggata ccgt                                          24

<210> SEQ ID NO 804
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 804
tgacttgatg gacctctaat tgct                                          24

<210> SEQ ID NO 805
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 805
tgacttgggc ggattctcag tggt                                          24

<210> SEQ ID NO 806
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 806
tgacttgtgt tgctgtgtgg atct                                          24

<210> SEQ ID NO 807
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 807
tgacttgaac cgcagagagg tagt                                            24

<210> SEQ ID NO 808
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
tgacttggca tcgactcacc ttct                                            24

<210> SEQ ID NO 809
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
tgacttggga acacgcacat ggct                                            24

<210> SEQ ID NO 810
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
tgacttggcc agcaatccta cagt                                            24

<210> SEQ ID NO 811
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811
tgacttgaac gcttatggca gtgt                                            24

<210> SEQ ID NO 812
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
tgacttgtgt tgcgtagtga tgct                                            24

<210> SEQ ID NO 813
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
```
tgacttgggc acgagatcct tgct                                              24

<210> SEQ ID NO 814
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
tgacttggtc aatggacgga tgct                                              24

<210> SEQ ID NO 815
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
tgacttggtc cgttgctata atct                                              24

<210> SEQ ID NO 816
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 816
tgacttgctg attcctgagt ccgt                                              24

<210> SEQ ID NO 817
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 817
tgacttgact agcacctcgt aatt                                              24

<210> SEQ ID NO 818
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818
tgacttggcg tataccgagt tggt                                              24

<210> SEQ ID NO 819
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 819

```
tgacttgtgg ttgattcaag aatt                                          24
```

<210> SEQ ID NO 820
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 820

```
tgacttgcgc atggatacca gcgt                                          24
```

<210> SEQ ID NO 821
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 821

```
tgacttgttc gtgtgagtct cgtt                                          24
```

<210> SEQ ID NO 822
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 822

```
tgacttgcat tctctgccga gagt                                          24
```

<210> SEQ ID NO 823
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 823

```
tgacttgggt tgttcgtgtg tcgt                                          24
```

<210> SEQ ID NO 824
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 824

```
tgacttgagt ccaggcattc gtct                                          24
```

<210> SEQ ID NO 825
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825

```
tgacttgtac aacggtgcga ctgt                                          24
```

<210> SEQ ID NO 826
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 826
tgacttgccg tatcgaggtg ccgt                                              24

<210> SEQ ID NO 827
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 827
tgacttgggt cctgtctagt ccgt                                              24

<210> SEQ ID NO 828
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 828
tgacttgcga tgacctgtcc atgt                                              24

<210> SEQ ID NO 829
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 829
tgacttgtgg ctctgaacct atct                                              24

<210> SEQ ID NO 830
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 830
tgacttggca cagtcctcca tgct                                              24

<210> SEQ ID NO 831
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 831
tgacttggtt gataagccga cggt                                              24

<210> SEQ ID NO 832
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
tgacttggag cgtgcagtgg aagt                                          24

<210> SEQ ID NO 833
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 833
tgacttgtga gctggacagg tggt                                          24

<210> SEQ ID NO 834
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 834
tgacttgtcc gcactctgat aatt                                          24

<210> SEQ ID NO 835
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 835
tgacttgcgc ctattgtact gcgt                                          24

<210> SEQ ID NO 836
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 836
tgacttggca caccatcgta ttct                                          24

<210> SEQ ID NO 837
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 837
tgacttgaat gcttcacacg gtgt                                          24

```
<210> SEQ ID NO 838
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 838
tgacttgatg tccgcctgca tggt                                              24

<210> SEQ ID NO 839
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 839
tgacttgtgg aacactctac tgct                                              24

<210> SEQ ID NO 840
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 840
tgacttgcta tcctgtcaac ggct                                              24

<210> SEQ ID NO 841
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 841
tgacttgagc ttgccgtagc gtgt                                              24

<210> SEQ ID NO 842
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 842
tgacttgtgt cgatattgat ccgt                                              24

<210> SEQ ID NO 843
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 843
tgacttggaa gcggaaggta tagt                                              24

<210> SEQ ID NO 844
```

```
<210> SEQ ID NO 844
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 844
tgacttggct acttccgaat cagt                                          24

<210> SEQ ID NO 845
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 845
tgacttgcgc acacgatcat ctgt                                          24

<210> SEQ ID NO 846
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 846
tgacttgact ggtgtcacgt ctct                                          24

<210> SEQ ID NO 847
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 847
tgacttggac tgttcgacac gtct                                          24

<210> SEQ ID NO 848
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 848
tgacttgacc acggagcctt ctct                                          24

<210> SEQ ID NO 849
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 849
tgacttgcct gttacgtccg ctgt                                          24

<210> SEQ ID NO 850
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 850
tgacttggac gctgtggcga ttct                                           24

<210> SEQ ID NO 851
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 851
tgacttgcgc tccagtcgta atct                                           24

<210> SEQ ID NO 852
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 852
agttgtcacg tcagccgcag tatc                                           24

<210> SEQ ID NO 853
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 853
agttgtcaca accttaatgt cacg                                           24

<210> SEQ ID NO 854
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 854
agttgtcacg cctagacgtg aggt                                           24

<210> SEQ ID NO 855
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 855
agttgtcacc gtggaacgta atca                                           24

<210> SEQ ID NO 856
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 856
agttgtcaca gaccgccacc tagt                                             24

<210> SEQ ID NO 857
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 857
agttgtcagc accatcattg atat                                             24

<210> SEQ ID NO 858
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 858
agttgtcagc atcgcagagg aatc                                             24

<210> SEQ ID NO 859
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 859
agttgtcaga tgacgtaagc tacc                                             24

<210> SEQ ID NO 860
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 860
agttgtcaga ttccagaacc taca                                             24

<210> SEQ ID NO 861
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 861
agttgtcaga accgtctagc ttga                                             24

<210> SEQ ID NO 862
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 862
agttgtcacg tagtggcagg actt                                              24

<210> SEQ ID NO 863
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 863
agttgtcagc actatcttgt tggt                                              24

<210> SEQ ID NO 864
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 864
agttgtcaga cgaactcgtg attc                                              24

<210> SEQ ID NO 865
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 865
agttgtcaac ggcaatatgg ttac                                              24

<210> SEQ ID NO 866
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 866
agttgtcaga ttctccaatc ctct                                              24

<210> SEQ ID NO 867
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 867
agttgtcacc gaacacacgc attg                                              24

<210> SEQ ID NO 868
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 868
agttgtcaga tggagtcacg gcac                                          24

<210> SEQ ID NO 869
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 869
agttgtcaac ctggagcact tcta                                          24

<210> SEQ ID NO 870
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 870
agttgtcact agaccagctc agcc                                          24

<210> SEQ ID NO 871
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 871
agttgtcacc tctcgcacta atcg                                          24

<210> SEQ ID NO 872
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 872
agttgtcaca gccttaacga agga                                          24

<210> SEQ ID NO 873
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 873
agttgtcacc actagatcct ccga                                          24

<210> SEQ ID NO 874
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 874
agttgtcacc tagttaatga agcc                                                24

<210> SEQ ID NO 875
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 875
agttgtcacg gtgtatagag cgtc                                                24

<210> SEQ ID NO 876
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 876
agttgtcaga cgacctggac tacg                                                24

<210> SEQ ID NO 877
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 877
agttgtcact gcctgtccta tgca                                                24

<210> SEQ ID NO 878
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 878
agttgtcaga gaggtgcttg agtt                                                24

<210> SEQ ID NO 879
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 879
agttgtcacg acctatacga tacc                                                24

<210> SEQ ID NO 880
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 880
agttgtcaac ctagtcagtc gtcg                                           24

<210> SEQ ID NO 881
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 881
agttgtcaat ggttgtggtg cgac                                           24

<210> SEQ ID NO 882
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 882
agttgtcacc ttatcatgcg acca                                           24

<210> SEQ ID NO 883
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 883
agttgtcacc tattagccaa gcgt                                           24

<210> SEQ ID NO 884
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 884
agttgtcact aattgcgatc ttct                                           24

<210> SEQ ID NO 885
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 885
agttgtcaga acatctagga gcgt                                           24

<210> SEQ ID NO 886
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 886
agttgtcacg gtgagcagta gtcg                                              24

<210> SEQ ID NO 887
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 887
agttgtcagc acgcaacaat ctat                                              24

<210> SEQ ID NO 888
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
agttgtcact tcagcggtgt agag                                              24

<210> SEQ ID NO 889
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
agttgtcacc agtaagccac ggaa                                              24

<210> SEQ ID NO 890
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 890
agttgtcacc tcagtcactt cacg                                              24

<210> SEQ ID NO 891
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 891
agttgtcaca cagcggatgt cggt                                              24

<210> SEQ ID NO 892
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 892
```
agttgtcact ccgcaaggct tgaa                                    24

<210> SEQ ID NO 893
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 893
agttgtcaca ctggtggcaa taac                                    24

<210> SEQ ID NO 894
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
agttgtcacg tcttgctaac tggc                                    24

<210> SEQ ID NO 895
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 895
agttgtcact ggaccaacga gcaa                                    24

<210> SEQ ID NO 896
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 896
agttgtcaca tcacggaagc aggt                                    24

<210> SEQ ID NO 897
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 897
agttgtcacg ccagttgaac gtgg                                    24

<210> SEQ ID NO 898
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 898
agttgtcact tatgagttcc agcg                                          24

<210> SEQ ID NO 899
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 899
agttgtcacg gtatccgaag actc                                          24

<210> SEQ ID NO 900
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 900
agttgtcagc aattagaggt ccat                                          24

<210> SEQ ID NO 901
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 901
agttgtcacc actgagaatc cgcc                                          24

<210> SEQ ID NO 902
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 902
agttgtcaga tccacacagc aaca                                          24

<210> SEQ ID NO 903
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 903
agttgtcact acctctctgc ggtt                                          24

<210> SEQ ID NO 904
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 904
agttgtcaga aggtgagtcg atgc                                          24

<210> SEQ ID NO 905
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 905
agttgtcagc catgtgcgtg ttcc                                           24

<210> SEQ ID NO 906
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 906
agttgtcact gtaggattgc tggc                                           24

<210> SEQ ID NO 907
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 907
agttgtcaca ctgccataag cgtt                                           24

<210> SEQ ID NO 908
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 908
agttgtcagc atcactacgc aaca                                           24

<210> SEQ ID NO 909
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 909
agttgtcagc aaggatctcg tgcc                                           24

<210> SEQ ID NO 910
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 910
agttgtcagc atccgtccat tgac                                           24

<210> SEQ ID NO 911
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 911
agttgtcaga ttatagcaac ggac                                        24

<210> SEQ ID NO 912
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 912
agttgtcacg gactcaggaa tcag                                        24

<210> SEQ ID NO 913
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 913
agttgtcaat tacgaggtgc tagt                                        24

<210> SEQ ID NO 914
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 914
agttgtcacc aactcggtat acgc                                        24

<210> SEQ ID NO 915
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 915
agttgtcaat tcttgaatca acca                                        24

<210> SEQ ID NO 916
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 916
agttgtcacg ctggtatcca tgcg                                        24

```
<210> SEQ ID NO 917
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 917
agttgtcaac gagactcaca cgaa                                              24

<210> SEQ ID NO 918
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 918
agttgtcact ctcggcagag aatg                                              24

<210> SEQ ID NO 919
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 919
agttgtcacg acacacgaac aacc                                              24

<210> SEQ ID NO 920
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 920
agttgtcaga cgaatgcctg gact                                              24

<210> SEQ ID NO 921
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 921
agttgtcaca gtcgcaccgt tgta                                              24

<210> SEQ ID NO 922
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 922
agttgtcacg gcacctcgat acgg                                              24

<210> SEQ ID NO 923
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 923
agttgtcacg gactagacag gacc                                           24

<210> SEQ ID NO 924
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 924
agttgtcaca tggacaggtc atcg                                           24

<210> SEQ ID NO 925
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 925
agttgtcaga taggttcaga gcca                                           24

<210> SEQ ID NO 926
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 926
agttgtcagc atggaggact gtgc                                           24

<210> SEQ ID NO 927
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 927
agttgtcacc gtcggcttat caac                                           24

<210> SEQ ID NO 928
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 928
agttgtcact tccactgcac gctc                                           24

<210> SEQ ID NO 929
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 929
agttgtcacc acctgtccag ctca                                            24

<210> SEQ ID NO 930
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 930
agttgtcaat tatcagagtg cgga                                            24

<210> SEQ ID NO 931
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 931
agttgtcacg cagtacaata ggcg                                            24

<210> SEQ ID NO 932
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 932
agttgtcaga atacgatggt gtgc                                            24

<210> SEQ ID NO 933
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 933
agttgtcaca ccgtgtgaag catt                                            24

<210> SEQ ID NO 934
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 934
agttgtcacc atgcaggcgg acat                                            24

<210> SEQ ID NO 935
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 935
agttgtcagc agtagagtgt tcca                                          24

<210> SEQ ID NO 936
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 936
agttgtcagc cgttgacagg atag                                          24

<210> SEQ ID NO 937
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 937
agttgtcaca cgctacggca agct                                          24

<210> SEQ ID NO 938
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 938
agttgtcacg gatcaatatc gaca                                          24

<210> SEQ ID NO 939
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 939
agttgtcact ataccttccg cttc                                          24

<210> SEQ ID NO 940
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 940
agttgtcact gattcggaag tagc                                          24

<210> SEQ ID NO 941
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 941
agttgtcaca gatgatcgtg tgcg                                          24

<210> SEQ ID NO 942
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 942
agttgtcaga gacgtgacac cagt                                          24

<210> SEQ ID NO 943
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 943
agttgtcaga cgtgtcgaac agtc                                          24

<210> SEQ ID NO 944
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 944
agttgtcaga gaaggctccg tggt                                          24

<210> SEQ ID NO 945
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
agttgtcaca gcggacgtaa cagg                                          24

<210> SEQ ID NO 946
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
agttgtcaga atcgccacag cgtc                                          24

<210> SEQ ID NO 947
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 947
agttgtcaga ttacgactgg agcg                                           24

<210> SEQ ID NO 948
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 948
gacaactctt cgtggaatct agct                                           24

<210> SEQ ID NO 949
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 949
gacaactgcc tacagaagta tctt                                           24

<210> SEQ ID NO 950
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 950
gacaactggt attactcata ggct                                           24

<210> SEQ ID NO 951
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 951
gacaactaga caagccacct tatt                                           24

<210> SEQ ID NO 952
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 952
gacaactgcc tctaactaag gatt                                           24

<210> SEQ ID NO 953
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 953
gacaactggt gtcaagcacc gctt                                            24

<210> SEQ ID NO 954
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 954
gacaactcac cgcaatataa ttgt                                            24

<210> SEQ ID NO 955
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 955
gacaactgct gtgtctgtca cctt                                            24

<210> SEQ ID NO 956
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 956
gacaacttcc tgtgcgttag agtt                                            24

<210> SEQ ID NO 957
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 957
gacaactgtc ggcaacagac catt                                            24

<210> SEQ ID NO 958
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 958
gacaactgcg gtcacgcctg agct                                            24

<210> SEQ ID NO 959
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 959
gacaactcgc cgtgcctcta actt                                          24

<210> SEQ ID NO 960
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 960
gacaacttat caatcgcagc ggtt                                          24

<210> SEQ ID NO 961
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 961
gacaactact aggtcgaatg cctt                                          24

<210> SEQ ID NO 962
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 962
gacaactaat caatgaacga ggct                                          24

<210> SEQ ID NO 963
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 963
gacaactttg gctaggttgt gtgt                                          24

<210> SEQ ID NO 964
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 964
gacaactcac tagaggtgtc cgtt                                          24

<210> SEQ ID NO 965
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 965
gacaactcgt gctataatct tgtt                                           24

<210> SEQ ID NO 966
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 966
gacaactttc gagtggagca attt                                           24

<210> SEQ ID NO 967
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 967
gacaacttgg ttgcttgcat tgtt                                           24

<210> SEQ ID NO 968
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 968
gacaactcgc catgcagtta cgct                                           24

<210> SEQ ID NO 969
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 969
gacaacttag ttcgtcaccg tgtt                                           24

<210> SEQ ID NO 970
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 970
gacaactagc gtcatcggac tctt                                           24

<210> SEQ ID NO 971
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 971
```
gacaacttcg gttcgttagg cgtt                                          24

<210> SEQ ID NO 972
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 972
gacaactata ctcggttagt cctt                                          24

<210> SEQ ID NO 973
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 973
gacaactagt agaacgctag gttt                                          24

<210> SEQ ID NO 974
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 974
gacaacttcc gcctagtgag gctt                                          24

<210> SEQ ID NO 975
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 975
gacaactcag caacgtccta ttgt                                          24

<210> SEQ ID NO 976
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 976
gacaactgtg cctacgacgt agct                                          24

<210> SEQ ID NO 977
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 977
gacaactcgt cacacgttga actt                                              24

<210> SEQ ID NO 978
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 978
gacaactaag gacgcagtga gatt                                              24

<210> SEQ ID NO 979
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 979
gacaacttat acggcaccta cttt                                              24

<210> SEQ ID NO 980
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 980
gacaactatc gttctcattc tgtt                                              24

<210> SEQ ID NO 981
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 981
gacaactcat cataccacgc cgct                                              24

<210> SEQ ID NO 982
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 982
gacaactatg atgtgataag gctt                                              24

<210> SEQ ID NO 983
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 983
gacaacttgg ttgcagcctc cgct                                              24

<210> SEQ ID NO 984
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 984
gacaacttac aatcaccgtg tatt                                          24

<210> SEQ ID NO 985
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 985
gacaactcat actctggtgc catt                                          24

<210> SEQ ID NO 986
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 986
gacaactgtt gaacacttcc gttt                                          24

<210> SEQ ID NO 987
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 987
gacaacttca cacgtcgagc gatt                                          24

<210> SEQ ID NO 988
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 988
gacaactaac gccgataagg actt                                          24

<210> SEQ ID NO 989
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 989
gacaactatc ctggacagtg agct                                          24

<210> SEQ ID NO 990
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 990
gacaactctt cttgtcttgg agct                                          24

<210> SEQ ID NO 991
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 991
gacaactcgt tcattacgtc agtt                                          24

<210> SEQ ID NO 992
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 992
gacaacttgc tcttcataag cctt                                          24

<210> SEQ ID NO 993
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 993
gacaactggt caccaagaga cgct                                          24

<210> SEQ ID NO 994
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 994
gacaactttg tgtaggagca agtt                                          24

<210> SEQ ID NO 995
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 995
gacaacttct caatctggat cgct                                          24

```
<210> SEQ ID NO 996
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 996
gacaactgct ggaagcctct agct                                              24

<210> SEQ ID NO 997
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 997
gacaactcgt tctccttaga gatt                                              24

<210> SEQ ID NO 998
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 998
gacaactctc aaggtgtccg agtt                                              24

<210> SEQ ID NO 999
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 999
gacaactata tgaatatgtg gctt                                              24

<210> SEQ ID NO 1000
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1000
gacaacttga atataggcac ttgt                                              24

<210> SEQ ID NO 1001
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1001
gacaactgcc ttccgcctcg tatt                                              24

<210> SEQ ID NO 1002
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1002
gacaactatt gcttaacgga ttgt                                          24

<210> SEQ ID NO 1003
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1003
gacaactctt ccaacacacg gatt                                          24

<210> SEQ ID NO 1004
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1004
gacaacttcg tgaggatcaa cgct                                          24

<210> SEQ ID NO 1005
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1005
gacaactacg ttccatgcta tctt                                          24

<210> SEQ ID NO 1006
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1006
gacaactgtc tcttgcatca cgct                                          24

<210> SEQ ID NO 1007
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1007
gacaactgtc actcggtgcg actt                                          24

<210> SEQ ID NO 1008
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1008
gacaactata tctgtgagcc gatt                                            24

<210> SEQ ID NO 1009
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1009
gacaacttag acagacggtc tatt                                            24

<210> SEQ ID NO 1010
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1010
gacaactgta tcgcactcat tgtt                                            24

<210> SEQ ID NO 1011
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1011
gacaactcct acatctgtcg agtt                                            24

<210> SEQ ID NO 1012
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1012
gacaacttga taccgtagca gatt                                            24

<210> SEQ ID NO 1013
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1013
gacaactgga tagcaccgtt catt                                            24

<210> SEQ ID NO 1014
<211> LENGTH: 24
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 1014
gacaactatg agtgccgcag actt                                          24

<210> SEQ ID NO 1015
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1015
gacaactgcc tagtagaaga cgtt                                          24

<210> SEQ ID NO 1016
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1016
gacaacttaa ttgaatacac cgtt                                          24

<210> SEQ ID NO 1017
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1017
gacaacttgc cattccactt agct                                          24

<210> SEQ ID NO 1018
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1018
gacaactcct ccagtgtcgt cgct                                          24

<210> SEQ ID NO 1019
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1019
gacaactgga gtgcgtgtta gctt                                          24

<210> SEQ ID NO 1020
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1020
gacaactttc taacacacag cctt                                              24

<210> SEQ ID NO 1021
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1021
gacaactgac caagcaccag actt                                              24

<210> SEQ ID NO 1022
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1022
gacaactcct attgcatctt catt                                              24

<210> SEQ ID NO 1023
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1023
gacaactgtg ctaacctaca catt                                              24

<210> SEQ ID NO 1024
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1024
gacaactcat atctcgaata ggct                                              24

<210> SEQ ID NO 1025
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1025
gacaactgac gaactccatg cgtt                                              24

<210> SEQ ID NO 1026
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1026
gacaactgtc cgatggacgc cgtt                                              24

<210> SEQ ID NO 1027
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1027
gacaactcaa cgaggtcagt cgct                                              24

<210> SEQ ID NO 1028
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1028
gacaacttag tggcacttca cctt                                              24

<210> SEQ ID NO 1029
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1029
gacaactacc ttcctatgct actt                                              24

<210> SEQ ID NO 1030
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1030
gacaactatc gaggatagcc tgtt                                              24

<210> SEQ ID NO 1031
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1031
gacaactact caggaaggct gatt                                              24

<210> SEQ ID NO 1032
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1032
gacaacttgg caacggctca tgtt        24

<210> SEQ ID NO 1033
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1033
gacaactcgg caagactgcc tatt        24

<210> SEQ ID NO 1034
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1034
gacaacttaa cgcaggatac tatt        24

<210> SEQ ID NO 1035
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1035
gacaactgct cttggaggta tctt        24

<210> SEQ ID NO 1036
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1036
gacaactcga agtggttcgg tctt        24

<210> SEQ ID NO 1037
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1037
gacaactcta acgctgtgaa ggct        24

<210> SEQ ID NO 1038
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1038
gacaactctc cgagatgatg tgtt                                          24

<210> SEQ ID NO 1039
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1039
gacaactcgc tgacataaga cctt                                          24

<210> SEQ ID NO 1040
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1040
gacaacttga gaggatgaat gctt                                          24

<210> SEQ ID NO 1041
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1041
gacaactcag actcaattag gctt                                          24

<210> SEQ ID NO 1042
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1042
gacaacttcg tgtcatcgct agtt                                          24

<210> SEQ ID NO 1043
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1043
gacaactaga agcctcggat tgtt                                          24

<210> SEQ ID NO 1044
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1044
caagtcaagc tagattccac gaag                                              24

<210> SEQ ID NO 1045
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1045
caagtcaaag atacttctgt aggc                                              24

<210> SEQ ID NO 1046
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1046
caagtcaagc ctatgagtaa tacc                                              24

<210> SEQ ID NO 1047
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1047
caagtcaaat aaggtggctt gtct                                              24

<210> SEQ ID NO 1048
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1048
caagtcaaat ccttagttag aggc                                              24

<210> SEQ ID NO 1049
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1049
caagtcaaag cggtgcttga cacc                                              24

<210> SEQ ID NO 1050
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1050
```
caagtcaaca attatattgc ggtg                                          24

<210> SEQ ID NO 1051
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1051
caagtcaaag gtgacagaca cagc                                          24

<210> SEQ ID NO 1052
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1052
caagtcaaac tctaacgcac agga                                          24

<210> SEQ ID NO 1053
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1053
caagtcaaat ggtctgttgc cgac                                          24

<210> SEQ ID NO 1054
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1054
caagtcaagc tcaggcgtga ccgc                                          24

<210> SEQ ID NO 1055
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1055
caagtcaaag ttagaggcac ggcg                                          24

<210> SEQ ID NO 1056
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1056
caagtcaaac cgctgcgatt gata                                            24

<210> SEQ ID NO 1057
<211> LENGTH: 24
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1057
caagtcaaag gcattcgacc tagt                                            24

<210> SEQ ID NO 1058
<211> LENGTH: 24
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1058
caagtcaagc ctcgttcatt gatt                                            24

<210> SEQ ID NO 1059
<211> LENGTH: 24
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1059
caagtcaaca cacaacctag ccaa                                            24

<210> SEQ ID NO 1060
<211> LENGTH: 24
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1060
caagtcaaac ggacacctct agtg                                            24

<210> SEQ ID NO 1061
<211> LENGTH: 24
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1061
caagtcaaac aagattatag cacg                                            24

<210> SEQ ID NO 1062
<211> LENGTH: 24
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1062
caagtcaaaa ttgctccact cgaa                                            24

<210> SEQ ID NO 1063
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1063
caagtcaaac aatgcaagca acca                                          24

<210> SEQ ID NO 1064
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1064
caagtcaagc gtaactgcat ggcg                                          24

<210> SEQ ID NO 1065
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1065
caagtcaaac acggtgacga acta                                          24

<210> SEQ ID NO 1066
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1066
caagtcaaag agtccgatga cgct                                          24

<210> SEQ ID NO 1067
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1067
caagtcaaac gcctaacgaa ccga                                          24

<210> SEQ ID NO 1068
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1068
caagtcaaag gactaaccga gtat                                          24

<210> SEQ ID NO 1069
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1069
caagtcaaaa cctagcgttc tact                                              24

<210> SEQ ID NO 1070
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1070
caagtcaaag cctcactagg cgga                                              24

<210> SEQ ID NO 1071
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1071
caagtcaaca ataggacgtt gctg                                              24

<210> SEQ ID NO 1072
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1072
caagtcaagc tacgtcgtag gcac                                              24

<210> SEQ ID NO 1073
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1073
caagtcaaag ttcaacgtgt gacg                                              24

<210> SEQ ID NO 1074
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1074
caagtcaaat ctcactgcgt cctt                                              24

```
<210> SEQ ID NO 1075
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1075
caagtcaaaa gtaggtgccg tata                                              24

<210> SEQ ID NO 1076
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1076
caagtcaaac agaatgagaa cgat                                              24

<210> SEQ ID NO 1077
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1077
caagtcaagc ggcgtggtat gatg                                              24

<210> SEQ ID NO 1078
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1078
caagtcaaag ccttatcaca tcat                                              24

<210> SEQ ID NO 1079
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1079
caagtcaagc ggaggctgca acca                                              24

<210> SEQ ID NO 1080
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1080
caagtcaaat acacggtgat tgta                                              24

<210> SEQ ID NO 1081
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1081
caagtcaaat ggcaccagag tatg                                            24

<210> SEQ ID NO 1082
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1082
caagtcaaaa cggaagtgtt caac                                            24

<210> SEQ ID NO 1083
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1083
caagtcaaat cgctcgacgt gtga                                            24

<210> SEQ ID NO 1084
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1084
caagtcaaag tccttatcgg cgtt                                            24

<210> SEQ ID NO 1085
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1085
caagtcaagc tcactgtcca ggat                                            24

<210> SEQ ID NO 1086
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1086
caagtcaagc tccaagacaa gaag                                            24

<210> SEQ ID NO 1087
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1087
caagtcaaac tgacgtaatg aacg                                              24

<210> SEQ ID NO 1088
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1088
caagtcaaag gcttatgaag agca                                              24

<210> SEQ ID NO 1089
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1089
caagtcaagc gtctcttggt gacc                                              24

<210> SEQ ID NO 1090
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1090
caagtcaaac ttgctcctac acaa                                              24

<210> SEQ ID NO 1091
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1091
caagtcaagc gatccagatt gaga                                              24

<210> SEQ ID NO 1092
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1092
caagtcaagc tagaggcttc cagc                                              24

<210> SEQ ID NO 1093
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1093
caagtcaaat ctctaaggag aacg                                          24

<210> SEQ ID NO 1094
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1094
caagtcaaac tcggacacct tgag                                          24

<210> SEQ ID NO 1095
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1095
caagtcaaag ccacatattc atat                                          24

<210> SEQ ID NO 1096
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1096
caagtcaaca agtgcctata ttca                                          24

<210> SEQ ID NO 1097
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1097
caagtcaaat acgaggcgga aggc                                          24

<210> SEQ ID NO 1098
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1098
caagtcaaca atccgttaag caat                                          24

<210> SEQ ID NO 1099
<211> LENGTH: 24
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 1099
caagtcaaat ccgtgtgttg gaag                                          24

<210> SEQ ID NO 1100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1100
caagtcaagc gttgatcctc acga                                          24

<210> SEQ ID NO 1101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1101
caagtcaaag atagcatgga acgt                                          24

<210> SEQ ID NO 1102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1102
caagtcaagc gtgatgcaag agac                                          24

<210> SEQ ID NO 1103
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1103
caagtcaaag tcgcaccgag tgac                                          24

<210> SEQ ID NO 1104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1104
caagtcaaat cggctcacag atat                                          24

<210> SEQ ID NO 1105
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 1105
caagtcaaat agaccgtctg tcta                                            24

<210> SEQ ID NO 1106
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1106
caagtcaaac aatgagtgcg atac                                            24

<210> SEQ ID NO 1107
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1107
caagtcaaac tcgacagatg tagg                                            24

<210> SEQ ID NO 1108
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1108
caagtcaaat ctgctacggt atca                                            24

<210> SEQ ID NO 1109
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1109
caagtcaaat gaacggtgct atcc                                            24

<210> SEQ ID NO 1110
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1110
caagtcaaag tctgcggcac tcat                                            24

<210> SEQ ID NO 1111
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1111
caagtcaaac gtcttctact aggc                                              24

<210> SEQ ID NO 1112
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1112
caagtcaaac ggtgtattca atta                                              24

<210> SEQ ID NO 1113
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1113
caagtcaagc taagtggaat ggca                                              24

<210> SEQ ID NO 1114
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1114
caagtcaagc gacgacactg gagg                                              24

<210> SEQ ID NO 1115
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1115
caagtcaaag ctaacacgca ctcc                                              24

<210> SEQ ID NO 1116
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1116
caagtcaaag gctgtgtgtt agaa                                              24

<210> SEQ ID NO 1117
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1117
caagtcaaag tctggtgctt ggtc                                          24

<210> SEQ ID NO 1118
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1118
caagtcaaat gaagatgcaa tagg                                          24

<210> SEQ ID NO 1119
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1119
caagtcaaat gtgtaggtta gcac                                          24

<210> SEQ ID NO 1120
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1120
caagtcaagc ctattcgaga tatg                                          24

<210> SEQ ID NO 1121
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1121
caagtcaaac gcatggagtt cgtc                                          24

<210> SEQ ID NO 1122
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1122
caagtcaaac ggcgtccatc ggac                                          24

<210> SEQ ID NO 1123
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1123
caagtcaagc gactgacctc gttg                                          24

<210> SEQ ID NO 1124
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1124
caagtcaaag gtgaagtgcc acta                                          24

<210> SEQ ID NO 1125
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1125
caagtcaaag tagcatagga aggt                                          24

<210> SEQ ID NO 1126
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1126
caagtcaaac aggctatcct cgat                                          24

<210> SEQ ID NO 1127
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1127
caagtcaaat cagccttcct gagt                                          24

<210> SEQ ID NO 1128
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1128
caagtcaaac atgagccgtt gcca                                          24

<210> SEQ ID NO 1129
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1129
```
caagtcaaat aggcagtctt gccg 24

<210> SEQ ID NO 1130
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1130
caagtcaaat agtatcctgc gtta 24

<210> SEQ ID NO 1131
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1131
caagtcaaag atacctccaa gagc 24

<210> SEQ ID NO 1132
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1132
caagtcaaag accgaaccac ttcg 24

<210> SEQ ID NO 1133
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1133
caagtcaagc cttcacagcg ttag 24

<210> SEQ ID NO 1134
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1134
caagtcaaac acatcatctc ggag 24

<210> SEQ ID NO 1135
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1135
caagtcaaag gtcttatgtc agcg 24

<210> SEQ ID NO 1136
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1136
caagtcaaag cattcatcct ctca 24

<210> SEQ ID NO 1137
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1137
caagtcaaag cctaattgag tctg 24

<210> SEQ ID NO 1138
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1138
caagtcaaac tagcgatgac acga 24

<210> SEQ ID NO 1139
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1139
caagtcaaac aatccgaggc ttct 24

<210> SEQ ID NO 1140
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1140
caagcagaag acggcatacg agatctctac ttgtgactgg agttcagacg tgtgctcttc 60
cgatct 66

<210> SEQ ID NO 1141
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1141

```
caagcagaag acggcatacg agatgatcgt gtgtgactgg agttcagacg tgtgctcttc    60
cgatct                                                               66

<210> SEQ ID NO 1142
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1142
caagcagaag acggcatacg agattcggaa cagtgactgg agttcagacg tgtgctcttc    60
cgatct                                                               66

<210> SEQ ID NO 1143
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1143
caagcagaag acggcatacg agatcgatca tggtgactgg agttcagacg tgtgctcttc    60
cgatct                                                               66

<210> SEQ ID NO 1144
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1144
caagcagaag acggcatacg agattggtaa cggtgactgg agttcagacg tgtgctcttc    60
cgatct                                                               66

<210> SEQ ID NO 1145
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1145
caagcagaag acggcatacg agataccaag gagtgactgg agttcagacg tgtgctcttc    60
cgatct                                                               66

<210> SEQ ID NO 1146
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1146
caagcagaag acggcatacg agataatgcg ttgtgactgg agttcagacg tgtgctcttc    60
cgatct                                                               66
```

<210> SEQ ID NO 1147
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1147
caagcagaag acggcatacg agatatacct gtgtgactgg agttcagacg tgtgctcttc    60
cgatct                                                              66

<210> SEQ ID NO 1148
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1148
caagcagaag acggcatacg agatccttac ctgtgactgg agttcagacg tgtgctcttc    60
cgatct                                                              66

<210> SEQ ID NO 1149
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1149
caagcagaag acggcatacg agatccattg ttgtgactgg agttcagacg tgtgctcttc    60
cgatct                                                              66

<210> SEQ ID NO 1150
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1150
caagcagaag acggcatacg agatgataca gtgtgactgg agttcagacg tgtgctcttc    60
cgatct                                                              66

<210> SEQ ID NO 1151
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1151
caagcagaag acggcatacg agattgcgac ctgtgactgg agttcagacg tgtgctcttc    60
cgatct                                                              66

<210> SEQ ID NO 1152
<211> LENGTH: 66

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1152
caagcagaag acggcatacg agattctgga ccgtgactgg agttcagacg tgtgctcttc    60
cgatct                                                              66

<210> SEQ ID NO 1153
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1153
caagcagaag acggcatacg agattaagca tggtgactgg agttcagacg tgtgctcttc    60
cgatct                                                              66

<210> SEQ ID NO 1154
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1154
caagcagaag acggcatacg agattagatc ctgtgactgg agttcagacg tgtgctcttc    60
cgatct                                                              66

<210> SEQ ID NO 1155
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1155
caagcagaag acggcatacg agattcgcca gagtgactgg agttcagacg tgtgctcttc    60
cgatct                                                              66

<210> SEQ ID NO 1156
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1156
caagcagaag acggcatacg agatgataac ctgtgactgg agttcagacg tgtgctcttc    60
cgatct                                                              66

<210> SEQ ID NO 1157
<211> LENGTH: 66
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 1157
caagcagaag acggcatacg agatcatcag acgtgactgg agttcagacg tgtgctcttc    60
cgatct    66

<210> SEQ ID NO 1158
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1158
caagcagaag acggcatacg agataatgtt gggtgactgg agttcagacg tgtgctcttc    60
cgatct    66

<210> SEQ ID NO 1159
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1159
caagcagaag acggcatacg agatgagagt tggtgactgg agttcagacg tgtgctcttc    60
cgatct    66

<210> SEQ ID NO 1160
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1160
caagcagaag acggcatacg agatagagga atgtgactgg agttcagacg tgtgctcttc    60
cgatct    66

<210> SEQ ID NO 1161
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1161
caagcagaag acggcatacg agatcgagtt aggtgactgg agttcagacg tgtgctcttc    60
cgatct    66

<210> SEQ ID NO 1162
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1162

```
caagcagaag acggcatacg agatatccgc aggtgactgg agttcagacg tgtgctcttc    60
cgatct                                                               66

<210> SEQ ID NO 1163
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1163
caagcagaag acggcatacg agatcctggt aggtgactgg agttcagacg tgtgctcttc    60
cgatct                                                               66

<210> SEQ ID NO 1164
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1164
caagcagaag acggcatacg agatagatgt gcgtgactgg agttcagacg tgtgctcttc    60
cgatct                                                               66

<210> SEQ ID NO 1165
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1165
caagcagaag acggcatacg agattgttat acgtgactgg agttcagacg tgtgctcttc    60
cgatct                                                               66

<210> SEQ ID NO 1166
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1166
caagcagaag acggcatacg agattcgcta tggtgactgg agttcagacg tgtgctcttc    60
cgatct                                                               66

<210> SEQ ID NO 1167
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1167
caagcagaag acggcatacg agatttactg tcgtgactgg agttcagacg tgtgctcttc    60
cgatct                                                               66
```

<210> SEQ ID NO 1168
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1168
caagcagaag acggcatacg agatgtgcgt aagtgactgg agttcagacg tgtgctcttc      60
cgatct                                                                66

<210> SEQ ID NO 1169
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1169
caagcagaag acggcatacg agattagatg acgtgactgg agttcagacg tgtgctcttc      60
cgatct                                                                66

<210> SEQ ID NO 1170
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1170
caagcagaag acggcatacg agatgattac aggtgactgg agttcagacg tgtgctcttc      60
cgatct                                                                66

<210> SEQ ID NO 1171
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1171
caagcagaag acggcatacg agattcgacg gcgtgactgg agttcagacg tgtgctcttc      60
cgatct                                                                66

<210> SEQ ID NO 1172
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1172
caagcagaag acggcatacg agatgatgtt acgtgactgg agttcagacg tgtgctcttc      60
cgatct                                                                66

<210> SEQ ID NO 1173
<211> LENGTH: 66
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 1173
caagcagaag acggcatacg agatcttcct tcgtgactgg agttcagacg tgtgctcttc     60
cgatct                                                               66

<210> SEQ ID NO 1174
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1174
caagcagaag acggcatacg agatgttagg tcgtgactgg agttcagacg tgtgctcttc     60
cgatct                                                               66

<210> SEQ ID NO 1175
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1175
caagcagaag acggcatacg agatcagttg gtgtgactgg agttcagacg tgtgctcttc     60
cgatct                                                               66

<210> SEQ ID NO 1176
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1176
caagcagaag acggcatacg agattcagcg aagtgactgg agttcagacg tgtgctcttc     60
cgatct                                                               66

<210> SEQ ID NO 1177
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1177
caagcagaag acggcatacg agatgtcgag cagtgactgg agttcagacg tgtgctcttc     60
cgatct                                                               66

<210> SEQ ID NO 1178
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 1178
caagcagaag acggcatacg agatggcata gggtgactgg agttcagacg tgtgctcttc    60
cgatct                                                               66

<210> SEQ ID NO 1179
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1179
caagcagaag acggcatacg agatggctcc tggtgactgg agttcagacg tgtgctcttc    60
cgatct                                                               66

<210> SEQ ID NO 1180
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1180
caagcagaag acggcatacg agattgcgaa gggtgactgg agttcagacg tgtgctcttc    60
cgatct                                                               66

<210> SEQ ID NO 1181
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1181
caagcagaag acggcatacg agatctattc aagtgactgg agttcagacg tgtgctcttc    60
cgatct                                                               66

<210> SEQ ID NO 1182
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1182
caagcagaag acggcatacg agatggcaga tagtgactgg agttcagacg tgtgctcttc    60
cgatct                                                               66

<210> SEQ ID NO 1183
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1183
caagcagaag acggcatacg agattgtgct tagtgactgg agttcagacg tgtgctcttc    60

```
cgatct                                                              66

<210> SEQ ID NO 1184
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1184
caagcagaag acggcatacg agattctagc gagtgactgg agttcagacg tgtgctcttc    60
cgatct                                                              66

<210> SEQ ID NO 1185
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1185
caagcagaag acggcatacg agattgatta cagtgactgg agttcagacg tgtgctcttc    60
cgatct                                                              66

<210> SEQ ID NO 1186
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1186
caagcagaag acggcatacg agatctgatt aagtgactgg agttcagacg tgtgctcttc    60
cgatct                                                              66

<210> SEQ ID NO 1187
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1187
caagcagaag acggcatacg agattacttg cagtgactgg agttcagacg tgtgctcttc    60
cgatct                                                              66

<210> SEQ ID NO 1188
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1188
caagcagaag acggcatacg agatgaattg ctgtgactgg agttcagacg tgtgctcttc    60
cgatct                                                              66
```

```
<210> SEQ ID NO 1189
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1189
caagcagaag acggcatacg agatgtcaag ttgtgactgg agttcagacg tgtgctcttc    60
cgatct                                                               66

<210> SEQ ID NO 1190
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1190
caagcagaag acggcatacg agatatccga cagtgactgg agttcagacg tgtgctcttc    60
cgatct                                                               66

<210> SEQ ID NO 1191
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1191
caagcagaag acggcatacg agatcaaggc gagtgactgg agttcagacg tgtgctcttc    60
cgatct                                                               66

<210> SEQ ID NO 1192
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1192
caagcagaag acggcatacg agatagtgtc ttgtgactgg agttcagacg tgtgctcttc    60
cgatct                                                               66

<210> SEQ ID NO 1193
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1193
caagcagaag acggcatacg agatgaccga gagtgactgg agttcagacg tgtgctcttc    60
cgatct                                                               66

<210> SEQ ID NO 1194
<211> LENGTH: 66
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1194
caagcagaag acggcatacg agatagaaca ttgtgactgg agttcagacg tgtgctcttc      60
cgatct                                                                66

<210> SEQ ID NO 1195
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1195
caagcagaag acggcatacg agatgtctta gtgtgactgg agttcagacg tgtgctcttc      60
cgatct                                                                66

<210> SEQ ID NO 1196
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1196
caagcagaag acggcatacg agatttgata atgtgactgg agttcagacg tgtgctcttc      60
cgatct                                                                66

<210> SEQ ID NO 1197
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1197
caagcagaag acggcatacg agattcaact gtgtgactgg agttcagacg tgtgctcttc      60
cgatct                                                                66

<210> SEQ ID NO 1198
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1198
caagcagaag acggcatacg agattccatg ctgtgactgg agttcagacg tgtgctcttc      60
cgatct                                                                66

<210> SEQ ID NO 1199
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1199
caagcagaag acggcatacg agattcgcac ctgtgactgg agttcagacg tgtgctcttc    60
cgatct                                                               66

<210> SEQ ID NO 1200
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1200
caagcagaag acggcatacg agataggatg tggtgactgg agttcagacg tgtgctcttc    60
cgatct                                                               66

<210> SEQ ID NO 1201
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1201
caagcagaag acggcatacg agataagcaa ctgtgactgg agttcagacg tgtgctcttc    60
cgatct                                                               66

<210> SEQ ID NO 1202
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1202
caagcagaag acggcatacg agatgacgct atgtgactgg agttcagacg tgtgctcttc    60
cgatct                                                               66

<210> SEQ ID NO 1203
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1203
caagcagaag acggcatacg agataacata atgtgactgg agttcagacg tgtgctcttc    60
cgatct                                                               66

<210> SEQ ID NO 1204
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1204
caagcagaag acggcatacg agatcagaca atgtgactgg agttcagacg tgtgctcttc    60
``` cgatct                                                                66

<210> SEQ ID NO 1205
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1205
caagcagaag acggcatacg agatccttgc tggtgactgg agttcagacg tgtgctcttc    60
cgatct                                                                66

<210> SEQ ID NO 1206
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1206
caagcagaag acggcatacg agatggaagg cggtgactgg agttcagacg tgtgctcttc    60
cgatct                                                                66

<210> SEQ ID NO 1207
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1207
caagcagaag acggcatacg agattaccgc tggtgactgg agttcagacg tgtgctcttc    60
cgatct                                                                66

<210> SEQ ID NO 1208
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1208
caagcagaag acggcatacg agatgactat tggtgactgg agttcagacg tgtgctcttc    60
cgatct                                                                66

<210> SEQ ID NO 1209
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1209
caagcagaag acggcatacg agatacgcat aggtgactgg agttcagacg tgtgctcttc    60
cgatct                                                                66

<210> SEQ ID NO 1210

-continued

```
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1210
caagcagaag acggcatacg agatcgccac aggtgactgg agttcagacg tgtgctcttc    60
cgatct                                                               66

<210> SEQ ID NO 1211
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1211
caagcagaag acggcatacg agatacatag cggtgactgg agttcagacg tgtgctcttc    60
cgatct                                                               66

<210> SEQ ID NO 1212
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1212
caagcagaag acggcatacg agatctaact gggtgactgg agttcagacg tgtgctcttc    60
cgatct                                                               66

<210> SEQ ID NO 1213
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1213
caagcagaag acggcatacg agatcattcc gagtgactgg agttcagacg tgtgctcttc    60
cgatct                                                               66

<210> SEQ ID NO 1214
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1214
caagcagaag acggcatacg agatatggta gggtgactgg agttcagacg tgtgctcttc    60
cgatct                                                               66

<210> SEQ ID NO 1215
<211> LENGTH: 66
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1215
caagcagaag acggcatacg agatacttct tcgtgactgg agttcagacg tgtgctcttc    60
cgatct                                                               66

<210> SEQ ID NO 1216
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1216
caagcagaag acggcatacg agatttgctg gagtgactgg agttcagacg tgtgctcttc    60
cgatct                                                               66

<210> SEQ ID NO 1217
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1217
caagcagaag acggcatacg agatctaggt tcgtgactgg agttcagacg tgtgctcttc    60
cgatct                                                               66

<210> SEQ ID NO 1218
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1218
caagcagaag acggcatacg agattcctgg tcgtgactgg agttcagacg tgtgctcttc    60
cgatct                                                               66

<210> SEQ ID NO 1219
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1219
caagcagaag acggcatacg agatggctag gcgtgactgg agttcagacg tgtgctcttc    60
cgatct                                                               66

<210> SEQ ID NO 1220
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1220
```

```
caagcagaag acggcatacg agatctgtgg acgtgactgg agttcagacg tgtgctcttc    60
cgatct                                                                66
```

<210> SEQ ID NO 1221
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1221

```
caagcagaag acggcatacg agatcaacgg tcgtgactgg agttcagacg tgtgctcttc    60
cgatct                                                                66
```

<210> SEQ ID NO 1222
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1222

```
caagcagaag acggcatacg agattggata tcgtgactgg agttcagacg tgtgctcttc    60
cgatct                                                                66
```

<210> SEQ ID NO 1223
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1223

```
caagcagaag acggcatacg agatgttgcg gcgtgactgg agttcagacg tgtgctcttc    60
cgatct                                                                66
```

<210> SEQ ID NO 1224
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1224

```
caagcagaag acggcatacg agatacatcc ttgtgactgg agttcagacg tgtgctcttc    60
cgatct                                                                66
```

<210> SEQ ID NO 1225
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1225

```
caagcagaag acggcatacg agataggctc aagtgactgg agttcagacg tgtgctcttc    60
cgatct                                                                66
```

<210> SEQ ID NO 1226
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1226
caagcagaag acggcatacg agatcctaga atgtgactgg agttcagacg tgtgctcttc      60
cgatct                                                                66

<210> SEQ ID NO 1227
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1227
caagcagaag acggcatacg agatgctaag tagtgactgg agttcagacg tgtgctcttc      60
cgatct                                                                66

<210> SEQ ID NO 1228
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1228
caagcagaag acggcatacg agatgttcat tagtgactgg agttcagacg tgtgctcttc      60
cgatct                                                                66

<210> SEQ ID NO 1229
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1229
caagcagaag acggcatacg agatagctct gggtgactgg agttcagacg tgtgctcttc      60
cgatct                                                                66

<210> SEQ ID NO 1230
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1230
caagcagaag acggcatacg agatcagcag cagtgactgg agttcagacg tgtgctcttc      60
cgatct                                                                66

<210> SEQ ID NO 1231
<211> LENGTH: 66

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1231
caagcagaag acggcatacg agatcctgga tagtgactgg agttcagacg tgtgctcttc    60
cgatct                                                               66

<210> SEQ ID NO 1232
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1232
caagcagaag acggcatacg agatcttgca gagtgactgg agttcagacg tgtgctcttc    60
cgatct                                                               66

<210> SEQ ID NO 1233
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1233
caagcagaag acggcatacg agatatagac aagtgactgg agttcagacg tgtgctcttc    60
cgatct                                                               66

<210> SEQ ID NO 1234
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1234
caagcagaag acggcatacg agatagatat aagtgactgg agttcagacg tgtgctcttc    60
cgatct                                                               66

<210> SEQ ID NO 1235
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1235
caagcagaag acggcatacg agatgagtta cagtgactgg agttcagacg tgtgctcttc    60
cgatct                                                               66

<210> SEQ ID NO 1236
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1236
aaacacccaa gatcggaaga gcgtcgtgta                                              30

<210> SEQ ID NO 1237
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1237
tgacttgtca tgtcttccga tcttgggtgt ttt                                          33

<210> SEQ ID NO 1238
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1238
caagtcaagc tagattccac gaagagttgt cacgtcagcc gcagtatc                          48

<210> SEQ ID NO 1239
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1239
tgacttggat actgcggctg acgtgacaac tcttcgtgga atctagct                          48

<210> SEQ ID NO 1240
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1240
agttgtcacc ataataagat cggaaga                                                 27

<210> SEQ ID NO 1241
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1241
cagacgtgtg ctcttccgat cttattatgg t                                            31

<210> SEQ ID NO 1242
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide -continued

```
<220> FEATURE:
<223> OTHER INFORMATION: Description of Combined DNA/RNA Molecule:
      Synthetic oligonucleotide

<400> SEQUENCE: 1242
aucagcaccc ggatgtagat aggatggact tagcgtcag                          39

<210> SEQ ID NO 1243
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1243
tgacttgctg acgctaagtc catcctatct acatccg                           37
```

METHODS FOR IDENTIFYING MACROMOLECULE INTERACTIONS

CROSS-REFERENCE TO RELATED APPLICATION(S)

The present application claims priority to and the benefit of U.S. Provisional Application Ser. No. 62/311,813 filed on Mar. 22, 2016, entitled "Mapping High-Dimensional Macromolecular Interactions in Cells," the entire content of which is incorporated herein by reference.

STATEMENT REGARDING FEDERALLY SPONSORED RESEARCH OR DEVELOPMENT

This invention was made with government support under Grant No. OD012190 and HL130007 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 31, 2017, is named 135069_402887-00585_SL.txt and is 303,128 bytes in size.

BACKGROUND

DNA is not randomly organized in the nucleus, but is instead structured around function. For decades, it has been known that DNA can change its compaction based on gene expression. For example, DNA is compacted into heterochromatin when genes are silenced, but is more accessible as open euchromatin when genes are activated. This compaction of DNA in the nucleus is thought to play an important role in gene regulation because it makes genes more or less accessible to regulatory proteins such as transcription factors, polymerase, and chromatin modifying proteins. However, it remains unclear how specific genes are positioned in the nucleus to achieve specific functions, such as regulating gene expression.

Over the past few decades, microscopy has identified another feature of nuclear structure called nuclear bodies. These are discrete structures in the nucleus where DNA, RNA, and proteins are brought together in the nucleus in 3D proximity. One of the most well known examples of a nuclear body is the nucleolus, where the transcription of ribosomal DNA genes occurs in a hub around nucleolar proteins and PolI. Another nuclear body, the speckle, has a high concentration of mRNAs and splicing proteins in discrete bodies in the nucleus, and another is the histone locus body where histone genes localize to a nuclear body with a high concentration of regulatory RNAs.

At a much higher resolution, chromosome confirmation capture C (3C)-based methods have been developed to map DNA-DNA interactions at higher resolution. These methods have identified several features of nuclear structure such as compartments where active and inactive genes interact more frequently with other active and inactive regions on the same chromosome. At a tens of kilobase scale, it has been observed that DNA is organized into neighborhoods of genes, called topologically associated domains, or TADs.

Nonetheless, current imaging methods are limited in the number of loci that can be observed at once, and because HiC (an extension of 3C) is limited in detection of pairwise interactions, both 3C and HiC methods are unable to detect whether these transcriptional hubs are a general feature of gene regulation. Specifically, there are no existing methods that can detect whether higher-order transcriptional hubs exist in single cells.

SUMMARY

In some embodiments of the present inventions, a method for identifying interactions of DNA, RNA, and/or protein molecules in a cell, includes lysing the cell to form a cell lysate, distributing the cell lysate into a plurality of lysate suspensions, adding a unique nucleotide tag to each of the lysate suspensions to tag the DNA, RNA, and/or protein molecules in the respective lysate suspension and thereby forming a plurality of tagged lysate suspensions, the unique nucleotide tag in each tagged lysate suspension being different from the unique nucleotide tags for the other tagged lysate suspensions, pooling the plurality of tagged lysate suspensions to form a tagged pool, distributing the tagged pool into a plurality of tagged suspensions and performing iii) and iv) n number of times on the plurality of tagged suspensions to form a plurality of tagged suspensions in which the DNA, RNA, and/or protein molecules have n+1 number of unique nucleotide tags, pooling the plurality of tagged suspensions to form a final tagged pool, sequencing each of the n+1 number of nucleotide tags in the final tagged pool; and identifying the DNA, RNA, and/or protein molecules having the same sequence and order of nucleotide tags.

In some embodiments of the present invention, a method for detecting interactions of molecules in a nucleus of a cell, includes, lysing the cell, isolating the nucleus from the cell lysate, shearing the chromatin in the nucleus forming a suspension of sheared chromatin, distributing the suspension into a first plurality of suspensions, adding a first unique nucleotide tag to the DNA, RNA, and/or protein molecules in each of the first plurality of suspensions, each unique nucleotide tag being different for each suspension, pooling the tagged first plurality of suspensions to form a first tagged pool, sequencing each of the first unique nucleotide tags in the first tagged pool, and identifying the DNA, RNA, and/or protein molecules having the same unique nucleotide tag.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 8D shows graphs of the number of reads obtained using SPRITE, according to embodiments of the present invention, in which the SPRITE method showed individual complexes that have reads containing all 3 histone gene clusters interacting in one tagged complex, in which examples are shown for 3 different SPRITE complexes that are tagged with different nucleotide tags depicted in different series of colors.

DETAILED DESCRIPTION

Figure 1:
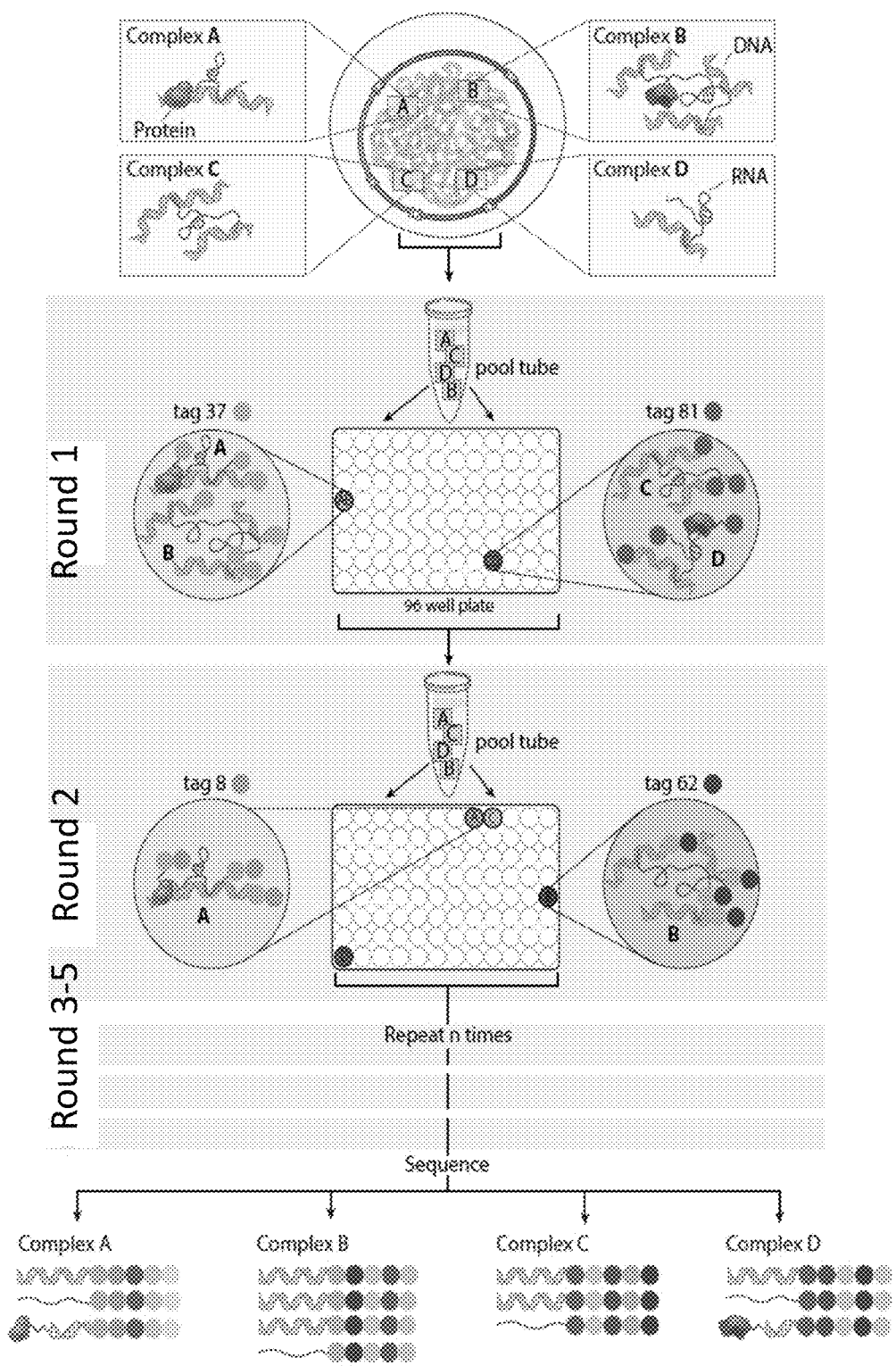
FIG. 1 is a conceptual diagram representing a method for detecting higher-order interactions of macromolecules using the split-and-pool nucleotide tagging of molecules according to embodiments of the present invention, in which cells are fragmented and single complexes are isolated in individual wells (e.g., a 96-well plate), where each well contains a unique nucleotide tag. In the example depicted, complexes A and B in one well and complexes C and D are tagged with a first unique tag in Round 1, where each well receives a different tag (e.g., unique tag 37 is shown as yellow, and unique tag 81 is shown as green). In some embodiments, the tagged molecules from Round 1 are pooled into one well and then randomly split again into wells (e.g., into a 96 well plate), where the complexes randomly distributed in each well are tagged with a second unique tag in Round 2 (e.g., unique tag 8 is shown as blue and unique tag 62 is shown as red). Any molecules that are in the same complex will sort together and be tagged with the same unique tags, and any molecules that are not in the same complex will randomly sort into different wells (e.g., of a 96-well plate) over the sequential rounds of split and pool tagging of complexes, and therefore receive a different set of unique tags. According to some embodiments of the present invention, the pool of molecules are tagged, pooled, and split at least once (Round 1), at least twice, (Round 2), or at least three times (Round 3). In some embodiments, the pool of molecules are tagged, pooled, and split at least 4 times (Round 4) and in still other embodiments, at least 5 times (Round 5). After the final round of nucleotide tagging, the tagged molecules are then sequenced, where any molecules that have the same set of nucleotide tags are matched to the same complex. This method is called Split-Pool Recognition of Interactions by Tag Extension (SPRITE), where each round of split-pool adds a nucleotide tag to a molecule, according to embodiments of the present invention.

A method for identifying DNA, RNA, and/or protein interactions in higher order structures in a cell includes a series of nucleotide tagging (or barcoding), pooling, and sorting of a cell lysate suspension such that interacting molecules sort together and thereby receive the same set of nucleotide tags (i.e., receive the same barcode), and molecules that do not interact are sorted apart, and thereby receive a different set of nucleotide tags (i.e., receive different barcodes), as shown in FIG. 1. Using this method, the probability that non-interacting molecules will receive all of the same nucleotide tags decreases exponentially with each additional round of tagging and sorting. In this way, interacting molecules may be identified by sequencing and matching identical barcodes. This method may also be referred to as Split-Pool Recognition of Interactions by Tag Extension (SPRITE).

As used herein, the term "DNA" refers to deoxyribonucleic acid. DNA may be double stranded including both complementary strands, unless the DNA is shown to be or indicated to be single stranded (ss) DNA.

As used herein, the term "RNA" refers to ribonucleic acid. RNA is a single stranded nucleic acid molecule, and as shown or indicated herein, may be a part of a double stranded molecule when complemented, for example, with copy DNA (cDNA) by reverse transcription.

As used herein, "suspension" refers to a liquid heterogeneous mixture. For example, a suspension may refer to a cell lysate having all of its cellular molecules in a liquid mixture. For example, a suspension may also include a cell lysate after homogenization, sonication, or chemical shearing.

As used herein, "adding," and like terms, refer to the combination of two components together, no matter the order of the addition. For example, "adding" a nucleotide tag to a molecule is the same as "adding" a molecule to a nucleotide tag so long as the nucleotide tag and the molecule are combined.

As used herein, "distributing" and "sorting" are used interchangeably to refer to the division of a whole quantity into a plurality of parts. For example, distributing or sorting a suspension involves the division of the whole suspension into multiple smaller suspensions.

As used herein, "pooling" refers to collecting and mixing together a plurality of components. For example, pooling of suspensions includes mixing multiple suspensions into one larger, pooled suspension.

As used herein, "shearing" or "fragmenting," and like terms, refer to chemical or mechanical means of separating or fragmenting a cell lysate. For example, shearing of chromatin (e.g., chromosomal DNA) may be carried out using mechanical means or chemical means. Non-limiting examples of mechanical shearing include sonication or homogenization. Non-limiting examples of chemical shearing, for example, of chromatin, include enzymatic fragmentation, using, for example DNase.

Figure 2A:
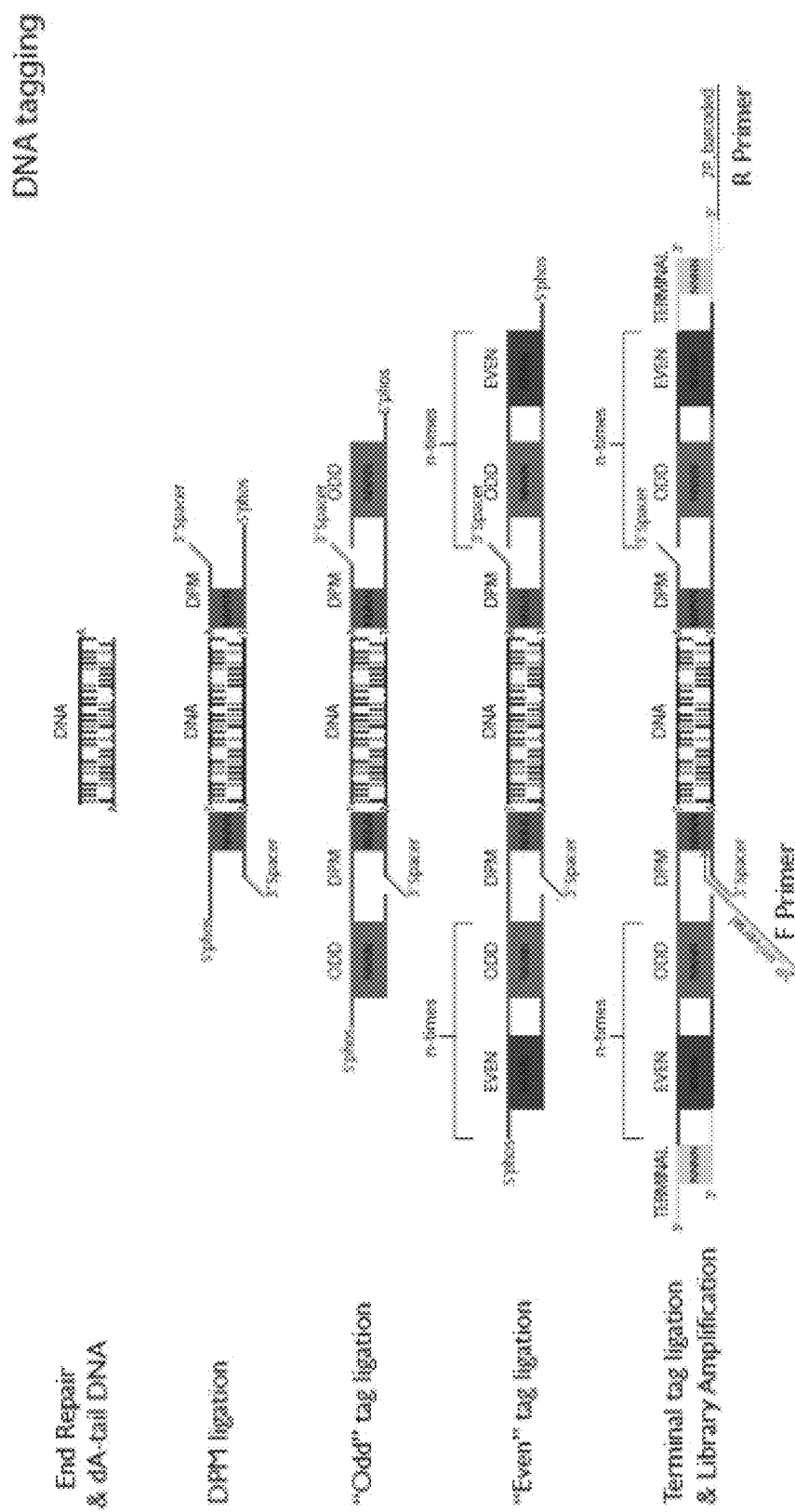
FIG. 2A is a schematic showing the molecular biology steps performed for ligating DNA molecules in a cell lysate with a series of unique nucleotide tags in order to barcode molecules in the same complex with the same barcode, according to embodiments of the present invention. As a first step, the DNA is end-repaired and dA-tailed, and then a complementary dT overhang DNA Phosphate modified (DPM) adaptor (shown in red) is ligated to both ends of the DNA molecule. After the DPM adaptor is ligated, all molecules are pooled and redistributed in a multi-well (e.g., 96-well) format and are then tagged with a first set of "Odd" nucleotide tags (shown in green) which are capable of ligating to the preceding DPM nucleotide tag (shown in red) on both ends of each DNA molecule. After the Odd nucleotide tag is ligated, all molecules are pooled and redistributed in a (e.g., 96-well) format and are then tagged with a first set of "Even" nucleotide tags (shown in blue) which are capable of ligating to the preceding Odd nucleotide tag on both ends of each DNA molecule. After the Even nucleotide tags have been ligated, all molecules are pooled and redistributed in a multi-well format and in the schematic shown, are tagged with a Terminal tag sequence capable of ligating to the preceding Even nucleotide tag.
Figure 3A:
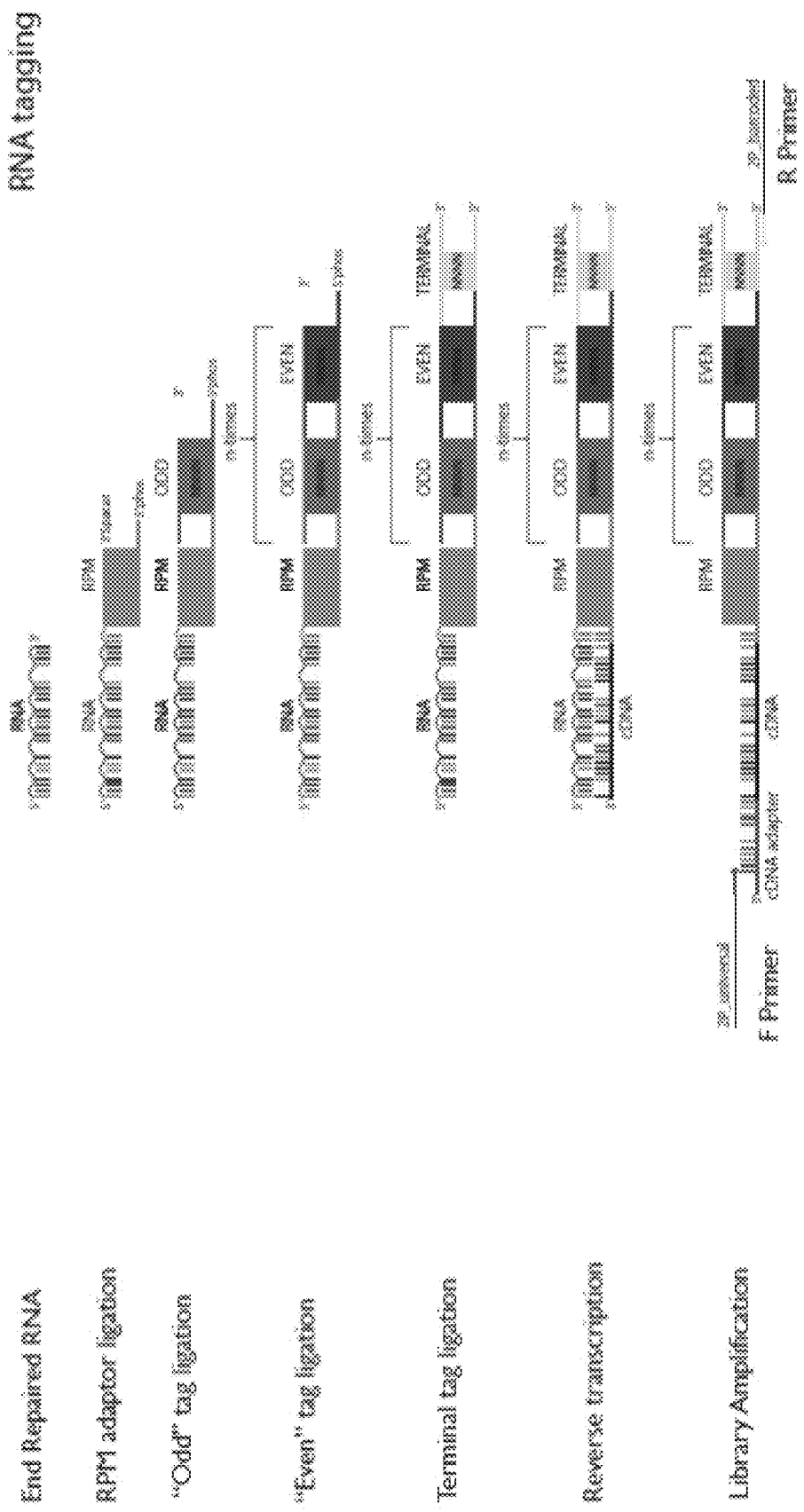
FIG. 3A is a schematic showing the molecular biology steps performed for ligating RNA molecules in a cell lysate with a series of unique nucleotide tags. As depicted, RNA is end repaired to obtain a 3'OH. A partially single-stranded RNA adaptor called RNA Phosphate Modified (RPM) adaptor is ligated to the RNA through a single-stranded RNA ligation. The 3'end of the RPM adaptor is synthesized with DNA bases and is annealed to a DNA adaptor to generate a double-stranded DNA overhang on the 3'end of the RPM adaptor. This double-stranded DNA sticky end on RNA allows for ligation of the same set of "Odd" and "Even" tags (as depicted and described in FIG. 2C) to be used for ligation of adaptors to RNA and DNA. A Terminal tag as depicted and described in FIG. 2D is ligated at the last step, and the primer sites are indicated.
Figure 4:
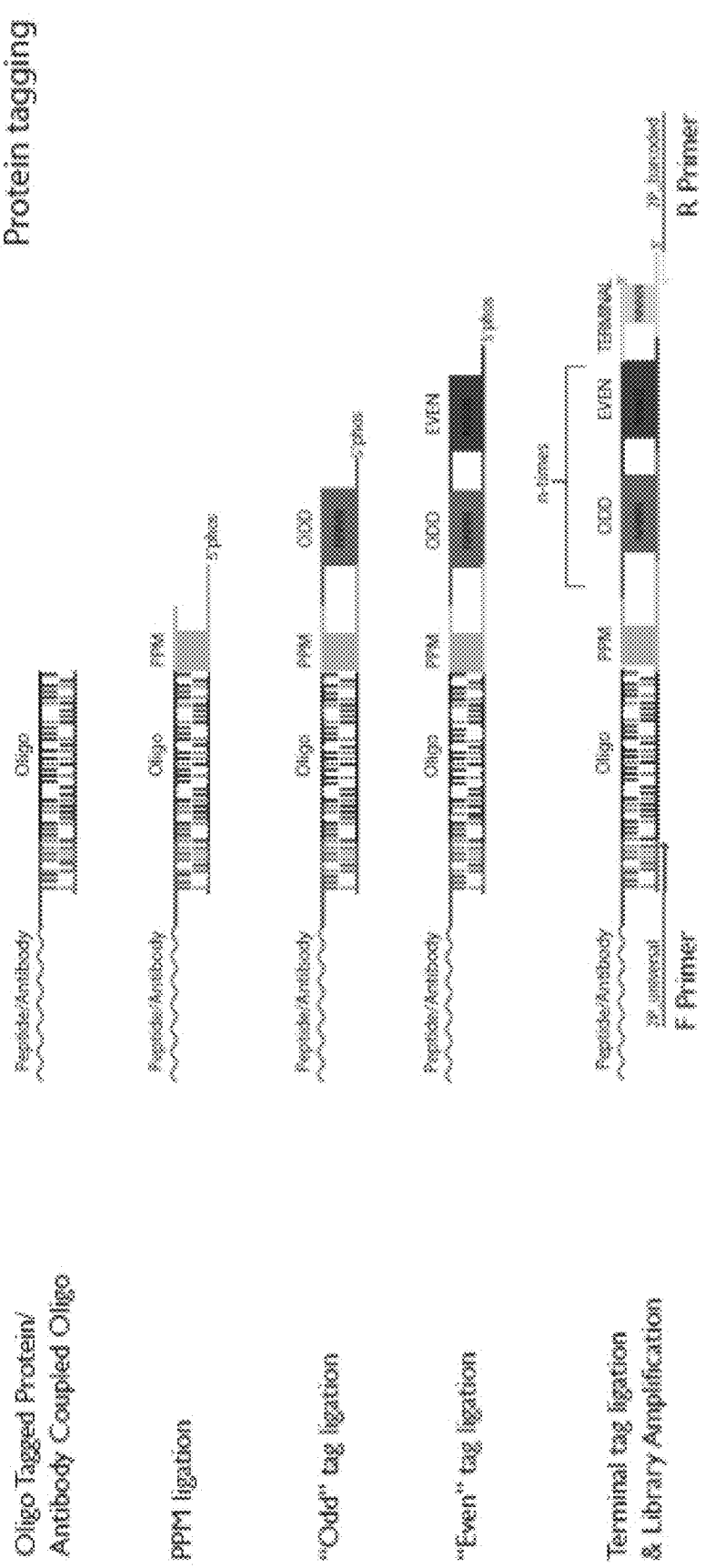
FIG. 4 is a schematic showing the molecular biology steps performed for ligating nucleotide tags to proteins or antibodies, according to embodiments of the present invention.

As used herein, the term "adaptor" refers to a molecule that may be coupled to a target molecule and enable or facilitate more effective nucleotide tagging (e.g., ligation), elongation, amplification, and/or sequencing of the target molecule. For example, DNA phosphate modified (DPM) adaptor according to embodiments of the present invention and shown in FIG. 2A, is a molecule that couples to the 5' and 3' end of a DNA molecule allowing for the DNA molecule to be effectively ligated with a subsequent nucleotide tag. Another example of an adaptor is the RNA phosphate modified (RPM) adaptor according to embodiments of the present invention and shown in FIG. 3A. The RPM adaptor couples to the 3' end of an RNA molecule allowing for the RNA molecule to be effectively ligated with a subsequent nucleotide tag. In some embodiments of the present invention, a protein phosphate modified (PPM) adaptor as shown in FIG. 4, is a molecule that couples to a target protein or to an antibody of a target protein, allowing for the protein to be effectively modified for subsequent nucleotide tagging. In some embodiments, the DPM, RPM, and/or PPM adaptor molecules may include a unique nucleotide sequence thereby also serving as a nucleotide tag.

Figure 3B:
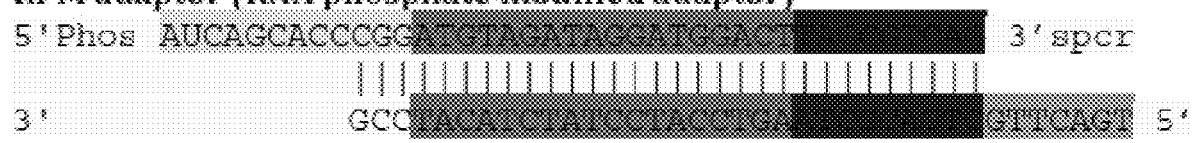
FIG. 3B is an example of one of the RNA Phosphate Modified (RPM) adaptor tags, according to embodiments of the present invention. The RPM adaptor is designed to specifically ligate RNA molecules using a single-stranded RNA ligase. The features and regions on the RPM as shown, have the following functions: the grey region in the RPM is synthesized using ribonucleotide bases, and it is also a single-stranded overhang on the 5'end of the molecule that allows for the 5'end of the RPM molecule to ligate RNA molecules; the pink region serves as a RNA-specific nucleotide tag to identify each read as RNA (if the pink sequence is read) or DNA (if the DPM sequence is read); the blue region may serve as an optionally unique nucleotide sequence making it possible to distinguish each RPM tag from another; the green region of the RPM (which is the same as the green region for the DPM as shown in FIG. 2B), is a sticky end sequence that renders the RPM capable of ligating to a first (e.g., Odd) nucleotide tag; the bottom strand of the RPM is phosphorylated (5 after ligation of the RPM adaptor to DNA to ensure that the RPM adaptor does not form chimeras and ligate to each other; and a 3'spacer (3' spcr) on the top strand of the RPM adaptor prevents ligation of single-stranded RPM molecules from ligating to the RPM adaptor and forming chimeras of several RPM molecules ligating to each other. Figure discloses SEQ ID NOS 1242-1243, respectively, in order of appearance.
Figure 3C:
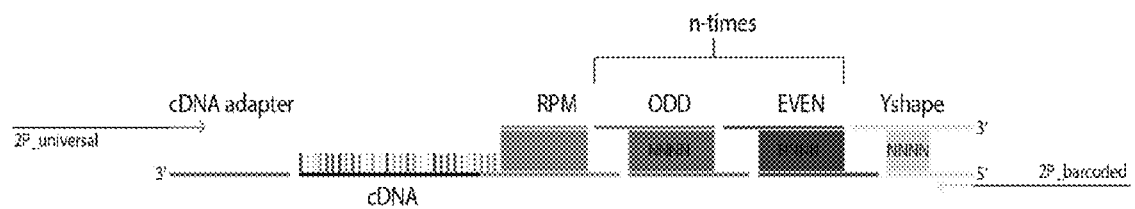
FIG. 3C is a schematic of the amplification of a tagged RNA molecule according to the embodiments of the present invention. For example, after performing a SPRITE ligation of an RPM adaptor molecule, an Odd nucleotide tag, an Even nucleotide tag, and a Terminal tag on the 3' end of an RNA molecule in the cell lysate, as depicted in FIGS. 1, 2C, 2D, 3A, and 3B, the RNA molecule is converted into cDNA such that a 2P universal primer may be used to amplify the tagged RNA after reverse transcription (RT) in preparation for sequencing of the nucleotide tags.
Figure 3D:
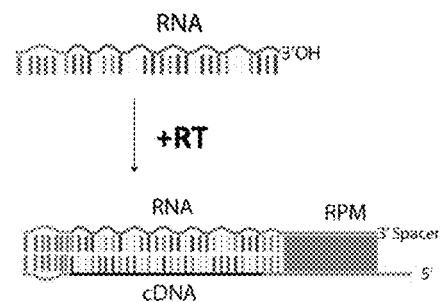
FIG. 3D is a schematic of the addition (i.e., ligation) of a single stranded (ss)RNA adaptor sequence (shown in blue) ligated to the 5'end of RNA through a single-stranded RNA ligase, according to embodiments of the present invention. Using this strategy, after RPM is ligated to an RNA molecule, the bottom strand of the RPM serves as the reverse-transcription primer, and during reverse transcription (+RT), the tagged RNA molecule and the 5' ssRNA adaptor is converted into cDNA, and the blue region may then serve as a priming site of the 3'end of the tagged cDNA.
Figure 3E:
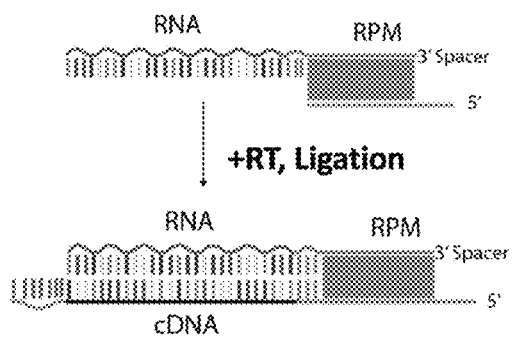
FIG. 3E is a schematic of the ligation of a 2P universal sequence to the cDNA as described and shown in FIG. 3C in which the blue represents a single-stranded DNA adaptor that is ligated to the cDNA through a single-stranded RNA/DNA ligase. Using this strategy, after RPM is ligated, the bottom strand of RPM serves as the reverse-transcription primer, and during reverse transcription (+RT), the tagged RNA is converted into cDNA in which the RNA is then degraded, leaving the cDNA as single-stranded DNA, to which the cDNA adaptor may be ligated through a single-stranded DNA ligation, and the blue region may then serve as a priming site of the 3'end of the tagged cDNA.
Figure 3F:
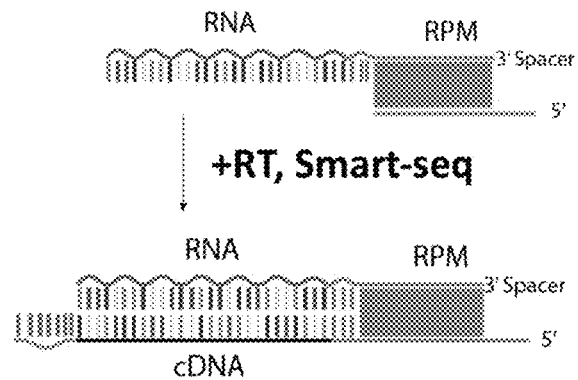
FIG. 3F is a schematic of the addition of a single-stranded adaptor to the cDNA through template switching using a reverse transcriptase that adds the cDNA adaptor to the 3'end of the cDNA using the Smart-seq strategy, according to embodiments of the present invention.

In addition to the tagging adaptors, a 5' single stranded RNA (ssRNA) adaptor, for example, as shown in FIG. 3D, may be used, which ssRNA adaptor allows for the elongation of the RNA molecule for amplification and sequencing after 3' nucleotide tagging of the RNA molecule.

As used herein, the terms "tagging" and "nucleotide tagging" refer to the coupling of oligonucleotides to DNA, RNA, and/or protein molecules in order to label molecules that are found to interact (directly or indirectly) in a complex. The tagging refers to the oligonucleotide label (tag) that identifies molecules that sort together thereby receiving the same tag. Additionally, coupling of oligonucleotides, according to embodiments of the present invention, may also be used to enable molecules to be tagged. For example, as shown in FIG. 4, a protein or antibody may be coupled with an oligonucleotide in order for the protein or antibody molecule to subsequently receive (e.g., ligate) a nucleotide tag or receive a protein phosphate modified (PPM) adaptor that is capable of ligating a nucleotide tag. The coupling of oligonucleotides to proteins or antibodies is shown herein, but is also described in Los et al., "HaloTag: a novel protein-labeling technology for cell imaging and protein analysis, *ACS Chem Biol.*, 2008, 3:373-382; Singh et al., "Genetically Encoded Multispectral Labeling of Proteins with Polyfluorophores on a DNA Backbone," *J. Am. Chem. Soc.*, 2013, 16:6184-6191; Blackstock et al., "Halo-Tag Mediated Self-Labeing of Fluorescent Proteins to Molecular Beacons for Nucleic Acid Detection," *Chem. Commun.*, 2014, 50: 1375-13738; Kozlov et al., "Efficient Strategies for the Conjugation of Oligonucleotides to Antibodies Enabling Highly Sensitive Protein Detection," *Biopolymers*, 2004, 73:621; and Solulink, "Antibody-Oligonucleotide Conjugate Preparation," Solulink.com, 4 pages, the entire contents of all of which are incorporated herein by reference.

According to embodiments of the present invention, a method for identifying interactions of DNA, RNA, and/or protein molecules in a cell, includes lysing the cell to form a cell lysate. In some embodiments, interactions may be identified using a whole cell lysate. In some embodiments, interactions may be identified using a fractionated cell lysate. For example, molecular interactions may be analyzed using the cytosol and/or any of the organelles. In some embodiments of the present invention, the nucleus may be isolated from the cell lysate for analysis of molecular interactions.

In some embodiments of the present invention, the cell or cell lysate may be treated with a crosslinker. The crosslinker may be added to the cell prior to cell lysis, or the crosslinker may be added to the cell lysate. Any suitable chemical crosslinker may be used. In some embodiments, disuccinimidyl glutarate (DSG) and/or formaldehyde crosslinkers may be used.

Following lysis, with or without crosslinking, the cell lysate, a cytosolic fraction of the cell lysate, or an organelle fraction of the cell lysate, all of which may be referred to as the suspension, may be distributed into a plurality of lysate suspensions for nucleotide tagging of the DNA, RNA, and/or protein molecules. Nucleotide tagging for each of DNA, RNA, and proteins may be carried out using any suitable method. Many means of nucleotide labeling are known. Examples of methods are shown, for example in FIGS. 2A-2D, 3A-3G, 4, and described in the examples disclosed herein.

Distribution or sorting of the suspension into the lysate suspensions may be performed using any suitable approach. As described in the examples disclosed herein, distribution of the suspension may be accomplished using a 96-well plate, thereby resulting in 96 suspensions and 96 unique nucleotide tags. The number of suspensions is not limited to a minimum or maximum. As is understood by the skilled person, an increase in the number of suspensions will increase the probability of sorting non-interacting molecules apart from each other. As used herein, a "well" refers to the well of a 96-plate, however, any number of wells or plates may be used. A well may also refer to the well of a tube or any similar vessel capable of holding the sorted lysate suspension separate from other sorted lysate suspensions. For example, a well may also include a flat surface.

To each of the distributed lysate suspensions, a unique nucleotide tag may be added. As used herein, "unique" means different from any other. As noted above in the definition of adding, either the unique nucleotide tag can be added to its respective distributed lysate suspension, or the distributed suspension may be added to a well containing its respective unique nucleotide tag. For example, in a 96-well set up, a plurality of lysate suspensions would refer to 96 suspensions receiving one of 96 different nucleotide tags. Each unique nucleotide tag is capable of tagging the DNA, RNA, and/or protein molecules in the lysate suspension. In some embodiments, the nucleotide tagging is facilitated by an adaptor molecule, such as the DPM, RPM, or PPM disclosed herein. In some embodiments, the nucleotide tagging of a protein molecule includes expressing a modified protein of interest in a cell, in which the expressed modified protein is capable of being coupled to an oligonucleotide. The oligonucleotide directly coupled to the protein may serve as a nucleotide tag for identification. In some embodiments, the oligonucleotide coupled to the protein may be ligated with subsequent nucleotide tags. In some embodiments, an antibody that binds to a target protein may be modified with an oligonucleotide. The antibody coupled oligonucleotide enables the protein to be labeled which may serve as a nucleotide tag for identification. In some embodiments, the oligonucleotide coupled to the antibody may be ligated with subsequent nucleotide tags. In some embodiments, an antibody modified with an oligonucleotide is incubated with the cell lysate prior to nucleotide tagging.

After a unique first nucleotide tag is coupled or ligated to each of the plurality of lysate suspensions, the lysate suspensions may be pooled, thereby forming a first tagged pool. In some embodiments, the first nucleotide tag may be any suitable oligonucleotide that is capable of being sequenced. In some embodiments, the first nucleotide tag is added to any one sorted lysate suspension is capable of binding to all DNA, RNA and/or protein molecules. In some embodiments, the first nucleotide tag is capable of ligating to all DNA, RNA, and/or protein molecules in the lysate suspension that have been modified with a DPM, RPM, or PPM adaptor as disclosed herein. This first nucleotide tag may be referred to as an "Odd" nucleotide tag as shown in FIGS. 2A, 3A, and 4. In some embodiments, depending on the approach and strategy used to target a complex, one distribution of the suspension may be adequate for identifying true interactions of molecules. Accordingly, the nucleotide tags in the first tagged pool may be amplified and subsequently sequenced for analysis. In some embodiments, the probability that non-interacting molecules will receive all of the same nucleotide tags decreases exponentially with each additional round of tagging and sorting. Accordingly, in some embodiments, the first tagged pool is distributed into a plurality of tagged pool suspensions. In some embodiments, the first tagged pool may be mixed thoroughly prior to redistribution to ensure separation of non-interacting complexes.

To each of the distributed plurality of tagged pool suspensions, a unique second nucleotide tag may be added (or each of the plurality of tagged pool suspensions may be added to its respective unique second nucleotide tag). In some embodiments, all of the second nucleotide tags are capable of ligating to any of the previously ligated first nucleotide tags. This second nucleotide tag is referred to as an "Even" nucleotide tag as shown in FIGS. 2A, 3A, and 4.

After a unique second nucleotide tag is coupled or ligated to each tagged pool suspension, the tagged pool suspensions may again be pooled forming a second tagged pool. In some embodiments, the nucleotide tags in the second tagged pool may be amplified and sequenced, or redistributed for another round of tagging. The pooling, distributing (sorting), and tagging may continue indefinitely so long as the integrity of the samples is maintained, and unique nucleotide tags remain available. In some embodiments, the second tagged pool is redistributed into a plurality of tagged re-pooled suspensions for a third nucleotide tagging in which the third nucleotide tag ligates to any of the second nucleotide tags. The third nucleotide tag may be referred to as an "Odd" tag as it can ligate to the previous "Even" tag. Nucleotide tagging may continue indefinitely so long as the previous tag is capable of ligating the subsequent tag. An example of this is the Odd to Even to Odd tagging as shown in FIGS. 2A and 2C. The ligation sequences of these tags alternate to ensure ligation fidelity. The third nucleotide tagging may be followed again by pooling of the tagged re-pooled suspensions to form a third tagged pool which may be amplified for sequencing. In some embodiments, the third tagged pool may be distributed into a plurality of tagged thrice pooled suspensions for a fourth nucleotide tagging in which the fourth nucleotide tag ligates to any of the previously ligated third nucleotide tags. The fourth nucleotide tagging may be followed again by pooling of the tagged thrice pooled suspensions to form a fourth tagged pool which may be amplified for sequencing. In some embodiments, the fourth tagged pool may be distributed into a plurality of tagged 4× pooled suspensions for a fifth nucleotide tagging.

In some embodiments, after the first nucleotide tagging, the pooling, distributing, and tagging may be carried out (n) number of times, such that the DNA, RNA, and/or protein molecules in the suspension receive (n)+1 number of nucleotide tags.

In some embodiments, after the desired number of sorting and tagging has been performed, the plurality of tagged (n)x pooled suspensions are pooled into a final pool and the tagged molecules in the final pool are amplified for sequencing. In some embodiments, after the last nucleotide tag is added, the final pool may be redistributed again into a plurality of tagged final pool suspensions for the addition of a Terminal nucleotide tag. As shown in FIG. 2D, a Terminal tag may provide an additional unique sequence and may also provide a primer site for amplification.

In some embodiments of the present invention, the tagged final pool is first amplified to make a library of amplified tags as disclosed herein. Amplified tags are then sequenced using next generation sequencing as disclosed.

The following Examples are presented for illustrative purposes only, and do not limit the scope or content of the present application.

EXAMPLES

Using one approach, SPRITE may be carried out using several molecular biology steps: (i) crosslinked complexes are coupled to magnetic beads at a loading frequency such that there is expected to be <1 complex per bead. (ii) A unique molecular sequence tag is ligated to double stranded DNA using T4 DNA Ligase and a distinct molecular sequence tag is ligated to single stranded RNA using RNA Ligase 1. These DNA and RNA tags each attach an identical "sticky end" overhang for efficient ligation of subsequent tags (FIGS. 2A, 3A, and 4). (iii) To enable an arbitrary number of rounds of tag extension, we make use of a set of 96 distinct "Even" and "Odd" tags. In this design, Even tags contain a sticky overhang that can anneal to an Odd tag; and Odd tags contain a sticky overhang that can anneal to Even tags. This enables the use of a small set of alternating tag sequences to extend the unique barcode, while simultaneously preventing multiple tags from being ligated in one round and enabling the ligation of tags over alternating rounds even if ligation does not occur over one round. (iv) Because each crosslinked complex is covalently coupled to a magnetic bead, after each round of tag extension, we can wash away free adaptors using stringent denaturing conditions that both inactivate residual enzymes and also solubilize chromatin to disrupt any aggregation that might lead to non-random sorting in the subsequent splitting round.

Figure 5A:
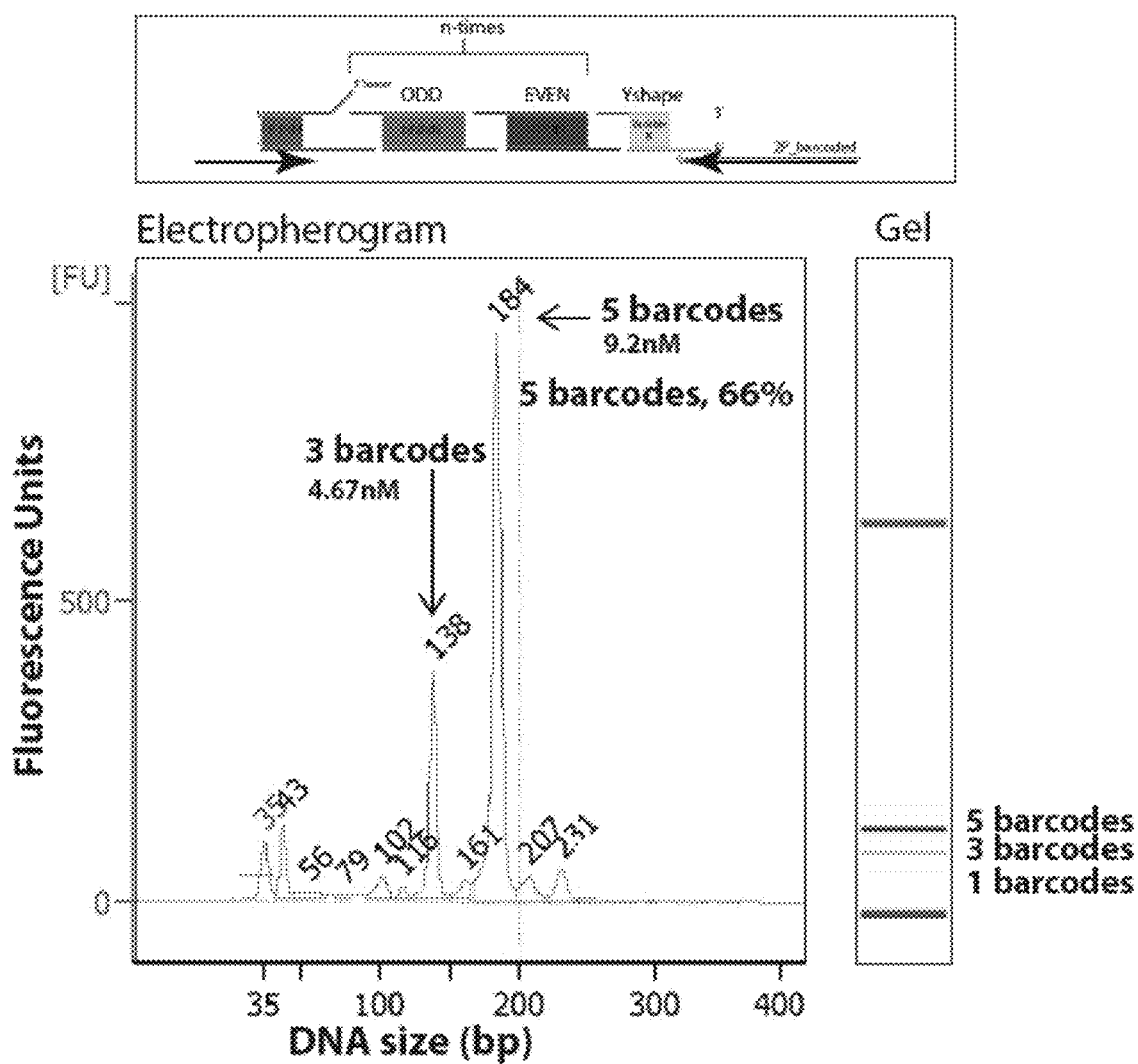
FIG. 5A. shows a graph of fluorescence units corresponding to the amount of DNA and the size of DNA in base pairs (bp) resulting from a PCR reaction for quality control on the ligation efficiency, according to embodiments of the present invention.
Figure 5B:
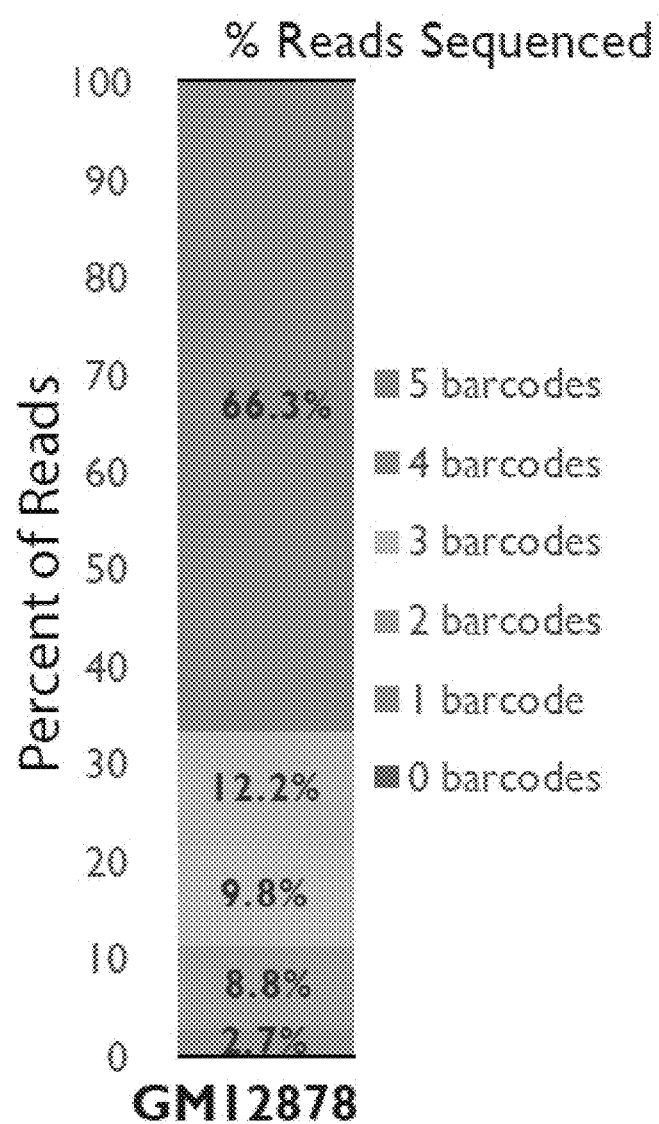
FIG. 5B shows the percent of sequencing reads with all 5, 4, 3, 2, and 1 barcodes (nucleotide tags) identified, for GM12878 barcoding reactions, according to embodiments of the present invention.
Figure 5C:
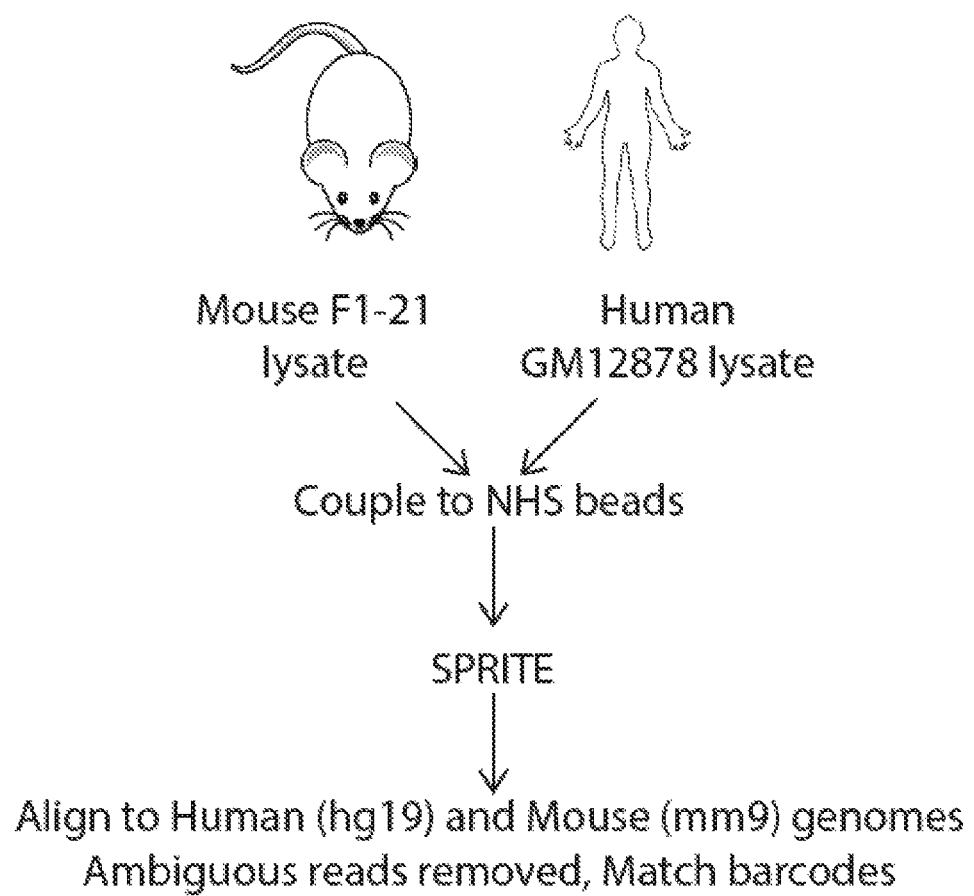
FIG. 5C depicts an experiment to determine on-bead noise using human and mouse lysates in which inter-species interactions are used to identify experimental noise, according to embodiments of the present invention.
Figure 5D:
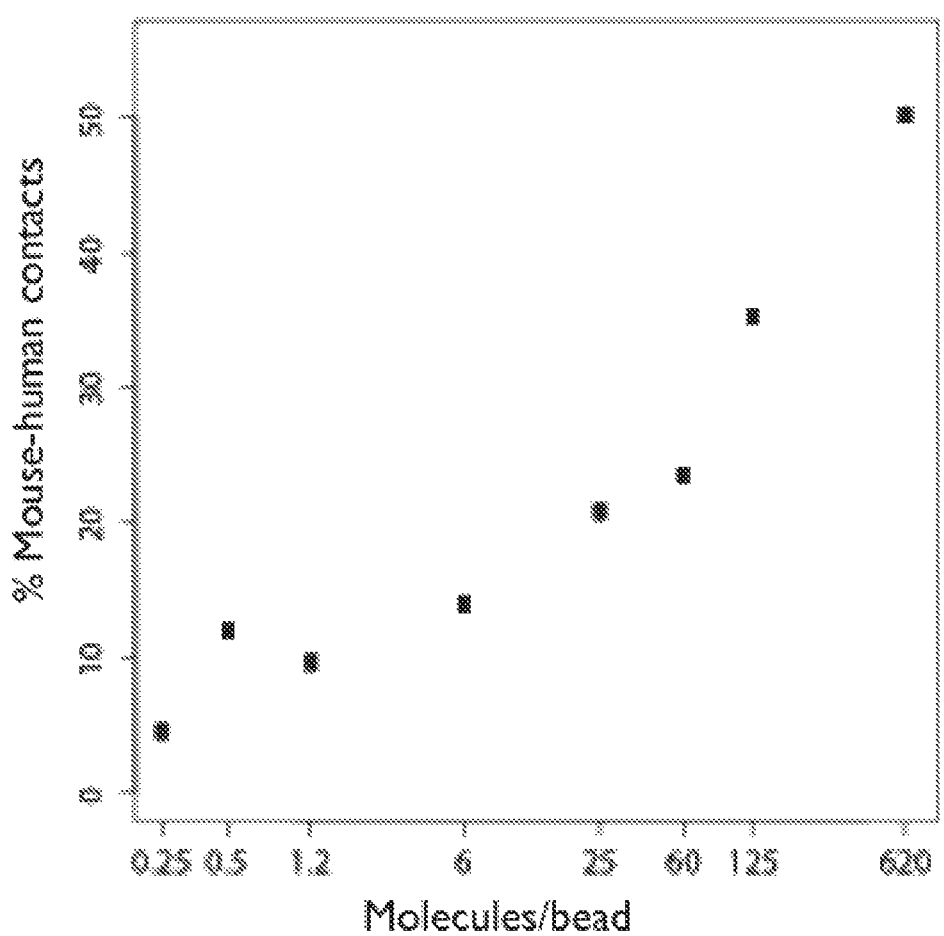
FIG. 5D. shows a graph of human-mouse contacts identified whenever two reads with the same barcodes come from both human and mouse, according to embodiments of the present invention in which any reads that did not uniquely map to mouse or human were excluded from this analysis.

To confirm that SPRITE successfully tags interacting molecules in vivo, several possible challenges were considered. (i) Because mapping interactions requires accurately assigning molecules to their original crosslinked complex, it needed to be ensured that most molecules present within the same crosslinked complex will contain a complete set of tags. To do this, the ligation conditions were optimized by designing a tag that contains a 7 nt overhang that anneals with a high Tm (Tm=20° C.) than a more-commonly used 2-3 nt sticky end (Tm=5-10° C.) to a complementary overhang present on the molecule. Using this approach, ~92% efficiency of tag extension was achieved in each round (FIGS. 5A-5B,) leading to >68% of interacting molecules containing the full barcode. (ii) It was ensured that molecules within independent complexes do not receive the same barcode by chance, which could occur due to random coupling to the same bead or through aggregation of complexes. To test this, we mixed human and mouse cells and performed SPRITE on these pooled samples. Because there should be no in vivo crosslinked complexes that should contain human and mouse sequences, we measured the number of such spurious interspecies contacts and identified that <5% of all interactions occurred between human and mouse molecules (FIGS. 5C-5D). (iii) Because SPRITE amplifies RNA and DNA in the same reaction, accurate discrimination between sequence reads arising from RNA or DNA was assayed. To do this, the strand of all molecules containing the RNA tag was determined and found that these reads align to known expressed regions (i.e. ribosomal RNA, messenger RNA, lncRNAs) and ~99% align to the sense strand as would be expect for RNA, but not DNA, reads. Together, these results demonstrate the specificity of SPRITE for identifying interactions that are crosslinked in the nucleus.

SPRITE accurately maps genome structure at various levels of resolution. To test whether SPRITE can be used for mapping genome structure, results obtained by SPRITE were compared to known DNA structures. To do this, data generated by HiC was used, a proximity-ligation method that enables genome-wide mapping of DNA-DNA interactions, which is currently the gold-standard approach for measuring DNA interactions.

To compare SPRITE to HiC, maps were generated in two mammalian cell types that have been well mapped by HiC (mouse ES cells and human lymphoblastoid cells). Because HiC observes pairwise interactions, interactions were downweighted from higher-order (>2 molecules each) clusters by the number of molecules in cluster minus 1 (n−1) such that larger clusters contribute the same number of contacts as pairwise clusters to compare SPRITE interactions directly with HiC interactions. Overall, these maps were found to be highly similar, such that at 200 Kb resolution we observe a spearman correlation of 0.92. This high correlation demonstrates that SPRITE produces comparable genome-wide maps to that observed by HiC.

Figure 6A:
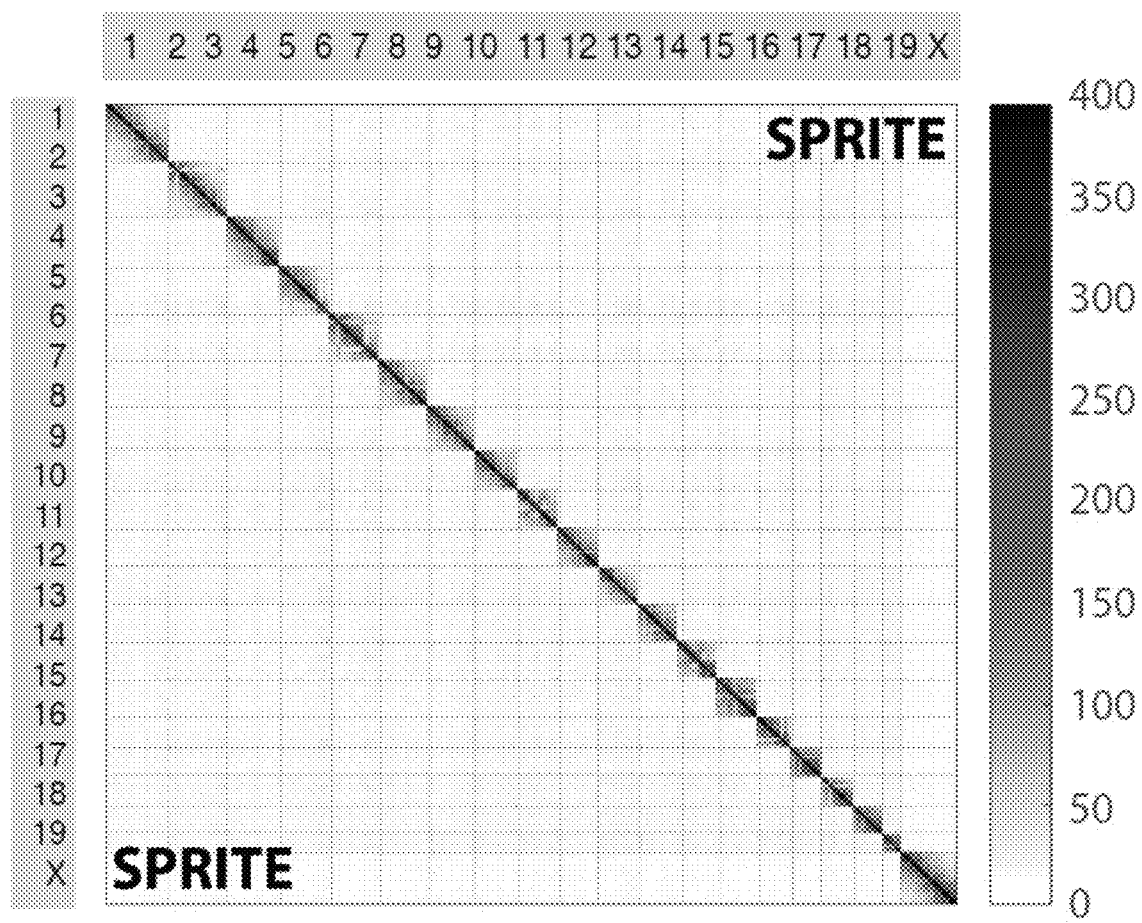
FIG. 6A graphically depicts a comparison of how SPRITE can observe known DNA interactions at various levels of nuclear structure in mouse embryonic stem (mES) cells that are similar to previously observed DNA interactions using HiC in mES cells in which chromosomes are known to form discrete territories, and where DNA on each chromosome interacts very highly with other regions on the same chromosome than with DNA different chromosomes, according to embodiments of the present invention.
Figure 6B:
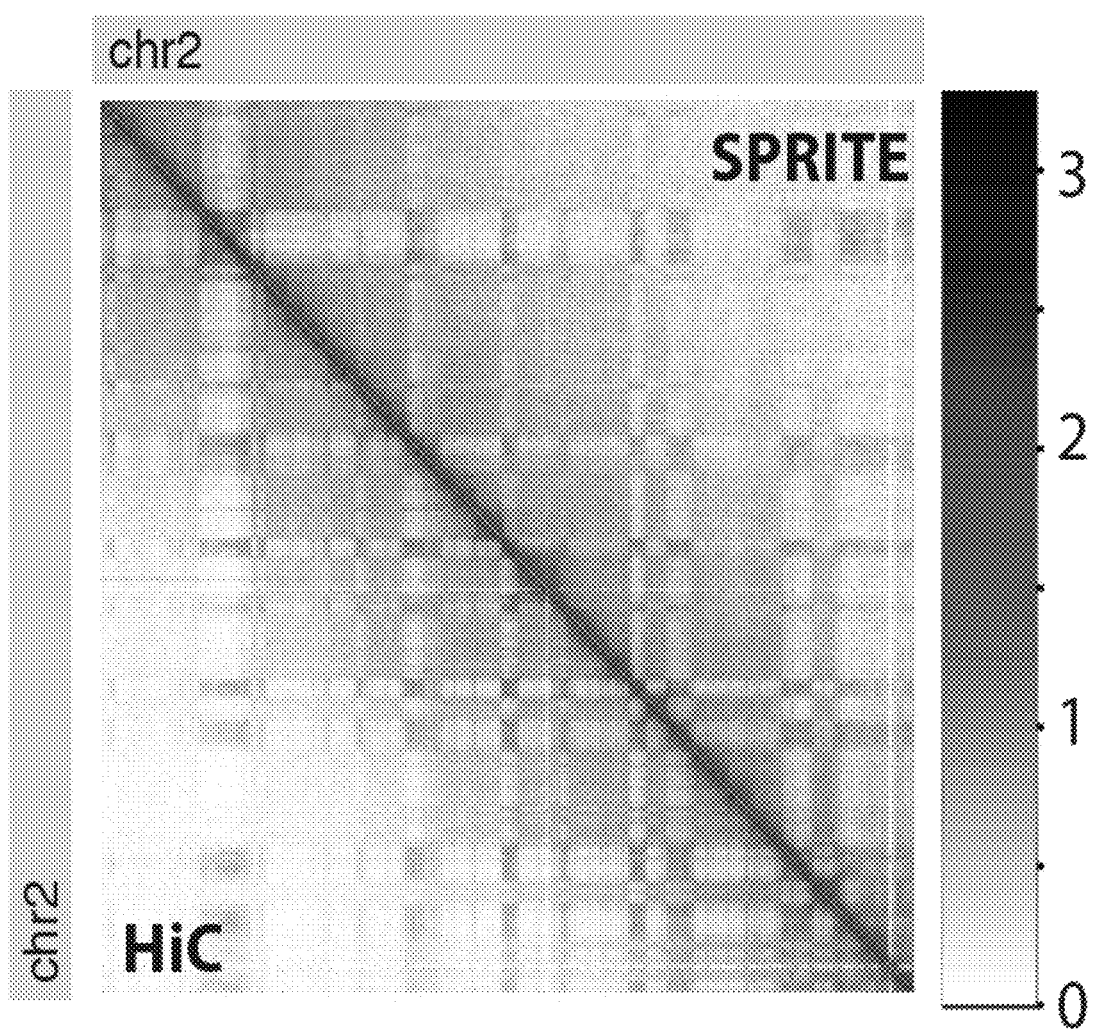
FIG. 6B graphically depicts a comparison at 200 kilobase (kb) resolution, in which SPRITE (upper half of diagonal) observes DNA interactions on the same chromosomes, such as compartment similar to those observed using HiC (lower half of diagonal), according to embodiments of the present invention.
Figure 6C:
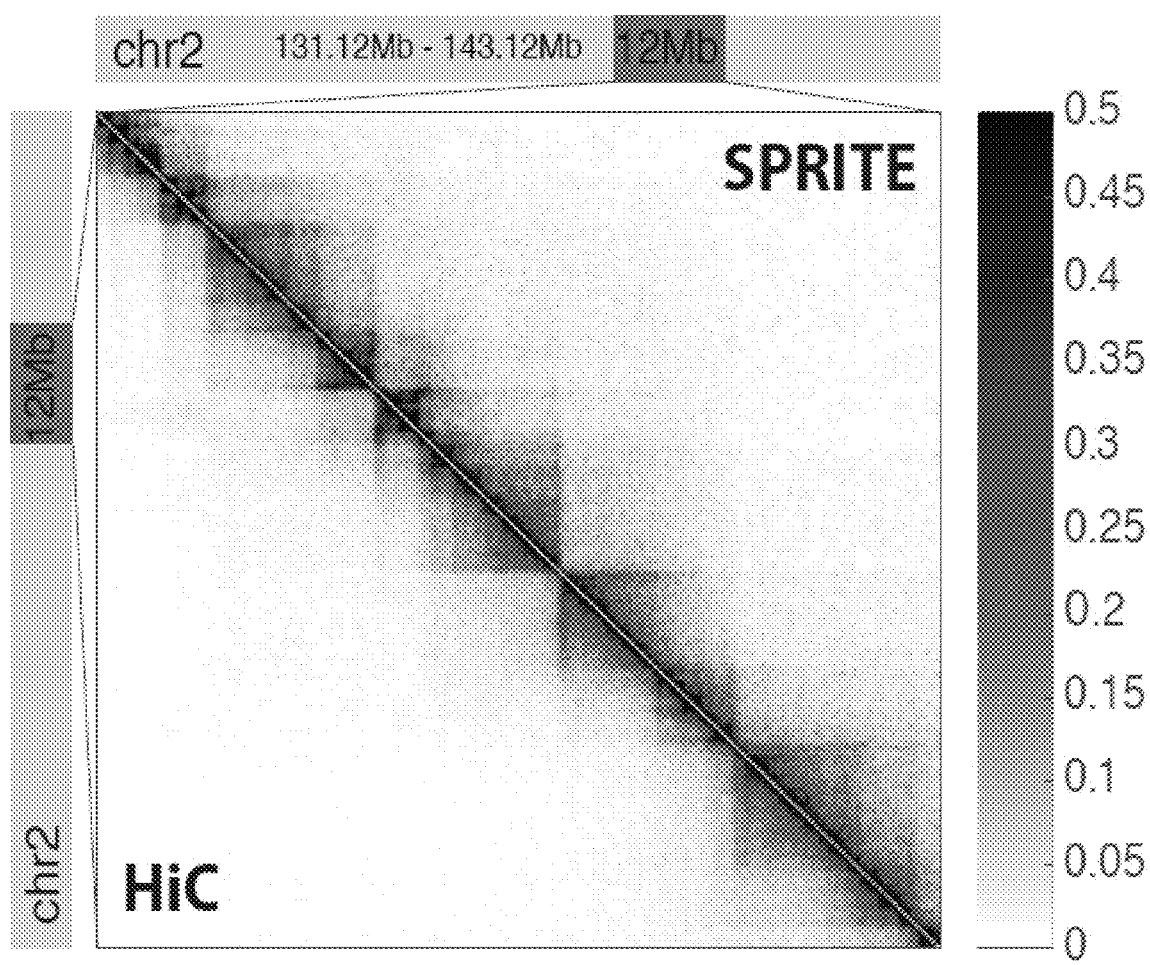
FIG. 6C graphically depicts a comparison at 40 kb resolution, in which similar topologically associated domains (TADs) are observed in both HiC (lower half of diagonal) and SPRITE (upper half of diagonal), according to embodiments of the present invention.

Using SPRITE, similar structural features of the genome that have been previously characterized using HiC were observed. For example, for interactions occurring across all chromosomes, it was observed that there is a clear preference for interactions to occur within the same chromosome (FIG. 6A). This is consistent with the fact that chromosomes have been previously shown to form discrete territories in the nucleus—often referred to as chromosome territories. At a megabase scale, an alternating interaction pattern was observed between regions on the chromosomes that correspond to "A" and "B" compartments, which segregate active and inactive regions of the genome (FIG. 6B). These compartments have previously been identified by performing principal component analysis on the matrix of contact frequencies between all pairs of genomic regions. Each genomic region is then assigned a compartment based on the sign of its value in the first principal component. To quantify the similarity between A and B compartments identified by SPRITE and HiC, the correlation coefficient was calculated between the first principal components for SPRITE and HiC and found that they are highly similar (R=XX), demonstrating that SPRITE can accurately map A and B compartments.

At sub-megabase resolution, it was observed that adjacent regions of DNA organize into discrete regions that are highly self-interacting and are separated by boundaries that preclude interaction with neighboring regions. These structures correspond to those previously mapped by HiC and have been referred to as topologically associated domains (TADs) (FIG. 6B). To compare these structures between SPRITE and HiC, an "insulation score" was calculated for each region in the genome, which quantifies how close a given region is to a TAD boundary. It was found that these insulation scores are highly similar between SPRITE and HiC, with a correlation coefficient of XX. These results demonstrate that SPRITE can accurately map genome structure across multiple levels of resolution.

SPRITE observes longer range interactions than those observed by HiC. In addition to accurately recapitulating HiC data, one key advantage of SPRITE is that it can map higher-order interactions that occur within a single region of the nucleus. Because 3C methods make use of proximity-ligation, they are intrinsically limited to measurements of pairs of DNA regions that interact. In contrast, SPRITE can map interactions between many DNA regions at once allowing us to directly measuring higher-order interactions. It was found that >45% of interactions observed by SPRITE occur between more than 2 interacting DNA molecules. We hypothesized that larger clusters might capture interactions across further genomic distances than those observed using HiC. To test this, SPRITE interactions were separated into groups consisting of tagged complexes containing 2-10 (~34%), 11-100 (~13%), 101-1000 (~8%), and 1001+(~9%) molecules (FIG. 7B). The distance decays were then calculated for interactions from clusters of different sizes compared to those observed using HiC. While clusters of 2-10 molecules showed a similar distance decay to HiC, interactions from larger cluster sizes (11+ molecules) spread across further genomic distances than HiC (FIG. 7C). These structures of various sizes allow observation of interactions across various scales in the nucleus to observe the hierarchical folding of chromatin. Specifically, larger clusters containing 10-100 accurately recapitulate known DNA structures observed across further genomic distances in HiC, such as interactions between neighboring TADs present within larger interacting A and B compartments of shared expression levels (active and inactive regions marked with similar histone acetylation marks) (FIG. 7D). In addition to interactions on the same chromosomes, clusters containing 100-1000 and 1000+ reads have sticking inter-chromosomal interactions between the centromeres and telomeres of different chromosomes. This is consistent with the observation of centromere clusters in mouse embryonic stem cells, suggesting that SPRITE can map long-range interactions between chromosomes (FIG. 7E). This suggests that SPRITE can both capture interactions similar to those observed using HiC using smaller clusters, as well as longer-range interactions in the nucleus.

Figure 7A:
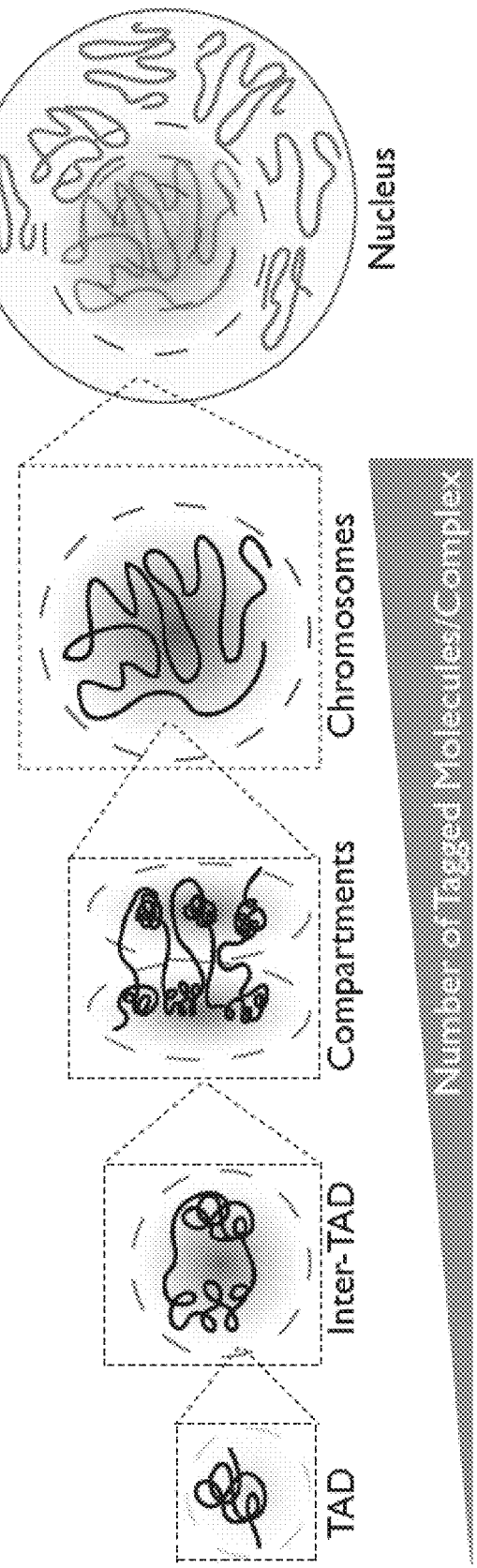
FIG. 7A is a schematic showing how SPRITE may be used to observe higher-order and longer-range interactions in the nucleus from clusters of tagged molecules of various sizes: 2-10, 10-100, 100-1000, and 1000+ reads in individual complexes, with all data shown from mES F1-21 cells, including interactions within TADs, between TADs, within compartments, and between chromosomes are observed with complexes of larger sizes, according to embodiments of the present invention.
Figure 7B:
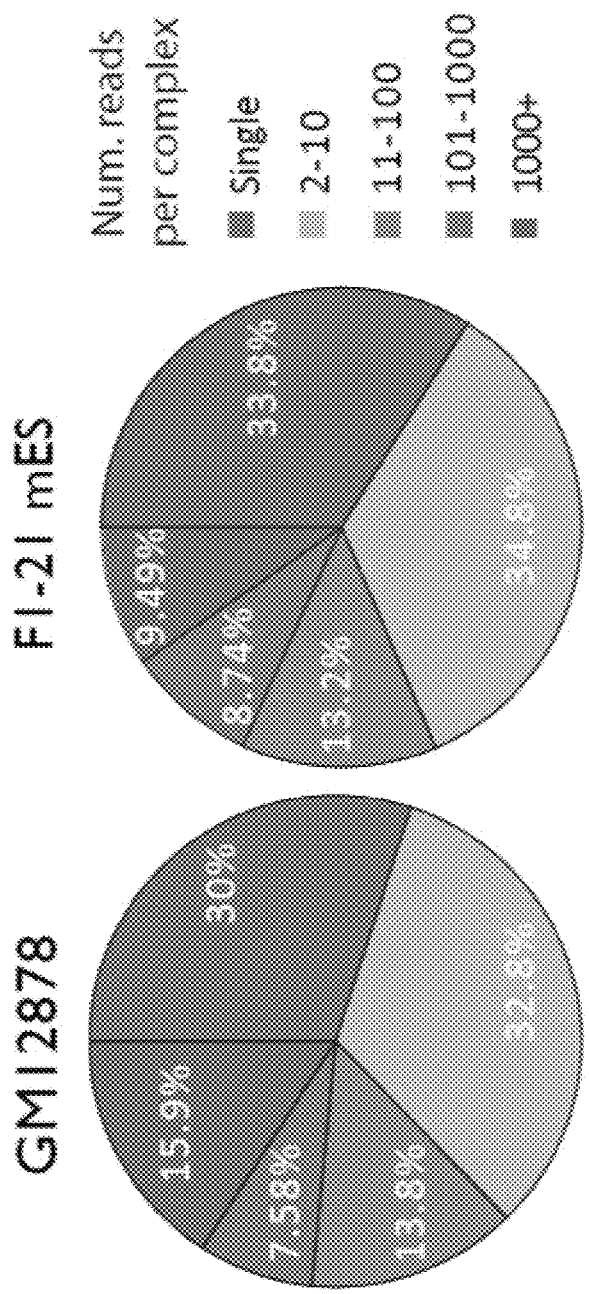
FIG. 7B is a graph showing percentage of reads in clusters of different sizes in two different cell types of human GM12878 lymphoblasts and mouse embryonic stem cell F1-21 hybrid cells, according to embodiments of the present invention.
Figure 7C:
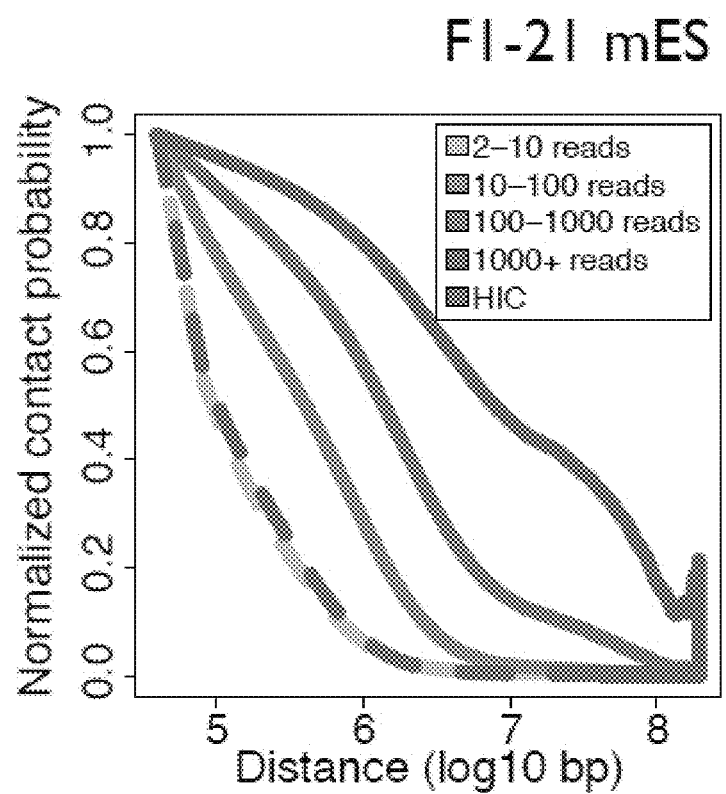
FIG. 7C is a graph showing longer range interactions observed on each chromosome from larger cluster sizes, according to embodiments of the present invention, with the number of reads indicated in yellow, green blue, purple, and red, as indicated, in which interactions across further genomic distances on each chromosome are observed from larger clusters sizes.
Figure 7D:
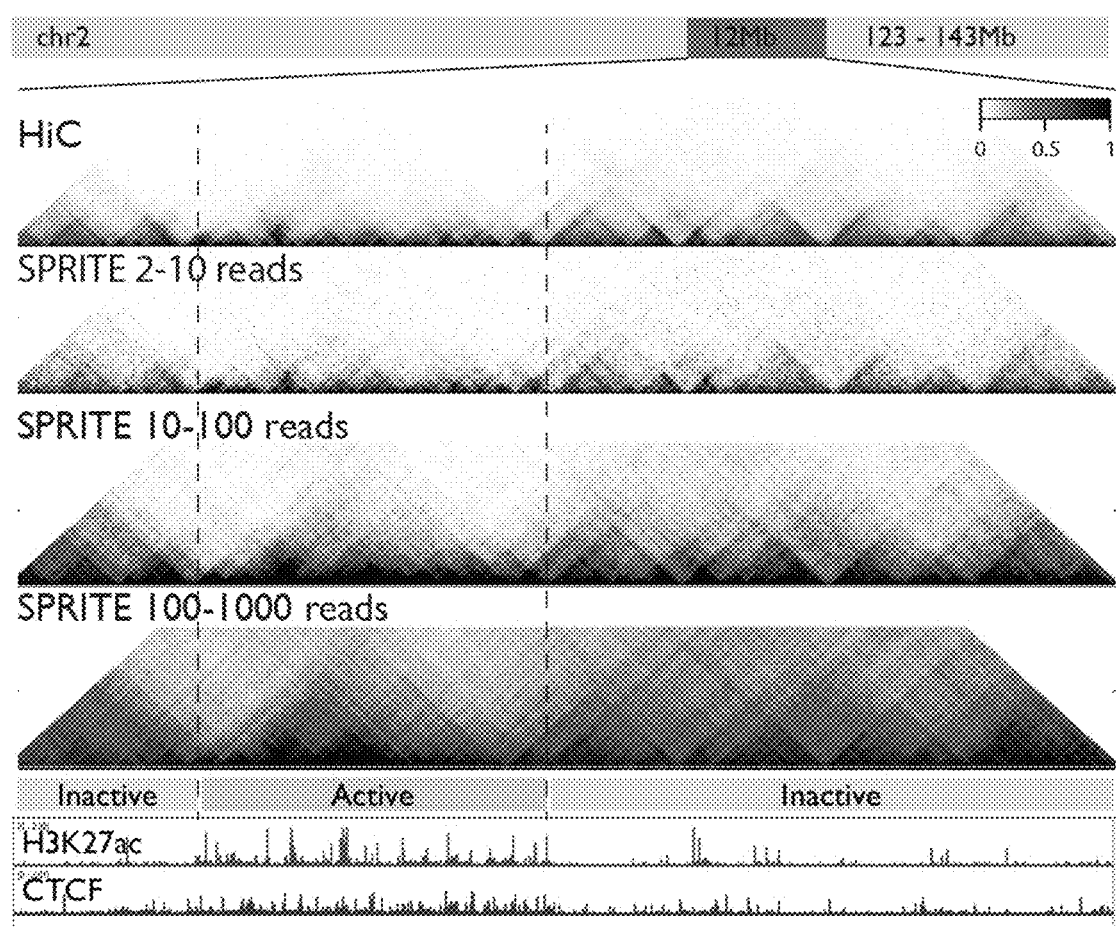
FIG. 7D is a graphical comparison of clusters containing 2-10 reads correspond to TAD structures similar to those observed using HiC, according to embodiments of the present invention, in which clusters containing 10-100 reads observe interactions between TADs of similar expression levels, where TADs within active histone marks such H3K27ac are highly interacting with each other, and TADs that are inactive and have much fewer H3K27ac marks are interacting more with each other than neighboring active regions, corresponding to interactions within active A compartments and inactive B compartments as indicated.
Figure 7E:
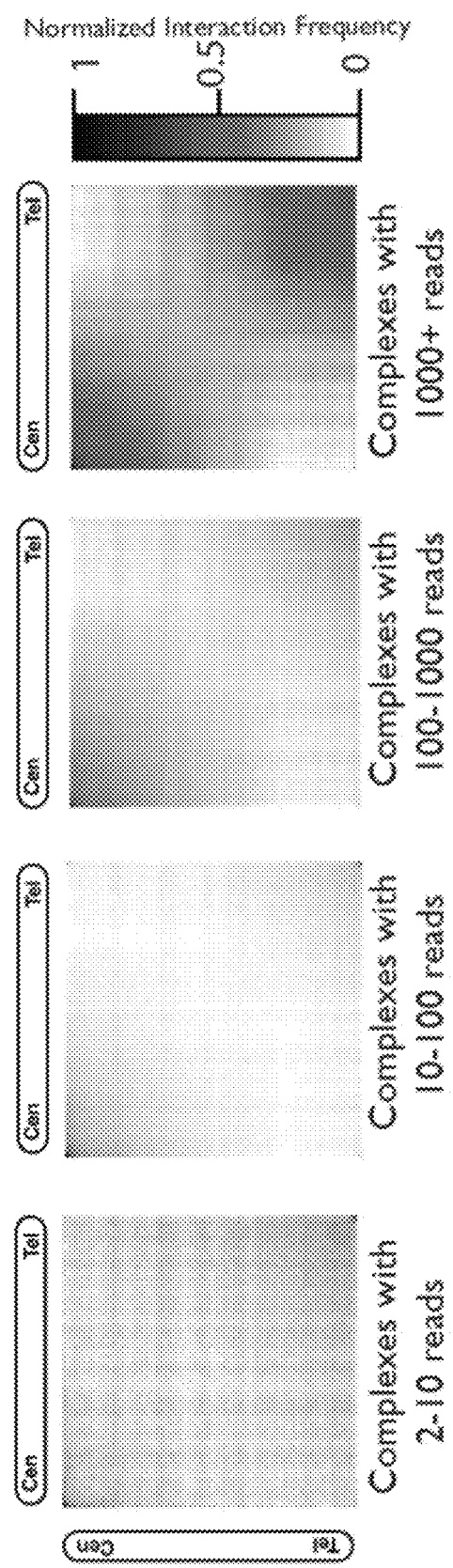
FIG. 7E is an inter-chromosomal interaction heatmap for all chromosomes, in which each chromosome was divided into 100 bins of equal size, and interactions were plotted between each chromosome, according to embodiments of the present invention, in which interactions were observed between centromeres of various chromosomes and telomeres of many chromosomes in clusters containing 100-1000 reads and 1000+ reads.

This distinction from HiC in the structures mapped using SPRITE likely reflects a difference in the molecular biology of these approaches—whereas HiC requires molecules to be close enough in some proportion of cells to touch (in order to ligate), SPRITE requires molecules to be close enough to crosslink, which corresponds more to the overall distance in the nucleus rather than frequency of contact (FIG. 7A). This is analogous to several recent discussions regarding FISH vs HiC, and as such SPRITE provides an orthogonal method that can provide additional and complementary information to that achieved by HiC alone.

Novel Higher-Order Interactions can be Mapped Using SPRITE.

Histone gene clusters exhibit higher-order intra- and inter-chromosomal interactions. Because SPRITE identifies clusters of interacting molecules and therefore provides direct information about higher-order interactions in the nucleus, it was tested whether once can observe interactions between several genes and DNA regions all crosslinked and interacting with each other. To explore whether one can observe higher-order interactions, the presence of higher-order contacts was investigated, corresponding to genes that are expected to be hubs of higher-order DNA contacts in the nucleus according to microscopy studies of nuclear bodies. These higher-order interactions at various scales were analyzed both within the same chromosome and across different chromosomes.

Figure 8A:
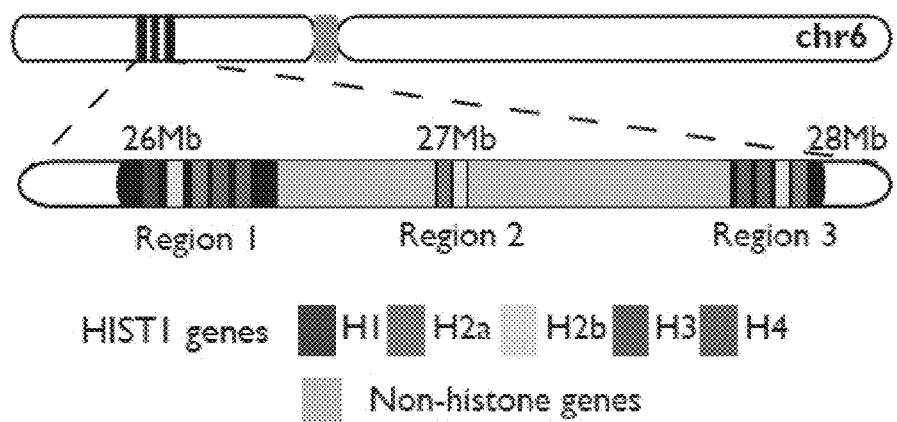
FIG. 8A is a schematic of how SPRITE method according to embodiments of the present invention may be used to observe higher-order interactions between the three histone gene clusters in human GM12878 cells, where the location of the HIST1 gene cluster in human cells is shown with 55 histone genes located within a 2 Mb region on chromosome 6, the histone gene clusters (Region 1, 2, and 3) are located in three separate histone gene clusters, and are separated by sites encoding genes other than histones.
Figure 8B:
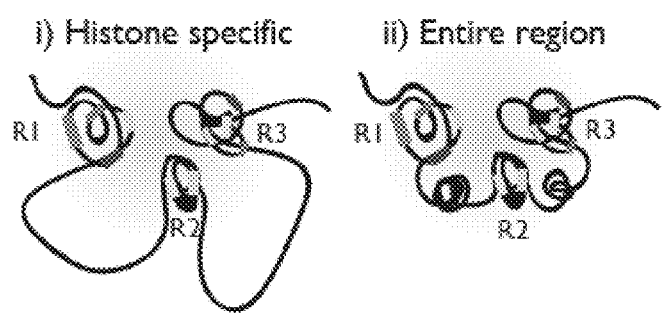
FIG. 8B is a schematic of how histone genes may be regulated either by bringing together the 3 histone gene clusters and excluding the non-histone genes, or by bringing the entire 2 Mb region into proximity.
Figure 8C:
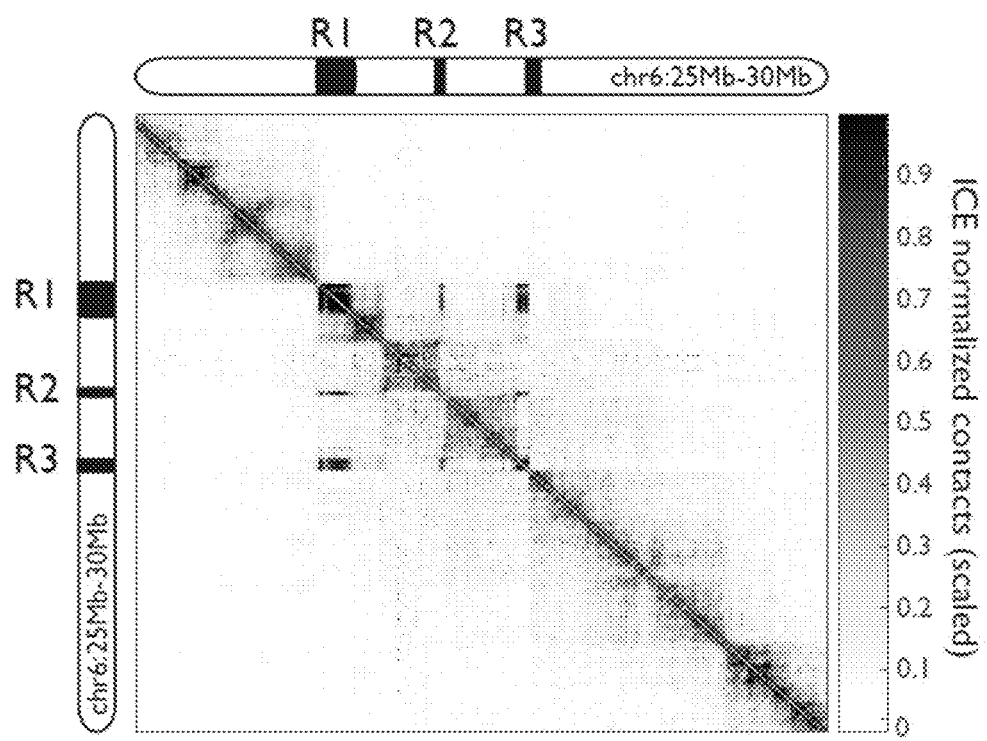
FIG. 8C is an interaction Heatmap in GM12878 lymphoblasts on chromosome 6 shows that the three histone gene regions (R1, R2, and R3) interact frequently with the other two gene clusters, according to embodiments of the present invention.
Figure 8E:
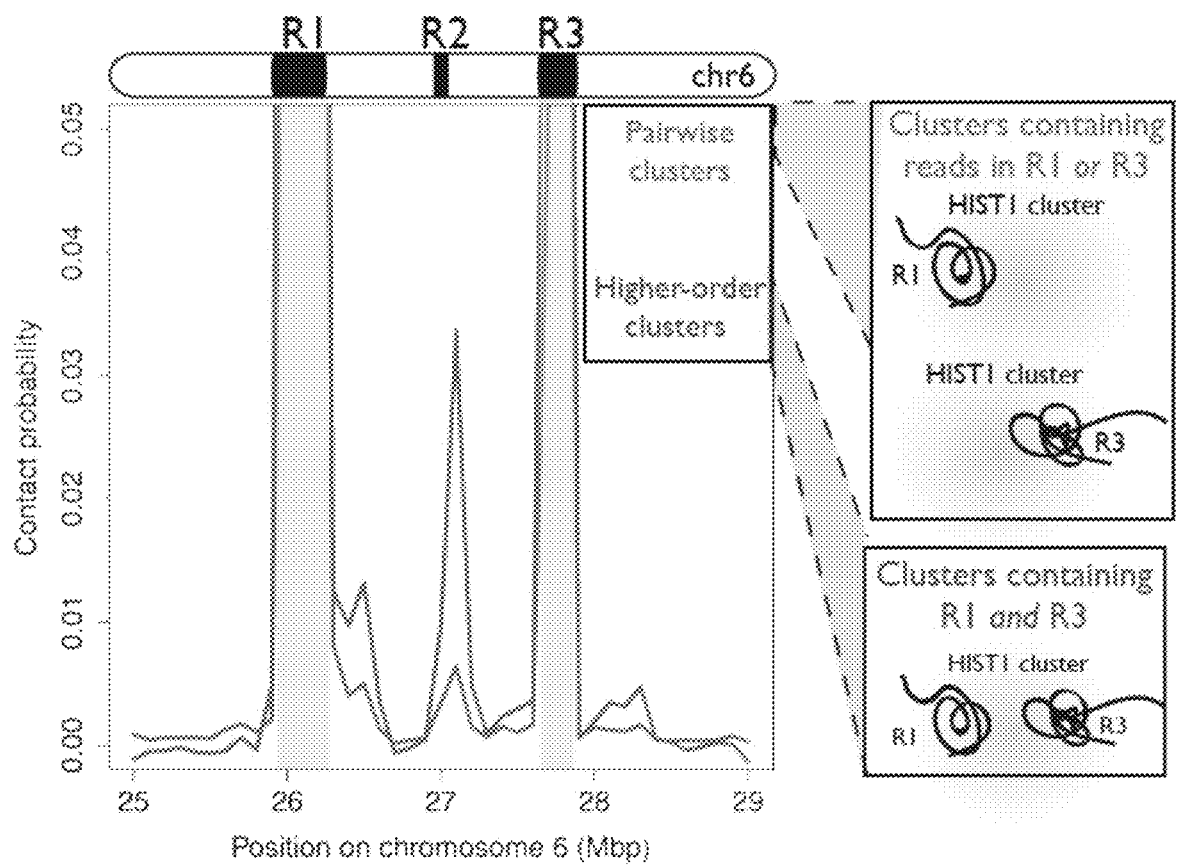
FIG. 8E is a graph showing contact probability of the three histone gene clusters interacting as a higher-order complex (shown in red) which is more than expected using a pairwise interaction method (shown in blue), where clusters containing reads in both R1 and R3 are 5-fold enriched for interactions at R2 more than was expected by pairwise interactions from clusters containing reads in R1 or R3, but not both R1 and R3 together, according to embodiments of the present invention.

One notable higher-order interaction that was observed with SPRITE occurs between histone gene clusters, known to interact with the histone locus nuclear body (also referred to as the cajal body). The histone locus body forms around replication-dependent histone genes in both mouse and human cells. These genes lack introns and a poly(A) tail, and are processed through interactions with the U7 snRNP, which is enriched at the Cajal body/histone locus bodies. Histone loci are thought to (at least transiently) localize to this nuclear body where a high concentration of processing proteins and RNAs can localize in proximity to their transcription loci. In mice and humans, 51 Hist1 and 55 histone HIST1 genes reside within a ~2 Mb region on chromosomes 13 and 6, respectively. Notably, despite being localized within a 2.1 Mb region, these Hist1 and HIST1 gene clusters contain a 1.3 Mb gap of non-histone genes between the Hist1 and HIST1 gene clusters, except for a small group of five histone genes in the middle of these two large clusters (FIG. 8A). This raises the question of whether any three-dimensional structure forms to co-regulate these linearly-separated histone gene clusters (FIG. 8B). To first determine whether Hist1 and HIST1 gene clusters interact, it was tested whether one could observe interactions between the three HIST1 clusters on the same chromosome. Notably, for human GM12878 lymphoblast cells, several (>100) individual SPRITE clusters containing reads from the three separate Histone gene clusters (FIG. 8D) were observed. Two possible modes of spatially localizing these genes into spatial proximity, if any, could occur to co-regulate these genes: either all genes spatially located between the histone genes could interact to bring these genes into spatial proximity, or the non-histone genes between the histone gene clusters could be excluded from this higher order interaction (FIG. 8B). Clear interactions were observed between the three separate histone gene clusters (FIG. 8C) in the aggregate heatmap suggesting that the three regions at least interact with each other in a pairwise manner. To determine whether these three histone gene clusters specifically interacted together in individual clusters, it was determined whether clusters containing reads from the two distal spatially segregated HIST1 gene loci were enriched for interactions with the middle HIST1 gene cluster. It was observed that clusters containing the two distal HIST1 clusters interacted with the middle HIST1 gene locus, while neighboring regions in the middle region did not contain histone genes were depleted (FIG. 8E). This indicates that higher-order interactions may be observed between cis-regulatory HIST1 gene clusters interacting together in individual complexes.

Figure 9A:
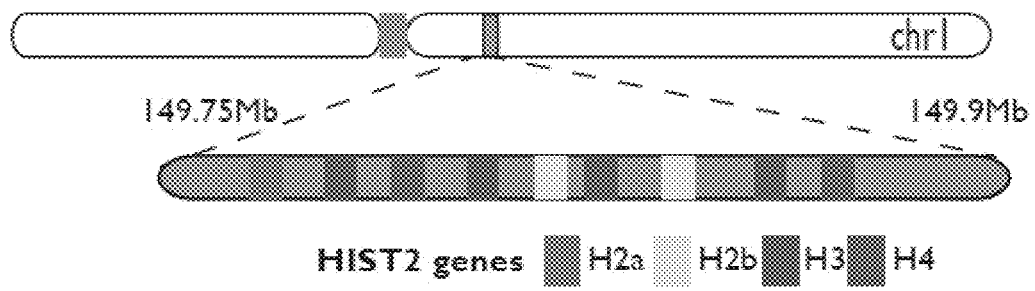
FIG. 9A is a schematic of how SPRITE method according to embodiments of the present invention may be used to observe higher-order interactions of the HIST2 gene cluster in human cells contains several histone genes in a contiguous 0.15 Mb region.
Figure 9B:
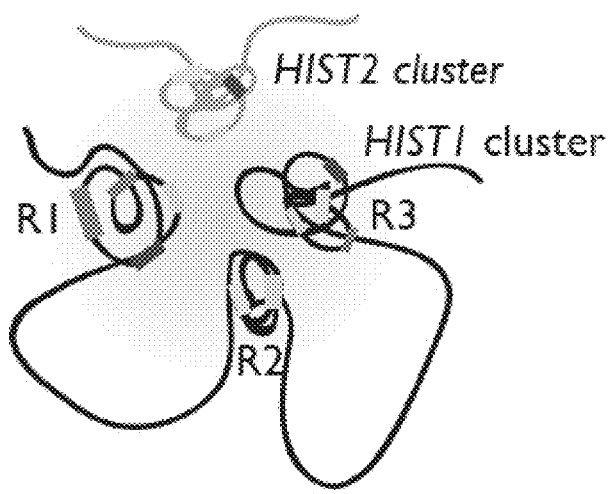
FIG. 9B. is a schematic of how histone genes are known to localize to a nuclear body called the histone locus body and from SPRITE observations demonstrate inter-chromosomal interactions between the two gene clusters, according to embodiments of the present invention.
Figure 9C:
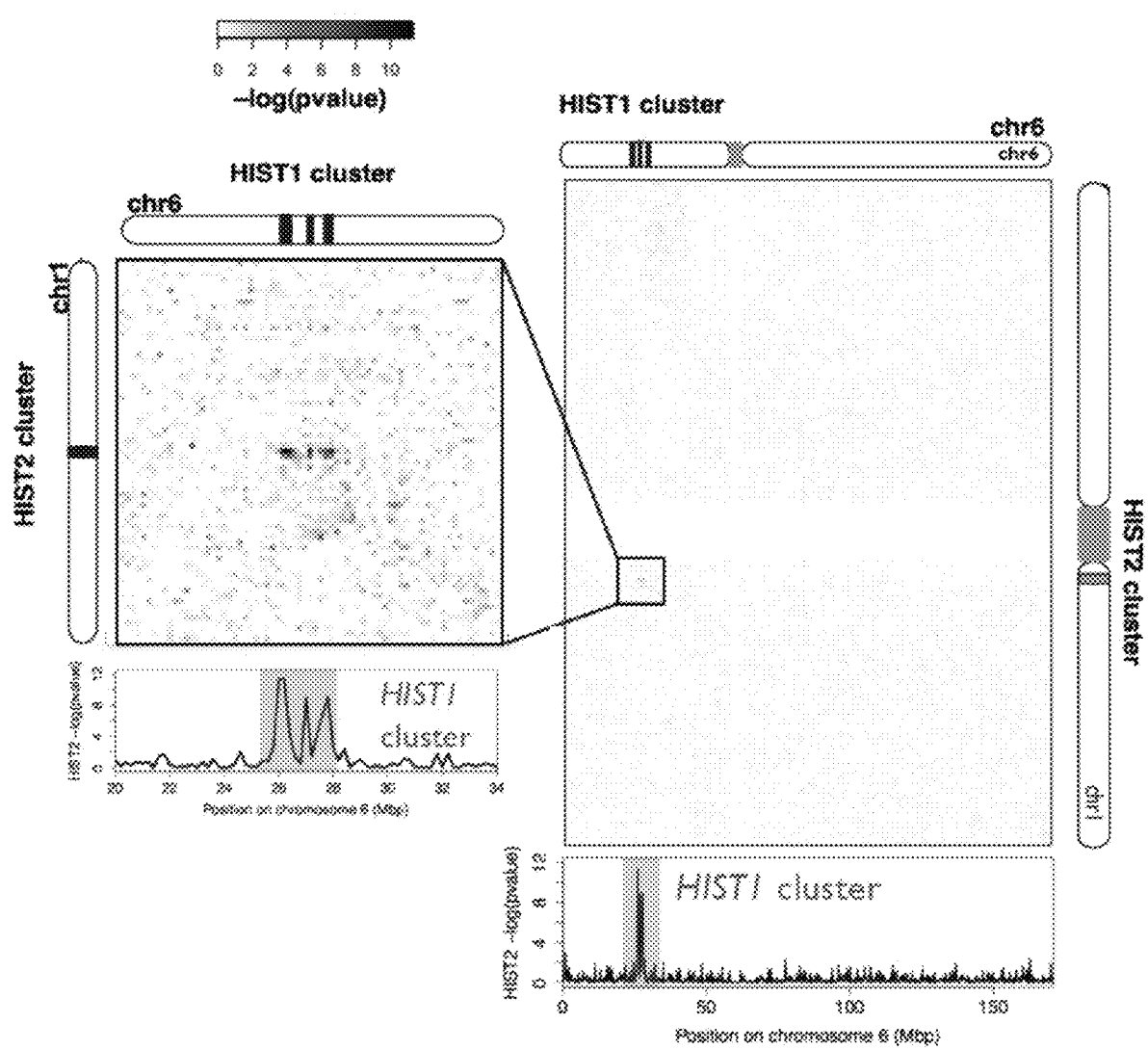
FIG. 9C is an inter-chromosomal heatmap plotting the −log(pvalue) of the HIST2 and HIST1 gene clusters interacting between the two chromosomes, according to embodiments of the present invention.

In both humans and mice, there is another locus containing core histone genes on chromosome 1 and chromosome 3 that correspond to the HIST2 and Hist2 gene clusters, respectively. In humans, the HIST2 gene cluster contains 6 histone genes in a 100-kb region with no other genes between them (FIG. 9A). It is known that both HIST2 and HIST1 genes localize to the cajal body/histone locus body. However, given that some cells contain multiple cajal bodies, it is unclear whether both the HIST1 and HIST2 can localize to the same nuclear body in individual cells. If so, we would expect to observe a higher-order inter-chromosomal interaction between the HIST2 gene cluster on chromosome 1 and three HIST1 gene clusters on chromosome 6 (FIG. 9B). Because the human HIST1 gene cluster contains the clearest 3-way interaction due to the spatial separation between the 3 histone gene clusters, the GM12878 interactions were chosen for the following analysis. All SPRITE clusters containing reads within the 200 kb bin around the HIST2 gene cluster were analyzed and plotted all inter-chromosomal interactions with these clusters on chromosome 6. A striking interaction was observed between the HIST2 gene cluster and all three HIST1 gene clusters (FIG. 9C). To determine whether these were observed as 3-way and 4-way interactions we counted how many triplets and quadruplet interactions were observed between at least 2 HIST1 clusters with the HIST2 cluster, and between all 3 HIST1 clusters and HIST2. XX and YY clusters containing 3-way and 4-way interactions at these histone clusters were observed, indicating that the histone loci on separate chromosomes come together and physically interact. This raises the possibly that these chromosomes come together and interact through the histone locus nuclear body. The histone locus body provides a sticking example of a conserved higher-order cis-regulatory gene cluster interaction on individual chromosomes as well as inter-chromosomal interaction between genes of similar function at a known nuclear body.

Centromere Clusters and the Nucleolus are Hubs for Inter-Chromosomal interactions.

Another set of higher-order interactions investigated was whether inter-chromosomal interactions could be observed at larger-scale nuclear bodies identified in the nucleus. As previously discussed, larger SPRITE clusters appear to span further genomic distances, and thus the focus was on clusters containing >1000 reads to investigate long-range interactions at large nuclear bodies. A striking feature of these higher-order maps is the frequency of inter-chromosomal interactions occurring in very large clusters that contain >1000 molecules. In analyzing these regions, we identified two interesting, well-defined, nuclear structures—interactions of pericentromeric heterochromatin regions and interactions of DNA sites at the nucleolus.

In both imaging- and HiC-based studies, pericentromeric heterochromatin has been shown to interact at a nuclear body described as centromere clusters in both mouse and human cells. Consistent with previous HiC-observations, SPRITE observes a sticking inter-chromosomal interaction between the 5'ends of several chromosomes (FIG. 7E).

Figure 10A:
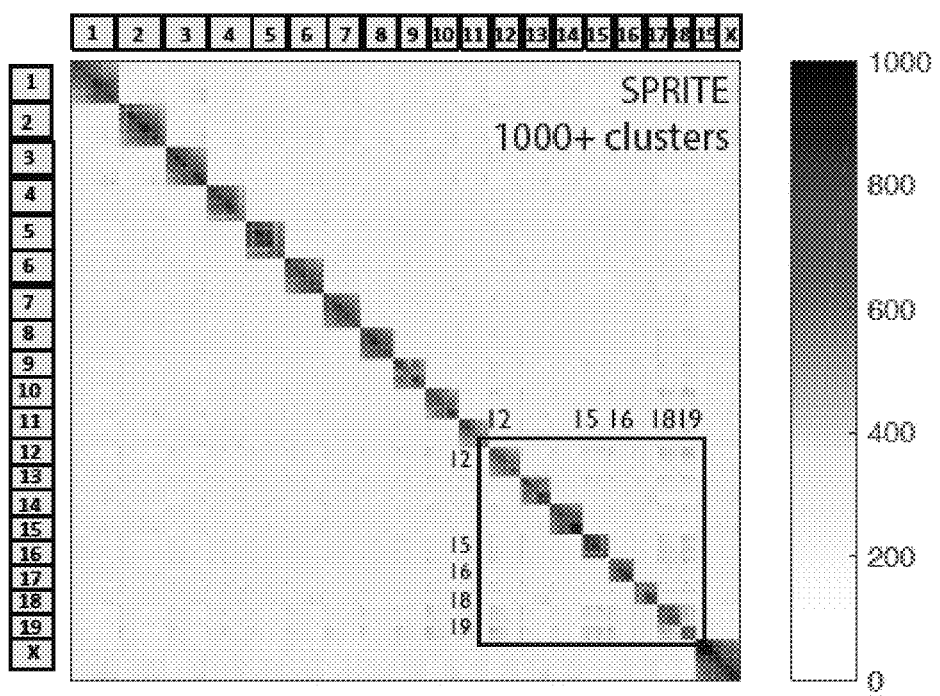
FIG. 10A is graph showing DNA interactions observed using SPRITE in mES cells in which the DNA interactions were of several different chromosomes in clusters containing greater than 1000 molecules.
Figure 10B:
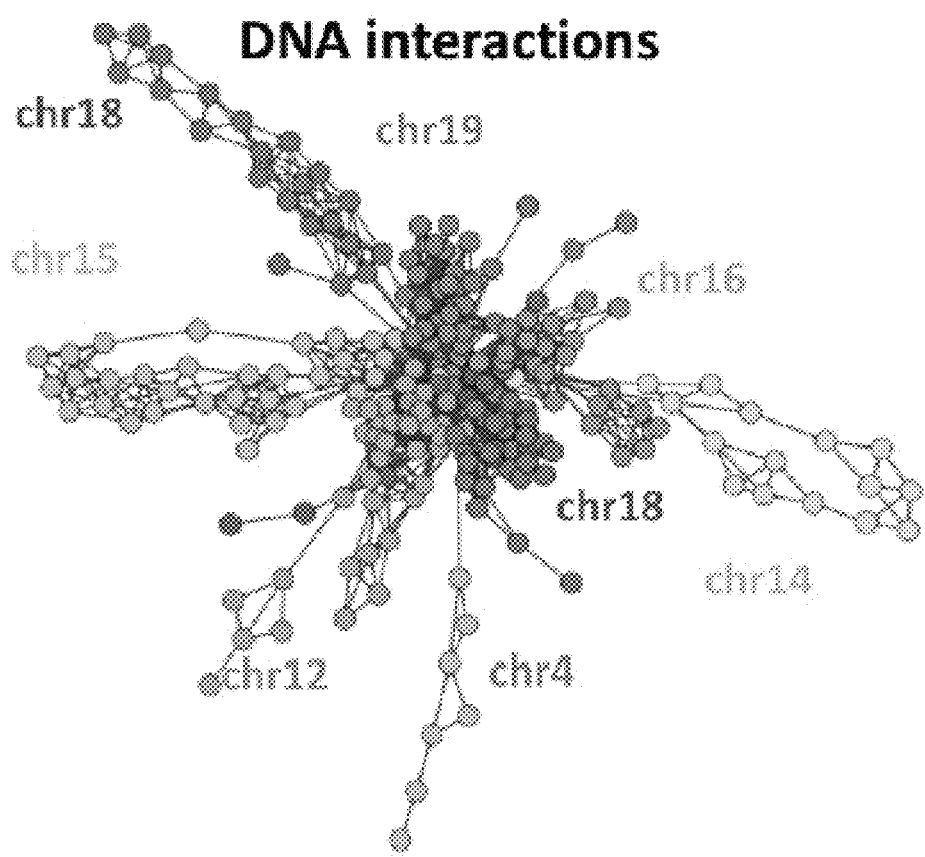
FIG. 10B is a schematic showing inter-chromosomal interactions observed using SPRITE, according to embodiments of the present invention, with the highest p-values (>1030) occur between chromosomes 12, 15, 16, 18, and 19, where a circle represents a 1 Mb bin, and each color corresponds to a different chromosome.
Figure 10C:
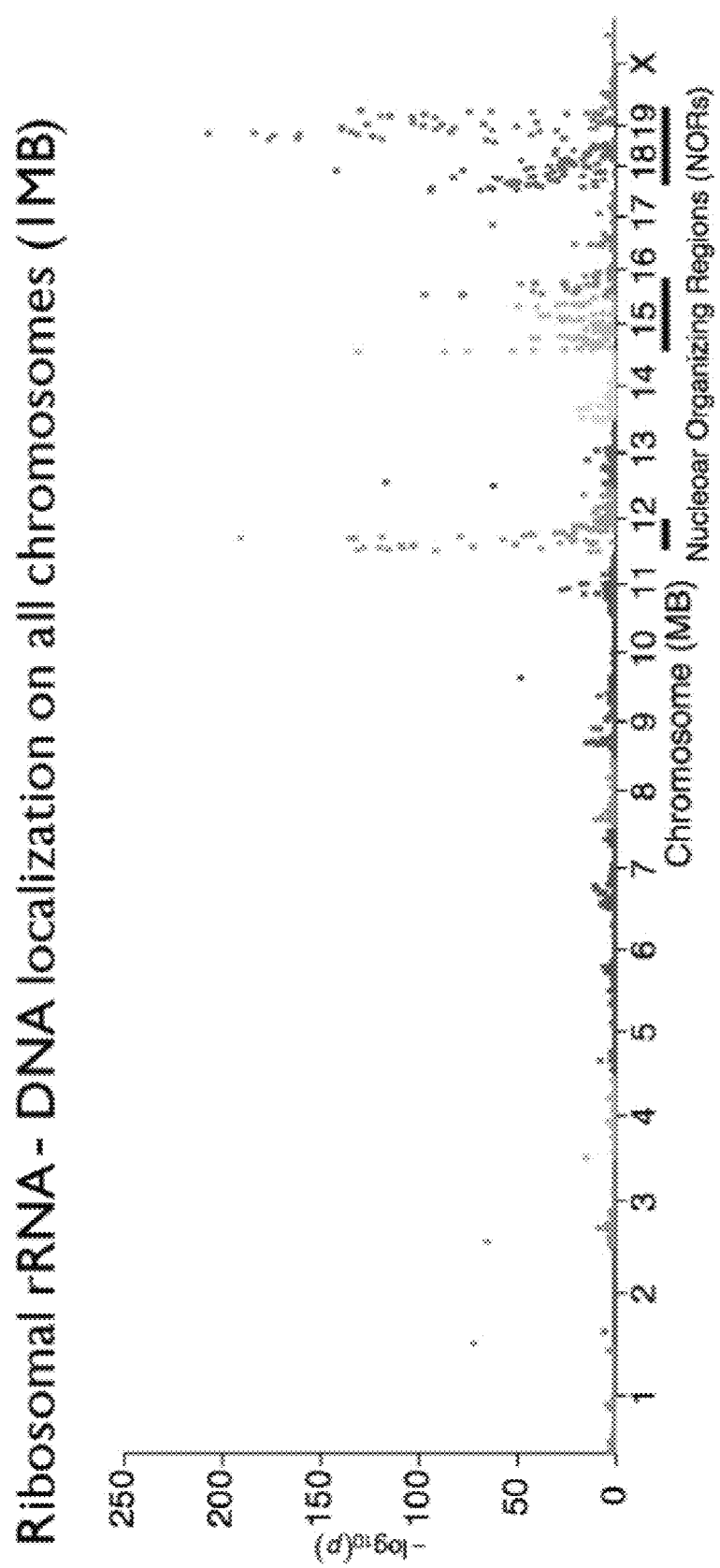
FIG. 10C is a map of RNA-DNA interactions in the nucleus derived from results obtained using SPRITE, according to embodiments of the present invention.

In addition to observing inter-chromosomal interactions at centromeric clusters, inter-chromosomal interactions at the nucleolus, another large nuclear body, were observed. In clusters containing >1000 reads, an enrichment for inter-chromosomal interactions between regions on chromosomes 12, 15, 16, 18, and 19 was observed (FIGS. 10A-10B). In mice, these chromosomes contain ribosomal DNA (rDNA) genes, and thus should localize to the nucleolus during the active transcription of rDNA. It was observed that these inter-chromosomal interactions extended tens of megabases beyond the rDNA transcriptional regions, previously defined as nucleolar organizing regions (FIG. 10C). As such, these large inter-chromosomal clusters between chromosomes 12, 15, 16, 18, and 19 may indeed correspond to long-range interactions the nucleolus, one of the largest nuclear bodies (~1 um in size). To test whether this is indeed the nucleolus, RNA-DNA maps were used to look at the localization of ribosomal RNAs on chromatin. It was found that ribosomal RNA specifically associates with these regions on chromosomes 12, 15, 16, 18, and 19 DNA—including the DNA identified in these clusters that were not previously defined as NORs (FIG. 10C). These results identifying rRNA-DNA interactions at NOR-containing chromosomes suggest that these large clusters on chromosomes 12, 15, 16, 18, and 19 correspond to DNA organized around the nucleolus.

Figure 10D:
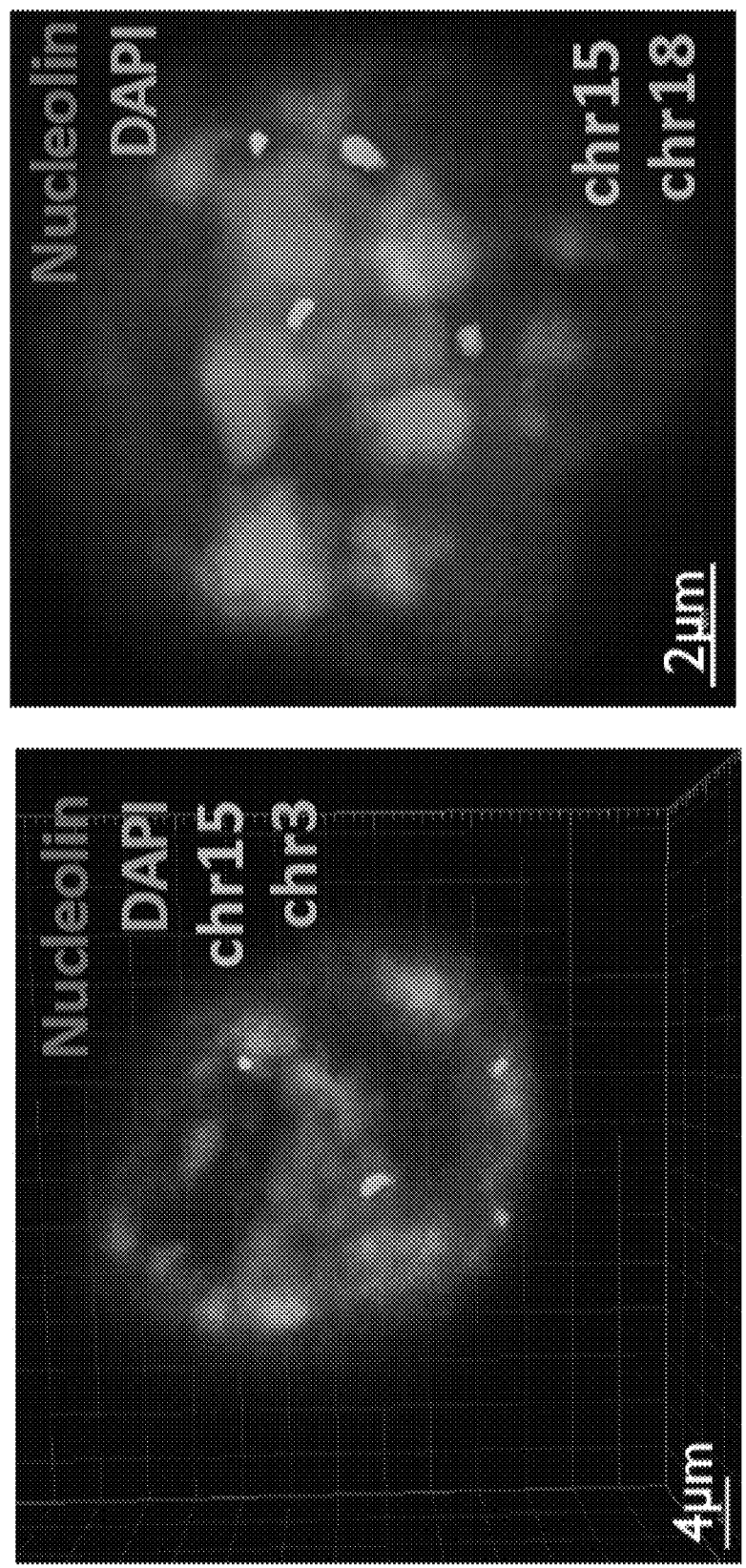
FIG. 10D shows DNA-Fluorescence in situ-hybridization (FISH) images for 2 Mb regions on chromosomes 3, 15, and 18 and immunofluorescence for nucleolin (shown in red) performed to measure the distance of each chromosome at the nucleolus, with Chromosome 3 as a negative control.
Figure 10E:
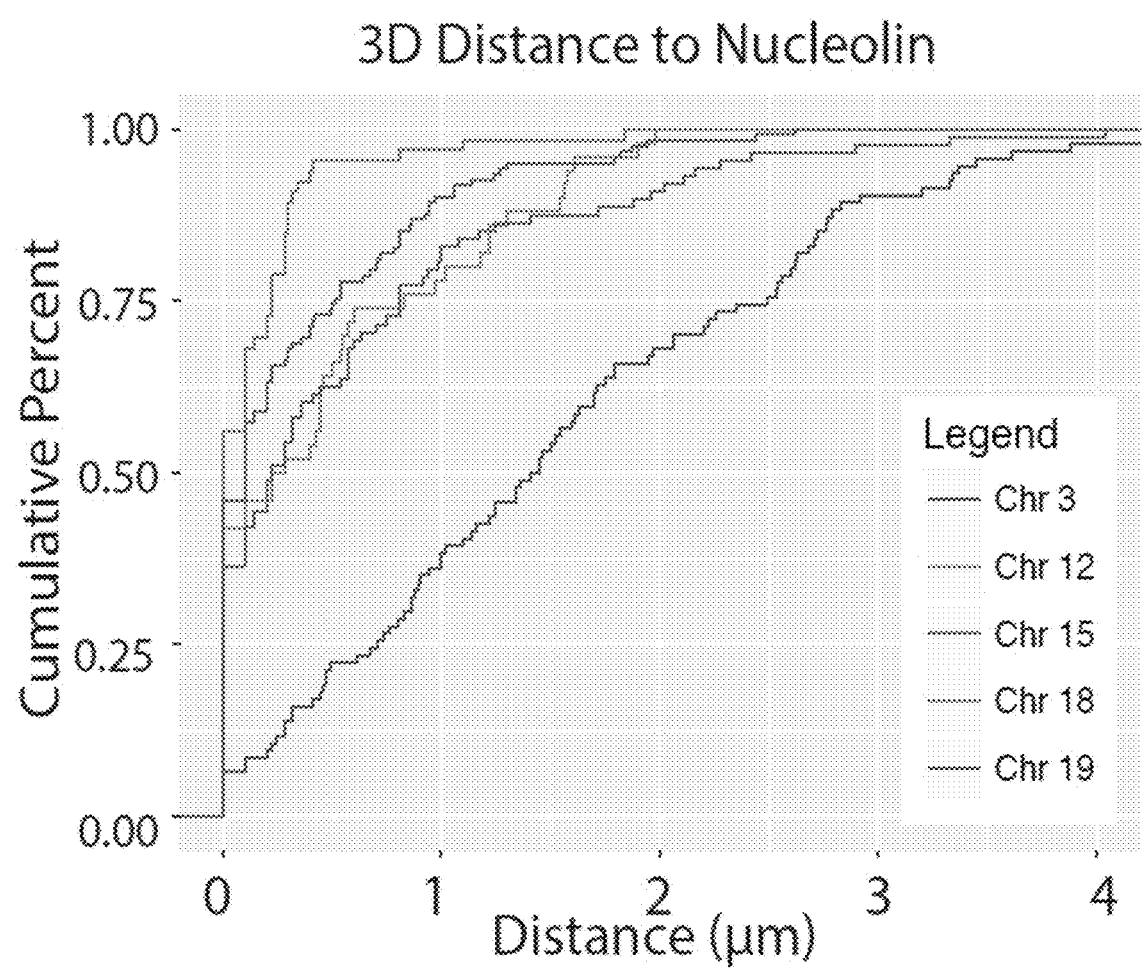
FIG. 10E is a graph showing the three-dimensional (3D) distance to the nucleolin from each indicated chromosome, according to embodiments of the present invention.

To further confirm that these rRNA-associated regions of DNA are indeed arranged around the nucleolus, immuno-fluorescence coupled with DNA FISH was used to calculate the 3D distance of each DNA regions relative to the nucleolus. Specifically, two sets of DNA regions: (i) DNA regions contained within these large inter-chromosomal clusters and enriched for rRNA-association (i.e. "nucleolar regions") and (ii) a control region on chromosome 3 not enriched in these clusters and not thought to contain NORs ("control region"). Two DNA regions were imaged together with the nucleophosmin protein, a well-defined nucleolar marker (FIG. 10D). It was found that the distance between the DNA in the nucleolar regions and the nucleolus was either directly interacting or physically in proximity to the nuclear body, with >90% of cells containing interactions within XX um distance (FIG. 10E). In contrast, the control regions had <YY % of cells containing an interaction within the same distance.

Figure 10F:
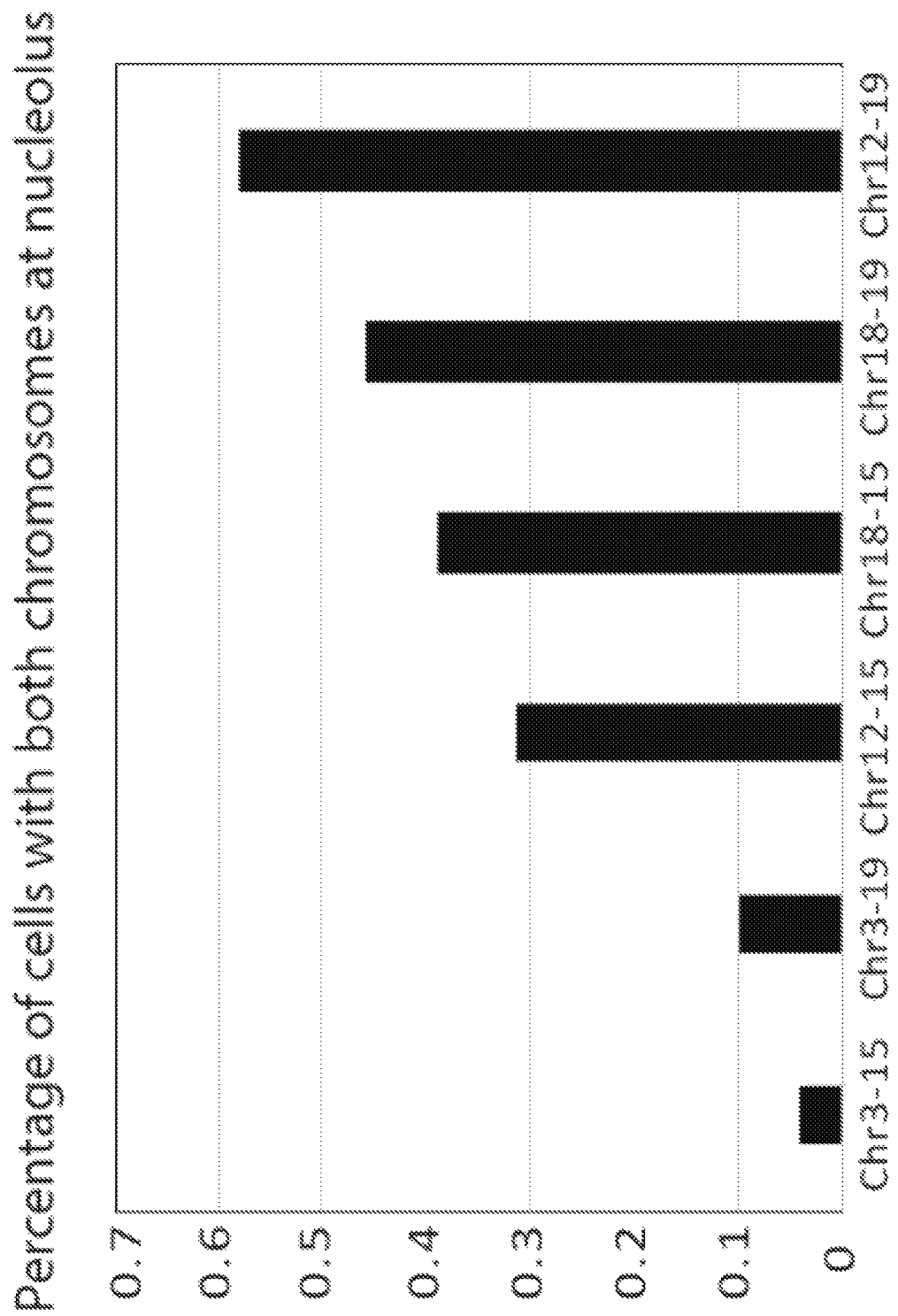
FIG. 10F is a graph quantifying the percentage of cells where both chromosomes localize to the same nucleolus (distance μm), according to embodiments of the present invention, showing that the nucleolar associated chromosomes 12, 15, 16, 18 and 19 are more frequently co-interacting at the same nucleolus than a negative control between chromosomes 3 and 15 or 19.

Inter-chromosomal interactions between chromosomes 12, 15, 16, 18, and 19 may occur through their shared interaction at the nucleolus. Thus, the distance between specific rRNA-enriched 1-2 Mb regions on chromosomes 12, 15, 16, 18, and 19 was measured using DNA FISH. As a negative control, the distance between these rRNA-associated regions was measured to the 1 Mb region on chr3. In 31-58% of the cells, the NOR chromosomes were both within 0 um from the same nucleolus, compared to 4-10% of the cells being the same distance away for the negative control regions (FIG. 10F). Because several NOR-bearing chromosomes are in spatial proximity around a large nuclear body, they would therefore result in a large, crosslinked complex of thousands of interacting molecules. These interactions are not observed in HiC, and this may be due to limitations in the distance of proximity ligation to capture interactions at a nuclear body across long distances in a crosslinked complex.

Materials and Methods

Mouse ES Cell Culture and Xist Induction.

All mouse ES cell lines were cultured in serum-free 2i/LIF medium as previously described in J. M. Engreitz et al., The Xist lncRNA exploits three-dimensional genome architecture to spread across the X chromosome. *Science* (80-89). 341, 1237973 (2013); C. A. McHugh et al., The Xist lncRNA interacts directly with SHARP to silence transcription through HDAC3. *Nature*. 521, 232-236 (2015); and C. Chen et al., Xist recruits the X chromosome to the nuclear lamina to enable chromosome-wide silencing. *Science*. 354, 468-472 (2016), the entire contents of all of which are herein incorporated by reference.

Female ES cells (F1 2-1 line, generously provided by K. Plath) are an F1 hybrid wild-type mouse ES cell line derived from a 129×CAST (castaneous) cross. Maintenance of 2× chromosomes in this line was monitored by X chromosome paint imaging, restriction length polymorphism analysis, as well as Sanger sequencing of SNPs on the X chromosome. The pSM33 ES cell line (kindly provided by K. Plath) is a male ES cell line, derived from the V6.5 ES cell line, expressing the lncRNA Xist from the endogenous locus under the transcriptional control of a tet-inducible promoter and the Tet transactivator (M2rtTA) from the Rosa26 locus. To induce Xist, doxycycline (Sigma, D9891) was added to cultures at a final concentration of 2 ug/ml for 6-24 hrs.

Human Lymphoblast Cell Culture.

GM12878 cells (Coriell Cell Repositories), a human lymphoblastoid cell line, was cultured in RPMI 1640 (Gibco, Life Technologies), 2 mM L-glutamine, 15% fetal bovine serum, and 1× penicillin-streptomycin and maintained at 37° C. under 5% CO2. Cells were seeded every 3-4 days at 200,000 cells/ml in T25 flasks and passaged or harvested before reaching 1,000,000 cells/ml.

Sample Preparation.

Crosslink cells to fix in vivo RNA-DNA-Protein complexes with disuccinimidyl glutarate (DSG) and formaldehyde crosslinkers. Lyse cells and fragment DNA and RNA to appropriate sizes via sonication and DNase.

"Optimization of lysis conditions (amount of sonication, amount/timing of DNase) is a critical step in establishing the protocol for the first time. The length of sonication might vary from 1-10 minutes and DNase treatment might vary from 10 to 20 minutes, depending on cell number, ploidy, crosslinking strength, and the desired [DNA] fragment size. To optimize DNase timing and conditions, remove 5 μL lysate aliquots every 2-4 minutes, quench with EDTA and EGTA on ice, and assay DNA sizes for each time point as described in the protocol. If an appropriate combination of solubilization and DNA fragment sizes cannot be obtained by varying the amount of sonication or DNase, then reducing the strength of the crosslinking may be necessary." (1) REF HERE.

DSG Crosslinking Solution
1×PBS
2 mM DSG in DMSO
Scraping Buffer
1×PBS pH 7.5
0.5% BSA
Store at 4° C.
Cell Lysis Buffer A
50 mM Hepes pH 7.4
1 mM EDTA
1 mM EGTA
140 mM NaCl
0.25% Triton-X
0.5% NP-40
10% Glycerol
Cell Lysis Buffer B
10 mM Tris pH 8
1.5 mM EDTA
1.5 mM EGTA
200 mM NaCl
10× Annealing Buffer
100 mM Tris-HCl pH 7.5
2M LiCl
2 mM EDgTA
Cell Lysis Buffer C
10 mM Tris pH 8
1.5 mM EDTA
1.5 mM EGTA
100 mM NaCl
0.1% DOC
0.5% NLS
10× DNase Buffer
200 mM Hepes pH 7.4
1M NaCl
0.5% NP-40
5 mM CaCl2
25 mM MnCl2
25× DNase Stop Solution
250 mM EDTA
125 mM EGTA
MyRNK Buffer
20 mM Tris pH 7.5
100 mM NaCl
10 mM EDTA
10 mM EGTA
0.5% Triton-X
0.2% SDS
Coupling Buffer
1×PBS
0.1% SDS
RLT++ Buffer
1× Buffer RLT supplied by Qiagen
10 mM Tris pH 7.5

1 mM EDTA
1 mM EGTA
0.2% NLS
0.1% Triton-X
0.1% NP-40
M2 Wash Buffer
20 mM Tris pH 7.5
50 mM NaCl
0.2% Triton-X
0.2% NP-40
0.2% DOC
PBLSD+ Wash Buffer
1×PBS
5 mM EDTA
5 mM EGTA
5 mM DTT (add fresh)
0.2% Triton-X
0.2% NP-40
0.2% DOC Formaldehyde-DSG Crosslinking.

Grow adherent cells on 15-cm plates.

Before crosslinking, count one plate. This protocol details crosslinking multiple plates of cells in one suspension, but it is important to maintain consistency in lysate batches. Typically cells are stored in 10M pellets. Lift cells from plate and wash: Remove media from plates. Add 5 mL TVP to each 15 cm plate and rock gently for 3-4 minutes. Afterwards, add 25 mL wash solution to each plate. Vigorously suspend cells in the wash solution and transfer from plate to a 50 mL conical tube. Rinse the plate with extra wash solution and add to the 50 mL conical. Pellet in a centrifuge for 3 minutes at 3300×G at room temperature. Wash cells by resuspending in 4 mL room temperature 1×PBS per 10M cells and transfer to a 15 mL conical, and pellet again. Resuspend cells in DSG Crosslinking Solution, 4 mL per 10M cells. Rock gently at room temperature for 45 minutes. Pellet cells for 4 minutes at 1000×G at room temperature, and discard supernatant. Wash cells with 4 mL 1×PBS per 10M cells. Pellet as before, discarding supernatant. Resuspend cell pellet in 3% formaldehyde in PBS. Rock gently at room temperature for 10 minutes. Add 200 uL of 2.5M glycine stop solution per 1 mL of cell suspension. Rock gently at room temperature for 5 minutes. Pellet cells at 4 C for 4 minutes at 1000×G at room temperature. Discard formaldehyde supernatant in an appropriate waste container. From here, keep cells at 4 C. Resuspend cell pellet in cold Scraping Buffer and gently rock for 1-2 minutes. Pellet cells at 4 C for 4 minutes at 1000×g. Discard supernatant in formaldehyde waste container. Resuspend cell pellet in cold Scraping Buffer again and gently rock for 1-2 minutes. Pellet as before and discard supernatant. Resuspend pellet in 1 mL of Scraping Buffer per 10M cells. Aliquot 10M cells each into Microcentrifuge tubes and pellet at 4 C for 5 minutes at 2000×g. Remove supernatant. Flash freeze in liquid nitrogen and store pellet at −80 C.

Cell Lysis.

Chill Lysis Buffers A, B, and C on ice. Thaw 10M cell pellets on ice. Add 1.4 mL of Lysis Buffer A supplemented with 1× Proteinase Cocktail Inhibitor (PIC) to each 10M cell pellet and resuspend. Incubate mixtures on ice for 10 minutes.

Pellet cells at 4 C for 9 minutes at 850×g. Discard the supernatant, taking care not to disturb the pellet. Add 1.4 mL of Lysis Buffer B supplemented with 1×PIC to each 10M cell pellet and resuspend. Incubate mixtures on ice for 10 minutes. Pellet cells at 4 C for 9 minutes at 850×g. Discard the supernatant, taking care not to disturb the pellet. Add 550 uL of Lysis Buffer C supplemented with 1×PIC to each 10M nuclei pellet and resuspend. Incubate mixture on ice for 8 minutes. Sonicate each sample at 5 watts for 1 minute: 1 pulse for 0.7 seconds ON, 3.3 seconds OFF. During and after sonication, keep lysate at 4 C. Pool all lysates together and split again into 10M aliquots. This ensures that all samples in each tube are equally lysed. Flash freeze lysate and store at −80 C.

DNA Fragmentation.

Thaw one tube of lysate on ice. To determine the optimal amount of DNase to use for DNA fragmentation, test varying DNase concentrations on 10 uL aliquots of lysate.

| Stock Solution | Volume |
|---|---|
| 10X DNase Buffer | 2 uL |
| Lysate | 10 uL |
| Turbo DNase from ThermoFisher | 2/3/4/5/6 uL |
| H20 | 6/5/4/3/2 uL |
| Total | 20 uL |

Incubate at 37 C for 20 minutes. Add 1 uL of 25× DNase Stop Solution to each sample to terminate the reaction. Reverse the crosslinks in each sample.

| Stock Solution | Volume |
|---|---|
| Lysate | 21 uL |
| MyRNK Buffer | 71 uL |
| Proteinase K | 8 uL |
| Total | 100 uL |

Incubate for at 65 C for three hours at the minimum, optimally overnight. Follow the protocol provided in the DNA Clean and Concentrator-5 Kit, binding in 6 volumes of DNA Binding Buffer. Elute in 10 uL of H20. Run each DNase sample on a gel with a 100 bp DNA ladder. An ideal fragmentation sample will have most DNA around 200 bp. Size should not greatly exceed 1 kb. If none of these concentrations of TURBO DNase result in ideal fragmentation, adjust concentrations and repeat the DNasing until optimal conditions are found. DNase the batch of crosslinked lysate at the identified optimal DNAase concentration.

| Stock Solution | Volume |
|---|---|
| 10X DNase Buffer | 110 uL |
| Lysate | 550 uL |
| Turbo DNase from ThermoFisher | X uL |
| H20 | X uL to reach final volume |
| Total | 1100 uL |

Incubate at 37 C for 20 minutes. Add 44 uL of 25× DNase Stop Solution to each sample to terminate the reaction. Flash freeze DNase lysate and store at −80 C.

Library Preparation.

Lysate is coupled to Pierce NHS-Activated Magnetic Beads to allow for easy DNA library preparation. DNA overhangs caused by fragmentation are repaired and blunted by a combination of T4 Polynucleoide Kinase, which adds phosphate onto 5' ends, and T4 DNA Polymerase, which has 5' to 3' polymerase activity as well as 3' to 5' exonuclease activity. Klenow fragment (-exo) is used to add adenine to 3' ends of each DNA molecule. This aids in ligation of the DPM adaptor, which has a 3' thymine overhang, without creating spurious ligation products.

It is helpful to have an optimal bead to molecule ratio for the library preparation and SPRITE processes. Ideally, binding at a 3:4 ratio of DNA molecules to beads is desired; and in general for these examples, around 50 billion molecules bound to 75 billion beads. Assuming 50% binding efficiency and further DNA loss during library clean ups, there remains a few billion molecules for sequencing. To determine the microliter amount of lysate to couple the lysate molarity was calculated by running a 5% aliquot on the Qubit Fluorometer to determine concentration and the Agilent Bioanalyzer to determine average size.

NHS Coupling.

All wash steps at 4 C are performed in a cold room. All wash steps above room temperature are performed on an Eppendorf Thermomixer. If a temperature is not specified, it is at room temperature. To wash beads, place the tube containing the beads on a magnetic rack to capture the beads. Wait until the solution is clear and all beads are captured before removing the liquid. Add the wash solution to the beads and remove the tube from the magnet. Gently pipette with a low-bind tip to mix thoroughly until all beads are in suspension. If using an Eppendorf Thermomixer, set the thermomixer to shake at 1200 RPM. Then place the tube back on the magnet to capture the beads again. Wait until the solution is clear and all beads are captured before removing the wash liquid.

The protocol may be stopped at any point of the process. To ensure the integrity of the DNA, resuspend the beads in 1 mL RLT++ and store at 4 C until you wish to resume. Wash three times with M2 Buffer to remove all RLT before proceeding with the protocol.

All steps involving bead pipetting should use low-bind pipette tips. Gently invert the bottle containing the NHS beads in DMAc until there is a uniform suspension. Being careful not to introduce water into the bottle, transfer 2 mL of NHS beads into a clean 1.7 mL tube. Place the tube on a magnetic rack to capture the beads. Remove the DMAc and wash beads with 1 mL ice-cold 1 mM HCl. Wash beads with 1 mL ice-cold 1×PBS. Add 1 mL Coupling Buffer to the beads. Before mixing, add the appropriate amount of lysate to the coupling buffer. Incubate the lysate and beads overnight at 4 C on a mixer. Place beads on a magnet and remove a 500 uL flowthrough aliquot to another tube. This aliquot can be analyzed to determine how much lysate was coupled.

Add 500 uL 1M Tris pH 7.5 to the beads and incubate on a mixer at 4 C for at least 45 minutes. This ensures that all beads will be quenched with protein, either from lysate or tris, and will not bind enzymes in the following steps. Wash beads four times in cold RLT++ Buffer at 4 C for 3-5 minutes each time. Wash beads twice in PBLSD+ Wash Buffer at 50 C for 4-5 minutes each time. Wash beads once at room temperature in PBLSD+ buffer. Wash beads three times with M2 Buffer. Spin the beads down quickly in a microcentrifuge and place back on the magnet to remove any remaining liquid.

FastAP to Repair Ends of RNA for Ligation of the RPM Adaptor.

1. Set up the following reaction

| Solution | Volume |
| --- | --- |
| 10x Fast A P Buffer | 20 ul |
| RNAse Inhibitor | 4 ul |
| FastAP Enzyme | 20 ul |
| H20 | 156 ul |
| Total | 200 ul |

2. Incubate on a thermomixer at 37 C for 30 min at 1200 rpm
3. Wash beads once in RLT++ to inactivate FastAP
4. Wash beads twice in M2 buffer Phosphorylation of RNA to Add a 5'Phosphate to RNA.

1. Set up the following reaction and add to beads

| Solution | Volume |
| --- | --- |
| H20 | 163.5 ul |
| 10x PNK Buffer | 20 ul |
| T4 PNK | 10 ul |
| RNase Inhibitor | 5 ul |
| TOTAL | 197.5 ul |

2. Incubate for 10 minutes at 37 C at 1200 rpm
3. Add 2.5 ul of 100 mM ATP after 10 minutes of incubation
4. Incubate 20 more minutes (for a total of 30 minutes) at 37 C at 1200 rpm
5. Rinse beads twice in M2 buffer End Repair of DNA to Blunt-End and Phosphorylate DNA.

1. Set up the following reaction and add to beads

| 10x End Repair Buffer | 30 ul |
| --- | --- |
| H20 | 215 ul |
| RNase Inhibitor | 10 ul |
| End Repair Enzyme | 25 ul |
| Total | 300 ul |

2. Incubate for 1 hr at 20 C, 1200 rpm
3. Rinse once in RLT++ buffer
4. Rinse twice in M2 buffer dA-tailing of DNA.

1. Set up the following reaction and add to beads

| 10x dA-tail Buffer | 30 ul |
| --- | --- |
| H20 | 256 ul |
| RNase Inhibitor | 6 ul |
| Klenow Fragment (exo-) | 12 ul |
| Total | 300 ul |

2. Incubate 1 hr, 37 C min, 1200 rpm
3. Rinse once in RLT++
4. Rinse twice in M2 Buffer DPM Adaptor Ligation.

There are 96 adaptors that are designed to ligate onto the DNA molecules. These DPM adaptors are kept in a 96-well stock plate at 45 uM. The ligation reaction between the adaptors and the DNA occurs in a 96-well plate. The following steps that detail set up are designed for optimum efficiency during the process.

All ligation steps include M2 buffer, which contains detergents, to prevent beads from aggregation of multiple beads, from sticking to the plastic tips and tubes, and for even distribution of the beads across a 96-well plate. We have verified that these detergents do not significantly inhibit ligation efficiency.

In the RNA and DNA tagging protocol, a non-phosphorylated version of the bottom strand of the DPM adaptor (with a sticky end for "Odd" and "Even" tagging) was ligated to prevent chimeras of DPM and RPM adaptors ligating each other in subsequent steps. DPM and RPM are subsequently phosphorylated in a later step after ligating both adaptors to add a 5'phosphate to the bottom strands of each adaptor.

Reaction conditions for DPM adaptor ligation:

| Solution | Volume |
| --- | --- |
| 2x Instant Sticky MM | 250 ul |
| DPM Pool Plate 6 (no 5'phosphate on DPM bottom) (45 uM) | 11 ul |
| H20 | 104 ul |
| M2 Buffer | 125 uL |
| RNAse Inhibitor | 10 ul |
| | 500 ul |

Make a mixture of 104 ul of H20, 125 ul of M2 buffer, and 10 ul of RNAse Inhibitor. Add mix of H20, M2 Buffer, and RNAse Inhibitor to the beads, and mix well to get beads into solution. Add 11 ul of 45 uM DPM adaptors to the beads and mix well. Add 250 ul of 2× Instant Sticky Mastermix and mix well. Incubate for 30 minutes at 20 C at 1200 rpm. Wash beads once with RLT++. Wash beads four times with PBLSD+ at 45 C for 3 minutes each wash. Wash beads twice in M2 buffer.

Ligation of Adaptor to the 5'End of the RNA Molecules.

An RNA adaptor called 5'ligtag is ligated to the 5'end of all RNA molecules to attach a priming site to RNA for the library amplification after tagging. The 5'ligtag sequence is rGrCrGrArGrGrGrArGrTrCrArGrGrCrArArG (SEQ ID NO: 1) where r indicates a ribose base.

Add 99 ul of H20 to NHS beads. Add 4 ul of 100% DMSO to beads and mix well. Add 4 ul of 5'ligTag adaptor (200 uM) to beads and mix well. Heat NHS beads in the DMSO, water, and 5'ligTag adaptor mix at 65 C for 2 minutes to melt secondary structure of RNA and to make 3'ends accessible for ligation. Immediately put on ice for 2 minutes to prevent secondary structure from re-annealing. Add the following components to NHS beads in the following order from first to last: i) PEG, ii) 100% DMSO, iii) Ligation Buffer, iv) ATP, v) and RNAse inhibitor. The entree ligation mix to beads and mix well. Then, add T4 RNA ligase 1 (high concentration) and mix again to get all of the ligation mixture into solution.

| Solution | Volume |
| --- | --- |
| 100% DMSO | 16 ul |
| 10x RNA Ligation Buffer | 20 ul |
| ATP (100 mM) | 2 ul |
| 50% PEG 8000 | 40 ul |
| Rnase Inhibitor | 3 ul |
| Add mastermix to beads at this step. | |
| T4 RNA ligase 1 (High Conc.) | 12 ul |
| Mixed with 99 ul H20 + 4 ul DMSO + 4 ul Adaptor total | 200 ul |

Put in small vortexer at 2000 rpm for 10 seconds to get into all ligation mix and beads into solution. Incubate ligation for 1 hr at 20 C, 1200 rpm. Wash beads once in RLT++ buffer. Wash beads four times for 3 min in PBLSD+ buffer at 45 C. Rinse beads twice in M2 buffer Ligation of RPM Adaptor to the 3'End of the RNA Molecules.

A double-stranded adaptor called RPM is ligated to the 3'end of all RNA molecules to add the RNA tag for SPRITE tagging of adaptors. The RPM adaptor is partially RNA for efficient RNA ligation of RPM to RNA. The rest of the RPM adaptor is double-stranded DNA for subsequent tagging with the "Odd" and "Even" adaptors.

Add 99 ul of H20 to NHS beads. Add 4 ul of 100% DMSO to beads and mix well. Heat NHS beads in the DMSO and water at 65 C for 2 minutes to melt secondary structure of RNA and to make 3'ends accessible for ligation. Immediately put on ice for 2 minutes to prevent secondary structure from re-annealing. Add the following components to NHS beads in the following order from first to last: i) PEG, ii) 100% DMSO, iii) Ligation Buffer, iv) ATP, v) and RNAse inhibitor. The entree ligation mix to beads and mix well. Then, add T4 RNA ligase 1 (high concentration) and the dsRPM adaptor. Mix again to get all of the ligation reaction into solution.

| Solution | Volume |
| --- | --- |
| 100% DMSO | 16 ul |
| 10x RNA Ligation Buffer | 20 ul |
| ATP (100 mM) | 2 ul |
| 50% PEG 8000 | 40 ul |
| Rnase Inhibitor | 3 ul |
| Add mastermix to beads at this step. | |
| 90 uM RPM adaptor | 8 ul |
| T4 RNA ligase 1 (High Conc.) | 12 ul |
| Mixed with 99 ul H20 + 4 ul DMSO + 4 uL Adaptor total | 200 ul |

Put in small vortexer at 2000 rpm for 10 seconds to get into all ligation mix and beads into solution. Incubate ligation for 1 hr at 20 C, 1200 rpm. Wash beads once in RLT++ buffer. Wash beads four times for 3 min in PBLSD+ buffer at 45 C. Rinse beads twice in M2 buffer.

Reverse Transcription of RNA on NHS Beads.

The double-stranded RPM adaptor is used to convert RNA into cDNA. Performing on-bead reverse transcription (RT) helps improve the stability of the RNA-DNA hybrid and reverse transcribes the RNA into cDNA to convert the molecule into cDNA prior to RNA degradation throughout the protocol. A manganese RT protocol is used to allow for reverse-transcription through formaldehyde crosslinks on RNA to convert the entire RNA molecule into cDNA. Add everything to RT mastermix except $MnCl_2$ until right before addition to mastermix.

Make the following 10× $MnCl_2$ RT master mix:

| 1M Tris pH 7.5 | 50 uL |
| --- | --- |
| 2M KCl | 37.5 uL |
| 1M $MnCl_2$ | 6.0 uL |
| H20 | 6.5 uL |
| Total | 100 uL |

Make the following Reverse Transcription Master Mix:
Add 10× buffer just prior to adding enzymes and adding to tubes

| Solutions | Volume |
| --- | --- |
| 10X MnCl$_2$ buffer | 30 ul |
| 100 mM DTT | 15 ul |
| dNTP mix (25 mM each) | 15 ul |
| Rnase Inhibitor | 15 ul |
| H20 | 210 ul |
| | 285 ul |

Add RT mastermix to beads, mix well. Add 15 ul of Superscript III enzyme. Incubate at 50 C for 1 hr on shaker, 1200 rpm. Rinse beads twice in M2 buffer.

Phosphorylation of RPM and DPM to Add a 5'Phosphate for Adaptor Ligation.

Set up the following reaction and add to beads

| Solution | Volume |
| --- | --- |
| H20 | 163.5 ul |
| 10x PNK Buffer | 20 ul |
| T4 PNK | 10 ul |
| RNase Inhibitor | 5 ul |
| TOTAL | 197.5 ul |

Incubate for 10 minutes at 37 C at 1200 rpm. Add 2.5 ul of 100 mM ATP after 10 minutes of incubation. Incubate 20 more minutes (for a total of 30 minutes) at 37 C at 1200 rpm. Rinse beads twice in M2 buffer.

Adaptor and Nucleotide Tag (Barcode) Design.

FIGS. 2A, 2C, 3A, and 4 depcit the adaptor and nucleotide tag scheme that is central to the SPRITE process. SPRITE in these examples uses a split-and-pool strategy to uniquely barcode all molecules within a crosslinked complex by repeatedly splitting all complexes into a 96-well plate, ligating a specific nucleotide tag sequence within each well, followed by pooling of these complexes such that the final product contains a series of tags ligated to each molecule, which we refer to as a barcode.

DNA Phosphate Modified (DPM) Adaptor.

Figure 2B:
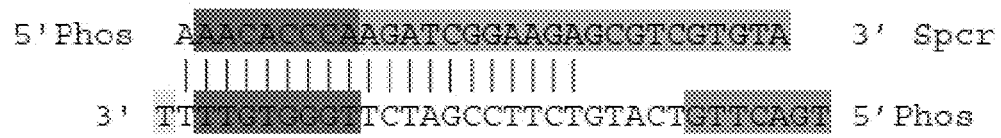
FIG. 2B is an example of one of the DNA Phosphate Modified (DPM) adaptor tags, according to embodiments of the present invention. The DPM Adaptor tags are double stranded (ds) DNA in which the 5' end of the molecule has a modified phosphate group (5' Phos) that allows for the ligation between the DPM adaptor tag and the target DNA molecules as well as the subsequent nucleotide tag (e.g., the first Odd nucleotide tag). The highlighted regions on the DPM have the following functions: the yellow T overhang is a mini-sticky-end that ligates to the end-repaired target DNA molecules; the pink region may serve as an optionally unique nucleotide sequence making it possible to distinguish each DPM tag; the green sequence is a sticky end that is capable of ligating to the first Odd nucleotide tag; and the grey sequence is complementary to the First Primer used for library amplification with a part of the grey sequence functioning as a 3' spacer (3' Spcr). Figure discloses SEQ ID NOS 1236-1237, respectively, in order of appearance.
Figure 2C:
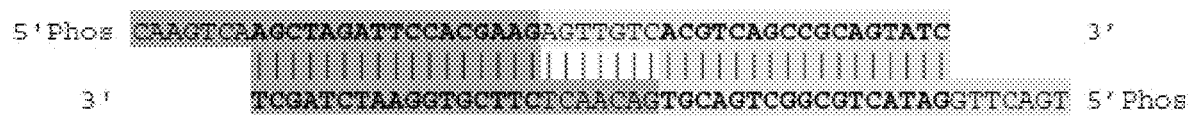
FIG. 2C is an example of an Odd tag (shown in grey) and an Even tag (shown in yellow) ligated together, according to embodiments of the present invention. Both the Odd and Even tags are dsDNA molecules which have, as depicted: 1) a 5' overhang on the top strand that is capable of ligating to either the DPM adaptor (the green sequence in FIG. 2B) or to the 5' overhang on the bottom strand of the Even tag, 2) both the Odd tag and Even tag have modified 5' phosphate groups (5' Phos) to allow for tag elongation, and 3) the bolded regions of complementarity on each tag are the sequences unique to each of the Odd tags (e.g., 96 Odd tags) and Even tags (e.g., 96 Even tags), resulting in many possible unique sequences amongst both the Odd and Even tags (e.g., 192 unique nucleotide tags). Figure discloses SEQ ID NOS 1238-1239, respectively, in order of appearance.
Figure 2D:
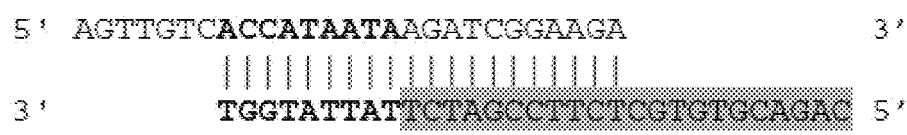
FIG. 2D is an example of a Terminal tag according to embodiments of the present invention. The Terminal tag as depicted is capable of ligating to an Odd tag and there is no modified 5' phosphate, making it so that the Terminal tag cannot ligate to itself. As depicted, the Terminal tag has a sequence complementary to a Second Primer (shown in grey) used for library amplification in which the Second Primer anneals to a daughter strand synthesized from a First Primer, and the bolded regions of complementarity on the Terminal tag are the sequences unique to each of the different Terminal tags, according to embodiments of the present invention. Figure discloses SEQ ID NOS 1240-1241, respectively, in order of appearance.

As shown in FIG. 2B, the dsDNA molecule is an example of one of the 96 DPM adaptors used during our process. The 5' end of the molecule has a modified phosphate group that allows for the ligation between DPM and the target DNA molecules as well as the subsequent tag. The highlighted regions on DPM in FIG. 2B have the following functions: The yellow T overhang is a sticky-end that ligates to our target DNA molecules, which are given a 5' A overhang following end repair. The pink region is the 9-nucleotide sequence unique to each of the 96 DPM adaptors. These unique sequences help to identify post-sequencing DNA molecules that are in a complex. The green sequence is a sticky end that ligates to the first tag. The grey sequence is complementary to the First Primer used for library amplification. Part of the grey sequence makes up a 3' spacer to prevent the top strand of the Odd tag from ligating, and only the bottom 5'phosphorylated sticky end of the Odd tag will ligate to the green tag.

RNA Phosphate Modified (RPM (Adaptor).

An RPM adaptor is shown in FIG. 3B. The key to tagging RNA and DNA molecules with the same tags is designing both DPM and RPM adaptors with the same sticky end on the bottom strand, which will ligate the Odd tags.

Additionally, the sequence for RPM is different from the DPM sequence, allowing each read off the sequencer to be identified as a RNA or DNA molecule depending on whether it contains a RPM or DPM adaptor, respectively. The RPM adaptor uniquely tags RNA through an RNA-specific ligation using single-stranded RNA ligase. The DPM adaptor uniquely tags DNA through a DNA-specific ligation using double-stranded DNA ligase.

The RPM adaptor is designed to specifically ligate RNA molecules using a single-stranded RNA ligase. This RNA-specific ligation tags RNA molecules to distinguish a molecule as RNA, rather than DNA, on the sequencer. With reference to FIGS. 3A and 3B, RPM has the following features: the grey sequence of RPM is synthesized using ribonucleotide bases. It is also a single-stranded overhang on the 5'end of the molecule. This allows for the 5'end of the molecule to ligate RNA molecules through an RNA-RNA single-stranded ligation using single-stranded RNA (ssRNA) ligase I, which ligates ssRNA to other ssRNA bases. The grey RNA bases are noted with an r letter before each RNA base:

(SEQ ID NO: 2)
rArUrCrArGrCrArCrCrCrGrGATGTAGATAGGATGGACTTAGCGT

CAG.

The pink sequence serves as a RNA-specific tag to identify each read as RNA (if the pink sequence is read) or DNA (if the DPM sequence is read). The blue sequence can serve as a 9 nucleotide barcode tag such that 96 different RPM tags can be ligated. However, it has currently only been used for ligation in a single well, and then an additional round of tag extension is performed than when the DNA SPRITE protocol is performed to achieve the same number of unique barcodes. The green sequence is a sticky end that ligates to the first tag. It contains the same sticky end as the DPM tag, so that both RNA and DNA molecules can be ligated with the same tags in one step when the complexes are split in a 96-well plate. The bottom strand of the RPM adaptor is phosphorylated after ligation of the RPM adaptor to DNA to ensure that the RPM adaptors do not form chimeras and ligate each other. The 3'spacer on the top strand of the RPM adaptor prevents ligation of single-stranded RPM molecules from ligating the RPM adaptor and forming chimeras of several RPM molecules ligating to each other.

cDNA Adaptor.

5'ligtag RNA 5' rGrCrGrArGrGrGrArGrTrCrArGrGrCrArArG 3' (SEQ ID NO: 3). In the 5'ligtagRNA adaptor (r letter indicates RNA bases) is designed for ligation to the 5'end of RNA through phosphorylation of the 5'end of RNA and ligation to the 5'ligtag using single-stranded RNA ligase I. An alternative adaptor rUrArCrArCrGrArCrGrCrUrCrUrCrCrGrArUrCrU (SEQ ID NO: 4) sequence primed by 2Puniversal (used for DNA amplification) can also be used for amplification of RNA and DNA with the same primer. The 5'adaptor is converted into cDNA during reverse transcription and is amplified during library amplification using a 5'ligtag primer:

(SEQ ID NO: 5)
5' AATGATACGGCGACCACCGAGATCTACACTCTTTCCCTACACGACGC

TCTTCCGATCT<u>GCGAGGGAGTCAGGCAAG</u> 3'

The highlighted regions on RPM have the following functions: The underlined sequence indicates the sequence of the 5'ligtag primer that amplifies the 3'end of the cDNA ligated with the 5'ligtag after the RNA has been reverse transcribed into cDNA. The bold sequence indicates the sequence of the 2P_universal adaptor that is used to amplify both the DNA and RNA for Illumina sequencing. It serves as the priming site for read 1 on during sequencing of the RNA and DNA molecules.\

Odd and Even Tags.

Odd and Even tags are so named because the Odd tag is ligated $1^{st}$, $3^{rd}$, $5^{th}$ etc. . . . during the SPRITE process and the Even tag is ligated $2^{nd}$, $4^{th}$, $6^{th}$, etc. . . . during SPRITE for however many rounds of tagging and pooling are completed. It is not necessary to ligate only an even number of tags or only an odd number of tags so long as there are two sets of Terminal tags; one that can ligate to Odd tags and one that can ligate to Even tags.

With reference to FIG. 2C, the dsDNA molecule shown in grey is an Odd tag and and an Even tag is shown in yellow in which the Odd and Even tag are ligated together. Features of these tags include: 1) the 5' overhang on the top strand ligates either to the DPM adaptor or the 5' overhang on the bottom strand of the Even tag; 2) both the Odd tags and Even tags have modified 5' phosphate groups to allow for tag elongation; and the bolded regions of complementarity on each tag are the sequences unique to each of the 96 tags (192 total, accounting for both Odd tags and Even tags).

Terminal Tag.

A terminal tag is shown in FIG. 2D. The terminal tags shown herein ligate to Odd tags, although a terminal tag may be made to ligate to Even tags. The key feature of the terminal tag is that there is no modified 5' phosphate on the bottom strand. With reference to FIG. 2D, additional features of the terminal tag include: 1) the grey sequence is complementary to the Second Primer used for library amplification; 2) since DNA cannot be synthesized in a 3' to 5' direction, the Second Primer anneals to a daughter strand synthesized from the First Primer; 3) the top strand is not primed because there is a break in the sequence generated by the 3'spacer on the DPM molecule and therefore priming the top strand of the terminal tag would terminate at the barcodes and would not PCR through to the gDNA sequence ligated to the barcodes; and 4) the bolded sequence on the Terminal tag is unique to each of the 96 tags. Examples of Terminal Tags are listed in Tables 1-2.

Library Amplification.

The DPM adaptor is designed with a 3' spacer to aid in final library amplification. If the 3' spacer is absent, each strand will form a hairpin loop during the initial denaturation due to reverse complementarity of the sequences on either side of the target DNA molecule. Instead, the 3' spacer allows the nucleotide tags to only ligate to the 5'end of each single-stranded DNA sequence, and not the 3'end, preventing these hairpin from forming.

```
2P_universal (F primer)
                                          (SEQ ID NO: 6)
5' AATGATACGGCGACCACCGAGATCTACACTCTTTCCCTACACGACGC

TCTTCCGATCT 3'

2P_barcoded_85 (R primer)
                                          (SEQ ID NO: 7)
5' CAAGCAGAAGACGGCATACGAGATGCCTAGCCGTGACTGGAGTTCAG

ACGTGTGCTCTTCCGATCT 3'
```

Due to reverse complementarity of the sequences, only one primer amplifies the tagged DNA in the first PCR cycle. This First Primer anneals to a sequence in the DPM adaptor and extends, synthesizing two daughter strands with reverse sequences. This first primer serves as the Read1 primer during Illumina sequencing. To synthesize the complement, the Second Primer anneals to the daughter strand extended from the First Primer in the second PCR cycle.

The 2P_barcoded primer contains an 8 nucleotide barcode as underlined above within the primer. This barcode is read from the illumina sequencer during the indexing priming step. This barcode effectively serves as an additional round of tag addition during SPRITE. Dilution of the sample into multiple wells is performed at the final step of SPRITE prior to proteinase K elution from NHS beads. Each dilution of the sample prior to proteinase K elution isolates a subset of the tagged complexes into different wells. Each dilution of complexes are amplified with a different 2P_barcoded primer.

Both the First and Second primers are around 30 nucleotides each. Yet the sequences they anneal to initially are ~20 nucleotides. For this reason, we set two different annealing temperatures during the final library PCR. The first annealing temperature is for the first four cycles until enough copies are made with fully extended primer regions. After these four cycles, the annealing temperature is raised for a remaining five cycles.

The 2P_universal primer and 2P_barcoded serve as the Read 1 and Read 2 primers for illumina sequencing, respectively. Read 1 sequences the DNA molecule and the DPM adaptor. Read 2 sequences the multiple tags, ie. unique barcode, ligated to the DNA molecules.

DPM and RPM Primers for Quality-Control (QC) of DPM and RPM Ligation.

The primers DPMQCprimerF, DPMQCprimerR, RPMQCprimerF, and RPMQCprimerR are used to ensure that the DPM and RPM adaptor has been successfully ligated to DNA and RNA of the lysate, respectively.

```
DPMQCprimerF
                                          (SEQ ID NO: 8)
5' TACACGACGCTCTTCCGATCT 3'

DPMQCprimerR
                                          (SEQ ID NO: 9)
5' TGACTTGTCATGTCTTCCGATCT 3'

RPMQCprimerF
                                          (SEQ ID NO: 10)
5' GCGAGGGAGTCAGGCAAG 3'

RPMQCprimerR
                                          (SEQ ID NO: 11)
5' TGACTTGCGCTAAGTCCATCCTATCTACATCCG 3'
```

If no libraries are obtained at this step after 14-16 cycles of PCR, it is likely that subsequent ligation of tags and amplification of tagged DNA and RNA during the SPRITE protocol will be unsuccessful.

The DPM Forward and Reverse primers amplify the top strand and bottom strand of the DPM adaptor, respectively. The RPM Forward and Reverse primers amplify the cDNA adaptor and bottom strand of the RPM adaptor, respectively.

Adaptor Annealing Program.

The following adaptors and tags are annealed to make the tags double-stranded adaptors for dsDNA adaptor ligation: DPM adaptors, Odd Nucleotide Tags (adaptors), Even Nucleotide Tags, and Terminal Tag adaptors.

Mix the top and bottom strands of each adaptor into a PCR tube or 96-well plate with 10× Annealing Buffer:

| Reagents | Volume |
| --- | --- |
| 10x Annealing Buffer | 10 ul |
| Top Adaptor (200 µM) | 45 ul |
| Bottom Adaptor (200 µM) | 45 ul |
| Total | 100 ul |

Incubate with the following conditions in a thermocycler for adapter annealing to denature any secondary structure within the top and bottom strands of each adaptor, then slowly cool to anneal each strand:

| | Temperature (° C.) | Time (min) | Ramp (° C./s) | Cycle |
| --- | --- | --- | --- | --- |
| Denaturation | 95 | 02:00 | | |
| Annealing | 85 | 00:10 | −1 | 60 |
| Hold | 25 | Infinite | | |

Split-Pool Recognition of Interactions by Tag Extension (SPRITE) and Library Preparation.

The SPRITE method provides each DNA, RNA, and/or protein complexes in the sample lysate with a unique nucleic acid barcode. When these complexes are de-crosslinked, the individual molecules that made up a single complex retain identical nucleotide tags or barcodes. These DNA libraries are sequenced on an Illumina Next-Generation sequencing platform and analyzed. Any DNA, RNA and/or protein molecules found to have the same barcode interact in-vivo.

In the examples shown here, the SPRITE method works by splitting into a 96-well plate a pooled sample of cross-linked lysate where DNA molecules are ligated to the DPM adaptor. Each well of the 96-well plate contains a unique tag (Odd) to which the DNA molecules are ligated. The ligation reactions are stopped, pooled, and split again into a new 96-well plate containing different, unique tags than the first (Even). If n rounds of tag ligation are performed, 96n unique barcodes are generated. We typically ligate 5 tags, creating over 8 billion unique barcodes. After all barcodes are ligated, the sample is split again into small m aliquots (100 wells of 1% aliquots up to 10 wells of 10% aliquots are typically used depending on the total material coupled) for PCR amplification. This final splitting of samples effectually sorts the DNA complexes once more, so that the chance that two different non-crosslinked complexes with the same barcode are amplified together is negligible. This last dilution into m wells effectively raises the number of unique tags to each molecule to m*96n. For example, if the sample is aliquoted into 1% aliquots, then over 815 billion unique barcodes are generated.

The first round of SPRITE was already completed with the ligation of 96 unique DPM adaptors (see Tables 3-5) that allow for the subsequent ligation of new barcodes. As disclosed herein, subsequent tag ligations are performed in the following order:

ODD Tag Ligation

EVEN Tag Ligation

ODD Tag Ligation

EVEN Tag Ligation

Terminal Tag Ligation

The give barcode ligations listed above are performed in the exact same manner with the only difference being the tag sequence. Thus, the following section will only detail one round of SPRITE.

It is noted that RNAse inhibitor has been added to the simultaneous tagging of RNA and DNA protocol to prevent degradation of RNA during the tagging protocol.

Example ODD and EVEN nucleotide tag nucleotides are listed in Tables 6-9. Aliquot 200 uL of Instant Sticky End Ligase Master Mix into each well of a 12-well strip tube. Keep on ice until ready to use. Centrifuge the nucleotide tag stock plate before removing the foil seal. Aliquot 2.4 uL from the stock plate of barcodes (nucleotide tags) to a new low-bind 96-well plate. Be careful to ensure that there is no mixing between wells at any point of the process. Use a new pipette tip for each well. After transfer is complete, seal both plates with a new foil seal. Create a diluted M2 Buffer by mixing 1100 uL of M2 Buffer with 682 uL of H20 and 110 ul of RNase Inhibitor.

Accounting for bead volume, add the M2+H20+RNase Inhibitor mix to the beads to achieve a final volume of 1700 uL. Ensure that the beads are equally suspended in the buffer. Aliquot 140 uL of the bead mix into each well of a 12-well strip tube. Centrifuge the 96-well plate containing the aliquoted barcodes, and then remove the foil seal. Aliquot 17.6 uL of beads into each well of the 96-well plate that contains 2.4 uL of the tags. Be careful to ensure that there is no mixing between wells at any point of the process. Use a new pipette tip for each well. Also be careful to ensure that there are no beads remaining in the pipette tip. Carefully add any remaining beads to individual wells on the plate in 1 uL aliquots. Aliquot 20 uL of Instant Sticky End Ligase Master Mix into each well, mixing by pipetting up and down 10 times. Be careful to ensure that there is no mixing between wells at any point of the process. Use a new pipette tip for each well.

The final reaction components and volumes for each well should be as follows:

| Stock Solution | Volume |
| --- | --- |
| Beads + M2 + H20 Mix | 16.6 uL |
| Tag (45 uM) | 2.4 uL |
| 2X Instant Sticky End Ligation Master Mix | 20 uL |
| Rnase inhibitor | 1 ul |
| Total | 40 uL |

Seal the plate with a foil seal and incubate on a thermo-mixer for 60 minutes at 20 C, shaking for 15 seconds at 1600 RPM every minute. After incubation, centrifuge the plate before removing the foil seal. Pour RLT++ Buffer into a sterile plastic reservoir, and transfer 100 uL of RLT++ into each well on the 96-well plate to stop the ligation reactions. It is not necessary to use new tips for each well. Pool all 96 stopped ligation reactions into a second sterile plastic reservoir. Place a 15 mL conical tube on an appropriately sized magnetic rack and transfer the pool into the conical. Capture all beads on the magnet, disposing all RLT++ in an appropriate waste receptacle. Remove the 15 mL conical containing the beads from the magnet and resuspend beads in 1 mL PBLSD+ Wash Buffer. Transfer the bead solution to a microcentrifuge tube. Wash three times with PBLSD+ Wash Buffer at 50 C, 1200 RPM for 3 minutes each time.

Wash three times with M2 Buffer. Repeat the process starting at Step 1 for the remaining four or more SPRITE rounds.

Library Preparation.

Resuspend the beads in MyRNK Buffer so that the final beads+buffer volume is 1 mL. Remove five aliquots into clean microcentrifuge tubes: 0.5%, 1%, 2.5%, 5%, and 7.5% (5 uL, 10 uL, 25 uL, 50 uL, and 75 uL) and elute the barcoded DNA and RNA from the beads.

| Stock Solution | Volume |
| --- | --- |
| Sample on beads in MyRNK Buffer | 5/10/25/50/75 uL |
| MyRNK Buffer | 87/82/67/42/17 uL |
| Proteinase K | 8 uL |
| Total | 100 uL |

Incubate at 65 C overnight. Place the microcentrifuge tubes on a magnet and capture the beads. Remove the flowthrough that contains the barcoded DNA and RNA and place in a clean microcentrifuge tube. Pipette 25 uL of H20 into the tube containing the beads. Vortex, and re-capture the beads. Remove the 25 uL of H20 that now contains any residual nucleic acid and add to the new sample tube. Discard the beads.

Follow the protocol provided in the DNA Clean and Concentrator-5 Kit, binding in 6 volumes of DNA Binding Buffer. Elute in 56 uL of H20.

Convert RNA into cDNA by reverse transcriptase, as detailed above. Follow the protocol provided in the DNA Clean and Concentrator-5 Kit, binding in 6 volumes of DNA Binding Buffer. Elute in 40 uL of H20. Amplify the final barcoded DNA and cDNA through PCR. The First Primer is a mix of 2P_Universal and 2P_Universal_5'LigTag to amplify both tagged DNA and RNA molecules, respectively. The Second Primer is 2P_Barcoded. Examples of unique primers are listed in Table 10. Before placing the reaction in the thermocycler, split the sample in in to two tubes with 50 uL in each tube.

| Stock Solution | Volume |
| --- | --- |
| Sample (cleaned) | 40 uL |
| First Primer (100 uM) | 2 uL |
| Second Primer (100 uM) | 2 uL |
| H20 | 6 uL |
| Q5 Hot Start Master Mix | 50 uL |
| Total | 100 uL |

PCR Program:
1. Initial denaturation: 98 C—180 seconds
2. 4 cycles:
    a. 98 C—10 seconds
    b. 67 C—30 seconds
    c. 72 C—90 seconds
3. 5 cycles:
    a. 98 C—10 seconds
    b. 70 C—30 seconds
    c. 72 C—90 seconds
4. Final extension: 72 C—180 seconds
5. Hold 4 C Clean the PCR reaction and size select for your target libraries. The total length of our barcode on one amplified product is around 160 base pairs and each target DNA molecules no less than 100 base pairs. Agencourt AMPure XP beads are able to size select while cleaning the PCR reaction of unwanted products.

Combine the two 50 uL PCR reactions back into one tube. Add 0.7×AMPure XP beads to the sample for a total volume of 170 uL and mix thoroughly. Incubate for 10 minutes at room temperature, mixing again at 5 minutes. Place the beads on an appropriately sized magnet to capture the beads and the bound DNA. Wait a few minutes until all the beads are captured. Remove the supernatant and discard. Wash beads twice with 70% ethanol by pipetting ethanol into the tube while beads are captured, moving the tube to the opposite side of the magnet so that beads pass through the ethanol, and then removing the ethanol solution. Quickly spin down the beads in a microcentrifuge, re-capture on magnet, and remove any remaining ethanol. Air-dry beads while the tube is on the magnet. Elute the amplified DNA from the beads by resuspending the beads in 100 uL of H20. Place the solution back on the magnet to capture the beads. Remove the eluted amplified DNA to a clean microcentrifuge tube. Repeat the clean up with 0.7×AMPure XP beads, eluting finally in 12 uL.

Determine the concentration of each library with the Qubit Fluorometer. The final libraries disclosed here are generally between 0.5 ng/uL and 1.5 ng/uL.

Load all samples on the Agilent BioAnalyzer, following the protocol provided with Agilent's High Sensitivity dsDNA Kit. Final library sizes range from around 260 base pairs to 1000 base pairs with peaks around 400 base pairs.

Using the concentrations gathered from Qubit and the average library size gathered from the BioAnalyzer, estimate the number of DNA molecules in each library. These numbers are used to determine the microliter amount to be sequenced.

Sequencing and Data Analysis.

The Illumina, Inc. HiSeq v2500 platform was employed for next generation sequencing of the generated libraries using a TruSeq Rapid SBS v1 Kit-HS (200 cycle) and TruSeq Rapid Paired End Cluster Kit-HS. All SPRITE data disclosed was generated using Illumina paired-end sequencing. Reads must be long enough to incorporate all tag information. Most read-pairs in this disclosure were (115 bp, 100 bp).

Tag Identification.

This step is performed using custom in-house software. The program takes as input both FASTQ files, sorted by name so that the record with a particular line number in the read 1 file corresponds with the record with the same line number in the read 2 file. The program also requires a text file containing the tag sequences with unique identifiers and an identification tolerance—the number of mismatches tolerated between the tag and the read when search for the tag.

The program first loads the tags from the tag file and stores them in a hashtable keyed by sequence. Storing these sequences in a hashtable allows rapid (O(1)) string matching. Additional tags are generated according to the given identification tolerances, and these are also stored. For example, if the tag TTTT has an identification tolerance of 1, the tag will be inserted into the table, keyed by all sequences at most one Hamming distance away:

TTTT
ATTT
TATT
TTAT
TTTA
CTTT
TCTT
TTCT
TTTC
GTTT
TGTT
TTGT

TTTG
NTTT
TNTT
TTNT
TTTN

After storing the tags, the program iterates through the read-pairs by advancing line-by-line through both FASTQ files simultaneously. For a given sequence, the program queries the hash table for substrings that correspond to known tag positions. (The exact details of this process depend on the barcoding scheme.) After the identification process for a record is complete, the tags are appended to the name of the record, and this modified record is output into new read 1 and read 2 FASTQ files.

Alignment.

In our barcoding schemes, only one of the reads in a read pair contains an appreciable amount of genomic sequence. These genomic-reads are aligned to the appropriate reference with Bowtie2 under the default parameters—except for the following. Only one of the two FASTQ files is aligned. A paired-end alignment is not run despite having paired-end reads. Before the genomic sequence on the read is an 11-mer DPM tag sequence. To account for this, a Bowtie2 with '--trim5 11' is run.

After the sequence, there are two possibilities. The read may extend into the tag sequences on the other end of the fragment if the fragment is too short, or the read may terminate before the tags if the fragment is long enough. To account for the inclusion of tag sequences, a Bowtie2 with '--local' was run. This also addresses the DPM tag at the start of the sequence. Alignment is made to both the reference chromosomes and unplaced scaffolds (typically end in "random").

The resulting SAM file is sorted and convert it to a BAM file. The names of each SAM record contain the identified tags, as these were present in the input FASTQ files.

Filtration.

The BAM file is then passed through successive filtration steps: Remove all alignments with a MAPQ score less than 30. This removes all unmapped reads. Note that the MAPQ score depends on the aligner used; it is not standardized. If a different aligner is used, this step will need to be replaced with a different quality-filtration step. Remove all alignments that align to the reference with a Hamming score >2. In these examples, only two mismatches were tolerated at most between the read and the reference. Remove all alignments that overlap (in any amount) any region in the repeat-mask BED file provided by B. Tabak. Bedtools intersect with the '-v' flag set were used.

Remove all alignments that overlap (in any amount) any region in the mask BED file generated by ComputeGenomeMask in the GATK package from the Broad. This mask file was generated by shredding the reference into 35-mers and BLASTting them against the reference. Any non-unique location that a 35-mer maps to is masked. The output of ComputeGenomeMask is not a BED file, but a FASTA file where all masked bases are represented with Os, and all unmasked bases are represented with 1 s. This mask file is converted to a BED file with a custom Python script.

Subsequence Post-Processing.

See the Github page.

Accessible on the world wide web at github.com/GuttmanLab/barcoding-post/wiki

TABLE 1

Top Strand of the Terminal Ligation Adaptor (Terminal Tag).
After annealing the "top" strand of the terminal adaptor with
the "bottom" strand of the terminal adaptor, the terminal
adaptor becomes a double stranded DNA oligo. The terminal
adaptor is ligated with a 5'phosphate (5Phos) to the tagged
DNA through the AGTTGTC sticky end. This set of terminal adaptors
is ligated to an Odd nucleotide tag, but another set of these
terminal adaptors may be designed with a different sticky end to
ligate an Even nucleotide tag. This terminal adaptor is primed by
the 2P_barcoded oligo for final library amplification.

| 96Well Position | Adaptor Name | Sequence |
|---|---|---|
| A1 | NYTop1_Stg | /5Phos/AGTTGTCACCATAATAAGATCGGAAGA (SEQ ID NO: 12) |
| A2 | NYTop2_Stg | /5Phos/AGTTGTCAAGGTAGCTAAGATCGGAAGA (SEQ ID NO: 13) |
| A3 | NYTop3_Stg | /5Phos/AGTTGTCATGAACAATAGATCGGAAGA (SEQ ID NO: 14) |
| A4 | NYTop4_Stg | /5Phos/AGTTGTCATTCGGTGGAGATCGGAAGA (SEQ ID NO: 15) |
| A5 | NYTop5_Stg | /5Phos/AGTTGTCACAACTGATGAGATCGGAAGA (SEQ ID NO: 16) |
| A6 | NYTop6_Stg | /5Phos/AGTTGTCCTCTCAAGGAGATCGGAAGA (SEQ ID NO: 17) |
| A7 | NYTop7_Stg | /5Phos/AGTTGTCACTTCCTGATAGATCGGAAGA (SEQ ID NO: 18) |
| A8 | NYTop8_Stg | /5Phos/AGTTGTCGCTACTTCGAGATCGGAAGA (SEQ ID NO: 19) |
| A9 | NYTop9_Stg | /5Phos/AGTTGTCAGTCGGTTAAAGATCGGAAGA (SEQ ID NO: 20) |
| A10 | NYTop10_Stg | /5Phos/AGTTGTCATGTATGAACAGATCGGAAGA (SEQ ID NO: 21) |
| A11 | NYTop11_Stg | /5Phos/AGTTGTCTTCTTCGTCAGATCGGAAGA (SEQ ID NO: 22) |
| A12 | NYTop12_Stg | /5Phos/AGTTGTCCACAGAGGCAAGATCGGAAGA (SEQ ID NO: 23) |
| B1 | NYTop13_Stg | /5Phos/AGTTGTCATCCATCTCAGATCGGAAGA (SEQ ID NO: 24) |

TABLE 1-continued

Top Strand of the Terminal Ligation Adaptor (Terminal Tag).
After annealing the "top" strand of the terminal adaptor with
the "bottom" strand of the terminal adaptor, the terminal
adaptor becomes a double stranded DNA oligo. The terminal
adaptor is ligated with a 5'phosphate (5Phos) to the tagged
DNA through the AGTTGTC sticky end. This set of terminal adaptors
is ligated to an Odd nucleotide tag, but another set of these
terminal adaptors may be designed with a different sticky end to
ligate an Even nucleotide tag. This terminal adaptor is primed by
the 2P_barcoded oligo for final library amplification.

| 96Well Position | Adaptor Name | Sequence |
| --- | --- | --- |
| B2 | NYTop14_Stg | /5Phos/AGTTGTCCACTATGGTAGATCGGAAGA (SEQ ID NO: 25) |
| B3 | NYTop15_Stg | /5Phos/AGTTGTCCCATTCGTACAGATCGGAAGA (SEQ ID NO: 26) |
| B4 | NYTop16_Stg | /5Phos/AGTTGTCCGTCTCCTTAGATCGGAAGA (SEQ ID NO: 27) |
| B5 | NYTop17_Stg | /5Phos/AGTTGTCGGTTAATGGAGATCGGAAGA (SEQ ID NO: 28) |
| B6 | NYTop18_Stg | /5Phos/AGTTGTCCGTAAGGAGAAGATCGGAAGA (SEQ ID NO: 29) |
| B7 | NYTop19_Stg | /5Phos/AGTTGTCTGGTGAGATAGATCGGAAGA (SEQ ID NO: 30) |
| B8 | NYTop20_Stg | /5Phos/AGTTGTCCTTAGTTACGAGATCGGAAGA (SEQ ID NO: 31) |
| B9 | NYTop21_Stg | /5Phos/AGTTGTCGAGCCAGTCTAGATCGGAAGA (SEQ ID NO: 32) |
| B10 | NYTop22_Stg | /5Phos/AGTTGTCGAGTGGTATTAGATCGGAAGA (SEQ ID NO: 33) |
| B11 | NYTop23_Stg | /5Phos/AGTTGTCATAATGCAGAGATCGGAAGA (SEQ ID NO: 34) |
| B12 | NYTop24_Stg | /5Phos/AGTTGTCCAGCTACAAAGATCGGAAGA (SEQ ID NO: 35) |
| C1 | NYTop25_Stg | /5Phos/AGTTGTCGATAACGGCAGATCGGAAGA (SEQ ID NO: 36) |
| C2 | NYTop26_Stg | /5Phos/AGTTGTCGGTTGTATTCAGATCGGAAGA (SEQ ID NO: 37) |
| C3 | NYTop27_Stg | /5Phos/AGTTGTCGTATTCTCCTAGATCGGAAGA (SEQ ID NO: 38) |
| C4 | NYTop28_Stg | /5Phos/AGTTGTCGTCTTAGATGAGATCGGAAGA (SEQ ID NO: 39) |
| C5 | NYTop29_Stg | /5Phos/AGTTGTCTTGTATTGAAGATCGGAAGA (SEQ ID NO: 40) |
| C6 | NYTop30_Stg | /5Phos/AGTTGTCTAACTTATCGAGATCGGAAGA (SEQ ID NO: 41) |
| C7 | NYTop31_Stg | /5Phos/AGTTGTCACTTGTCAAAGATCGGAAGA (SEQ ID NO: 42) |
| C8 | NYTop32_Stg | /5Phos/AGTTGTCTAGAACTACAAGATCGGAAGA (SEQ ID NO: 43) |
| C9 | NYTop33_Stg | /5Phos/AGTTGTCAGGATAGGCAGATCGGAAGA (SEQ ID NO: 44) |
| C10 | NYTop34_Stg | /5Phos/AGTTGTCTATTGCCGCCAGATCGGAAGA (SEQ ID NO: 45) |
| C11 | NYTop35_Stg | /5Phos/AGTTGTCTTGGCCGTAAAGATCGGAAGA (SEQ ID NO: 46) |
| C12 | NYTop36_Stg | /5Phos/AGTTGTCTGAGGATTCCAGATCGGAAGA (SEQ ID NO: 47) |
| D1 | NYTop37_Stg | /5Phos/AGTTGTCTTAACATGAGAGATCGGAAGA (SEQ ID NO: 48) |
| D2 | NYTop38_Stg | /5Phos/AGTTGTCTAATCAATCAGATCGGAAGA (SEQ ID NO: 49) |
| D3 | NYTop39_Stg | /5Phos/AGTTGTCTCAGTATATAGATCGGAAGA (SEQ ID NO: 50) |
| D4 | NYTop40_Stg | /5Phos/AGTTGTCGAAGGAGCGAGATCGGAAGA (SEQ ID NO: 51) |
| D5 | NYTop41_Stg | /5Phos/AGTTGTCATCGCGTACTAGATCGGAAGA (SEQ ID NO: 52) |
| D6 | NYTop42_Stg | /5Phos/AGTTGTCCAGATCCGTGAGATCGGAAGA (SEQ ID NO: 53) |
| D7 | NYTop43_Stg | /5Phos/AGTTGTCGATACCAGGAAGATCGGAAGA (SEQ ID NO: 54) |
| D8 | NYTop44_Stg | /5Phos/AGTTGTCCGAAGACCTAGATCGGAAGA (SEQ ID NO: 55) |
| D9 | NYTop45_Stg | /5Phos/AGTTGTCGGCCTTGGAAAGATCGGAAGA (SEQ ID NO: 56) |
| D10 | NYTop46_Stg | /5Phos/AGTTGTCGGATGCTACAGATCGGAAGA (SEQ ID NO: 57) |

TABLE 1-continued

Top Strand of the Terminal Ligation Adaptor (Terminal Tag).
After annealing the "top" strand of the terminal adaptor with
the "bottom" strand of the terminal adaptor, the terminal
adaptor becomes a double stranded DNA oligo. The terminal
adaptor is ligated with a 5'phosphate (5Phos) to the tagged
DNA through the AGTTGTC sticky end. This set of terminal adaptors
is ligated to an Odd nucleotide tag, but another set of these
terminal adaptors may be designed with a different sticky end to
ligate an Even nucleotide tag. This terminal adaptor is primed by
the 2P_barcoded oligo for final library amplification.

| 96Well Position | Adaptor Name | Sequence |
|---|---|---|
| D11 | NYTop47_Stg | /5Phos/AGTTGTCGGCCGTAGGAGATCGGAAGA (SEQ ID NO: 58) |
| D12 | NYTop48_Stg | /5Phos/AGTTGTCTCAAGCGTAAGATCGGAAGA (SEQ ID NO: 59) |
| E1 | NYTop49_Stg | /5Phos/AGTTGTCATGGTCGCCAAGAGATCGGAAGA (SEQ ID NO: 60) |
| E2 | NYTop50_Stg | /5Phos/AGTTGTCTGCCGGTTTAAGAGATCGGAAGA (SEQ ID NO: 61) |
| E3 | NYTop51_Stg | /5Phos/AGTTGTCGCAACAACAGAGAGATCGGAAGA (SEQ ID NO: 62) |
| E4 | NYTop52_Stg | /5Phos/AGTTGTCCAAACAACAGAGAGATCGGAAGA (SEQ ID NO: 63) |
| E5 | NYTop53_Stg | /5Phos/AGTTGTCATATGTGAAACGAGATCGGAAGA (SEQ ID NO: 64) |
| E6 | NYTop54_Stg | /5Phos/AGTTGTCTGCTTAGAAGCGAGATCGGAAGA (SEQ ID NO: 65) |
| E7 | NYTop55_Stg | /5Phos/AGTTGTCGCTAGCAGTCGGAGATCGGAAGA (SEQ ID NO: 66) |
| E8 | NYTop56_Stg | /5Phos/AGTTGTCCATGACTGGATGAGATCGGAAGA (SEQ ID NO: 67) |
| E9 | NYTop57_Stg | /5Phos/AGTTGTCACTTCGGAGCTGAGATCGGAAGA (SEQ ID NO: 68) |
| E10 | NYTop58_Stg | /5Phos/AGTTGTCTTAACGTTGTTGAGATCGGAAGA (SEQ ID NO: 69) |
| E11 | NYTop59_Stg | /5Phos/AGTTGTCGCTAGTCTAATGAGATCGGAAGA (SEQ ID NO: 70) |
| E12 | NYTop60_Stg | /5Phos/AGTTGTCCGCAAGTGCTGGAGATCGGAAGA (SEQ ID NO: 71) |
| F1 | NYTop61_Stg | /5Phos/AGTTGTCAACGTACATCACAGATCGGAAGA (SEQ ID NO: 72) |
| F2 | NYTop62_Stg | /5Phos/AGTTGTCTGGGACGACTACAGATCGGAAGA (SEQ ID NO: 73) |
| F3 | NYTop63_Stg | /5Phos/AGTTGTCGCGAGTTGGACCAGATCGGAAGA (SEQ ID NO: 74) |
| F4 | NYTop64_Stg | /5Phos/AGTTGTCCTGTATGGCGCCAGATCGGAAGA (SEQ ID NO: 75) |
| F5 | NYTop65_Stg | /5Phos/AGTTGTCAGGGTGCTCTCCAGATCGGAAGA (SEQ ID NO: 76) |
| F6 | NYTop66_Stg | /5Phos/AGTTGTCTCATTGCAGAGCAGATCGGAAGA (SEQ ID NO: 77) |
| F7 | NYTop67_Stg | /5Phos/AGTTGTCGGAAACGTTCGCAGATCGGAAGA (SEQ ID NO: 78) |
| F8 | NYTop68_Stg | /5Phos/AGTTGTCCCGACTCGATGCAGATCGGAAGA (SEQ ID NO: 79) |
| F9 | NYTop69_Stg | /5Phos/AGTTGTCATCTACGTCATCAGATCGGAAGA (SEQ ID NO: 80) |
| F10 | NYTop70_Stg | /5Phos/AGTTGTCTATGTTCTGCTCAGATCGGAAGA (SEQ ID NO: 81) |
| F11 | NYTop71_Stg | /5Phos/AGTTGTCGCACGGGGTGTCAGATCGGAAGA (SEQ ID NO: 82) |
| F12 | NYTop72_Stg | /5Phos/AGTTGTCCGGTCGAACAACAGATCGGAAGA (SEQ ID NO: 83) |
| G1 | NYTop73_Stg | /5Phos/AGTTGTCACACATATAAAAGATCGGAAGA (SEQ ID NO: 84) |
| G2 | NYTop74_Stg | /5Phos/AGTTGTCTGTGATGTCAAAGATCGGAAGA (SEQ ID NO: 85) |
| G3 | NYTop75_Stg | /5Phos/AGTTGTCGTGGGGATAAAGATCGGAAGA (SEQ ID NO: 86) |
| G4 | NYTop76_Stg | /5Phos/AGTTGTCCACTGGTCACAAGATCGGAAGA (SEQ ID NO: 87) |
| G5 | NYTop77_Stg | /5Phos/AGTTGTCAGGAGCATCCAAGATCGGAAGA (SEQ ID NO: 88) |
| G6 | NYTop78_Stg | /5Phos/AGTTGTCTTAATTACTCAAGATCGGAAGA (SEQ ID NO: 89) |
| G7 | NYTop79_Stg | /5Phos/AGTTGTCCCAATATGAGAAGATCGGAAGA (SEQ ID NO: 90) |

TABLE 1-continued

Top Strand of the Terminal Ligation Adaptor (Terminal Tag).
After annealing the "top" strand of the terminal adaptor with
the "bottom" strand of the terminal adaptor, the terminal
adaptor becomes a double stranded DNA oligo. The terminal
adaptor is ligated with a 5'phosphate (5Phos) to the tagged
DNA through the AGTTGTC sticky end. This set of terminal adaptors
is ligated to an Odd nucleotide tag, but another set of these
terminal adaptors may be designed with a different sticky end to
ligate an Even nucleotide tag. This terminal adaptor is primed by
the 2P_barcoded oligo for final library amplification.

| 96Well Position | Adaptor Name | Sequence |
| --- | --- | --- |
| G8 | NYTop80_Stg | /5Phos/AGTTGTCCATATGTTCGAAGATCGGAAGA (SEQ ID NO: 91) |
| G9 | NYTop81_Stg | /5Phos/AGTTGTCATGTAGTATGAAGATCGGAAGA (SEQ ID NO: 92) |
| G10 | NYTop82_Stg | /5Phos/AGTTGTCTGACGTCGATAAGATCGGAAGA (SEQ ID NO: 93) |
| G11 | NYTop83_Stg | /5Phos/AGTTGTCGCCCTGGTCTAAGATCGGAAGA (SEQ ID NO: 94) |
| G12 | NYTop84_Stg | /5Phos/AGTTGTCCATCCACATTAAGATCGGAAGA (SEQ ID NO: 95) |
| H1 | NYTop85_Stg | /5Phos/AGTTGTCAACATACTAATAGATCGGAAGA (SEQ ID NO: 96) |
| H2 | NYTop86_Stg | /5Phos/AGTTGTCTTGGATAGGATAGATCGGAAGA (SEQ ID NO: 97) |
| H3 | NYTop87_Stg | /5Phos/AGTTGTCGGGCGTGTAATAGATCGGAAGA (SEQ ID NO: 98) |
| H4 | NYTop88_Stg | /5Phos/AGTTGTCCTATTTCAACTAGATCGGAAGA (SEQ ID NO: 99) |
| H5 | NYTop89_Stg | /5Phos/AGTTGTCACAAAGGGCCTAGATCGGAAGA (SEQ ID NO: 100) |
| H6 | NYTop90_Stg | /5Phos/AGTTGTCTACGCTCATCTAGATCGGAAGA (SEQ ID NO: 101) |
| H7 | NYTop91_Stg | /5Phos/AGTTGTCGGAAGAAGAGTAGATCGGAAGA (SEQ ID NO: 102) |
| H8 | NYTop92_Stg | /5Phos/AGTTGTCCCAATAATGGTAGATCGGAAGA (SEQ ID NO: 103) |
| H9 | NYTop93_Stg | /5Phos/AGTTGTCACTGAGTCTGTAGATCGGAAGA (SEQ ID NO: 104) |
| H10 | NYTop94_Stg | /5Phos/AGTTGTCTACAGACAATTAGATCGGAAGA (SEQ ID NO: 105) |
| H11 | NYTop95_Stg | /5Phos/AGTTGTCGGTGAGGCCTTAGATCGGAAGA (SEQ ID NO: 106) |
| H12 | NYTop96_Stg | /5Phos/AGTTGTCCTCTGTTCGTTAGATCGGAAGA (SEQ ID NO: 107) |

TABLE 2

Bottom Strand of the Terminal Ligation Adaptor.
After annealing the "top" strand of the terminal adaptor with the
"bottom" strand of the terminal adaptor, the terminal adaptor
becomes a double stranded DNA oligo. The terminal adaptor is ligated
with a 5'phosphate to the tagged DNA through the AGTTGTC
sticky end on the top strand of the oligo. This set of terminal adaptors
is ligated to an Odd barcode, but another set of these terminal
adaptors can be designed with a different sticky end to ligate an Even
barcode. This terminal adaptor is primed by the 2P_barcoded oligo
for final library amplification. There are 96 different terminal tags.
The 96 different unique sequences are in column 4. The barcodes
have been generated with a "stagger" such that each
barcode is of variable length and then causes the sticky end to be
at a variable position +/- 0-4 nts in the read. This is
necessary to prevent a monotemplate the all sticky ends producing
the same signal on the sequencer.

| 96Well Position | Adaptor Name | Sequence | Unique Barcode |
| --- | --- | --- | --- |
| A1 | NYBot1_Stg | CAGACGTGTGCTCTTCCGATCTTATTATGGT (SEQ ID NO: 108) | TATTATGGT |
| A2 | NYBot2_Stg | CAGACGTGTGCTCTTCCGATCTTAGCTACCTT (SEQ ID NO: 109) | TAGCTACCTT (SEQ ID NO: 204) |

TABLE 2-continued

Bottom Strand of the Terminal Ligation Adaptor.
After annealing the "top" strand of the terminal adaptor with the "bottom" strand of the terminal adaptor, the terminal adaptor becomes a double stranded DNA oligo. The terminal adaptor is ligated with a 5'phosphate to the tagged DNA through the AGTTGTC sticky end on the top strand of the oligo. This set of terminal adaptors is ligated to an Odd barcode, but another set of these terminal adaptors can be designed with a different sticky end to ligate an Even barcode. This terminal adaptor is primed by the 2P_barcoded oligo for final library amplification. There are 96 different terminal tags. The 96 different unique sequences are in column 4. The barcodes have been generated with a "stagger" such that each barcode is of variable length and then causes the sticky end to be at a variable position +/- 0-4 nts in the read. This is necessary to prevent a monotemplate the all sticky ends producing the same signal on the sequencer.

| 96Well Position | Adaptor Name | Sequence | Unique Barcode |
|---|---|---|---|
| A3 | NYBot3_Stg | CAGACGTGTGCTCTTCCGATCTATTGTTCAT (SEQ ID NO: 110) | ATTGTTCAT |
| A4 | NYBot4_Stg | CAGACGTGTGCTCTTCCGATCTCCACCGAAT (SEQ ID NO: 111) | CCACCGAAT |
| A5 | NYBot5_Stg | CAGACGTGTGCTCTTCCGATCTCATCAGTTGT (SEQ ID NO: 112) | CATCAGTTGT (SEQ ID NO: 205) |
| A6 | NYBot6_Stg | CAGACGTGTGCTCTTCCGATCTCCTTGAGAG (SEQ ID NO: 113) | CCTTGAGAG |
| A7 | NYBot7_Stg | CAGACGTGTGCTCTTCCGATCTATCAGGAAGT (SEQ ID NO: 114) | ATCAGGAAGT (SEQ ID NO: 206) |
| A8 | NYBot8_Stg | CAGACGTGTGCTCTTCCGATCTCGAAGTAGC (SEQ ID NO: 115) | CGAAGTAGC |
| A9 | NYBot9_Stg | CAGACGTGTGCTCTTCCGATCTTTAACCGACT (SEQ ID NO: 116) | TTAACCGACT (SEQ ID NO: 207) |
| A10 | NYBot10_Stg | CAGACGTGTGCTCTTCCGATCTGTTCATACAT (SEQ ID NO: 117) | GTTCATACAT (SEQ ID NO: 208) |
| A11 | NYBot11_Stg | CAGACGTGTGCTCTTCCGATCTGACGAAGAA (SEQ ID NO: 118) | GACGAAGAA |
| A12 | NYBot12_Stg | CAGACGTGTGCTCTTCCGATCTTGCCTCTGTG (SEQ ID NO: 119) | TGCCTCTGTG (SEQ ID NO: 209) |
| B1 | NYBot13_Stg | CAGACGTGTGCTCTTCCGATCTGAGATGGAT (SEQ ID NO: 120) | GAGATGGAT |
| B2 | NYBot14_Stg | CAGACGTGTGCTCTTCCGATCTACCATAGTG (SEQ ID NO: 121) | ACCATAGTG |
| B3 | NYBot15_Stg | CAGACGTGTGCTCTTCCGATCTGTACGAATGG (SEQ ID NO: 122) | GTACGAATGG (SEQ ID NO: 210) |
| B4 | NYBot16_Stg | CAGACGTGTGCTCTTCCGATCTAAGGAGACG (SEQ ID NO: 123) | AAGGAGACG |
| B5 | NYBot17_Stg | CAGACGTGTGCTCTTCCGATCTCCATTAACC (SEQ ID NO: 124) | CCATTAACC |
| B6 | NYBot18_Stg | CAGACGTGTGCTCTTCCGATCTTCTCCTTACG (SEQ ID NO: 125) | TCTCCTTACG (SEQ ID NO: 211) |
| B7 | NYBot19_Stg | CAGACGTGTGCTCTTCCGATCTATCTCACCA (SEQ ID NO: 126) | ATCTCACCA |

TABLE 2-continued

Bottom Strand of the Terminal Ligation Adaptor.
After annealing the "top" strand of the terminal adaptor with the
"bottom" strand of the terminal adaptor, the terminal adaptor
becomes a double stranded DNA oligo. The terminal adaptor is ligated
with a 5'phosphate to the tagged DNA through the AGTTGTC
sticky end on the top strand of the oligo. This set of terminal adaptors
is ligated to an Odd barcode, but another set of these terminal
adaptors can be designed with a different sticky end to ligate an Even
barcode. This terminal adaptor is primed by the 2P_barcoded oligo
for final library amplification. There are 96 different terminal tags.
The 96 different unique sequences are in column 4. The barcodes
have been generated with a "stagger" such that each
barcode is of variable length and then causes the sticky end to be
at a variable position +/- 0-4 nts in the read. This is
necessary to prevent a monotemplate the all sticky ends producing
the same signal on the sequencer.

| 96Well Position | Adaptor Name | Sequence | Unique Barcode |
|---|---|---|---|
| B8 | NYBot20_Stg | CAGACGTGTGCTCTTCCGATCTCGTAACTAAG (SEQ ID NO: 127) | CGTAACTAAG (SEQ ID NO: 212) |
| B9 | NYBot21_Stg | CAGACGTGTGCTCTTCCGATCTAGACTGGCTC (SEQ ID NO: 128) | AGACTGGCTC (SEQ ID NO: 213) |
| B10 | NYBot22_Stg | CAGACGTGTGCTCTTCCGATCTAATACCACTC (SEQ ID NO: 129) | AATACCACTC (SEQ ID NO: 214) |
| B11 | NYBot23_Stg | CAGACGTGTGCTCTTCCGATCTCTGCATTAT (SEQ ID NO: 130) | CTGCATTAT |
| B12 | NYBot24_Stg | CAGACGTGTGCTCTTCCGATCTTTGTAGCTG (SEQ ID NO: 131) | TTGTAGCTG |
| C1 | NYBot25_Stg | CAGACGTGTGCTCTTCCGATCTGCCGTTATC (SEQ ID NO: 132) | GCCGTTATC |
| C2 | NYBot26_Stg | CAGACGTGTGCTCTTCCGATCTGAATACAACC (SEQ ID NO: 133) | GAATACAACC (SEQ ID NO: 215) |
| C3 | NYBot27_Stg | CAGACGTGTGCTCTTCCGATCTAGGAGAATAC (SEQ ID NO: 134) | AGGAGAATAC (SEQ ID NO: 216) |
| C4 | NYBot28_Stg | CAGACGTGTGCTCTTCCGATCTCATCTAAGAC (SEQ ID NO: 135) | CATCTAAGAC (SEQ ID NO: 217) |
| C5 | NYBot29_Stg | CAGACGTGTGCTCTTCCGATCTTCAATACAA (SEQ ID NO: 136) | TCAATACAA |
| C6 | NYBot30_Stg | CAGACGTGTGCTCTTCCGATCTCGATAAGTTA (SEQ ID NO: 137) | CGATAAGTTA (SEQ ID NO: 218) |
| C7 | NYBot31_Stg | CAGACGTGTGCTCTTCCGATCTTTGACAAGT (SEQ ID NO: 138) | TTGACAAGT |
| C8 | NYBot32_Stg | CAGACGTGTGCTCTTCCGATCTTGTAGTTCTA (SEQ ID NO: 139) | TGTAGTTCTA (SEQ ID NO: 219) |
| C9 | NYBot33_Stg | CAGACGTGTGCTCTTCCGATCTGCCTATCCT (SEQ ID NO: 140) | GCCTATCCT |
| C10 | NYBot34_Stg | CAGACGTGTGCTCTTCCGATCTGGCGGCAATA (SEQ ID NO: 141) | GGCGGCAATA (SEQ ID NO: 220) |
| C11 | NYBot35_Stg | CAGACGTGTGCTCTTCCGATCTTTACGGCCAA (SEQ ID NO: 142) | TTACGGCCAA (SEQ ID NO: 221) |

TABLE 2-continued

Bottom Strand of the Terminal Ligation Adaptor.
After annealing the "top" strand of the terminal adaptor with the
"bottom" strand of the terminal adaptor, the terminal adaptor
becomes a double stranded DNA oligo. The terminal adaptor is ligated
with a 5'phosphate to the tagged DNA through the AGTTGTC
sticky end on the top strand of the oligo. This set of terminal adaptors
is ligated to an Odd barcode, but another set of these terminal
adaptors can be designed with a different sticky end to ligate an Even
barcode. This terminal adaptor is primed by the 2P_barcoded oligo
for final library amplification. There are 96 different terminal tags.
The 96 different unique sequences are in column 4. The barcodes
have been generated with a "stagger" such that each
barcode is of variable length and then causes the sticky end to be
at a variable position +/- 0-4 nts in the read. This is
necessary to prevent a monotemplate the all sticky ends producing
the same signal on the sequencer.

| 96Well Position | Adaptor Name | Sequence | Unique Barcode |
|---|---|---|---|
| C12 | NYBot36_Stg | CAGACGTGTGCTCTTCCGATCTGGAATCCTCA (SEQ ID NO: 143) | GGAATCCTCA (SEQ ID NO: 222) |
| D1 | NYBot37_Stg | CAGACGTGTGCTCTTCCGATCTCTCATGTTAA (SEQ ID NO: 144) | CTCATGTTAA (SEQ ID NO: 223) |
| D2 | NYBot38_Stg | CAGACGTGTGCTCTTCCGATCTGATTGATTA (SEQ ID NO: 145) | GATTGATTA |
| D3 | NYBot39_Stg | CAGACGTGTGCTCTTCCGATCTATATACTGA (SEQ ID NO: 146) | ATATACTGA |
| D4 | NYBot40_Stg | CAGACGTGTGCTCTTCCGATCTCGCTCCTTC (SEQ ID NO: 147) | CGCTCCTTC |
| D5 | NYBot41_Stg | CAGACGTGTGCTCTTCCGATCTAGTACGCGAT (SEQ ID NO: 148) | AGTACGCGAT (SEQ ID NO: 224) |
| D6 | NYBot42_Stg | CAGACGTGTGCTCTTCCGATCTCACGGATCTG (SEQ ID NO: 149) | CACGGATCTG (SEQ ID NO: 225) |
| D7 | NYBot43_Stg | CAGACGTGTGCTCTTCCGATCTTCCTGGTATC (SEQ ID NO: 150) | TCCTGGTATC (SEQ ID NO: 226) |
| D8 | NYBot44_Stg | CAGACGTGTGCTCTTCCGATCTAGGTCTTCG (SEQ ID NO: 151) | AGGTCTTCG |
| D9 | NYBot45_Stg | CAGACGTGTGCTCTTCCGATCTTTCCAAGGCC (SEQ ID NO: 152) | TTCCAAGGCC (SEQ ID NO: 227) |
| D10 | NYBot46_Stg | CAGACGTGTGCTCTTCCGATCTGTAGCATCC (SEQ ID NO: 153) | GTAGCATCC |
| D11 | NYBot47_Stg | CAGACGTGTGCTCTTCCGATCTCCTACGGCC (SEQ ID NO: 154) | CCTACGGCC |
| D12 | NYBot48_Stg | CAGACGTGTGCTCTTCCGATCTTACGCTTGA (SEQ ID NO: 155) | TACGCTTGA |
| E1 | NYBot49_Stg | CAGACGTGTGCTCTTCCGATCTCTTGGCGACCAT (SEQ ID NO: 156) | CTTGGCGACCAT (SEQ ID NO: 228) |
| E2 | NYBot50_Stg | CAGACGTGTGCTCTTCCGATCTCTTAAACCGGCA (SEQ ID NO: 157) | CTTAAACCGGCA (SEQ ID NO: 229) |
| E3 | NYBot51_Stg | CAGACGTGTGCTCTTCCGATCTCTCTGTTGTTGC (SEQ ID NO: 158) | CTCTGTTGTTGC (SEQ ID NO: 230) |

TABLE 2-continued

Bottom Strand of the Terminal Ligation Adaptor.
After annealing the "top" strand of the terminal adaptor with the
"bottom" strand of the terminal adaptor, the terminal adaptor
becomes a double stranded DNA oligo. The terminal adaptor is ligated
with a 5'phosphate to the tagged DNA through the AGTTGTC
sticky end on the top strand of the oligo. This set of terminal adaptors
is ligated to an Odd barcode, but another set of these terminal
adaptors can be designed with a different sticky end to ligate an Even
barcode. This terminal adaptor is primed by the 2P_barcoded oligo
for final library amplification. There are 96 different terminal tags.
The 96 different unique sequences are in column 4. The barcodes
have been generated with a "stagger" such that each
barcode is of variable length and then causes the sticky end to be
at a variable position +/- 0-4 nts in the read. This is
necessary to prevent a monotemplate the all sticky ends producing
the same signal on the sequencer.

| 96Well Position | Adaptor Name | Sequence | Unique Barcode |
|---|---|---|---|
| E4 | NYBot52_Stg | CAGACGTGTGCTCTTCCGATCTCTCTGTTGTTTG (SEQ ID NO: 159) | CTCTGTTGTTTG (SEQ ID NO: 231) |
| E5 | NYBot53_Stg | CAGACGTGTGCTCTTCCGATCTCGTTTCACATAT (SEQ ID NO: 160) | CGTTTCACATAT (SEQ ID NO: 232) |
| E6 | NYBot54_Stg | CAGACGTGTGCTCTTCCGATCTCGCTTCTAAGCA (SEQ ID NO: 161) | CGCTTCTAAGCA (SEQ ID NO: 233) |
| E7 | NYBot55_Stg | CAGACGTGTGCTCTTCCGATCTCCGACTGCTAGC (SEQ ID NO: 162) | CCGACTGCTAGC (SEQ ID NO: 234) |
| E8 | NYBot56_Stg | CAGACGTGTGCTCTTCCGATCTCATCCAGTCATG (SEQ ID NO: 163) | CATCCAGTCATG (SEQ ID NO: 235) |
| E9 | NYBot57_Stg | CAGACGTGTGCTCTTCCGATCTCAGCTCCGAAGT (SEQ ID NO: 164) | CAGCTCCGAAGT (SEQ ID NO: 236) |
| E10 | NYBot58_Stg | CAGACGTGTGCTCTTCCGATCTCAACAACGTTAA (SEQ ID NO: 165) | CAACAACGTTAA (SEQ ID NO: 237) |
| E11 | NYBot59_Stg | CAGACGTGTGCTCTTCCGATCTCATTAGACTAGC (SEQ ID NO: 166) | CATTAGACTAGC (SEQ ID NO: 238) |
| E12 | NYBot60_Stg | CAGACGTGTGCTCTTCCGATCTCCAGCACTTGCG (SEQ ID NO: 167) | CCAGCACTTGCG (SEQ ID NO: 239) |
| F1 | NYBot61_Stg | CAGACGTGTGCTCTTCCGATCTGTGATGTACGTT (SEQ ID NO: 168) | GTGATGTACGTT (SEQ ID NO: 240) |
| F2 | NYBot62_Stg | CAGACGTGTGCTCTTCCGATCTGTAGTCGTCCCA (SEQ ID NO: 169) | GTAGTCGTCCCA (SEQ ID NO: 241) |
| F3 | NYBot63_Stg | CAGACGTGTGCTCTTCCGATCTGGTCCAACTCGC (SEQ ID NO: 170) | GGTCCAACTCGC (SEQ ID NO: 242) |
| F4 | NYBot64_Stg | CAGACGTGTGCTCTTCCGATCTGGCGCCATACAG (SEQ ID NO: 171) | GGCGCCATACAG (SEQ ID NO: 243) |
| F5 | NYBot65_Stg | CAGACGTGTGCTCTTCCGATCTGGAGAGCACCCT (SEQ ID NO: 172) | GGAGAGCACCCT (SEQ ID NO: 244) |
| F6 | NYBot66_Stg | CAGACGTGTGCTCTTCCGATCTGCTCTGCAATGA (SEQ ID NO: 173) | GCTCTGCAATGA (SEQ ID NO: 245) |

TABLE 2-continued

Bottom Strand of the Terminal Ligation Adaptor.
After annealing the "top" strand of the terminal adaptor with the
"bottom" strand of the terminal adaptor, the terminal adaptor
becomes a double stranded DNA oligo. The terminal adaptor is ligated
with a 5'phosphate to the tagged DNA through the AGTTGTC
sticky end on the top strand of the oligo. This set of terminal adaptors
is ligated to an Odd barcode, but another set of these terminal
adaptors can be designed with a different sticky end to ligate an Even
barcode. This terminal adaptor is primed by the 2P_barcoded oligo
for final library amplification. There are 96 different terminal tags.
The 96 different unique sequences are in column 4. The barcodes
have been generated with a "stagger" such that each
barcode is of variable length and then causes the sticky end to be
at a variable position +/- 0-4 nts in the read. This is
necessary to prevent a monotemplate the all sticky ends producing
the same signal on the sequencer.

| 96Well Position | Adaptor Name | Sequence | Unique Barcode |
|---|---|---|---|
| F7 | NYBot67_Stg | CAGACGTGTGCTCTTCCGATCTGCGAACGTTTCC (SEQ ID NO: 174) | GCGAACGTTTCC (SEQ ID NO: 246) |
| F8 | NYBot68_Stg | CAGACGTGTGCTCTTCCGATCTGCATCGAGTCGG (SEQ ID NO: 175) | GCATCGAGTCGG (SEQ ID NO: 247) |
| F9 | NYBot69_Stg | CAGACGTGTGCTCTTCCGATCTGATGACGTAGAT (SEQ ID NO: 176) | GATGACGTAGAT (SEQ ID NO: 248) |
| F10 | NYBot70_Stg | CAGACGTGTGCTCTTCCGATCTGAGCAGAACATA (SEQ ID NO: 177) | GAGCAGAACATA (SEQ ID NO: 249) |
| F11 | NYBot71_Stg | CAGACGTGTGCTCTTCCGATCTGACACCCCGTGC (SEQ ID NO: 178) | GACACCCCGTGC (SEQ ID NO: 250) |
| F12 | NYBot72_Stg | CAGACGTGTGCTCTTCCGATCTGTTGTTCGACCG (SEQ ID NO: 179) | GTTGTTCGACCG (SEQ ID NO: 251) |
| G1 | NYBot73_Stg | CAGACGTGTGCTCTTCCGATCTTTTATATGTGT (SEQ ID NO: 180) | TTTATATGTGT (SEQ ID NO: 252) |
| G2 | NYBot74_Stg | CAGACGTGTGCTCTTCCGATCTTTGACATCACA (SEQ ID NO: 181) | TTGACATCACA (SEQ ID NO: 253) |
| G3 | NYBot75_Stg | CAGACGTGTGCTCTTCCGATCTTTATCCCCCAC (SEQ ID NO: 182) | TTATCCCCCAC (SEQ ID NO: 254) |
| G4 | NYBot76_Stg | CAGACGTGTGCTCTTCCGATCTTGTGACCAGTG (SEQ ID NO: 183) | TGTGACCAGTG (SEQ ID NO: 255) |
| G5 | NYBot77_Stg | CAGACGTGTGCTCTTCCGATCTTGGATGCTCCT (SEQ ID NO: 184) | TGGATGCTCCT (SEQ ID NO: 256) |
| G6 | NYBot78_Stg | CAGACGTGTGCTCTTCCGATCTTGAGTAATTAA (SEQ ID NO: 185) | TGATAATTAA (SEQ ID NO: 257) |
| G7 | NYBot79_Stg | CAGACGTGTGCTCTTCCGATCTTCTCATATTGG (SEQ ID NO: 186) | TCTCATATTGG (SEQ ID NO: 258) |
| G8 | NYBot80_Stg | CAGACGTGTGCTCTTCCGATCTTCGAACATATG (SEQ ID NO: 187) | TCGAACATATG (SEQ ID NO: 259) |
| G9 | NYBot81_Stg | CAGACGTGTGCTCTTCCGATCTTCATACTACAT (SEQ ID NO: 188) | TCATACTACAT (SEQ ID NO: 260) |

TABLE 2-continued

Bottom Strand of the Terminal Ligation Adaptor.
After annealing the "top" strand of the terminal adaptor with the
"bottom" strand of the terminal adaptor, the terminal adaptor
becomes a double stranded DNA oligo. The terminal adaptor is ligated
with a 5'phosphate to the tagged DNA through the AGTTGTC
sticky end on the top strand of the oligo. This set of terminal adaptors
is ligated to an Odd barcode, but another set of these terminal
adaptors can be designed with a different sticky end to ligate an Even
barcode. This terminal adaptor is primed by the 2P_barcoded oligo
for final library amplification. There are 96 different terminal tags.
The 96 different unique sequences are in column 4. The barcodes
have been generated with a "stagger" such that each
barcode is of variable length and then causes the sticky end to be
at a variable position +/- 0-4 nts in the read. This is
necessary to prevent a monotemplate the all sticky ends producing
the same signal on the sequencer.

| 96Well Position | Adaptor Name | Sequence | Unique Barcode |
|---|---|---|---|
| G10 | NYBot82_Stg | CAGACGTGTGCTCTTCCGATCTTATCGACGTCA (SEQ ID NO: 189) | TATCGACGTCA (SEQ ID NO: 261) |
| G11 | NYBot83_Stg | CAGACGTGTGCTCTTCCGATCTTAGACCAGGGC (SEQ ID NO: 190) | TAGACCAGGGC (SEQ ID NO: 262) |
| G12 | NYBot84_Stg | CAGACGTGTGCTCTTCCGATCTTAATGTGGATG (SEQ ID NO: 191) | TAATGTGGATG (SEQ ID NO: 263) |
| H1 | NYBot85_Stg | CAGACGTGTGCTCTTCCGATCTATTAGTATGTT (SEQ ID NO: 192) | ATTAGTATGTT (SEQ ID NO: 264) |
| H2 | NYBot86_Stg | CAGACGTGTGCTCTTCCGATCTATCCTATCCAA (SEQ ID NO: 193) | ATCCTATCCAA (SEQ ID NO: 265) |
| H3 | NYBot87_Stg | CAGACGTGTGCTCTTCCGATCTATTACACGCCC (SEQ ID NO: 194) | ATTACACGCCC (SEQ ID NO: 266) |
| H4 | NYBot88_Stg | CAGACGTGTGCTCTTCCGATCTAGTTGAAATAG (SEQ ID NO: 195) | AGTTGAAATAG (SEQ ID NO: 267) |
| H5 | NYBot89_Stg | CAGACGTGTGCTCTTCCGATCTAGGCCCTTTGT (SEQ ID NO: 196) | AGGCCCTTTGT (SEQ ID NO: 268) |
| H6 | NYBot90_Stg | CAGACGTGTGCTCTTCCGATCTAGATGAGCGTA (SEQ ID NO: 197) | AGATGAGCGTA (SEQ ID NO: 269) |
| H7 | NYBot91_Stg | CAGACGTGTGCTCTTCCGATCTACTCTTCTTCC (SEQ ID NO: 198) | ACTCTTCTTCC (SEQ ID NO: 270) |
| H8 | NYBot92_Stg | CAGACGTGTGCTCTTCCGATCTACCATTATTGG (SEQ ID NO: 199) | ACCATTATTGG (SEQ ID NO: 271) |
| H9 | NYBot93_Stg | CAGACGTGTGCTCTTCCGATCTACAGACTCAGT (SEQ ID NO: 200) | ACAGACTCAGT (SEQ ID NO: 272) |
| H10 | NYBot94_Stg | CAGACGTGTGCTCTTCCGATCTAATTGTCTGTA (SEQ ID NO: 201) | AATTGTCTGTA (SEQ ID NO: 273) |
| H11 | NYBot95_Stg | CAGACGTGTGCTCTTCCGATCTAAGGCCTCACC (SEQ ID NO: 202) | AAGGCCTCACC (SEQ ID NO: 274) |

TABLE 2-continued

Bottom Strand of the Terminal Ligation Adaptor.
After annealing the "top" strand of the terminal adaptor with the
"bottom" strand of the terminal adaptor, the terminal adaptor
becomes a double stranded DNA oligo. The terminal adaptor is ligated
with a 5'phosphate to the tagged DNA through the AGTTGTC
sticky end on the top strand of the oligo. This set of terminal adaptors
is ligated to an Odd barcode, but another set of these terminal
adaptors can be designed with a different sticky end to ligate an Even
barcode. This terminal adaptor is primed by the 2P_barcoded oligo
for final library amplification. There are 96 different terminal tags.
The 96 different unique sequences are in column 4. The barcodes
have been generated with a "stagger" such that each
barcode is of variable length and then causes the sticky end to be
at a variable position +/- 0-4 nts in the read. This is
necessary to prevent a monotemplate the all sticky ends producing
the same signal on the sequencer.

| 96Well Position | Adaptor Name | Sequence | Unique Barcode |
|---|---|---|---|
| H12 | NYBot96_Stg | CAGACGTGTGCTCTTCCGATCTAACGAACAGAG (SEQ ID NO: 203) | AACGAACAGAG (SEQ ID NO: 275) |

TABLE 3

Phosphorylated Bottom Strand of the DPM adaptor.
The bottom and top strands of the DPM adaptor are annealed
to make a double-stranded DNA oligo. This is the first oligo
that is ligated to the DNA after End repair and dA-tailing. This
version of DPM bottom has a 5'phosphate (5Phos) and
sticky-end for ligation of the Odd tag. Another version of this
plate has been made without a 5'phosphate for
the RNA-DNA protocol.
DPMbotPlate6_P

| 96Well Position | Adaptor Name | Sequence | Unique Barcode |
|---|---|---|---|
| A1 | DPM6bot1 | /5Phos/TGACTTGTCATGTCTTCCGATCTTGGGTGTTTT (SEQ ID NO: 276) | TGGGTGTTTT (SEQ ID NO: 372) |
| B1 | DPM6bot2 | /5Phos/TGACTTGTCATGTCTTCCGATCTTCGAGTCTTT (SEQ ID NO: 277) | TCGAGTCTTT (SEQ ID NO: 373) |
| C1 | DPM6bot3 | /5Phos/TGACTTGTCATGTCTTCCGATCTGCAGATTGTT (SEQ ID NO: 278) | GCAGATTGTT (SEQ ID NO: 374) |
| D1 | DPM6bot4 | /5Phos/TGACTTGTCATGTCTTCCGATCTTCTATGCGTT (SEQ ID NO: 279) | TCTATGCGTT (SEQ ID NO: 375) |
| E1 | DPM6bot5 | /5Phos/TGACTTGTCATGTCTTCCGATCTGGACTTTCTT (SEQ ID NO: 280) | GGACTTTCTT (SEQ ID NO: 376) |
| F1 | DPM6bot6 | /5Phos/TGACTTGTCATGTCTTCCGATCTGCCGTGCCTT (SEQ ID NO: 281) | GCCGTGCCTT (SEQ ID NO: 377) |
| G1 | DPM6bot7 | /5Phos/TGACTTGTCATGTCTTCCGATCTAGTGTTTATT (SEQ ID NO: 282) | AGTGTTTATT (SEQ ID NO: 378) |
| H1 | DPM6bot8 | /5Phos/TGACTTGTCATGTCTTCCGATCTGACTGGCATT (SEQ ID NO: 283) | GACTGGCATT (SEQ ID NO: 379) |
| A2 | DPM6bot9 | /5Phos/TGACTTGTCATGTCTTCCGATCTTGACATGTTT (SEQ ID NO: 284) | TGACATGTTT (SEQ ID NO: 380) |
| B2 | DPM6bot10 | /5Phos/TGACTTGTCATGTCTTCCGATCTCCCTTTATTT (SEQ ID NO: 285) | CCCTTTATTT (SEQ ID NO: 381) |
| C2 | DPM6bot11 | /5Phos/TGACTTGTCATGTCTTCCGATCTTTGGTTGGTT (SEQ ID NO: 286) | TTGGTTGGTT (SEQ ID NO: 382) |
| D2 | DPM6bot12 | /5Phos/TGACTTGTCATGTCTTCCGATCTATAAGTAGTT (SEQ ID NO: 287) | ATAAGTAGTT (SEQ ID NO: 383) |

TABLE 3-continued

Phosphorylated Bottom Strand of the DPM adaptor.
The bottom and top strands of the DPM adaptor are annealed
to make a double-stranded DNA oligo. This is the first oligo
that is ligated to the DNA after End repair and dA-tailing. This
version of DPM bottom has a 5'phosphate (5Phos) and
sticky-end for ligation of the Odd tag. Another version of this
plate has been made without a 5'phosphate for
the RNA-DNA protocol.
DPMbotPlate6_P

| 96Well Position | Adaptor Name | Sequence | Unique Barcode |
|---|---|---|---|
| E2 | DPM6bot13 | /5Phos/TGACTTGTCATGTCTTCCGATCTCCTCTTGCTT (SEQ ID NO: 288) | CCTCTTGCTT (SEQ ID NO: 384) |
| F2 | DPM6bot14 | /5Phos/TGACTTGTCATGTCTTCCGATCTAAGCTTACTT (SEQ ID NO: 289) | AAGCTTACTT (SEQ ID NO: 385) |
| G2 | DPM6bot15 | /5Phos/TGACTTGTCATGTCTTCCGATCTGGCATTGATT (SEQ ID NO: 290) | GGCATTGATT (SEQ ID NO: 386) |
| H2 | DPM6bot16 | /5Phos/TGACTTGTCATGTCTTCCGATCTTGCCTGAATT (SEQ ID NO: 291) | TGCCTGAATT (SEQ ID NO: 387) |
| A3 | DPM6bot17 | /5Phos/TGACTTGTCATGTCTTCCGATCTGCGCGGTTTT (SEQ ID NO: 292) | GCGCGGTTTT (SEQ ID NO: 388) |
| B3 | DPM6bot18 | /5Phos/TGACTTGTCATGTCTTCCGATCTCAGCATCTTT (SEQ ID NO: 293) | CAGCATCTTT (SEQ ID NO: 389) |
| C3 | DPM6bot19 | /5Phos/TGACTTGTCATGTCTTCCGATCTTGCAATTGTT (SEQ ID NO: 294) | TGCAATTGTT (SEQ ID NO: 390) |
| D3 | DPM6bot20 | /5Phos/TGACTTGTCATGTCTTCCGATCTGGCCAGCGTT (SEQ ID NO: 295) | GGCCAGCGTT (SEQ ID NO: 391) |
| E3 | DPM6bot21 | /5Phos/TGACTTGTCATGTCTTCCGATCTATCCATTCTT (SEQ ID NO: 296) | ATCCATTCTT (SEQ ID NO: 392) |
| F3 | DPM6bot22 | /5Phos/TGACTTGTCATGTCTTCCGATCTAATCTGCCTT (SEQ ID NO: 297) | AATCTGCCTT (SEQ ID NO: 393) |
| G3 | DPM6bot23 | /5Phos/TGACTTGTCATGTCTTCCGATCTCCGATTTATT (SEQ ID NO: 298) | CCGATTTATT (SEQ ID NO: 394) |
| H3 | DPM6bot24 | /5Phos/TGACTTGTCATGTCTTCCGATCTCGGGGCATT (SEQ ID NO: 299) | CGGGGCATT (SEQ ID NO: 395) |
| A4 | DPM6bot25 | /5Phos/TGACTTGTCATGTCTTCCGATCTCGCCGGGTTT (SEQ ID NO: 300) | CGCCGGGTTT (SEQ ID NO: 396) |
| B4 | DPM6bot26 | /5Phos/TGACTTGTCATGTCTTCCGATCTAGGTCTATTT (SEQ ID NO: 301) | AGGTCTATTT (SEQ ID NO: 397) |
| C4 | DPM6bot27 | /5Phos/TGACTTGTCATGTCTTCCGATCTGACGCTGGTT (SEQ ID NO: 302) | GACGCTGGTT (SEQ ID NO: 398) |
| D4 | DPM6bot28 | /5Phos/TGACTTGTCATGTCTTCCGATCTCATAATAGTT (SEQ ID NO: 303) | CATAATAGTT (SEQ ID NO: 399) |
| E4 | DPM6bot29 | /5Phos/TGACTTGTCATGTCTTCCGATCTATGTGGGCTT (SEQ ID NO: 304) | ATGTGGGCTT (SEQ ID NO: 400) |
| F4 | DPM6bot30 | /5Phos/TGACTTGTCATGTCTTCCGATCTGCGACTACTT (SEQ ID NO: 305) | GCGACTACTT (SEQ ID NO: 401) |
| G4 | DPM6bot31 | /5Phos/TGACTTGTCATGTCTTCCGATCTGTACTGGATT (SEQ ID NO: 306) | GTACTGGATT (SEQ ID NO: 402) |
| H4 | DPM6bot32 | /5Phos/TGACTTGTCATGTCTTCCGATCTAAAGCGAATT (SEQ ID NO: 307) | AAAGCGAATT (SEQ ID NO: 403) |
| A5 | DPM6bot33 | /5Phos/TGACTTGTCATGTCTTCCGATCTCTGTCGTTTT (SEQ ID NO: 308) | CTGTCGTTTT (SEQ ID NO: 404) |
| B5 | DPM6bot34 | /5Phos/TGACTTGTCATGTCTTCCGATCTAGAAGGCTTT (SEQ ID NO: 309) | AGAAGGCTTT (SEQ ID NO: 405) |

TABLE 3-continued

Phosphorylated Bottom Strand of the DPM adaptor.
The bottom and top strands of the DPM adaptor are annealed
to make a double-stranded DNA oligo. This is the first oligo
that is ligated to the DNA after End repair and dA-tailing. This
version of DPM bottom has a 5'phosphate (5Phos) and
sticky-end for ligation of the Odd tag. Another version of this
plate has been made without a 5'phosphate for
the RNA-DNA protocol.
DPMbotPlate6_P

| 96Well Position | Adaptor Name | Sequence | Unique Barcode |
|---|---|---|---|
| C5 | DPM6bot35 | /5Phos/TGACTTGTCATGTCTTCCGATCTTTACAGTGTT (SEQ ID NO: 310) | TTACAGTGTT (SEQ ID NO: 406) |
| D5 | DPM6bot36 | /5Phos/TGACTTGTCATGTCTTCCGATCTCTGATCCGTT (SEQ ID NO: 311) | CTGATCCGTT (SEQ ID NO: 407) |
| E5 | DPM6bot37 | /5Phos/TGACTTGTCATGTCTTCCGATCTCCTAGGTCTT (SEQ ID NO: 312) | CCTAGGTCTT (SEQ ID NO: 408) |
| F5 | DPM6bot38 | /5Phos/TGACTTGTCATGTCTTCCGATCTCTACCGCCTT (SEQ ID NO: 313) | CTACCGCCTT (SEQ ID NO: 409) |
| G5 | DPM6bot39 | /5Phos/TGACTTGTCATGTCTTCCGATCTTACGGTTATT (SEQ ID NO: 314) | TACGGTTATT (SEQ ID NO: 410) |
| H5 | DPM6bot40 | /5Phos/TGACTTGTCATGTCTTCCGATCTTTTGCGCATT (SEQ ID NO: 315) | TTTGCGCATT (SEQ ID NO: 411) |
| A6 | DPM6bot41 | /5Phos/TGACTTGTCATGTCTTCCGATCTGAAGAGGTTT (SEQ ID NO: 316) | GAAGAGGTTT (SEQ ID NO: 412) |
| B6 | DPM6bot42 | /5Phos/TGACTTGTCATGTCTTCCGATCTGGTTTGATTT (SEQ ID NO: 317) | GGTTTGATTT (SEQ ID NO: 413) |
| C6 | DPM6bot43 | /5Phos/TGACTTGTCATGTCTTCCGATCTACGAATGGTT (SEQ ID NO: 318) | ACGAATGGTT (SEQ ID NO: 414) |
| D6 | DPM6bot44 | /5Phos/TGACTTGTCATGTCTTCCGATCTGTTGGGAGTT (SEQ ID NO: 319) | GTTGGGAGTT (SEQ ID NO: 415) |
| E6 | DPM6bot45 | /5Phos/TGACTTGTCATGTCTTCCGATCTTCGCCGGCTT (SEQ ID NO: 320) | TCGCCGGCTT (SEQ ID NO: 416) |
| F6 | DPM6bot46 | /5Phos/TGACTTGTCATGTCTTCCGATCTCCTTCCACTT (SEQ ID NO: 321) | CCTTCCACTT (SEQ ID NO: 417) |
| G6 | DPM6bot47 | /5Phos/TGACTTGTCATGTCTTCCGATCTCCCGCGGATT (SEQ ID NO: 322) | CCCGCGGATT (SEQ ID NO: 418) |
| H6 | DPM6bot48 | /5Phos/TGACTTGTCATGTCTTCCGATCTGCTAAGAATT (SEQ ID NO: 323) | GCTAAGAATT (SEQ ID NO: 419) |
| A7 | DPM6bot49 | /5Phos/TGACTTGTCATGTCTTCCGATCTAAGAAGTTTT (SEQ ID NO: 324) | AAGAAGTTTT (SEQ ID NO: 420) |
| B7 | DPM6bot50 | /5Phos/TGACTTGTCATGTCTTCCGATCTGAACTCCTTT (SEQ ID NO: 325) | GAACTCCTTT (SEQ ID NO: 421) |
| C7 | DPM6bot51 | /5Phos/TGACTTGTCATGTCTTCCGATCTGTCTTCTGTT (SEQ ID NO: 326) | GTCTTCTGTT (SEQ ID NO: 422) |
| D7 | DPM6bot52 | /5Phos/TGACTTGTCATGTCTTCCGATCTTGGCCCCGTT (SEQ ID NO: 327) | TGGCCCCGTT (SEQ ID NO: 423) |
| E7 | DPM6bot53 | /5Phos/TGACTTGTCATGTCTTCCGATCTTTGAGCTCTT (SEQ ID NO: 328) | TTGAGCTCTT (SEQ ID NO: 424) |
| F7 | DPM6bot54 | /5Phos/TGACTTGTCATGTCTTCCGATCTTGTTAGCCTT (SEQ ID NO: 329) | TGTTAGCCTT (SEQ ID NO: 425) |
| G7 | DPM6bot55 | /5Phos/TGACTTGTCATGTCTTCCGATCTAAACGCTATT (SEQ ID NO: 330) | AAACGCTATT (SEQ ID NO: 426) |
| H7 | DPM6bot56 | /5Phos/TGACTTGTCATGTCTTCCGATCTCCCCGCCATT (SEQ ID NO: 331) | CCCCGCCATT (SEQ ID NO: 427) |

TABLE 3-continued

Phosphorylated Bottom Strand of the DPM adaptor.
The bottom and top strands of the DPM adaptor are annealed
to make a double-stranded DNA oligo. This is the first oligo
that is ligated to the DNA after End repair and dA-tailing. This
version of DPM bottom has a 5'phosphate (5Phos) and
sticky-end for ligation of the Odd tag. Another version of this
plate has been made without a 5'phosphate for
the RNA-DNA protocol.
DPMbotPlate6_P

| 96Well Position | Adaptor Name | Sequence | Unique Barcode |
|---|---|---|---|
| A8 | DPM6bot57 | /5Phos/TGACTTGTCATGTCTTCCGATCTTTCAAGGTTT (SEQ ID NO: 332) | TTCAAGGTTT (SEQ ID NO: 428) |
| B8 | DPM6bot58 | /5Phos/TGACTTGTCATGTCTTCCGATCTCTTCTCATTT (SEQ ID NO: 333) | CTTCTCATTT (SEQ ID NO: 429) |
| C8 | DPM6bot59 | /5Phos/TGACTTGTCATGTCTTCCGATCTGCATCGGGTT (SEQ ID NO: 334) | GCATCGGGTT (SEQ ID NO: 430) |
| D8 | DPM6bot60 | /5Phos/TGACTTGTCATGTCTTCCGATCTTACTCGAGTT (SEQ ID NO: 335) | TACTCGAGTT (SEQ ID NO: 431) |
| E8 | DPM6bot61 | /5Phos/TGACTTGTCATGTCTTCCGATCTCACTAGGCTT (SEQ ID NO: 336) | CACTAGGCTT (SEQ ID NO: 432) |
| F8 | DPM6bot62 | /5Phos/TGACTTGTCATGTCTTCCGATCTTAACACACTT (SEQ ID NO: 337) | TAACACACTT (SEQ ID NO: 433) |
| G8 | DPM6bot63 | /5Phos/TGACTTGTCATGTCTTCCGATCTCGATTCGATT (SEQ ID NO: 338) | CGATTCGATT (SEQ ID NO: 434) |
| H8 | DPM6bot64 | /5Phos/TGACTTGTCATGTCTTCCGATCTGGGCGCAATT (SEQ ID NO: 339) | GGGCGCAATT (SEQ ID NO: 435) |
| A9 | DPM6bot65 | /5Phos/TGACTTGTCATGTCTTCCGATCTTCCCTCTTTT (SEQ ID NO: 340) | TCCCTCTTTT (SEQ ID NO: 436) |
| B9 | DPM6bot66 | /5Phos/TGACTTGTCATGTCTTCCGATCTACTTGCCTTT (SEQ ID NO: 341) | ACTTGCCTTT (SEQ ID NO: 437) |
| C9 | DPM6bot67 | /5Phos/TGACTTGTCATGTCTTCCGATCTAGCGCCTGTT (SEQ ID NO: 342) | AGCGCCTGTT (SEQ ID NO: 438) |
| D9 | DPM6bot68 | /5Phos/TGACTTGTCATGTCTTCCGATCTACGTTACGTT (SEQ ID NO: 343) | ACGTTACGTT (SEQ ID NO: 439) |
| E9 | DPM6bot69 | /5Phos/TGACTTGTCATGTCTTCCGATCTGACAACTCTT (SEQ ID NO: 344) | GACAACTCTT (SEQ ID NO: 440) |
| F9 | DPM6bot70 | /5Phos/TGACTTGTCATGTCTTCCGATCTATAGTCCCTT (SEQ ID NO: 345) | ATAGTCCCTT (SEQ ID NO: 441) |
| G9 | DPM6bot71 | /5Phos/TGACTTGTCATGTCTTCCGATCTACCAGATATT (SEQ ID NO: 346) | ACCAGATATT (SEQ ID NO: 442) |
| H9 | DPM6bot72 | /5Phos/TGACTTGTCATGTCTTCCGATCTAGTACCCATT (SEQ ID NO: 347) | AGTACCCATT (SEQ ID NO: 443) |
| A10 | DPM6bot73 | /5Phos/TGACTTGTCATGTCTTCCGATCTTATGCCGTTT (SEQ ID NO: 348) | TATGCCGTTT (SEQ ID NO: 444) |
| B10 | DPM6bot74 | /5Phos/TGACTTGTCATGTCTTCCGATCTTGATGCATTT (SEQ ID NO: 349) | TGATGCATTT (SEQ ID NO: 445) |
| C10 | DPM6bot75 | /5Phos/TGACTTGTCATGTCTTCCGATCTTAAAGAGGTT (SEQ ID NO: 350) | TAAAGAGGTT (SEQ ID NO: 446) |
| D10 | DPM6bot76 | /5Phos/TGACTTGTCATGTCTTCCGATCTACGGGCAGTT (SEQ ID NO: 351) | ACGGGCAGTT (SEQ ID NO: 447) |
| E10 | DPM6bot77 | /5Phos/TGACTTGTCATGTCTTCCGATCTTGTATCGCTT (SEQ ID NO: 352) | TGTATCGCTT (SEQ ID NO: 448) |
| F10 | DPM6bot78 | /5Phos/TGACTTGTCATGTCTTCCGATCTCAAATAACTT (SEQ ID NO: 353) | CAAATAACTT (SEQ ID NO: 449) |

TABLE 3-continued

Phosphorylated Bottom Strand of the DPM adaptor.
The bottom and top strands of the DPM adaptor are annealed
to make a double-stranded DNA oligo. This is the first oligo
that is ligated to the DNA after End repair and dA-tailing. This
version of DPM bottom has a 5'phosphate (5Phos) and
sticky-end for ligation of the Odd tag. Another version of this
plate has been made without a 5'phosphate for
the RNA-DNA protocol.
DPMbotPlate6 P

| 96Well Position | Adaptor Name | Sequence | Unique Barcode |
|---|---|---|---|
| G10 | DPM6bot79 | /5Phos/TGACTTGTCATGTCTTCCGATCTTTTCGCGATT (SEQ ID NO: 354) | TTTCGCGATT (SEQ ID NO: 450) |
| H10 | DPM6bot80 | /5Phos/TGACTTGTCATGTCTTCCGATCTTCAACCAATT (SEQ ID NO: 355) | TCAACCAATT (SEQ ID NO: 451) |
| A11 | DPM6bot81 | /5Phos/TGACTTGTCATGTCTTCCGATCTGTATGATTTT (SEQ ID NO: 356) | GTATGATTTT (SEQ ID NO: 452) |
| B11 | DPM6bot82 | /5Phos/TGACTTGTCATGTCTTCCGATCTAACCCACTTT (SEQ ID NO: 357) | AACCCACTTT (SEQ ID NO: 453) |
| C11 | DPM6bot83 | /5Phos/TGACTTGTCATGTCTTCCGATCTCATTTATGTT (SEQ ID NO: 358) | CATTTATGTT (SEQ ID NO: 454) |
| D11 | DPM6bot84 | /5Phos/TGACTTGTCATGTCTTCCGATCTCGCTCACGTT (SEQ ID NO: 359) | CGCTCACGTT (SEQ ID NO: 455) |
| E11 | DPM6bot85 | /5Phos/TGACTTGTCATGTCTTCCGATCTTGTCGATCTT (SEQ ID NO: 360) | TGTCGATCTT (SEQ ID NO: 456) |
| F11 | DPM6bot86 | /5Phos/TGACTTGTCATGTCTTCCGATCTGGATCCCCTT (SEQ ID NO: 361) | GGATCCCCTT (SEQ ID NO: 457) |
| G11 | DPM6bot87 | /5Phos/TGACTTGTCATGTCTTCCGATCTGAAACATATT (SEQ ID NO: 362) | GAAACATATT (SEQ ID NO: 458) |
| H11 | DPM6bot88 | /5Phos/TGACTTGTCATGTCTTCCGATCTTCACAACATT (SEQ ID NO: 363) | TCACAACATT (SEQ ID NO: 459) |
| A12 | DPM6bot89 | /5Phos/TGACTTGTCATGTCTTCCGATCTATTATAGTTT (SEQ ID NO: 364) | ATTATAGTTT (SEQ ID NO: 460) |
| B12 | DPM6bot90 | /5Phos/TGACTTGTCATGTCTTCCGATCTCGAGCAATTT (SEQ ID NO: 365) | CGAGCAATTT (SEQ ID NO: 461) |
| C12 | DPM6bot91 | /5Phos/TGACTTGTCATGTCTTCCGATCTGTGCCAGGTT (SEQ ID NO: 366) | GTGCCAGGTT (SEQ ID NO: 462) |
| D12 | DPM6bot92 | /5Phos/TGACTTGTCATGTCTTCCGATCTGAGTACAGTT (SEQ ID NO: 367) | GAGTACAGTT (SEQ ID NO: 463) |
| E12 | DPM6bot93 | /5Phos/TGACTTGTCATGTCTTCCGATCTGAGGGAGCTT (SEQ ID NO: 368) | GAGGGAGCTT (SEQ ID NO: 464) |
| F12 | DPM6bot94 | /5Phos/TGACTTGTCATGTCTTCCGATCTTCCAAAACTT (SEQ ID NO: 369) | TCCAAAACTT (SEQ ID NO: 465) |
| G12 | DPM6bot95 | /5Phos/TGACTTGTCATGTCTTCCGATCTAATTAAGATT (SEQ ID NO: 370) | AATTAAGATT (SEQ ID NO: 466) |
| H12 | DPM6bot96 | /5Phos/TGACTTGTCATGTCTTCCGATCTATGAACAATT (SEQ ID NO: 371) | ATGAACAATT (SEQ ID NO: 467) |

TABLE 4

Unphosphorylated Bottom Strand of the DPM adaptor.
The bottom and top strands of the DPM adaptor are annealed
to make a double-stranded DNA oligo. This is the first oligo
that is ligated to the DNA after End repair and dA-tailing. This
version of DPM bottom has no 5'phosphate. In the RNA-DNA
protocol, the DPM oligo is phosphorylated using T4 Polynucleoide
Kinase for add a 5'phosphate enzymatically to the DPM
bottom. It has sticky-end for ligation of the Odd tag.

| 96Well Position | Adaptor Name | Sequence | Barcode |
|---|---|---|---|
| A1 | DPM6bot1 | TGACTTGTCATGTCTTCCGATCTTGGGTGTTTT (SEQ ID NO: 468) | TGGGTGTTTT (SEQ ID NO: 564) |
| B1 | DPM6bot2 | TGACTTGTCATGTCTTCCGATCTTCGAGTCTTT (SEQ ID NO: 469) | TCGAGTCTTT (SEQ ID NO: 565) |
| C1 | DPM6bot3 | TGACTTGTCATGTCTTCCGATCTGCAGATTGTT (SEQ ID NO: 470) | GCAGATTGTT (SEQ ID NO: 566) |
| D1 | DPM6bot4 | TGACTTGTCATGTCTTCCGATCTTCTATGCGTT (SEQ ID NO: 471) | TCTATGCGTT (SEQ ID NO: 567) |
| E1 | DPM6bot5 | TGACTTGTCATGTCTTCCGATCTGGACTTTCTT (SEQ ID NO: 472) | GGACTTTCTT (SEQ ID NO: 568) |
| F1 | DPM6bot6 | TGACTTGTCATGTCTTCCGATCTGCCGTGCCTT (SEQ ID NO: 473) | GCCGTGCCTT (SEQ ID NO: 569) |
| G1 | DPM6bot7 | TGACTTGTCATGTCTTCCGATCTAGTGTTTATT (SEQ ID NO: 474) | AGTGTTTATT (SEQ ID NO: 570) |
| H1 | DPM6bot8 | TGACTTGTCATGTCTTCCGATCTGACTGGCATT (SEQ ID NO: 475) | GACTGGCATT (SEQ ID NO: 571) |
| A2 | DPM6bot9 | TGACTTGTCATGTCTTCCGATCTTGACATGTTT (SEQ ID NO: 476) | TGACATGTTT (SEQ ID NO: 572) |
| B2 | DPM6bot10 | TGACTTGTCATGTCTTCCGATCTCCCTTTATTT (SEQ ID NO: 477) | CCCTTTATTT (SEQ ID NO: 573) |
| C2 | DPM6bot11 | TGACTTGTCATGTCTTCCGATCTTTGGTTGGTT (SEQ ID NO: 478) | TTGGTTGGTT (SEQ ID NO: 574) |
| D2 | DPM6bot12 | TGACTTGTCATGTCTTCCGATCTATAAGTAGTT (SEQ ID NO: 479) | ATAAGTAGTT (SEQ ID NO: 575) |
| E2 | DPM6bot13 | TGACTTGTCATGTCTTCCGATCTCCTCTTGCTT (SEQ ID NO: 480) | CCTCTTGCTT (SEQ ID NO: 576) |
| F2 | DPM6bot14 | TGACTTGTCATGTCTTCCGATCTAAGCTTACTT (SEQ ID NO: 481) | AAGCTTACTT (SEQ ID NO: 577) |
| G2 | DPM6bot15 | TGACTTGTCATGTCTTCCGATCTGGCATTGATT (SEQ ID NO: 482) | GGCATTGATT (SEQ ID NO: 578) |
| H2 | DPM6bot16 | TGACTTGTCATGTCTTCCGATCTTGCCTGAATT (SEQ ID NO: 483) | TGCCTGAATT (SEQ ID NO: 579) |
| A3 | DPM6bot17 | TGACTTGTCATGTCTTCCGATCTGCGCGGTTTT (SEQ ID NO: 484) | GCGCGGTTTT (SEQ ID NO: 580) |
| B3 | DPM6bot18 | TGACTTGTCATGTCTTCCGATCTCAGCATCTTT (SEQ ID NO: 485) | CAGCATCTTT (SEQ ID NO: 581) |
| C3 | DPM6bot19 | TGACTTGTCATGTCTTCCGATCTTGCAATTGTT (SEQ ID NO: 486) | TGCAATTGTT (SEQ ID NO: 582) |
| D3 | DPM6bot20 | TGACTTGTCATGTCTTCCGATCTGGCCAGCGTT (SEQ ID NO: 487) | GGCCAGCGTT (SEQ ID NO: 583) |
| E3 | DPM6bot21 | TGACTTGTCATGTCTTCCGATCTATCCATTCTT (SEQ ID NO: 488) | ATCCATTCTT (SEQ ID NO: 584) |
| F3 | DPM6bot22 | TGACTTGTCATGTCTTCCGATCTAATCTGCCTT (SEQ ID NO: 489) | AATCTGCCTT (SEQ ID NO: 585) |
| G3 | DPM6bot23 | TGACTTGTCATGTCTTCCGATCTCCGATTTATT (SEQ ID NO: 490) | CCGATTTATT (SEQ ID NO: 586) |

TABLE 4-continued

Unphosphorylated Bottom Strand of the DPM adaptor.
The bottom and top strands of the DPM adaptor are annealed
to make a double-stranded DNA oligo. This is the first oligo
that is ligated to the DNA after End repair and dA-tailing. This
version of DPM bottom has no 5'phosphate. In the RNA-DNA
protocol, the DPM oligo is phosphorylated using T4 Polynucleoide
Kinase for add a 5'phosphate enzymatically to the DPM
bottom. It has sticky-end for ligation of the Odd tag.

| 96Well Position | Adaptor Name | Sequence | Barcode |
|---|---|---|---|
| H3 | DPM6bot24 | TGACTTGTCATGTCTTCCGATCTCGGGGGCATT (SEQ ID NO: 491) | CGGGGGCATT (SEQ ID NO: 587) |
| A4 | DPM6bot25 | TGACTTGTCATGTCTTCCGATCTCGCCGGGTTT (SEQ ID NO: 492) | CGCCGGGTTT (SEQ ID NO: 588) |
| B4 | DPM6bot26 | TGACTTGTCATGTCTTCCGATCTAGGTCTATTT (SEQ ID NO: 493) | AGGTCTATTT (SEQ ID NO: 589) |
| C4 | DPM6bot27 | TGACTTGTCATGTCTTCCGATCTGACGCTGGTT (SEQ ID NO: 494) | GACGCTGGTT (SEQ ID NO: 590) |
| D4 | DPM6bot28 | TGACTTGTCATGTCTTCCGATCTCATAATAGTT (SEQ ID NO: 495) | CATAATAGTT (SEQ ID NO: 591) |
| E4 | DPM6bot29 | TGACTTGTCATGTCTTCCGATCTATGTGGGCTT (SEQ ID NO: 496) | ATGTGGGCTT (SEQ ID NO: 592) |
| F4 | DPM6bot30 | TGACTTGTCATGTCTTCCGATCTGCGACTACTT (SEQ ID NO: 497) | GCGACTACTT (SEQ ID NO: 593) |
| G4 | DPM6bot31 | TGACTTGTCATGTCTTCCGATCTGTACTGGATT (SEQ ID NO: 498) | GTACTGGATT (SEQ ID NO: 594) |
| H4 | DPM6bot32 | TGACTTGTCATGTCTTCCGATCTAAAGCGAATT (SEQ ID NO: 499) | AAAGCGAATT (SEQ ID NO: 595) |
| A5 | DPM6bot33 | TGACTTGTCATGTCTTCCGATCTCTGTCGTTTT (SEQ ID NO: 500) | CTGTCGTTTT (SEQ ID NO: 596) |
| B5 | DPM6bot34 | TGACTTGTCATGTCTTCCGATCTAGAAGGCTTT (SEQ ID NO: 501) | AGAAGGCTTT (SEQ ID NO: 597) |
| C5 | DPM6bot35 | TGACTTGTCATGTCTTCCGATCTTTACAGTGTT (SEQ ID NO: 502) | TTACAGTGTT (SEQ ID NO: 598) |
| D5 | DPM6bot36 | TGACTTGTCATGTCTTCCGATCTCTGATCCGTT (SEQ ID NO: 503) | CTGATCCGTT (SEQ ID NO: 599) |
| E5 | DPM6bot37 | TGACTTGTCATGTCTTCCGATCTCCTAGGTCTT (SEQ ID NO: 504) | CCTAGGTCTT (SEQ ID NO: 600) |
| F5 | DPM6bot38 | TGACTTGTCATGTCTTCCGATCTCTACCGCCTT (SEQ ID NO: 505) | CTACCGCCTT (SEQ ID NO: 601) |
| G5 | DPM6bot39 | TGACTTGTCATGTCTTCCGATCTTACGGTTATT (SEQ ID NO: 506) | TACGGTTATT (SEQ ID NO: 602) |
| H5 | DPM6bot40 | TGACTTGTCATGTCTTCCGATCTTTTGCGCATT (SEQ ID NO: 507) | TTTGCGCATT (SEQ ID NO: 603) |
| A6 | DPM6bot41 | TGACTTGTCATGTCTTCCGATCTGAAGAGGTTT (SEQ ID NO: 508) | GAAGAGGTTT (SEQ ID NO: 604) |
| B6 | DPM6bot42 | TGACTTGTCATGTCTTCCGATCTGGTTTGATTT (SEQ ID NO: 509) | GGTTTGATTT (SEQ ID NO: 605) |
| C6 | DPM6bot43 | TGACTTGTCATGTCTTCCGATCTACGAATGGTT (SEQ ID NO: 510) | ACGAATGGTT (SEQ ID NO: 606) |
| D6 | DPM6bot44 | TGACTTGTCATGTCTTCCGATCTGTTGGGAGTT (SEQ ID NO: 511) | GTTGGGAGTT (SEQ ID NO: 607) |
| E6 | DPM6bot45 | TGACTTGTCATGTCTTCCGATCTTCGCCGGCTT (SEQ ID NO: 512) | TCGCCGGCTT (SEQ ID NO: 608) |

TABLE 4-continued

Unphosphorylated Bottom Strand of the DPM adaptor.
The bottom and top strands of the DPM adaptor are annealed
to make a double-stranded DNA oligo. This is the first oligo
that is ligated to the DNA after End repair and dA-tailing. This
version of DPM bottom has no 5'phosphate. In the RNA-DNA
protocol, the DPM oligo is phosphorylated using T4 Polynucleoide
Kinase for add a 5'phosphate enzymatically to the DPM
bottom. It has sticky-end for ligation of the Odd tag.

| 96Well Position | Adaptor Name | Sequence | Barcode |
|---|---|---|---|
| F6 | DPM6bot46 | TGACTTGTCATGTCTTCCGATCTCCTTCCACTT (SEQ ID NO: 513) | CCTTCCACTT (SEQ ID NO: 609) |
| G6 | DPM6bot47 | TGACTTGTCATGTCTTCCGATCTCCCGCGGATT (SEQ ID NO: 514) | CCCGCGGATT (SEQ ID NO: 610) |
| H6 | DPM6bot48 | TGACTTGTCATGTCTTCCGATCTGCTAAGAATT (SEQ ID NO: 515) | GCTAAGAATT (SEQ ID NO: 611) |
| A7 | DPM6bot49 | TGACTTGTCATGTCTTCCGATCTAAGAAGTTTT (SEQ ID NO: 516) | AAGAAGTTTT (SEQ ID NO: 612) |
| B7 | DPM6bot50 | TGACTTGTCATGTCTTCCGATCTGAACTCCTTT (SEQ ID NO: 517) | GAACTCCTTT (SEQ ID NO: 613) |
| C7 | DPM6bot51 | TGACTTGTCATGTCTTCCGATCTGTCTTCTGTT (SEQ ID NO: 518) | GTCTTCTGTT (SEQ ID NO: 614) |
| D7 | DPM6bot52 | TGACTTGTCATGTCTTCCGATCTTGGCCCCGTT (SEQ ID NO: 519) | TGGCCCCGTT (SEQ ID NO: 615) |
| E7 | DPM6bot53 | TGACTTGTCATGTCTTCCGATCTTTGAGCTCTT (SEQ ID NO: 520) | TTGAGCTCTT (SEQ ID NO: 616) |
| F7 | DPM6bot54 | TGACTTGTCATGTCTTCCGATCTTGTTAGCCTT (SEQ ID NO: 521) | TGTTAGCCTT (SEQ ID NO: 617) |
| G7 | DPM6bot55 | TGACTTGTCATGTCTTCCGATCTAAACGCTATT (SEQ ID NO: 522) | AAACGCTATT (SEQ ID NO: 618) |
| H7 | DPM6bot56 | TGACTTGTCATGTCTTCCGATCTCCCCGCCATT (SEQ ID NO: 523) | CCCCGCCATT (SEQ ID NO: 619) |
| A8 | DPM6bot57 | TGACTTGTCATGTCTTCCGATCTTTCAAGGTTT (SEQ ID NO: 524) | TTCAAGGTTT (SEQ ID NO: 620) |
| B8 | DPM6bot58 | TGACTTGTCATGTCTTCCGATCTCTTCTCATTT (SEQ ID NO: 525) | CTTCTCATTT (SEQ ID NO: 621) |
| C8 | DPM6bot59 | TGACTTGTCATGTCTTCCGATCTGCATCGGGTT (SEQ ID NO: 526) | GCATCGGGTT (SEQ ID NO: 622) |
| D8 | DPM6bot60 | TGACTTGTCATGTCTTCCGATCTTACTCGAGTT (SEQ ID NO: 527) | TACTCGAGTT (SEQ ID NO: 623) |
| E8 | DPM6bot61 | TGACTTGTCATGTCTTCCGATCTCACTAGGCTT (SEQ ID NO: 528) | CACTAGGCTT (SEQ ID NO: 624) |
| F8 | DPM6bot62 | TGACTTGTCATGTCTTCCGATCTTAACACACTT (SEQ ID NO: 529) | TAACACACTT (SEQ ID NO: 625) |
| G8 | DPM6bot63 | TGACTTGTCATGTCTTCCGATCTCGATTCGATT (SEQ ID NO: 530) | CGATTCGATT (SEQ ID NO: 626) |
| H8 | DPM6bot64 | TGACTTGTCATGTCTTCCGATCTGGGCGCAATT (SEQ ID NO: 531) | GGGCGCAATT (SEQ ID NO: 627) |
| A9 | DPM6bot65 | TGACTTGTCATGTCTTCCGATCTTCCCTCTTTT (SEQ ID NO: 532) | TCCCTCTTTT (SEQ ID NO: 628) |
| B9 | DPM6bot66 | TGACTTGTCATGTCTTCCGATCTACTTGCCTTT (SEQ ID NO: 533) | ACTTGCCTTT (SEQ ID NO: 629) |
| C9 | DPM6bot67 | TGACTTGTCATGTCTTCCGATCTAGCGCCTGTT (SEQ ID NO: 534) | AGCGCCTGTT (SEQ ID NO: 630) |

TABLE 4-continued

Unphosphorylated Bottom Strand of the DPM adaptor.
The bottom and top strands of the DPM adaptor are annealed
to make a double-stranded DNA oligo. This is the first oligo
that is ligated to the DNA after End repair and dA-tailing. This
version of DPM bottom has no 5'phosphate. In the RNA-DNA
protocol, the DPM oligo is phosphorylated using T4 Polynucleoide
Kinase for add a 5'phosphate enzymatically to the DPM
bottom. It has sticky-end for ligation of the Odd tag.

| 96Well Position | Adaptor Name | Sequence | Barcode |
|---|---|---|---|
| D9 | DPM6bot68 | TGACTTGTCATGTCTTCCGATCTACGTTACGTT (SEQ ID NO: 535) | ACGTTACGTT (SEQ ID NO: 631) |
| E9 | DPM6bot69 | TGACTTGTCATGTCTTCCGATCTGACAACTCTT (SEQ ID NO: 536) | GACAACTCTT (SEQ ID NO: 632) |
| F9 | DPM6bot70 | TGACTTGTCATGTCTTCCGATCTATAGTCCCTT (SEQ ID NO: 537) | ATAGTCCCTT (SEQ ID NO: 633) |
| G9 | DPM6bot71 | TGACTTGTCATGTCTTCCGATCTACCAGATATT (SEQ ID NO: 538) | ACCAGATATT (SEQ ID NO: 634) |
| H9 | DPM6bot72 | TGACTTGTCATGTCTTCCGATCTAGTACCCATT (SEQ ID NO: 539) | AGTACCCATT (SEQ ID NO: 635) |
| A10 | DPM6bot73 | TGACTTGTCATGTCTTCCGATCTTATGCCGTTT (SEQ ID NO: 540) | TATGCCGTTT (SEQ ID NO: 636) |
| B10 | DPM6bot74 | TGACTTGTCATGTCTTCCGATCTTGATGCATTT (SEQ ID NO: 541) | TGATGCATTT (SEQ ID NO: 637) |
| C10 | DPM6bot75 | TGACTTGTCATGTCTTCCGATCTTAAAGAGGTT (SEQ ID NO: 542) | TAAAGAGGTT (SEQ ID NO: 638) |
| D10 | DPM6bot76 | TGACTTGTCATGTCTTCCGATCTACGGGCAGTT (SEQ ID NO: 543) | ACGGGCAGTT (SEQ ID NO: 639) |
| E10 | DPM6bot77 | TGACTTGTCATGTCTTCCGATCTTGTATCGCTT (SEQ ID NO: 544) | TGTATCGCTT (SEQ ID NO: 640) |
| F10 | DPM6bot78 | TGACTTGTCATGTCTTCCGATCTCAAATAACTT (SEQ ID NO: 545) | CAAATAACTT (SEQ ID NO: 641) |
| G10 | DPM6bot79 | TGACTTGTCATGTCTTCCGATCTTTTCGCGATT (SEQ ID NO: 546) | TTTCGCGATT (SEQ ID NO: 642) |
| H10 | DPM6bot80 | TGACTTGTCATGTCTTCCGATCTTCAACCAATT (SEQ ID NO: 547) | TCAACCAATT (SEQ ID NO: 643) |
| A11 | DPM6bot81 | TGACTTGTCATGTCTTCCGATCTGTATGATTTT (SEQ ID NO: 548) | GTATGATTTT (SEQ ID NO: 644) |
| B11 | DPM6bot82 | TGACTTGTCATGTCTTCCGATCTAACCCACTTT (SEQ ID NO: 549) | AACCCACTTT (SEQ ID NO: 645) |
| C11 | DPM6bot83 | TGACTTGTCATGTCTTCCGATCTCATTTATGTT (SEQ ID NO: 550) | CATTTATGTT (SEQ ID NO: 646) |
| D11 | DPM6bot84 | TGACTTGTCATGTCTTCCGATCTCGCTCACGTT (SEQ ID NO: 551) | CGCTCACGTT (SEQ ID NO: 647) |
| E11 | DPM6bot85 | TGACTTGTCATGTCTTCCGATCTTGTCGATCTT (SEQ ID NO: 552) | TGTCGATCTT (SEQ ID NO: 648) |
| F11 | DPM6bot86 | TGACTTGTCATGTCTTCCGATCTGGATCCCCTT (SEQ ID NO: 553) | GGATCCCCTT (SEQ ID NO: 649) |
| G11 | DPM6bot87 | TGACTTGTCATGTCTTCCGATCTGAAACATATT (SEQ ID NO: 554) | GAAACATATT (SEQ ID NO: 650) |
| H11 | DPM6bot88 | TGACTTGTCATGTCTTCCGATCTTCACAACATT (SEQ ID NO: 555) | TCACAACATT (SEQ ID NO: 651) |
| A12 | DPM6bot89 | TGACTTGTCATGTCTTCCGATCTATTATAGTTT (SEQ ID NO: 556) | ATTATAGTTT (SEQ ID NO: 652) |

TABLE 4-continued

Unphosphorylated Bottom Strand of the DPM adaptor.
The bottom and top strands of the DPM adaptor are annealed
to make a double-stranded DNA oligo. This is the first oligo
that is ligated to the DNA after End repair and dA-tailing. This
version of DPM bottom has no 5'phosphate. In the RNA-DNA
protocol, the DPM oligo is phosphorylated using T4 Polynucleoide
Kinase for add a 5'phosphate enzymatically to the DPM
bottom. It has sticky-end for ligation of the Odd tag.

| 96Well Position | Adaptor Name | Sequence | Barcode |
|---|---|---|---|
| B12 | DPM6bot90 | TGACTTGTCATGTCTTCCGATCTCGAGCAATTT (SEQ ID NO: 557) | CGAGCAATTT (SEQ ID NO: 653) |
| C12 | DPM6bot91 | TGACTTGTCATGTCTTCCGATCTGTGCCAGGTT (SEQ ID NO: 558) | GTGCCAGGTT (SEQ ID NO: 654) |
| D12 | DPM6bot92 | TGACTTGTCATGTCTTCCGATCTGAGTACAGTT (SEQ ID NO: 559) | GAGTACAGTT (SEQ ID NO: 655) |
| E12 | DPM6bot93 | TGACTTGTCATGTCTTCCGATCTGAGGGAGCTT (SEQ ID NO: 560) | GAGGGAGCTT (SEQ ID NO: 656) |
| F12 | DPM6bot94 | TGACTTGTCATGTCTTCCGATCTTCCAAAACTT (SEQ ID NO: 561) | TCCAAAACTT (SEQ ID NO: 657) |
| G12 | DPM6bot95 | TGACTTGTCATGTCTTCCGATCTAATTAAGATT (SEQ ID NO: 562) | AATTAAGATT (SEQ ID NO: 658) |
| H12 | DPM6bot96 | TGACTTGTCATGTCTTCCGATCTATGAACAATT (SEQ ID NO: 563) | ATGAACAATT (SEQ ID NO: 659) |

TABLE 5

Top Strand of the DPM adaptor.
The top and bottom (with and without a 5'phosphate
modification) strands of the DPM adaptor are annealed to make
a double-stranded DNA oligo. This is the first oligo that is
ligated to the DNA after End Repair and dA-tailing. This has a
5'phosphate (5Phos) for ligation to DNA. The 3'spacer
(3SpC3) on DPM top prevents ligation of the Odd barcode to the
top strand of DPM, but ligates to the bottom strand of DPM.
The spacer is designed to prevent a hairpin from forming upon
ligation of a series of tags to both ends of the DNA such that
the tags only ligate to the 5'end of DNA. This top strand
also has a contstant sequence for a priming site for the
2P universal primer during final amplification.

| 96Well Column | 96Well Row | Barcode | Sequence |
|---|---|---|---|
| A | 1 | AACACCCA | /5Phos/AAACACCCAAGATCGGAAGAGCGTCGTGTA/3SpC3/ (SEQ ID NO: 660) |
| B | 1 | AGACTCGA | /5Phos/AAGACTCGAAGATCGGAAGAGCGTCGTGTA/3SpC3/ (SEQ ID NO: 661) |
| C | 1 | CAATCTGC | /5Phos/ACAATCTGCAGATCGGAAGAGCGTCGTGTA/3SpC3/ (SEQ ID NO: 662) |
| D | 1 | CGCATAGA | /5Phos/ACGCATAGAAGATCGGAAGAGCGTCGTGTA/3SpC3/ (SEQ ID NO: 663) |
| E | 1 | GAAAGTCC | /5Phos/AGAAAGTCCAGATCGGAAGAGCGTCGTGTA/3SpC3/ (SEQ ID NO: 664) |
| F | 1 | GGCACGGC | /5Phos/AGGCACGGCAGATCGGAAGAGCGTCGTGTA/3SpC3/ (SEQ ID NO: 665) |
| G | 1 | TAAACACT | /5Phos/ATAAACACTAGATCGGAAGAGCGTCGTGTA/3SpC3/ (SEQ ID NO: 666) |
| H | 1 | TGCCAGTC | /5Phos/ATGCCAGTCAGATCGGAAGAGCGTCGTGTA/3SpC3/ (SEQ ID NO: 667) |

TABLE 5-continued

Top Strand of the DPM adaptor.
The top and bottom (with and without a 5'phosphate modification) strands of the DPM adaptor are annealed to make a double-stranded DNA oligo. This is the first oligo that is ligated to the DNA after End Repair and dA-tailing. This has a 5'phosphate (5Phos) for ligation to DNA. The 3'spacer (3SpC3) on DPM top prevents ligation of the Odd barcode to the top strand of DPM, but ligates to the bottom strand of DPM. The spacer is designed to prevent a hairpin from forming upon ligation of a series of tags to both ends of the DNA such that the tags only ligate to the 5'end of DNA. This top strand also has a contstant sequence for a priming site for the 2P universal primer during final amplification.

| 96Well Column | 96Well Row | Barcode | Sequence |
|---|---|---|---|
| A | 2 | ACATGTCA | /5Phos/AACATGTCAAGATCGGAAGAGCGTCGTGTA/3SpC3/ (SEQ ID NO: 668) |
| B | 2 | ATAAAGGG | /5Phos/AATAAAGGGAGATCGGAAGAGCGTCGTGTA/3SpC3/ (SEQ ID NO: 669) |
| C | 2 | CCAACCAA | /5Phos/ACCAACCAAAGATCGGAAGAGCGTCGTGTA/3SpC3/ (SEQ ID NO: 670) |
| D | 2 | CTACTTAT | /5Phos/ACTACTTATAGATCGGAAGAGCGTCGTGTA/3SpC3/ (SEQ ID NO: 671) |
| E | 2 | GCAAGAGG | /5Phos/AGCAAGAGGAGATCGGAAGAGCGTCGTGTA/3SpC3/ (SEQ ID NO: 672) |
| F | 2 | GTAAGCTT | /5Phos/AGTAAGCTTAGATCGGAAGAGCGTCGTGTA/3SpC3/ (SEQ ID NO: 673) |
| G | 2 | TCAATGCC | /5Phos/ATCAATGCCAGATCGGAAGAGCGTCGTGTA/3SpC3/ (SEQ ID NO: 674) |
| H | 2 | TTCAGGCA | /5Phos/ATTCAGGCAAGATCGGAAGAGCGTCGTGTA/3SpC3/ (SEQ ID NO: 675) |
| A | 3 | AACCGCGC | /5Phos/AAACCGCGCAGATCGGAAGAGCGTCGTGTA/3SpC3/ (SEQ ID NO: 676) |
| B | 3 | AGATGCTG | /5Phos/AAGATGCTGAGATCGGAAGAGCGTCGTGTA/3SpC3/ (SEQ ID NO: 677) |
| C | 3 | CAATTGCA | /5Phos/ACAATTGCAAGATCGGAAGAGCGTCGTGTA/3SpC3/ (SEQ ID NO: 678) |
| D | 3 | CGCTGGCC | /5Phos/ACGCTGGCCAGATCGGAAGAGCGTCGTGTA/3SpC3/ (SEQ ID NO: 679) |
| E | 3 | GAATGGAT | /5Phos/AGAATGGATAGATCGGAAGAGCGTCGTGTA/3SpC3/ (SEQ ID NO: 680) |
| F | 3 | GGCAGATT | /5Phos/AGGCAGATTAGATCGGAAGAGCGTCGTGTA/3SpC3/ (SEQ ID NO: 681) |
| G | 3 | TAAATCGG | /5Phos/ATAAATCGGAGATCGGAAGAGCGTCGTGTA/3SpC3/ (SEQ ID NO: 682) |
| H | 3 | TGCCCCCG | /5Phos/ATGCCCCCGAGATCGGAAGAGCGTCGTGTA/3SpC3/ (SEQ ID NO: 683) |
| A | 4 | ACCCGGCG | /5Phos/AACCCGGCGAGATCGGAAGAGCGTCGTGTA/3SpC3/ (SEQ ID NO: 684) |
| B | 4 | ATAGACCT | /5Phos/AATAGACCTAGATCGGAAGAGCGTCGTGTA/3SpC3/ (SEQ ID NO: 685) |
| C | 4 | CCAGCGTC | /5Phos/ACCAGCGTCAGATCGGAAGAGCGTCGTGTA/3SpC3/ (SEQ ID NO: 686) |
| D | 4 | CTATTATG | /5Phos/ACTATTATGAGATCGGAAGAGCGTCGTGTA/3SpC3/ (SEQ ID NO: 687) |
| E | 4 | GCCCACAT | /5Phos/AGCCCACATAGATCGGAAGAGCGTCGTGTA/3SpC3/ (SEQ ID NO: 688) |

TABLE 5-continued

Top Strand of the DPM adaptor.
The top and bottom (with and without a 5'phosphate modification) strands of the DPM adaptor are annealed to make a double-stranded DNA oligo. This is the first oligo that is ligated to the DNA after End Repair and dA-tailing. This has a 5'phosphate (5Phos) for ligation to DNA. The 3'spacer (3SpC3) on DPM top prevents ligation of the Odd barcode to the top strand of DPM, but ligates to the bottom strand of DPM. The spacer is designed to prevent a hairpin from forming upon ligation of a series of tags to both ends of the DNA such that the tags only ligate to the 5'end of DNA. This top strand also has a contstant sequence for a priming site for the 2P universal primer during final amplification.

| 96Well Column | 96Well Row | Barcode | Sequence |
|---|---|---|---|
| F | 4 | GTAGTCGC | /5Phos/AGTAGTCGCAGATCGGAAGAGCGTCGTGTA/3SpC3/ (SEQ ID NO: 689) |
| G | 4 | TCCAGTAC | /5Phos/ATCCAGTACAGATCGGAAGAGCGTCGTGTA/3SpC3/ (SEQ ID NO: 690) |
| H | 4 | TTCGCTTT | /5Phos/ATTCGCTTTAGATCGGAAGAGCGTCGTGTA/3SpC3/ (SEQ ID NO: 691) |
| A | 5 | AACGACAG | /5Phos/AAACGACAGAGATCGGAAGAGCGTCGTGTA/3SpC3/ (SEQ ID NO: 692) |
| B | 5 | AGCCTTCT | /5Phos/AAGCCTTCTAGATCGGAAGAGCGTCGTGTA/3SpC3/ (SEQ ID NO: 693) |
| C | 5 | CACTGTAA | /5Phos/ACACTGTAAAGATCGGAAGAGCGTCGTGTA/3SpC3/ (SEQ ID NO: 694) |
| D | 5 | CGGATCAG | /5Phos/ACGGATCAGAGATCGGAAGAGCGTCGTGTA/3SpC3/ (SEQ ID NO: 695) |
| E | 5 | GACCTAGG | /5Phos/AGACCTAGGAGATCGGAAGAGCGTCGTGTA/3SpC3/ (SEQ ID NO: 696) |
| F | 5 | GGCGGTAG | /5Phos/AGGCGGTAGAGATCGGAAGAGCGTCGTGTA/3SpC3/ (SEQ ID NO: 697) |
| G | 5 | TAACCGTA | /5Phos/ATAACCGTAAGATCGGAAGAGCGTCGTGTA/3SpC3/ (SEQ ID NO: 698) |
| H | 5 | TGCGCAAA | /5Phos/ATGCGCAAAAGATCGGAAGAGCGTCGTGTA/3SpC3/ (SEQ ID NO: 699) |
| A | 6 | ACCTCTTC | /5Phos/AACCTCTTCAGATCGGAAGAGCGTCGTGTA/3SpC3/ (SEQ ID NO: 700) |
| B | 6 | ATCAAACC | /5Phos/AATCAAACCAGATCGGAAGAGCGTCGTGTA/3SpC3/ (SEQ ID NO: 701) |
| C | 6 | CCATTCGT | /5Phos/ACCATTCGTAGATCGGAAGAGCGTCGTGTA/3SpC3/ (SEQ ID NO: 702) |
| D | 6 | CTCCCAAC | /5Phos/ACTCCCAACAGATCGGAAGAGCGTCGTGTA/3SpC3/ (SEQ ID NO: 703) |
| E | 6 | GCCGGCGA | /5Phos/AGCCGGCGAAGATCGGAAGAGCGTCGTGTA/3SpC3/ (SEQ ID NO: 704) |
| F | 6 | GTGGAAGG | /5Phos/AGTGGAAGGAGATCGGAAGAGCGTCGTGTA/3SpC3/ (SEQ ID NO: 705) |
| G | 6 | TCCGCGGG | /5Phos/ATCCGCGGGAGATCGGAAGAGCGTCGTGTA/3SpC3/ (SEQ ID NO: 706) |
| H | 6 | TTCTTAGC | /5Phos/ATTCTTAGCAGATCGGAAGAGCGTCGTGTA/3SpC3/ (SEQ ID NO: 707) |
| A | 7 | AACTTCTT | /5Phos/AAACTTCTTAGATCGGAAGAGCGTCGTGTA/3SpC3/ (SEQ ID NO: 708) |
| B | 7 | AGGAGTTC | /5Phos/AAGGAGTTCAGATCGGAAGAGCGTCGTGTA/3SpC3/ (SEQ ID NO: 709) |

TABLE 5-continued

Top Strand of the DPM adaptor.
The top and bottom (with and without a 5'phosphate modification) strands of the DPM adaptor are annealed to make a double-stranded DNA oligo. This is the first oligo that is ligated to the DNA after End Repair and dA-tailing. This has a 5'phosphate (5Phos) for ligation to DNA. The 3'spacer (3SpC3) on DPM top prevents ligation of the Odd barcode to the top strand of DPM, but ligates to the bottom strand of DPM. The spacer is designed to prevent a hairpin from forming upon ligation of a series of tags to both ends of the DNA such that the tags only ligate to the 5'end of DNA. This top strand also has a contstant sequence for a priming site for the 2P universal primer during final amplification.

| 96Well Column | 96Well Row | Barcode | Sequence |
|---|---|---|---|
| C | 7 | CAGAAGAC | /5Phos/ACAGAAGACAGATCGGAAGAGCGTCGTGTA/3SpC3/ (SEQ ID NO: 710) |
| D | 7 | CGGGGCCA | /5Phos/ACGGGGCCAAGATCGGAAGAGCGTCGTGTA/3SpC3/ (SEQ ID NO: 711) |
| E | 7 | GAGCTCAA | /5Phos/AGAGCTCAAAGATCGGAAGAGCGTCGTGTA/3SpC3/ (SEQ ID NO: 712) |
| F | 7 | GGCTAACA | /5Phos/AGGCTAACAAGATCGGAAGAGCGTCGTGTA/3SpC3/ (SEQ ID NO: 713) |
| G | 7 | TAGCGTTT | /5Phos/ATAGCGTTTAGATCGGAAGAGCGTCGTGTA/3SpC3/ (SEQ ID NO: 714) |
| H | 7 | TGGCGGGG | /5Phos/ATGGCGGGGAGATCGGAAGAGCGTCGTGTA/3SpC3/ (SEQ ID NO: 715) |
| A | 8 | ACCTTGAA | /5Phos/AACCTTGAAAGATCGGAAGAGCGTCGTGTA/3SpC3/ (SEQ ID NO: 716) |
| B | 8 | ATGAGAAG | /5Phos/AATGAGAAGAGATCGGAAGAGCGTCGTGTA/3SpC3/ (SEQ ID NO: 717) |
| C | 8 | CCCGATGC | /5Phos/ACCCGATGCAGATCGGAAGAGCGTCGTGTA/3SpC3/ (SEQ ID NO: 718) |
| D | 8 | CTCGAGTA | /5Phos/ACTCGAGTAAGATCGGAAGAGCGTCGTGTA/3SpC3/ (SEQ ID NO: 719) |
| E | 8 | GCCTAGTG | /5Phos/AGCCTAGTGAGATCGGAAGAGCGTCGTGTA/3SpC3/ (SEQ ID NO: 720) |
| F | 8 | GTGTGTTA | /5Phos/AGTGTGTTAAGATCGGAAGAGCGTCGTGTA/3SpC3/ (SEQ ID NO: 721) |
| G | 8 | TCGAATCG | /5Phos/ATCGAATCGAGATCGGAAGAGCGTCGTGTA/3SpC3/ (SEQ ID NO: 722) |
| H | 8 | TTGCGCCC | /5Phos/ATTGCGCCCAGATCGGAAGAGCGTCGTGTA/3SpC3/ (SEQ ID NO: 723) |
| A | 9 | AAGAGGGA | /5Phos/AAAGAGGGAAGATCGGAAGAGCGTCGTGTA/3SpC3/ (SEQ ID NO: 724) |
| B | 9 | AGGCAAGT | /5Phos/AAGGCAAGTAGATCGGAAGAGCGTCGTGTA/3SpC3/ (SEQ ID NO: 725) |
| C | 9 | CAGGCGCT | /5Phos/ACAGGCGCTAGATCGGAAGAGCGTCGTGTA/3SpC3/ (SEQ ID NO: 726) |
| D | 9 | CGTAACGT | /5Phos/ACGTAACGTAGATCGGAAGAGCGTCGTGTA/3SpC3/ (SEQ ID NO: 727) |
| E | 9 | GAGTTGTC | /5Phos/AGAGTTGTCAGATCGGAAGAGCGTCGTGTA/3SpC3/ (SEQ ID NO: 728) |
| F | 9 | GGGACTAT | /5Phos/AGGGACTATAGATCGGAAGAGCGTCGTGTA/3SpC3/ (SEQ ID NO: 729) |
| G | 9 | TATCTGGT | /5Phos/ATATCTGGTAGATCGGAAGAGCGTCGTGTA/3SpC3/ (SEQ ID NO: 730) |

TABLE 5-continued

Top Strand of the DPM adaptor.
The top and bottom (with and without a 5'phosphate modification) strands of the DPM adaptor are annealed to make a double-stranded DNA oligo. This is the first oligo that is ligated to the DNA after End Repair and dA-tailing. This has a 5'phosphate (5Phos) for ligation to DNA. The 3'spacer (3SpC3) on DPM top prevents ligation of the Odd barcode to the top strand of DPM, but ligates to the bottom strand of DPM. The spacer is designed to prevent a hairpin from forming upon ligation of a series of tags to both ends of the DNA such that the tags only ligate to the 5'end of DNA. This top strand also has a contstant sequence for a priming site for the 2P universal primer during final amplification.

| 96Well Column | 96Well Row | Barcode | Sequence |
|---|---|---|---|
| H | 9 | TGGGTACT | /5Phos/ATGGGTACTAGATCGGAAGAGCGTCGTGTA/3SpC3/ (SEQ ID NO: 731) |
| A | 10 | ACGGCATA | /5Phos/AACGGCATAAGATCGGAAGAGCGTCGTGTA/3SpC3/ (SEQ ID NO: 732) |
| B | 10 | ATGCATCA | /5Phos/AATGCATCAAGATCGGAAGAGCGTCGTGTA/3SpC3/ (SEQ ID NO: 733) |
| C | 10 | CCTCTTTA | /5Phos/ACCTCTTTAAGATCGGAAGAGCGTCGTGTA/3SpC3/ (SEQ ID NO: 734) |
| D | 10 | CTGCCCGT | /5Phos/ACTGCCCGTAGATCGGAAGAGCGTCGTGTA/3SpC3/ (SEQ ID NO: 735) |
| E | 10 | GCGATACA | /5Phos/AGCGATACAAGATCGGAAGAGCGTCGTGTA/3SpC3/ (SEQ ID NO: 736) |
| F | 10 | GTTATTTG | /5Phos/AGTTATTTGAGATCGGAAGAGCGTCGTGTA/3SpC3/ (SEQ ID NO: 737) |
| G | 10 | TCGCGAAA | /5Phos/ATCGCGAAAAGATCGGAAGAGCGTCGTGTA/3SpC3/ (SEQ ID NO: 738) |
| H | 10 | TTGGTTGA | /5Phos/ATTGGTTGAAGATCGGAAGAGCGTCGTGTA/3SpC3/ (SEQ ID NO: 739) |
| A | 11 | AATCATAC | /5Phos/AAATCATACAGATCGGAAGAGCGTCGTGTA/3SpC3/ (SEQ ID NO: 740) |
| B | 11 | AGTGGGTT | /5Phos/AAGTGGGTTAGATCGGAAGAGCGTCGTGTA/3SpC3/ (SEQ ID NO: 741) |
| C | 11 | CATAAATG | /5Phos/ACATAAATGAGATCGGAAGAGCGTCGTGTA/3SpC3/ (SEQ ID NO: 742) |
| D | 11 | CGTGAGCG | /5Phos/ACGTGAGCGAGATCGGAAGAGCGTCGTGTA/3SpC3/ (SEQ ID NO: 743) |
| E | 11 | GATCGACA | /5Phos/AGATCGACAAGATCGGAAGAGCGTCGTGTA/3SpC3/ (SEQ ID NO: 744) |
| F | 11 | GGGGATCC | /5Phos/AGGGGATCCAGATCGGAAGAGCGTCGTGTA/3SpC3/ (SEQ ID NO: 745) |
| G | 11 | TATGTTTC | /5Phos/ATATGTTTCAGATCGGAAGAGCGTCGTGTA/3SpC3/ (SEQ ID NO: 746) |
| H | 11 | TGTTGTGA | /5Phos/ATGTTGTGAAGATCGGAAGAGCGTCGTGTA/3SpC3/ (SEQ ID NO: 747) |
| A | 12 | ACTATAAT | /5Phos/AACTATAATAGATCGGAAGAGCGTCGTGTA/3SpC3/ (SEQ ID NO: 748) |
| B | 12 | ATTGCTCG | /5Phos/AATTGCTCGAGATCGGAAGAGCGTCGTGTA/3SpC3/ (SEQ ID NO: 749) |
| C | 12 | CCTGGCAC | /5Phos/ACCTGGCACAGATCGGAAGAGCGTCGTGTA/3SpC3/ (SEQ ID NO: 750) |
| D | 12 | CTGTACTC | /5Phos/ACTGTACTCAGATCGGAAGAGCGTCGTGTA/3SpC3/ (SEQ ID NO: 751) |

TABLE 5-continued

Top Strand of the DPM adaptor.
The top and bottom (with and without a 5'phosphate modification) strands of the DPM adaptor are annealed to make a double-stranded DNA oligo. This is the first oligo that is ligated to the DNA after End Repair and dA-tailing. This has a 5'phosphate (5Phos) for ligation to DNA. The 3'spacer (3SpC3) on DPM top prevents ligation of the Odd barcode to the top strand of DPM, but ligates to the bottom strand of DPM. The spacer is designed to prevent a hairpin from forming upon ligation of a series of tags to both ends of the DNA such that the tags only ligate to the 5'end of DNA. This top strand also has a contstant sequence for a priming site for the 2P universal primer during final amplification.

| 96Well Column | 96Well Row | Barcode | Sequence |
| --- | --- | --- | --- |
| E | 12 | GCTCCCTC | /5Phos/AGCTCCCTCAGATCGGAAGAGCGTCGTGTA/3SpC3/ (SEQ ID NO: 752) |
| F | 12 | GTTTTGGA | /5Phos/AGTTTTGGAAGATCGGAAGAGCGTCGTGTA/3SpC3/ (SEQ ID NO: 753) |
| G | 12 | TCTTAATT | /5Phos/ATCTTAATTAGATCGGAAGAGCGTCGTGTA/3SpC3/ (SEQ ID NO: 754) |
| H | 12 | TTGTTCAT | /5Phos/ATTGTTCATAGATCGGAAGAGCGTCGTGTA/3SpC3/ (SEQ ID NO: 755) |

TABLE 6

Bottom Strand of the Even tag.
The bottom and top strands of the Even tag are annealed to make a double-stranded DNA oligo. It has a TGACTTG overhang and 5'phosphate (5Phos) to ligate to an Odd tag.

| 96Well Position | Adaptor Name | Sequence |
| --- | --- | --- |
| A1 | Even2Bo1 | /5Phos/TGACTTGGATACTGCGGCTGACGT (SEQ ID NO: 756) |
| B1 | Even2Bo2 | /5Phos/TGACTTGCGTGACATTAAGGTTGT (SEQ ID NO: 757) |
| C1 | Even2Bo3 | /5Phos/TGACTTGACCTCACGTCTAGGCGT (SEQ ID NO: 758) |
| D1 | Even2Bo4 | /5Phos/TGACTTGTGATTACGTTCCACGGT (SEQ ID NO: 759) |
| E1 | Even2Bo5 | /5Phos/TGACTTGACTAGGTGGCGGTCTGT (SEQ ID NO: 760) |
| F1 | Even2Bo6 | /5Phos/TGACTTGATATCAATGATGGTGCT (SEQ ID NO: 761) |
| G1 | Even2Bo7 | /5Phos/TGACTTGGATTCCTCTGCGATGCT (SEQ ID NO: 762) |
| H1 | Even2Bo8 | /5Phos/TGACTTGGGTAGCTTACGTCATCT (SEQ ID NO: 763) |
| A2 | Even2Bo9 | /5Phos/TGACTTGTGTAGGTTCTGGAATCT (SEQ ID NO: 764) |
| B2 | Even2Bo10 | /5Phos/TGACTTGTCAAGCTAGACGGTTCT (SEQ ID NO: 765) |
| C2 | Even2Bo11 | /5Phos/TGACTTGAAGTCCTGCCACTACGT (SEQ ID NO: 766) |
| D2 | Even2Bo12 | /5Phos/TGACTTGACCAACAAGATAGTGCT (SEQ ID NO: 767) |
| E2 | Even2Bo13 | /5Phos/TGACTTGGAATCACGAGTTCGTCT (SEQ ID NO: 768) |
| F2 | Even2Bo14 | /5Phos/TGACTTGGTAACCATATTGCCGTT (SEQ ID NO: 769) |
| G2 | Even2Bo15 | /5Phos/TGACTTGAGAGGATTGGAGAATCT (SEQ ID NO: 770) |
| H2 | Even2Bo16 | /5Phos/TGACTTGCAATGCGTGTGTTCGGT (SEQ ID NO: 771) |
| A3 | Even2Bo17 | /5Phos/TGACTTGGTGCCGTGACTCCATCT (SEQ ID NO: 772) |
| B3 | Even2Bo18 | /5Phos/TGACTTGTAGAAGTGCTCCAGGTT (SEQ ID NO: 773) |
| C3 | Even2Bo19 | /5Phos/TGACTTGGGCTGAGCTGGTCTAGT (SEQ ID NO: 774) |
| D3 | Even2Bo20 | /5Phos/TGACTTGCGATTAGTGCGAGAGGT (SEQ ID NO: 775) |
| E3 | Even2Bo21 | /5Phos/TGACTTGTCCTTCGTTAAGGCTGT (SEQ ID NO: 776) |
| F3 | Even2Bo22 | /5Phos/TGACTTGTCGGAGGATCTAGTGGT (SEQ ID NO: 777) |
| G3 | Even2Bo23 | /5Phos/TGACTTGGGCTTCATTAACTAGGT (SEQ ID NO: 778) |
| H3 | Even2Bo24 | /5Phos/TGACTTGGACGCTCTATACACCGT (SEQ ID NO: 779) |

TABLE 6-continued

Bottom Strand of the Even tag.
The bottom and top strands of the Even tag are
annealed to make a double-stranded DNA oligo.
It has a TGACTTG overhang and 5'phosphate
(5Phos) to ligate to an Odd tag.

| 96Well Position | Adaptor Name | Sequence |
|---|---|---|
| A4 | Even2Bo25 | /5Phos/TGACTTGCGTAGTCCAGGTCGTCT (SEQ ID NO: 780) |
| B4 | Even2Bo26 | /5Phos/TGACTTGTGCATAGGACAGGCAGT (SEQ ID NO: 781) |
| C4 | Even2Bo27 | /5Phos/TGACTTGAACTCAAGCACCTCTCT (SEQ ID NO: 782) |
| D4 | Even2Bo28 | /5Phos/TGACTTGGGTATCGTATAGGTCGT (SEQ ID NO: 783) |
| E4 | Even2Bo29 | /5Phos/TGACTTGCGACGACTGACTAGGTT (SEQ ID NO: 784) |
| F4 | Even2Bo30 | /5Phos/TGACTTGGTCGCACCACAACCATT (SEQ ID NO: 785) |
| G4 | Even2Bo31 | /5Phos/TGACTTGTGGTCGCATGATAAGGT (SEQ ID NO: 786) |
| H4 | Even2Bo32 | /5Phos/TGACTTGACGCTTGGCTAATAGGT (SEQ ID NO: 787) |
| A5 | Even2Bo33 | /5Phos/TGACTTGAGAAGATCGCAATTAGT (SEQ ID NO: 788) |
| B5 | Even2Bo34 | /5Phos/TGACTTGACGCTCCTAGATGTTCT (SEQ ID NO: 789) |
| C5 | Even2Bo35 | /5Phos/TGACTTGCGACTACTGCTCACCGT (SEQ ID NO: 790) |
| D5 | Even2Bo36 | /5Phos/TGACTTGATAGATTGTTGCGTGCT (SEQ ID NO: 791) |
| E5 | Even2Bo37 | /5Phos/TGACTTGCTCTACACCGCTGAAGT (SEQ ID NO: 792) |
| F5 | Even2Bo38 | /5Phos/TGACTTGTTCCGTGGCTTACTGGT (SEQ ID NO: 793) |
| G5 | Even2Bo39 | /5Phos/TGACTTGCGTGAAGTGACTGAGGT (SEQ ID NO: 794) |
| H5 | Even2Bo40 | /5Phos/TGACTTGACCGACATCCGCTGTGT (SEQ ID NO: 795) |
| A6 | Even2Bo41 | /5Phos/TGACTTGTTCAAGCCTTGCGGAGT (SEQ ID NO: 796) |
| B6 | Even2Bo42 | /5Phos/TGACTTGGTTATTGCCACCAGTGT (SEQ ID NO: 797) |
| C6 | Even2Bo43 | /5Phos/TGACTTGGCCAGTTAGCAAGACGT (SEQ ID NO: 798) |
| D6 | Even2Bo44 | /5Phos/TGACTTGTTGCTCGTTGGTCCAGT (SEQ ID NO: 799) |
| E6 | Even2Bo45 | /5Phos/TGACTTGACCTGCTTCCGTGATGT (SEQ ID NO: 800) |
| F6 | Even2Bo46 | /5Phos/TGACTTGCCACGTTCAACTGGCGT (SEQ ID NO: 801) |
| G6 | Even2Bo47 | /5Phos/TGACTTGCGCTGGAACTCATAAGT (SEQ ID NO: 802) |
| H6 | Even2Bo48 | /5Phos/TGACTTGGAGTCTTCGGATACCGT (SEQ ID NO: 803) |
| A7 | Even2Bo49 | /5Phos/TGACTTGATGGACCTCTAATTGCT (SEQ ID NO: 804) |
| B7 | Even2Bo50 | /5Phos/TGACTTGGGCGGATTCTCAGTGGT (SEQ ID NO: 805) |
| C7 | Even2Bo51 | /5Phos/TGACTTGTGTTGCTGTGTGGATCT (SEQ ID NO: 806) |
| D7 | Even2Bo52 | /5Phos/TGACTTGAACCGCAGAGAGGTAGT (SEQ ID NO: 807) |
| E7 | Even2Bo53 | /5Phos/TGACTTGGCATCGACTCACCTTCT (SEQ ID NO: 808) |
| F7 | Even2Bo54 | /5Phos/TGACTTGGGAACACGCACATGGCT (SEQ ID NO: 809) |
| G7 | Even2Bo55 | /5Phos/TGACTTGGCCAGCAATCCTACAGT (SEQ ID NO: 810) |
| H7 | Even2Bo56 | /5Phos/TGACTTGAACGCTTATGGCAGTGT (SEQ ID NO: 811) |
| A8 | Even2Bo57 | /5Phos/TGACTTGTGTTGCGTAGTGATGCT (SEQ ID NO: 812) |
| B8 | Even2Bo58 | /5Phos/TGACTTGGGCACGAGATCCTTGCT (SEQ ID NO: 813) |
| C8 | Even2Bo59 | /5Phos/TGACTTGGTCAATGGACGGATGCT (SEQ ID NO: 814) |
| D8 | Even2Bo60 | /5Phos/TGACTTGGTCCGTTGCTATAATCT (SEQ ID NO: 815) |
| E8 | Even2Bo61 | /5Phos/TGACTTGCTGATTCCTGAGTCCGT (SEQ ID NO: 816) |
| F8 | Even2Bo62 | /5Phos/TGACTTGACTAGCACCTCGTAATT (SEQ ID NO: 817) |
| G8 | Even2Bo63 | /5Phos/TGACTTGGCGTATACCGAGTTGGT (SEQ ID NO: 818) |
| H8 | Even2Bo64 | /5Phos/TGACTTGTGGTTGATTCAAGAATT (SEQ ID NO: 819) |
| A9 | Even2Bo65 | /5Phos/TGACTTGCGCATGGATACCAGCGT (SEQ ID NO: 820) |
| B9 | Even2Bo66 | /5Phos/TGACTTGTTCGTGTGAGTCTCGTT (SEQ ID NO: 821) |
| C9 | Even2Bo67 | /5Phos/TGACTTGCATTCTCTGCCGAGAGT (SEQ ID NO: 822) |
| D9 | Even2Bo68 | /5Phos/TGACTTGGGTTGTTCGTGTGTCGT (SEQ ID NO: 823) |
| E9 | Even2Bo69 | /5Phos/TGACTTGAGTCCAGGCATTCGTCT (SEQ ID NO: 824) |
| F9 | Even2Bo70 | /5Phos/TGACTTGTACAACGGTGCGACTGT (SEQ ID NO: 825) |

TABLE 6-continued

Bottom Strand of the Even tag.
The bottom and top strands of the Even tag are
annealed to make a double-stranded DNA oligo.
It has a TGACTTG overhang and 5'phosphate
(5Phos) to ligate to an Odd tag.

| 96Well Position | Adaptor Name | Sequence |
|---|---|---|
| G9 | Even2Bo71 | /5Phos/TGACTTGCCGTATCGAGGTGCCGT (SEQ ID NO: 826) |
| H9 | Even2Bo72 | /5Phos/TGACTTGGGTCCTGTCTAGTCCGT (SEQ ID NO: 827) |
| A10 | Even2Bo73 | /5Phos/TGACTTGCGATGACCTGTCCATGT (SEQ ID NO: 828) |
| B10 | Even2Bo74 | /5Phos/TGACTTGTGGCTCTGAACCTATCT (SEQ ID NO: 829) |
| C10 | Even2Bo75 | /5Phos/TGACTTGGCACAGTCCTCCATGCT (SEQ ID NO: 830) |
| D10 | Even2Bo76 | /5Phos/TGACTTGGTTGATAAGCCGACGGT (SEQ ID NO: 831) |
| E10 | Even2Bo77 | /5Phos/TGACTTGGAGCGTGCAGTGGAAGT (SEQ ID NO: 832) |
| F10 | Even2Bo78 | /5Phos/TGACTTGTGAGCTGGACAGGTGGT (SEQ ID NO: 833) |
| G10 | Even2Bo79 | /5Phos/TGACTTGTCCGCACTCTGATAATT (SEQ ID NO: 834) |
| H10 | Even2Bo80 | /5Phos/TGACTTGCGCCTATTGTACTGCGT (SEQ ID NO: 835) |
| A11 | Even2Bo81 | /5Phos/TGACTTGGCACACCATCGTATTCT (SEQ ID NO: 836) |
| B11 | Even2Bo82 | /5Phos/TGACTTGAATGCTTCACACGGTGT (SEQ ID NO: 837) |
| C11 | Even2Bo83 | /5Phos/TGACTTGATGTCCGCCTGCATGGT (SEQ ID NO: 838) |

TABLE 6-continued

Bottom Strand of the Even tag.
The bottom and top strands of the Even tag are
annealed to make a double-stranded DNA oligo.
It has a TGACTTG overhang and 5'phosphate
(5Phos) to ligate to an Odd tag.

| 96Well Position | Adaptor Name | Sequence |
|---|---|---|
| D11 | Even2Bo84 | /5Phos/TGACTTGTGGAACACTCTACTGCT (SEQ ID NO: 839) |
| E11 | Even2Bo85 | /5Phos/TGACTTGCTATCCTGTCAACGGCT (SEQ ID NO: 840) |
| F11 | Even2Bo86 | /5Phos/TGACTTGAGCTTGCCGTAGCGTGT (SEQ ID NO: 841) |
| G11 | Even2Bo87 | /5Phos/TGACTTGTGTCGATATTGATCCGT (SEQ ID NO: 842) |
| H11 | Even2Bo88 | /5Phos/TGACTTGGAAGCGGAAGGTATAGT (SEQ ID NO: 843) |
| A12 | Even2Bo89 | /5Phos/TGACTTGGCTACTTCCGAATCAGT (SEQ ID NO: 844) |
| B12 | Even2Bo90 | /5Phos/TGACTTGCGCACACGATCATCTGT (SEQ ID NO: 845) |
| C12 | Even2Bo91 | /5Phos/TGACTTGACTGGTGTCACGTCTCT (SEQ ID NO: 846) |
| D12 | Even2Bo92 | /5Phos/TGACTTGGACTGTTCGACACGTCT (SEQ ID NO: 847) |
| E12 | Even2Bo93 | /5Phos/TGACTTGACCACGGAGCCTTCTCT (SEQ ID NO: 848) |
| F12 | Even2Bo94 | /5Phos/TGACTTGCCTGTTACGTCCGCTGT (SEQ ID NO: 849) |
| G12 | Even2Bo95 | /5Phos/TGACTTGGACGCTGTGGCGATTCT (SEQ ID NO: 850) |
| H12 | Even2Bo96 | /5Phos/TGACTTGCGCTCCAGTCGTAATCT (SEQ ID NO: 851) |

TABLE 7

Top Strand of the Even tag.
The bottom and top strands of the Even tag are annealed to make a
double-stranded DNA oligo. It has a AGTTGTC overhang and
5'phosphate (5Phos) to be ligated by an Odd tag in the
subsequent round of split-and-pool tagging.

| 96Well Position | Adaptor Name | Sequence |
|---|---|---|
| A1 | Even2Top1 | /5Phos/AGTTGTCACGTCAGCCGCAGTATC (SEQ ID NO: 852) |
| B1 | Even2Top2 | /5Phos/AGTTGTCACAACCTTAATGTCACG (SEQ ID NO: 853) |
| C1 | Even2Top3 | /5Phos/AGTTGTCACGCCTAGACGTGAGGT (SEQ ID NO: 854) |
| D1 | Even2Top4 | /5Phos/AGTTGTCACCGTGGAACGTAATCA (SEQ ID NO: 855) |
| E1 | Even2Top5 | /5Phos/AGTTGTCACAGACCGCCACCTAGT (SEQ ID NO: 856) |
| F1 | Even2Top6 | /5Phos/AGTTGTCAGCACCATCATTGATAT (SEQ ID NO: 857) |
| G1 | Even2Top7 | /5Phos/AGTTGTCAGCATCGCAGAGGAATC (SEQ ID NO: 858) |
| H1 | Even2Top8 | /5Phos/AGTTGTCAGATGACGTAAGCTACC (SEQ ID NO: 859) |
| A2 | Even2Top9 | /5Phos/AGTTGTCAGATTCCAGAACCTACA (SEQ ID NO: 860) |

TABLE 7-continued

Top Strand of the Even tag.
The bottom and top strands of the Even tag are annealed to make a double-stranded DNA oligo. It has a AGTTGTC overhang and 5'phosphate (5Phos) to be ligated by an Odd tag in the subsequent round of split-and-pool tagging.

| 96Well Position | Adaptor Name | Sequence |
|---|---|---|
| B2 | Even2Top10 | /5Phos/AGTTGTCAGAACCGTCTAGCTTGA (SEQ ID NO: 861) |
| C2 | Even2Top11 | /5Phos/AGTTGTCACGTAGTGGCAGGACTT (SEQ ID NO: 862) |
| D2 | Even2Top12 | /5Phos/AGTTGTCAGCACTATCTTGTTGGT (SEQ ID NO: 863) |
| E2 | Even2Top13 | /5Phos/AGTTGTCAGACGAACTCGTGATTC (SEQ ID NO: 864) |
| F2 | Even2Top14 | /5Phos/AGTTGTCAACGGCAATATGGTTAC (SEQ ID NO: 865) |
| G2 | Even2Top15 | /5Phos/AGTTGTCAGATTCTCCAATCCTCT (SEQ ID NO: 866) |
| H2 | Even2Top16 | /5Phos/AGTTGTCACCGAACACACGCATTG (SEQ ID NO: 867) |
| A3 | Even2Top17 | /5Phos/AGTTGTCAGATGGAGTCACGGCAC (SEQ ID NO: 868) |
| B3 | Even2Top18 | /5Phos/AGTTGTCAACCTGGAGCACTTCTA (SEQ ID NO: 869) |
| C3 | Even2Top19 | /5Phos/AGTTGTCACTAGACCAGCTCAGCC (SEQ ID NO: 870) |
| D3 | Even2Top20 | /5Phos/AGTTGTCACCTCTCGCACTAATCG (SEQ ID NO: 871) |
| E3 | Even2Top21 | /5Phos/AGTTGTCAGCCTTAACGAAGGA (SEQ ID NO: 872) |
| F3 | Even2Top22 | /5Phos/AGTTGTCACCACTAGATCCTCCGA (SEQ ID NO: 873) |
| G3 | Even2Top23 | /5Phos/AGTTGTCACCTAGTTAATGAAGCC (SEQ ID NO: 874) |
| H3 | Even2Top24 | /5Phos/AGTTGTCACGGTGTATAGAGCGTC (SEQ ID NO: 875) |
| A4 | Even2Top25 | /5Phos/AGTTGTCAGACGACCTGGACTACG (SEQ ID NO: 876) |
| B4 | Even2Top26 | /5Phos/AGTTGTCACTGCCTGTCCTATGCA (SEQ ID NO: 877) |
| C4 | Even2Top27 | /5Phos/AGTTGTCAGAGAGGTGCTTGAGTT (SEQ ID NO: 878) |
| D4 | Even2Top28 | /5Phos/AGTTGTCACGACCTATACGATACC (SEQ ID NO: 879) |
| E4 | Even2Top29 | /5Phos/AGTTGTCAACCTAGTCAGTCGTCG (SEQ ID NO: 880) |
| F4 | Even2Top30 | /5Phos/AGTTGTCAATGGTTGTGGTGCGAC (SEQ ID NO: 881) |
| G4 | Even2Top31 | /5Phos/AGTTGTCACCTTATCATGCGACCA (SEQ ID NO: 882) |
| H4 | Even2Top32 | /5Phos/AGTTGTCACCTATTAGCCAAGCGT (SEQ ID NO: 883) |
| A5 | Even2Top33 | /5Phos/AGTTGTCACTAATTGCGATCTTCT (SEQ ID NO: 884) |
| B5 | Even2Top34 | /5Phos/AGTTGTCAGAACATCTAGGAGCGT (SEQ ID NO: 885) |
| C5 | Even2Top35 | /5Phos/AGTTGTCACGGTGAGCAGTAGTCG (SEQ ID NO: 886) |
| D5 | Even2Top36 | /5Phos/AGTTGTCAGCACGCAACAATCTAT (SEQ ID NO: 887) |
| E5 | Even2Top37 | /5Phos/AGTTGTCACTTCAGCGGTGTAGAG (SEQ ID NO: 888) |
| F5 | Even2Top38 | /5Phos/AGTTGTCACCAGTAAGCCACGGAA (SEQ ID NO: 889) |
| G5 | Even2Top39 | /5Phos/AGTTGTCACCTCAGTCACTTCACG (SEQ ID NO: 890) |
| H5 | Even2Top40 | /5Phos/AGTTGTCACACAGCGGATGTCGGT (SEQ ID NO: 891) |
| A6 | Even2Top41 | /5Phos/AGTTGTCACTCCGCAAGGCTTGAA (SEQ ID NO: 892) |
| B6 | Even2Top42 | /5Phos/AGTTGTCACACTGGTGGCAATAAC (SEQ ID NO: 893) |
| C6 | Even2Top43 | /5Phos/AGTTGTCACGTCTTGCTAACTGGC (SEQ ID NO: 894) |
| D6 | Even2Top44 | /5Phos/AGTTGTCACTGGACCAACGAGCAA (SEQ ID NO: 895) |

TABLE 7-continued

Top Strand of the Even tag.
The bottom and top strands of the Even tag are annealed to make a double-stranded DNA oligo. It has a AGTTGTC overhang and 5'phosphate (5Phos) to be ligated by an Odd tag in the subsequent round of split-and-pool tagging.

| 96Well Position | Adaptor Name | Sequence |
|---|---|---|
| E6 | Even2Top45 | /5Phos/AGTTGTCACATCACGGAAGCAGGT (SEQ ID NO: 896) |
| F6 | Even2Top46 | /5Phos/AGTTGTCACGCCAGTTGAACGTGG (SEQ ID NO: 897) |
| G6 | Even2Top47 | /5Phos/AGTTGTCACTTATGAGTTCCAGCG (SEQ ID NO: 898) |
| H6 | Even2Top48 | /5Phos/AGTTGTCACGGTATCCGAAGACTC (SEQ ID NO: 899) |
| A7 | Even2Top49 | /5Phos/AGTTGTCAGCAATTAGAGGTCCAT (SEQ ID NO: 900) |
| B7 | Even2Top50 | /5Phos/AGTTGTCACCACTGAGAATCCGCC (SEQ ID NO: 901) |
| C7 | Even2Top51 | /5Phos/AGTTGTCAGATCCACACAGCAACA (SEQ ID NO: 902) |
| D7 | Even2Top52 | /5Phos/AGTTGTCACTACCTCTCTGCGGTT (SEQ ID NO: 903) |
| E7 | Even2Top53 | /5Phos/AGTTGTCAGAAGGTGAGTCGATGC (SEQ ID NO: 904) |
| F7 | Even2Top54 | /5Phos/AGTTGTCAGCCATGTGCGTGTTCC (SEQ ID NO: 905) |
| G7 | Even2Top55 | /5Phos/AGTTGTCACTGTAGGATTGCTGGC (SEQ ID NO: 906) |
| H7 | Even2Top56 | /5Phos/AGTTGTCACACTGCCATAAGCGTT (SEQ ID NO: 907) |
| A8 | Even2Top57 | /5Phos/AGTTGTCAGCATCACTACGCAACA (SEQ ID NO: 908) |
| B8 | Even2Top58 | /5Phos/AGTTGTCAGCAAGGATCTCGTGCC (SEQ ID NO: 909) |
| C8 | Even2Top59 | /5Phos/AGTTGTCAGCATCCGTCCATTGAC (SEQ ID NO: 910) |
| D8 | Even2Top60 | /5Phos/AGTTGTCAGATTATAGCAACGGAC (SEQ ID NO: 911) |
| E8 | Even2Top61 | /5Phos/AGTTGTCACGGACTCAGGAATCAG (SEQ ID NO: 912) |
| F8 | Even2Top62 | /5Phos/AGTTGTCAATTACGAGGTGCTAGT (SEQ ID NO: 913) |
| G8 | Even2Top63 | /5Phos/AGTTGTCACCAACTCGGTATACGC (SEQ ID NO: 914) |
| H8 | Even2Top64 | /5Phos/AGTTGTCAATTCTTGAATCAACCA (SEQ ID NO: 915) |
| A9 | Even2Top65 | /5Phos/AGTTGTCACGCTGGTATCCATGCG (SEQ ID NO: 916) |
| B9 | Even2Top66 | /5Phos/AGTTGTCAACGAGACTCACACGAA (SEQ ID NO: 917) |
| C9 | Even2Top67 | /5Phos/AGTTGTCACTCTCGGCAGAGAATG (SEQ ID NO: 918) |
| D9 | Even2Top68 | /5Phos/AGTTGTCACGACACACGAACAACC (SEQ ID NO: 919) |
| E9 | Even2Top69 | /5Phos/AGTTGTCAGACGAATGCCTGGACT (SEQ ID NO: 920) |
| F9 | Even2Top70 | /5Phos/AGTTGTCACAGTCGCACCGTTGTA (SEQ ID NO: 921) |
| G9 | Even2Top71 | /5Phos/AGTTGTCACGGCACCTCGATACGG (SEQ ID NO: 922) |
| H9 | Even2Top72 | /5Phos/AGTTGTCACGGACTAGACAGGACC (SEQ ID NO: 923) |
| A10 | Even2Top73 | /5Phos/AGTTGTCACATGGACAGGTCATCG (SEQ ID NO: 924) |
| B10 | Even2Top74 | /5Phos/AGTTGTCAGATAGGTTCAGAGCCA (SEQ ID NO: 925) |
| C10 | Even2Top75 | /5Phos/AGTTGTCAGCATGGAGGACTGTGC (SEQ ID NO: 926) |
| D10 | Even2Top76 | /5Phos/AGTTGTCACCGTCGGCTTATCAAC (SEQ ID NO: 927) |
| E10 | Even2Top77 | /5Phos/AGTTGTCACTTCCACTGCACGCTC (SEQ ID NO: 928) |
| F10 | Even2Top78 | /5Phos/AGTTGTCACCACCTGTCCAGCTCA (SEQ ID NO: 929) |
| G10 | Even2Top79 | /5Phos/AGTTGTCAATTATCAGAGTGCGGA (SEQ ID NO: 930) |
| H10 | Even2Top80 | /5Phos/AGTTGTCACGCAGTACAATAGGCG (SEQ ID NO: 931) |

TABLE 7-continued

Top Strand of the Even tag.
The bottom and top strands of the Even tag are annealed to make a double-stranded DNA oligo. It has a AGTTGTC overhang and 5'phosphate (5Phos) to be ligated by an Odd tag in the subsequent round of split-and-pool tagging.

| 96Well Position | Adaptor Name | Sequence |
|---|---|---|
| A11 | Even2Top81 | /5Phos/AGTTGTCAGAATACGATGGTGTGC (SEQ ID NO: 932) |
| B11 | Even2Top82 | /5Phos/AGTTGTCACACCGTGTGAAGCATT (SEQ ID NO: 933) |
| C11 | Even2Top83 | /5Phos/AGTTGTCACCATGCAGGCGGACAT (SEQ ID NO: 934) |
| D11 | Even2Top84 | /5Phos/AGTTGTCAGCAGTAGAGTGTTCCA (SEQ ID NO: 935) |
| E11 | Even2Top85 | /5Phos/AGTTGTCAGCCGTTGACAGGATAG (SEQ ID NO: 936) |
| F11 | Even2Top86 | /5Phos/AGTTGTCACACGCTACGGCAAGCT (SEQ ID NO: 937) |
| G11 | Even2Top87 | /5Phos/AGTTGTCACGGATCAATATCGACA (SEQ ID NO: 938) |
| H11 | Even2Top88 | /5Phos/AGTTGTCACTATACCTTCCGCTTC (SEQ ID NO: 939) |
| A12 | Even2Top89 | /5Phos/AGTTGTCACTGATTCGGAAGTAGC (SEQ ID NO: 940) |
| B12 | Even2Top90 | /5Phos/AGTTGTCACAGATGATCGTGTGCG (SEQ ID NO: 941) |
| C12 | Even2Top91 | /5Phos/AGTTGTCAGAGACGTGACACCAGT (SEQ ID NO: 942) |
| D12 | Even2Top92 | /5Phos/AGTTGTCAGACGTGTCGAACAGTC (SEQ ID NO: 943) |
| E12 | Even2Top93 | /5Phos/AGTTGTCAGAGAAGGCTCCGTGGT (SEQ ID NO: 944) |
| F12 | Even2Top94 | /5Phos/AGTTGTCACAGCGGACGTAACAGG (SEQ ID NO: 945) |
| G12 | Even2Top95 | /5Phos/AGTTGTCAGAATCGCCACAGCGTC (SEQ ID NO: 946) |
| H12 | Even2Top96 | /5Phos/AGTTGTCAGATTACGACTGGAGCG (SEQ ID NO: 947) |

TABLE 8

Bottom Strand of the Odd tag.
The bottom and top strands of the Even tag are annealed to make a double-stranded DNA oligo. It has a GACAACT overhang and 5'phosphate (5Phos) to ligate to an Odd tag.

| 96Well Position | Adaptor Name | Sequence |
|---|---|---|
| A1 | Odd2Bo1 | /5Phos/GACAACTCTTCGTGGAATCTAGCT (SEQ ID NO: 948) |
| B1 | Odd2Bo2 | /5Phos/GACAACTGCCTACAGAAGTATCTT (SEQ ID NO: 949) |
| C1 | Odd2Bo3 | /5Phos/GACAACTGGTATTACTCATAGGCT (SEQ ID NO: 950) |
| D1 | Odd2Bo4 | /5Phos/GACAACTAGACAAGCCACCTTATT (SEQ ID NO: 951) |
| E1 | Odd2Bo5 | /5Phos/GACAACTGCCTCTAACTAAGGATT (SEQ ID NO: 952) |
| F1 | Odd2Bo6 | /5Phos/GACAACTGGTGTCAAGCACCGCTT (SEQ ID NO: 953) |
| G1 | Odd2Bo7 | /5Phos/GACAACTCACCGCAATATAATTGT (SEQ ID NO: 954) |
| H1 | Odd2Bo8 | /5Phos/GACAACTGCTGTGTCTGTCACCTT (SEQ ID NO: 955) |
| A2 | Odd2Bo9 | /5Phos/GACAACTTCCTGTGCGTTAGAGTT (SEQ ID NO: 956) |
| B2 | Odd2Bo10 | /5Phos/GACAACTGTCGGCAACAGACCATT (SEQ ID NO: 957) |
| C2 | Odd2Bo11 | /5Phos/GACAACTGCGGTCACGCCTGAGCT (SEQ ID NO: 958) |
| D2 | Odd2Bo12 | /5Phos/GACAACTCGCCGTGCCTCTAACTT (SEQ ID NO: 959) |
| E2 | Odd2Bo13 | /5Phos/GACAACTTATCAATCGCAGCGGTT (SEQ ID NO: 960) |

TABLE 8-continued

Bottom Strand of the Odd tag.
The bottom and top strands of the Even tag are annealed to make a double-stranded DNA oligo. It has a GACAACT overhang and 5'phosphate (5Phos) to ligate to an Odd tag.

| 96Well Position | Adaptor Name | Sequence |
|---|---|---|
| F2 | Odd2Bo14 | /5Phos/GACAACTACTAGGTCGAATGCCTT (SEQ ID NO: 961) |
| G2 | Odd2Bo15 | /5Phos/GACAACTAATCAATGAACGAGGCT (SEQ ID NO: 962) |
| H2 | Odd2Bo16 | /5Phos/GACAACTTTGGCTAGGTTGTGTGT (SEQ ID NO: 963) |
| A3 | Odd2Bo17 | /5Phos/GACAACTCACTAGAGGTGTCCGTT (SEQ ID NO: 964) |
| B3 | Odd2Bo18 | /5Phos/GACAACTCGTGCTATAATCTTGTT (SEQ ID NO: 965) |
| C3 | Odd2Bo19 | /5Phos/GACAACTTTCGAGTGGAGCAATTT (SEQ ID NO: 966) |
| D3 | Odd2Bo20 | /5Phos/GACAACTTGGTTGCTTGCATTGTT (SEQ ID NO: 967) |
| E3 | Odd2Bo21 | /5Phos/GACAACTCGCCATGCAGTTACGCT (SEQ ID NO: 968) |
| F3 | Odd2Bo22 | /5Phos/GACAACTTAGTTCGTCACCGTGTT (SEQ ID NO: 969) |
| G3 | Odd2Bo23 | /5Phos/GACAACTAGCGTCATCGGACTCTT (SEQ ID NO: 970) |
| H3 | Odd2Bo24 | /5Phos/GACAACTTCGGTTCGTTAGGCGTT (SEQ ID NO: 971) |
| A4 | Odd2Bo25 | /5Phos/GACAACTATACTCGGTTAGTCCTT (SEQ ID NO: 972) |
| B4 | Odd2Bo26 | /5Phos/GACAACTAGTAGAACGCTAGGTTT (SEQ ID NO: 973) |
| C4 | Odd2Bo27 | /5Phos/GACAACTTCCGCCTAGTGAGGCTT (SEQ ID NO: 974) |
| D4 | Odd2Bo28 | /5Phos/GACAACTCAGCAACGTCCTATTGT (SEQ ID NO: 975) |
| E4 | Odd2Bo29 | /5Phos/GACAACTGTGCCTACGACGTAGCT (SEQ ID NO: 976) |
| F4 | Odd2Bo30 | /5Phos/GACAACTCGTCACACGTTGAACTT (SEQ ID NO: 977) |
| G4 | Odd2Bo31 | /5Phos/GACAACTAAGGACGCAGTGAGATT (SEQ ID NO: 978) |
| H4 | Odd2Bo32 | /5Phos/GACAACTTATACGGCACCTACTTT (SEQ ID NO: 979) |
| A5 | Odd2Bo33 | /5Phos/GACAACTATCGTTCTCATTCTGTT (SEQ ID NO: 980) |
| B5 | Odd2Bo34 | /5Phos/GACAACTCATCATACCACGCCGCT (SEQ ID NO: 981) |
| C5 | Odd2Bo35 | /5Phos/GACAACTATGATGTGATAAGGCTT (SEQ ID NO: 982) |
| D5 | Odd2Bo36 | /5Phos/GACAACTTGGTTGCAGCCTCCGCT (SEQ ID NO: 983) |
| E5 | Odd2Bo37 | /5Phos/GACAACTTACAATCACCGTGTATT (SEQ ID NO: 984) |
| F5 | Odd2Bo38 | /5Phos/GACAACTCATACTCTGGTGCCATT (SEQ ID NO: 985) |
| G5 | Odd2Bo39 | /5Phos/GACAACTGTTGAACACTTCCGTTT (SEQ ID NO: 986) |
| H5 | Odd2Bo40 | /5Phos/GACAACTTCACACGTCGAGCGATT (SEQ ID NO: 987) |
| A6 | Odd2Bo41 | /5Phos/GACAACTAACGCCGATAAGGACTT (SEQ ID NO: 988) |
| B6 | Odd2Bo42 | /5Phos/GACAACTATCCTGGACAGTGAGCT (SEQ ID NO: 989) |
| C6 | Odd2Bo43 | /5Phos/GACAACTCTTCTTGTCTTGGAGCT (SEQ ID NO: 990) |
| D6 | Odd2Bo44 | /5Phos/GACAACTCGTTCATTACGTCAGTT (SEQ ID NO: 991) |
| E6 | Odd2Bo45 | /5Phos/GACAACTTGCTCTTCATAAGCCTT (SEQ ID NO: 992) |
| F6 | Odd2Bo46 | /5Phos/GACAACTGGTCACCAAGAGACGCT (SEQ ID NO: 993) |
| G6 | Odd2Bo47 | /5Phos/GACAACTTTGTGTAGGAGCAAGTT (SEQ ID NO: 994) |
| H6 | Odd2Bo48 | /5Phos/GACAACTTCTCAATCTGGATCGCT (SEQ ID NO: 995) |
| A7 | Odd2Bo49 | /5Phos/GACAACTGCTGGAAGCCTCTAGCT (SEQ ID NO: 996) |

TABLE 8-continued

Bottom Strand of the Odd tag.
The bottom and top strands of the Even tag are annealed to make a double-stranded DNA oligo. It has a GACAACT overhang and 5'phosphate (5Phos) to ligate to an Odd tag.

| 96Well Position | Adaptor Name | Sequence |
|---|---|---|
| B7 | Odd2Bo50 | /5Phos/GACAACTCGTTCTCCTTAGAGATT (SEQ ID NO: 997) |
| C7 | Odd2Bo51 | /5Phos/GACAACTCTCAAGGTGTCCGAGTT (SEQ ID NO: 998) |
| D7 | Odd2Bo52 | /5Phos/GACAACTATATGAATATGTGGCTT (SEQ ID NO: 999) |
| E7 | Odd2Bo53 | /5Phos/GACAACTTGAATATAGGCACTTGT (SEQ ID NO: 1000) |
| F7 | Odd2Bo54 | /5Phos/GACAACTGCCTTCCGCCTCGTATT (SEQ ID NO: 1001) |
| G7 | Odd2Bo55 | /5Phos/GACAACTATTGCTTAACGGATTGT (SEQ ID NO: 1002) |
| H7 | Odd2Bo56 | /5Phos/GACAACTCTTCCAACACACGGATT (SEQ ID NO: 1003) |
| A8 | Odd2Bo57 | /5Phos/GACAACTTCGTGAGGATCAACGCT (SEQ ID NO: 1004) |
| B8 | Odd2Bo58 | /5Phos/GACAACTACGTTCCATGCTATCTT (SEQ ID NO: 1005) |
| C8 | Odd2Bo59 | /5Phos/GACAACTGTCTCTTGCATCACGCT (SEQ ID NO: 1006) |
| D8 | Odd2Bo60 | /5Phos/GACAACTGTCACTCGGTGCGACTT (SEQ ID NO: 1007) |
| E8 | Odd2Bo61 | /5Phos/GACAACTATATCTGTGAGCCGATT (SEQ ID NO: 1008) |
| F8 | Odd2Bo62 | /5Phos/GACAACTTAGACAGACGGTCTATT (SEQ ID NO: 1009) |
| G8 | Odd2Bo63 | /5Phos/GACAACTGTATCGCACTCATTGTT (SEQ ID NO: 1010) |
| H8 | Odd2Bo64 | /5Phos/GACAACTCCTACATCTGTCGAGTT (SEQ ID NO: 1011) |
| A9 | Odd2Bo65 | /5Phos/GACAACTTGATACCGTAGCAGATT (SEQ ID NO: 1012) |
| B9 | Odd2Bo66 | /5Phos/GACAACTGGATAGCACCGTTCATT (SEQ ID NO: 1013) |
| C9 | Odd2Bo67 | /5Phos/GACAACTATGAGTGCCGCAGACTT (SEQ ID NO: 1014) |
| D9 | Odd2Bo68 | /5Phos/GACAACTGCCTAGTAGAAGACGTT (SEQ ID NO: 1015) |
| E9 | Odd2Bo69 | /5Phos/GACAACTTAATTGAATACACCGTT (SEQ ID NO: 1016) |
| F9 | Odd2Bo70 | /5Phos/GACAACTTGCCATTCCACTTAGCT (SEQ ID NO: 1017) |
| G9 | Odd2Bo71 | /5Phos/GACAACTCCTCCAGTGTCGTCGCT (SEQ ID NO: 1018) |
| H9 | Odd2Bo72 | /5Phos/GACAACTGGAGTGCGTGTTAGCTT (SEQ ID NO: 1019) |
| A10 | Odd2Bo73 | /5Phos/GACAACTTTCTAACACACAGCCTT (SEQ ID NO: 1020) |
| B10 | Odd2Bo74 | /5Phos/GACAACTGACCAAGCACCAGACTT (SEQ ID NO: 1021) |
| C10 | Odd2Bo75 | /5Phos/GACAACTCCTATTGCATCTTCATT (SEQ ID NO: 1022) |
| D10 | Odd2Bo76 | /5Phos/GACAACTGTGCTAACCTACACATT (SEQ ID NO: 1023) |
| E10 | Odd2Bo77 | /5Phos/GACAACTCATATCTCGAATAGGCT (SEQ ID NO: 1024) |
| F10 | Odd2Bo78 | /5Phos/GACAACTGACGAACTCCATGCGTT (SEQ ID NO: 1025) |
| G10 | Odd2Bo79 | /5Phos/GACAACTGTCCGATGGACGCCGTT (SEQ ID NO: 1026) |
| H10 | Odd2Bo80 | /5Phos/GACAACTCAACGAGGTCAGTCGCT (SEQ ID NO: 1027) |
| A11 | Odd2Bo81 | /5Phos/GACAACTTAGTGGCACTTCACCTT (SEQ ID NO: 1028) |
| B11 | Odd2Bo82 | /5Phos/GACAACTACCTTCCTATGCTACTT (SEQ ID NO: 1029) |
| C11 | Odd2Bo83 | /5Phos/GACAACTATCGAGGATAGCCTGTT (SEQ ID NO: 1030) |
| D11 | Odd2Bo84 | /5Phos/GACAACTACTCAGGAAGGCTGATT (SEQ ID NO: 1031) |
| E11 | Odd2Bo85 | /5Phos/GACAACTTGGCAACGGCTCATGTT (SEQ ID NO: 1032) |

TABLE 8-continued

Bottom Strand of the Odd tag.
The bottom and top strands of the Even tag are annealed to make a double-stranded DNA oligo. It has a GACAACT overhang and 5'phosphate (5Phos) to ligate to an Odd tag.

| 96Well Position | Adaptor Name | Sequence |
|---|---|---|
| F11 | Odd2Bo86 | /5Phos/GACAACTCGGCAAGACTGCCTATT (SEQ ID NO: 1033) |
| G11 | Odd2Bo87 | /5Phos/GACAACTTAACGCAGGATACTATT (SEQ ID NO: 1034) |
| H11 | Odd2Bo88 | /5Phos/GACAACTGCTCTTGGAGGTATCTT (SEQ ID NO: 1035) |
| A12 | Odd2Bo89 | /5Phos/GACAACTCGAAGTGGTTCGGTCTT (SEQ ID NO: 1036) |
| B12 | Odd2Bo90 | /5Phos/GACAACTCTAACGCTGTGAAGGCT (SEQ ID NO: 1037) |
| C12 | Odd2Bo91 | /5Phos/GACAACTCTCCGAGATGATGTGTT (SEQ ID NO: 1038) |
| D12 | Odd2Bo92 | /5Phos/GACAACTCGCTGACATAAGACCTT (SEQ ID NO: 1039) |
| E12 | Odd2Bo93 | /5Phos/GACAACTTGAGAGGATGAATGCTT (SEQ ID NO: 1040) |
| F12 | Odd2Bo94 | /5Phos/GACAACTCAGACTCAATTAGGCTT (SEQ ID NO: 1041) |
| G12 | Odd2Bo95 | /5Phos/GACAACTTCGTGTCATCGCTAGTT (SEQ ID NO: 1042) |
| H12 | Odd2Bo96 | /5Phos/GACAACTAGAAGCCTCGGATTGTT (SEQ ID NO: 1043) |

TABLE 9

Top Strand of the Odd tag.
The bottom and top strands of the Odd tag are annealed to make a double-stranded DNA oligo. It has a GAACTCA overhang and 5'phosphate (5Phos) to be ligated by an Even tag or Terminal tag in the subsequent round of split-and-pool tagging.

| 96Well Position | Adaptor Name | Sequence |
|---|---|---|
| A1 | Odd2Top1 | /5Phos/CAAGTCAAGCTAGATTCCACGAAG (SEQ ID NO: 1044) |
| B1 | Odd2Top2 | /5Phos/CAAGTCAAAGATACTTCTGTAGGC (SEQ ID NO: 1045) |
| C1 | Odd2Top3 | /5Phos/CAAGTCAAGCCTATGAGTAATACC (SEQ ID NO: 1046) |
| D1 | Odd2Top4 | /5Phos/CAAGTCAAATAAGGTGGCTTGTCT (SEQ ID NO: 1047) |
| E1 | Odd2Top5 | /5Phos/CAAGTCAAATCCTTAGTTAGAGGC (SEQ ID NO: 1048) |
| F1 | Odd2Top6 | /5Phos/CAAGTCAAAGCGGTGCTTGACACC (SEQ ID NO: 1049) |
| G1 | Odd2Top7 | /5Phos/CAAGTCAACAATTATATTGCGGTG (SEQ ID NO: 1050) |
| H1 | Odd2Top8 | /5Phos/CAAGTCAAAGGTGACAGACACAGC (SEQ ID NO: 1051) |
| A2 | Odd2Top9 | /5Phos/CAAGTCAAACTCTAACGCACAGGA (SEQ ID NO: 1052) |
| B2 | Odd2Top10 | /5Phos/CAAGTCAAATGGTCTGTTGCCGAC (SEQ ID NO: 1053) |
| C2 | Odd2Top11 | /5Phos/CAAGTCAAGCTCAGGCGTGACCGC (SEQ ID NO: 1054) |
| D2 | Odd2Top12 | /5Phos/CAAGTCAAAGTTAGAGGCACGGCG (SEQ ID NO: 1055) |
| E2 | Odd2Top13 | /5Phos/CAAGTCAAACCGCTGCGATTGATA (SEQ ID NO: 1056) |
| F2 | Odd2Top14 | /5Phos/CAAGTCAAAGGCATTCGACCTAGT (SEQ ID NO: 1057) |
| G2 | Odd2Top15 | /5Phos/CAAGTCAAGCCTCGTTCATTGATT (SEQ ID NO: 1058) |
| H2 | Odd2Top16 | /5Phos/CAAGTCAACACACAACCTAGCCAA (SEQ ID NO: 1059) |
| A3 | Odd2Top17 | /5Phos/CAAGTCAAACGGACACCTCTAGTG (SEQ ID NO: 1060) |
| B3 | Odd2Top18 | /5Phos/CAAGTCAAACAAGATTATAGCACG (SEQ ID NO: 1061) |
| C3 | Odd2Top19 | /5Phos/CAAGTCAAAATTGCTCCACTCGAA (SEQ ID NO: 1062) |
| D3 | Odd2Top20 | /5Phos/CAAGTCAAACAATGCAAGCAACCA (SEQ ID NO: 1063) |
| E3 | Odd2Top21 | /5Phos/CAAGTCAAGCGTAACTGCATGGCG (SEQ ID NO: 1064) |
| F3 | Odd2Top22 | /5Phos/CAAGTCAAACACGGTGACGAACTA (SEQ ID NO: 1065) |

TABLE 9-continued

Top Strand of the Odd tag.
The bottom and top strands of the Odd tag are
annealed to make a double-stranded DNA oligo. It
has a GAACTCA overhang and 5'phosphate (5Phos)
to be ligated by an Even tag or Terminal tag in
the subsequent round of split-and-pool tagging.

| 96Well Position | Adaptor Name | Sequence |
|---|---|---|
| G3 | Odd2Top23 | /5Phos/CAAGTCAAAGAGTCCGATGACGCT (SEQ ID NO: 1066) |
| H3 | Odd2Top24 | /5Phos/CAAGTCAAACGCCTAACGAACCGA (SEQ ID NO: 1067) |
| A4 | Odd2Top25 | /5Phos/CAAGTCAAAGGACTAACCGAGTAT (SEQ ID NO: 1068) |
| B4 | Odd2Top26 | /5Phos/CAAGTCAAAACCTAGCGTTCTACT (SEQ ID NO: 1069) |
| C4 | Odd2Top27 | /5Phos/CAAGTCAAAGCCTCACTAGGCGGA (SEQ ID NO: 1070) |
| D4 | Odd2Top28 | /5Phos/CAAGTCAACAATAGGACGTTGCTG (SEQ ID NO: 1071) |
| E4 | Odd2Top29 | /5Phos/CAAGTCAAGCTACGTCGTAGGCAC (SEQ ID NO: 1072) |
| F4 | Odd2Top30 | /5Phos/CAAGTCAAAGTTCAACGTGTGACG (SEQ ID NO: 1073) |
| G4 | Odd2Top31 | /5Phos/CAAGTCAAATCTCACTGCGTCCTT (SEQ ID NO: 1074) |
| H4 | Odd2Top32 | /5Phos/CAAGTCAAAAGTAGGTGCCGTATA (SEQ ID NO: 1075) |
| A5 | Odd2Top33 | /5Phos/CAAGTCAAACAGAATGAGAACGAT (SEQ ID NO: 1076) |
| B5 | Odd2Top34 | /5Phos/CAAGTCAAGCGGCGTGGTATGATG (SEQ ID NO: 1077) |
| C5 | Odd2Top35 | /5Phos/CAAGTCAAAGCCTTATCACATCAT (SEQ ID NO: 1078) |
| D5 | Odd2Top36 | /5Phos/CAAGTCAAGCGGAGGCTGCAACCA (SEQ ID NO: 1079) |
| E5 | Odd2Top37 | /5Phos/CAAGTCAAATACACGGTGATTGTA (SEQ ID NO: 1080) |
| F5 | Odd2Top38 | /5Phos/CAAGTCAAATGGCACCAGAGTATG (SEQ ID NO: 1081) |
| G5 | Odd2Top39 | /5Phos/CAAGTCAAAACGGAAGTGTTCAAC (SEQ ID NO: 1082) |
| H5 | Odd2Top40 | /5Phos/CAAGTCAAATCGCTCGACGTGTGA (SEQ ID NO: 1083) |
| A6 | Odd2Top41 | /5Phos/CAAGTCAAAGTCCTTATCGGCGTT (SEQ ID NO: 1084) |
| B6 | Odd2Top42 | /5Phos/CAAGTCAAGCTCACTGTCCAGGAT (SEQ ID NO: 1085) |
| C6 | Odd2Top43 | /5Phos/CAAGTCAAGCTCCAAGACAAGAAG (SEQ ID NO: 1086) |
| D6 | Odd2Top44 | /5Phos/CAAGTCAAACTGACGTAATGAACG (SEQ ID NO: 1087) |
| E6 | Odd2Top45 | /5Phos/CAAGTCAAAGGCTTATGAAGAGCA (SEQ ID NO: 1088) |
| F6 | Odd2Top46 | /5Phos/CAAGTCAAGCGTCTCTTGGTGACC (SEQ ID NO: 1089) |
| G6 | Odd2Top47 | /5Phos/CAAGTCAAACTTGCTCCTACACAA (SEQ ID NO: 1090) |
| H6 | Odd2Top48 | /5Phos/CAAGTCAAGCGATCCAGATTGAGA (SEQ ID NO: 1091) |
| A7 | Odd2Top49 | /5Phos/CAAGTCAAGCTAGAGGCTTCCAGC (SEQ ID NO: 1092) |
| B7 | Odd2Top50 | /5Phos/CAAGTCAAATCTCTAAGGAGAACG (SEQ ID NO: 1093) |
| C7 | Odd2Top51 | /5Phos/CAAGTCAAACTCGGACACCTTGAG (SEQ ID NO: 1094) |
| D7 | Odd2Top52 | /5Phos/CAAGTCAAAGCCACATATTCATAT (SEQ ID NO: 1095) |
| E7 | Odd2Top53 | /5Phos/CAAGTCAACAAGTGCCTATATTCA (SEQ ID NO: 1096) |
| F7 | Odd2Top54 | /5Phos/CAAGTCAAATACGAGGCGGAAGGC (SEQ ID NO: 1097) |
| G7 | Odd2Top55 | /5Phos/CAAGTCAACAATCCGTTAAGCAAT (SEQ ID NO: 1098) |
| H7 | Odd2Top56 | /5Phos/CAAGTCAAATCCGTGTGTTGGAAG (SEQ ID NO: 1099) |
| A8 | Odd2Top57 | /5Phos/CAAGTCAAGCGTTGATCCTCACGA (SEQ ID NO: 1100) |
| B8 | Odd2Top58 | /5Phos/CAAGTCAAAGATAGCATGGAACGT (SEQ ID NO: 1101) |
| C8 | Odd2Top59 | /5Phos/CAAGTCAAGCGTGATGCAAGAGAC (SEQ ID NO: 1102) |
| D8 | Odd2Top60 | /5Phos/CAAGTCAAAGTCGCACCGAGTGAC (SEQ ID NO: 1103) |
| E8 | Odd2Top61 | /5Phos/CAAGTCAAATCGGCTCACAGATAT (SEQ ID NO: 1104) |
| F8 | Odd2Top62 | /5Phos/CAAGTCAAATAGACCGTCTGTCTA (SEQ ID NO: 1105) |
| G8 | Odd2Top63 | /5Phos/CAAGTCAAACAATGAGTGCGATAC (SEQ ID NO: 1106) |
| H8 | Odd2Top64 | /5Phos/CAAGTCAAACTCGACAGATGTAGG (SEQ ID NO: 1107) |
| A9 | Odd2Top65 | /5Phos/CAAGTCAAATCTGCTACGGTATCA (SEQ ID NO: 1108) |
| B9 | Odd2Top66 | /5Phos/CAAGTCAAATGAACGGTGCTATCC (SEQ ID NO: 1109) |
| C9 | Odd2Top67 | /5Phos/CAAGTCAAAGTCTGCGGCACTCAT (SEQ ID NO: 1110) |
| D9 | Odd2Top68 | /5Phos/CAAGTCAAACGTCTTCTACTAGGC (SEQ ID NO: 1111) |

TABLE 9-continued

Top Strand of the Odd tag.
The bottom and top strands of the Odd tag are
annealed to make a double-stranded DNA oligo. It
has a GAACTCA overhang and 5'phosphate (5Phos)
to be ligated by an Even tag or Terminal tag in
the subsequent round of split-and-pool tagging.

| 96Well Position | Adaptor Name | Sequence |
|---|---|---|
| E9 | Odd2Top69 | /5Phos/CAAGTCAAACGGTGTATTCAATTA (SEQ ID NO: 1112) |
| F9 | Odd2Top70 | /5Phos/CAAGTCAAGCTAAGTGGAATGGCA (SEQ ID NO: 1113) |
| G9 | Odd2Top71 | /5Phos/CAAGTCAAGCGACGACACTGGAGG (SEQ ID NO: 1114) |
| H9 | Odd2Top72 | /5Phos/CAAGTCAAAGCTAACACGCACTCC (SEQ ID NO: 1115) |
| A10 | Odd2Top73 | /5Phos/CAAGTCAAAGGCTGTGTGTTAGAA (SEQ ID NO: 1116) |
| B10 | Odd2Top74 | /5Phos/CAAGTCAAAGTCTGGTGCTTGGTC (SEQ ID NO: 1117) |
| C10 | Odd2Top75 | /5Phos/CAAGTCAAATGAAGATGCAATAGG (SEQ ID NO: 1118) |
| D10 | Odd2Top76 | /5Phos/CAAGTCAAATGTGTAGGTTAGCAC (SEQ ID NO: 1119) |
| E10 | Odd2Top77 | /5Phos/CAAGTCAAGCCTATTCGAGATATG (SEQ ID NO: 1120) |
| F10 | Odd2Top78 | /5Phos/CAAGTCAAACGCATGGAGTTCGTC (SEQ ID NO: 1121) |
| G10 | Odd2Top79 | /5Phos/CAAGTCAAACGGCGTCCATCGGAC (SEQ ID NO: 1122) |
| H10 | Odd2Top80 | /5Phos/CAAGTCAAGCGACTGACCTCGTTG (SEQ ID NO: 1123) |
| A11 | Odd2Top81 | /5Phos/CAAGTCAAAGGTGAAGTGCCACTA (SEQ ID NO: 1124) |
| B11 | Odd2Top82 | /5Phos/CAAGTCAAAGTAGCATAGGAAGGT (SEQ ID NO: 1125) |
| C11 | Odd2Top83 | /5Phos/CAAGTCAAACAGGCTATCCTCGAT (SEQ ID NO: 1126) |
| D11 | Odd2Top84 | /5Phos/CAAGTCAAATCAGCCTTCCTGAGT (SEQ ID NO: 1127) |
| E11 | Odd2Top85 | /5Phos/CAAGTCAAACATGAGCCGTTGCCA (SEQ ID NO: 1128) |
| F11 | Odd2Top86 | /5Phos/CAAGTCAAATAGGCAGTCTTGCCG (SEQ ID NO: 1129) |
| G11 | Odd2Top87 | /5Phos/CAAGTCAAATAGTATCCTGCGTTA (SEQ ID NO: 1130) |
| H11 | Odd2Top88 | /5Phos/CAAGTCAAAGATACCTCCAAGAGC (SEQ ID NO: 1131) |
| A12 | Odd2Top89 | /5Phos/CAAGTCAAAGACCGAACCACTTCG (SEQ ID NO: 1132) |
| B12 | Odd2Top90 | /5Phos/CAAGTCAAGCCTTCACAGCGTTAG (SEQ ID NO: 1133) |
| C12 | Odd2Top91 | /5Phos/CAAGTCAAACACATCATCTCGGAG (SEQ ID NO: 1134) |
| D12 | Odd2Top92 | /5Phos/CAAGTCAAAGGTCTTATGTCAGCG (SEQ ID NO: 1135) |
| E12 | Odd2Top93 | /5Phos/CAAGTCAAAGCATTCATCCTCTCA (SEQ ID NO: 1136) |
| F12 | Odd2Top94 | /5Phos/CAAGTCAAAGCCTAATTGAGTCTG (SEQ ID NO: 1137) |
| G12 | Odd2Top95 | /5Phos/CAAGTCAAACTAGCGATGACACGA (SEQ ID NO: 1138) |
| H12 | Odd2Top96 | /5Phos/CAAGTCAAACAATCCGAGGCTTCT (SEQ ID NO: 1139) |

TABLE 10

2P barcoded Primer for Library Amplification
The 2P barcoded primer in combination with the 2P universal primer will amplify from
the terminal tag in the last library amplification stage. If dilution of complexes
into multiple wells is performed prior to the library amplification stage,
this 2P_barcoded primer adds an additional round of tagging to each complex.
This barcode is read off during Illumina sequencing during the indexing step.

| 96 Well Position | Adaptor Name | Barcode Sequence |
|---|---|---|
| A1 | 2P_57 | CTCTACTT CAAGCAGAAGACGGCATACGAGATCTCTACTTGTGACTGGAGTTCAGACGTGTGCTCTTCCGATCT (SEQ ID NO: 1140) |
| A2 | 2P_100 | GATCGTGT CAAGCAGAAGACGGCATACGAGATGATCGTGTGTGACTGGAGTTCAGACGTGTGCTCTTCCGATCT (SEQ ID NO: 1141) |
| A3 | 2P_930 | TCGGAACA CAAGCAGAAGACGGCATACGAGATTCGGAACAGTGACTGGAGTTCAGACGTGTGCTCTTCCGATCT (SEQ ID NO: 1142) |
| A4 | 2P_373 | CGATCATG CAAGCAGAAGACGGCATACGAGATCGATCATGGTGACTGGAGTTCAGACGTGTGCTCTTCCGATCT (SEQ ID NO: 1143) |

TABLE 10-continued 2P barcoded Primer for Library Amplification
The 2P barcoded primer in combination with the 2P universal primer will amplify from the terminal tag in the last library amplification stage. If dilution of complexes into multiple wells is performed prior to the library amplification stage, this 2P_barcoded primer adds an additional round of tagging to each complex. This barcode is read off during Illumina sequencing during the indexing step.

| 96 Well Position | Adaptor Name | Barcode Sequence |
|---|---|---|
| A5 | 2P_498 | TGGTAACG CAAGCAGAAGACGGCATACGAGATTGGTAACGGTGACTGGAGTTCAGACGTGTGCTCTTCCGATCT (SEQ ID NO: 1144) |
| A6 | 2P_861 | ACCAAGGA CAAGCAGAAGACGGCATACGAGATACCAAGGAGTGACTGGAGTTCAGACGTGTGCTCTTCCGATCT (SEQ ID NO: 1145) |
| A7 | 2P_23 | AATGCGTT CAAGCAGAAGACGGCATACGAGATAATGCGTTGTGACTGGAGTTCAGACGTGTGCTCTTCCGATCT (SEQ ID NO: 1146) |
| A8 | 2P_109 | ATACCTGT CAAGCAGAAGACGGCATACGAGATATACCTGTGTGACTGGAGTTCAGACGTGTGCTCTTCCGATCT (SEQ ID NO: 1147) |
| A9 | 2P_218 | CCTTACCT CAAGCAGAAGACGGCATACGAGATCCTTACCTGTGACTGGAGTTCAGACGTGTGCTCTTCCGATCT (SEQ ID NO: 1148) |
| A10 | 2Ped_3 | CCATTGTT CAAGCAGAAGACGGCATACGAGATCCATTGTTGTGACTGGAGTTCAGACGTGTGCTCTTCCGATCT (SEQ ID NO: 1149) |
| A11 | 2P_163 | GATACAGT CAAGCAGAAGACGGCATACGAGATGATACAGTGTGACTGGAGTTCAGACGTGTGCTCTTCCGATCT (SEQ ID NO: 1150) |
| A12 | 2P_220 | TGCGACCT CAAGCAGAAGACGGCATACGAGATTGCGACCTGTGACTGGAGTTCAGACGTGTGCTCTTCCGATCT (SEQ ID NO: 1151) |
| B1 | 2P_726 | TCTGGACC CAAGCAGAAGACGGCATACGAGATTCTGGACCGTGACTGGAGTTCAGACGTGTGCTCTTCCGATCT (SEQ ID NO: 1152) |
| B2 | 2P_375 | TAAGCATG CAAGCAGAAGACGGCATACGAGATTAAGCATGGTGACTGGAGTTCAGACGTGTGCTCTTCCGATCT (SEQ ID NO: 1153) |
| B3 | 2P_214 | TAGATCCT CAAGCAGAAGACGGCATACGAGATTAGATCCTGTGACTGGAGTTCAGACGTGTGCTCTTCCGATCT (SEQ ID NO: 1154) |
| B4 | 2P_880 | TCGCCAGA CAAGCAGAAGACGGCATACGAGATTCGCCAGAGTGACTGGAGTTCAGACGTGTGCTCTTCCGATCT (SEQ ID NO: 1155) |
| B5 | 2P_223 | GATAACCT CAAGCAGAAGACGGCATACGAGATGATAACCTGTGACTGGAGTTCAGACGTGTGCTCTTCCGATCT (SEQ ID NO: 1156) |
| B6 | 2P_754 | CATCAGAC CAAGCAGAAGACGGCATACGAGATCATCAGACGTGACTGGAGTTCAGACGTGTGCTCTTCCGATCT (SEQ ID NO: 1157) |
| B7 | 2P_379 | AATGTTGG CAAGCAGAAGACGGCATACGAGATAATGTTGGGTGACTGGAGTTCAGACGTGTGCTCTTCCGATCT (SEQ ID NO: 1158) |
| B8 | 2P_309 | GAGAGTTG CAAGCAGAAGACGGCATACGAGATGAGAGTTGGTGACTGGAGTTCAGACGTGTGCTCTTCCGATCT (SEQ ID NO: 1159) |
| B9 | 2P_291 | AGAGGAAT CAAGCAGAAGACGGCATACGAGATAGAGGAATGTGACTGGAGTTCAGACGTGTGCTCTTCCGATCT (SEQ ID NO: 1160) |
| B10 | 2P_500 | CGAGTTAG CAAGCAGAAGACGGCATACGAGATCGAGTTAGGTGACTGGAGTTCAGACGTGTGCTCTTCCGATCT (SEQ ID NO: 1161) |
| B11 | 2P_534 | ATCCGCAG CAAGCAGAAGACGGCATACGAGATATCCGCAGGTGACTGGAGTTCAGACGTGTGCTCTTCCGATCT (SEQ ID NO: 1162) |
| B12 | 2P_504 | CCTGGTAG CAAGCAGAAGACGGCATACGAGATCCTGGTAGGTGACTGGAGTTCAGACGTGTGCTCTTCCGATCT (SEQ ID NO: 1163) |
| C1 | 2P_630 | AGATGTGC CAAGCAGAAGACGGCATACGAGATAGATGTGCGTGACTGGAGTTCAGACGTGTGCTCTTCCGATCT (SEQ ID NO: 1164) |
| C2 | 2P_741 | TGTTATAC CAAGCAGAAGACGGCATACGAGATTGTTATACGTGACTGGAGTTCAGACGTGTGCTCTTCCGATCT (SEQ ID NO: 1165) |
| C3 | 2P_367 | TCGCTATG CAAGCAGAAGACGGCATACGAGATTCGCTATGGTGACTGGAGTTCAGACGTGTGCTCTTCCGATCT (SEQ ID NO: 1166) |

TABLE 10-continued 2P barcoded Primer for Library Amplification
The 2P barcoded primer in combination with the 2P universal primer will amplify from the terminal tag in the last library amplification stage. If dilution of complexes into multiple wells is performed prior to the library amplification stage, this 2P_barcoded primer adds an additional round of tagging to each complex. This barcode is read off during Illumina sequencing during the indexing step.

| 96 Well Position | Adaptor Name | Barcode Sequence |
|---|---|---|
| C4 | 2P_579 | TTACTGTC CAAGCAGAAGACGGCATACGAGATTTACTGTCGTGACTGGAGTTCAGACGTGTGCTCTTCCGATCT (SEQ ID NO: 1167) |
| C5 | 2P_938 | GTGCGTAA CAAGCAGAAGACGGCATACGAGATGTGCGTAAGTGACTGGAGTTCAGACGTGTGCTCTTCCGATCT (SEQ ID NO: 1168) |
| C6 | 2P_745 | TAGATGAC CAAGCAGAAGACGGCATACGAGATTAGATGACGTGACTGGAGTTCAGACGTGTGCTCTTCCGATCT (SEQ ID NO: 1169) |
| C7 | 2P_542 | GATTACAG CAAGCAGAAGACGGCATACGAGATGATTACAGGTGACTGGAGTTCAGACGTGTGCTCTTCCGATCT (SEQ ID NO: 1170) |
| C8 | 2P_655 | TCGACGGC CAAGCAGAAGACGGCATACGAGATTCGACGGCGTGACTGGAGTTCAGACGTGTGCTCTTCCGATCT (SEQ ID NO: 1171) |
| C9 | 2P_732 | GATGTTAC CAAGCAGAAGACGGCATACGAGATGATGTTACGTGACTGGAGTTCAGACGTGTGCTCTTCCGATCT (SEQ ID NO: 1172) |
| C10 | 2P_567 | CTTCCTTC CAAGCAGAAGACGGCATACGAGATCTTCCTTCGTGACTGGAGTTCAGACGTGTGCTCTTCCGATCT (SEQ ID NO: 1173) |
| C11 | 2P_584 | GTTAGGTC CAAGCAGAAGACGGCATACGAGATGTTAGGTCGTGACTGGAGTTCAGACGTGTGCTCTTCCGATCT (SEQ ID NO: 1174) |
| C12 | 2P_117 | CAGTTGGT CAAGCAGAAGACGGCATACGAGATCAGTTGGTGTGACTGGAGTTCAGACGTGTGCTCTTCCGATCT (SEQ ID NO: 1175) |
| D1 | 2P_954 | TCAGCGAA CAAGCAGAAGACGGCATACGAGATTCAGCGAAGTGACTGGAGTTCAGACGTGTGCTCTTCCGATCT (SEQ ID NO: 1176) |
| D2 | 2P_908 | GTCGAGCA CAAGCAGAAGACGGCATACGAGATGTCGAGCAGTGACTGGAGTTCAGACGTGTGCTCTTCCGATCT (SEQ ID NO: 1177) |
| D3 | 2P_426 | GGCATAGG CAAGCAGAAGACGGCATACGAGATGGCATAGGGTGACTGGAGTTCAGACGTGTGCTCTTCCGATCT (SEQ ID NO: 1178) |
| D4 | 2P_357 | GGCTCCTG CAAGCAGAAGACGGCATACGAGATGGCTCCTGGTGACTGGAGTTCAGACGTGTGCTCTTCCGATCT (SEQ ID NO: 1179) |
| D5 | 2P_438 | TGCGAAGG CAAGCAGAAGACGGCATACGAGATTGCGAAGGGTGACTGGAGTTCAGACGTGTGCTCTTCCGATCT (SEQ ID NO: 1180) |
| D6 | 2P_959 | CTATTCAA CAAGCAGAAGACGGCATACGAGATCTATTCAAGTGACTGGAGTTCAGACGTGTGCTCTTCCGATCT (SEQ ID NO: 1181) |
| D7 | 2P_821 | GGCAGATA CAAGCAGAAGACGGCATACGAGATGGCAGATAGTGACTGGAGTTCAGACGTGTGCTCTTCCGATCT (SEQ ID NO: 1182) |
| D8 | 2P_778 | TGTGCTTA CAAGCAGAAGACGGCATACGAGATTGTGCTTAGTGACTGGAGTTCAGACGTGTGCTCTTCCGATCT (SEQ ID NO: 1183) |
| D9 | 2P_868 | TCTAGCGA CAAGCAGAAGACGGCATACGAGATTCTAGCGAGTGACTGGAGTTCAGACGTGTGCTCTTCCGATCT (SEQ ID NO: 1184) |
| D10 | 2P_924 | TGATTACA CAAGCAGAAGACGGCATACGAGATTGATTACAGTGACTGGAGTTCAGACGTGTGCTCTTCCGATCT (SEQ ID NO: 1185) |
| D11 | 2P_934 | CTGATTAA CAAGCAGAAGACGGCATACGAGATCTGATTAAGTGACTGGAGTTCAGACGTGTGCTCTTCCGATCT (SEQ ID NO: 1186) |
| D12 | 2P_899 | TACTTGCA CAAGCAGAAGACGGCATACGAGATTACTTGCAGTGACTGGAGTTCAGACGTGTGCTCTTCCGATCT (SEQ ID NO: 1187) |
| E1 | 2P_190 | GAATTGCT CAAGCAGAAGACGGCATACGAGATGAATTGCTGTGACTGGAGTTCAGACGTGTGCTCTTCCGATCT (SEQ ID NO: 1188) |
| E2 | 2P_34 | GTCAAGTT CAAGCAGAAGACGGCATACGAGATGTCAAGTTGTGACTGGAGTTCAGACGTGTGCTCTTCCGATCT (SEQ ID NO: 1189) |

TABLE 10-continued 2P barcoded Primer for Library Amplification
The 2P barcoded primer in combination with the 2P universal primer will amplify from the terminal tag in the last library amplification stage. If dilution of complexes into multiple wells is performed prior to the library amplification stage, this 2P_barcoded primer adds an additional round of tagging to each complex. This barcode is read off during Illumina sequencing during the indexing step.

| 96 Well Position | Adaptor Name | Barcode Sequence |
|---|---|---|
| E3 | 2P_927 | ATCCGACA CAAGCAGAAGACGGCATACGAGATATCCGACAGTGACTGGAGTTCAGACGTGTGCTCTTCCGATCT (SEQ ID NO: 1190) |
| E4 | 2P_866 | CAAGGCGA CAAGCAGAAGACGGCATACGAGATCAAGGCGAGTGACTGGAGTTCAGACGTGTGCTCTTCCGATCT (SEQ ID NO: 1191) |
| E5 | 2P_38 | AGTGTCTT CAAGCAGAAGACGGCATACGAGATAGTGTCTTGTGACTGGAGTTCAGACGTGTGCTCTTCCGATCT (SEQ ID NO: 1192) |
| E6 | 2P_875 | GACCGAGA CAAGCAGAAGACGGCATACGAGATGACCGAGAGTGACTGGAGTTCAGACGTGTGCTCTTCCGATCT (SEQ ID NO: 1193) |
| E7 | 2P_78 | AGAACATT CAAGCAGAAGACGGCATACGAGATAGAACATTGTGACTGGAGTTCAGACGTGTGCTCTTCCGATCT (SEQ ID NO: 1194) |
| E8 | 2P_151 | GTCTTAGT CAAGCAGAAGACGGCATACGAGATGTCTTAGTGTGACTGGAGTTCAGACGTGTGCTCTTCCGATCT (SEQ ID NO: 1195) |
| E9 | 2P_288 | TTGATAAT CAAGCAGAAGACGGCATACGAGATTTGATAATGTGACTGGAGTTCAGACGTGTGCTCTTCCGATCT (SEQ ID NO: 1196) |
| E10 | 2P_110 | TCAACTGT CAAGCAGAAGACGGCATACGAGATTCAACTGTGTGACTGGAGTTCAGACGTGTGCTCTTCCGATCT (SEQ ID NO: 1197) |
| E11 | 2P_195 | TCCATGCT CAAGCAGAAGACGGCATACGAGATTCCATGCTGTGACTGGAGTTCAGACGTGTGCTCTTCCGATCT (SEQ ID NO: 1198) |
| E12 | 2P_222 | TCGCACCT CAAGCAGAAGACGGCATACGAGATTCGCACCTGTGACTGGAGTTCAGACGTGTGCTCTTCCGATCT (SEQ ID NO: 1199) |
| F1 | 2P_332 | AGGATGTG CAAGCAGAAGACGGCATACGAGATAGGATGTGGTGACTGGAGTTCAGACGTGTGCTCTTCCGATCT (SEQ ID NO: 1200) |
| F2 | 2P_236 | AAGCAACT CAAGCAGAAGACGGCATACGAGATAAGCAACTGTGACTGGAGTTCAGACGTGTGCTCTTCCGATCT (SEQ ID NO: 1201) |
| F3 | 2P_250 | GACGCTAT CAAGCAGAAGACGGCATACGAGATGACGCTATGTGACTGGAGTTCAGACGTGTGCTCTTCCGATCT (SEQ ID NO: 1202) |
| F4 | 2P_289 | AACATAAT CAAGCAGAAGACGGCATACGAGATAACATAATGTGACTGGAGTTCAGACGTGTGCTCTTCCGATCT (SEQ ID NO: 1203) |
| F5 | 2P_298 | CAGACAAT CAAGCAGAAGACGGCATACGAGATCAGACAATGTGACTGGAGTTCAGACGTGTGCTCTTCCGATCT (SEQ ID NO: 1204) |
| F6 | 2P_352 | CCTTGCTG CAAGCAGAAGACGGCATACGAGATCCTTGCTGGTGACTGGAGTTCAGACGTGTGCTCTTCCGATCT (SEQ ID NO: 1205) |
| F7 | 2P_469 | GGAAGGCG CAAGCAGAAGACGGCATACGAGATGGAAGGCGGTGACTGGAGTTCAGACGTGTGCTCTTCCGATCT (SEQ ID NO: 1206) |
| F8 | 2P_355 | TACCGCTG CAAGCAGAAGACGGCATACGAGATTACCGCTGGTGACTGGAGTTCAGACGTGTGCTCTTCCGATCT (SEQ ID NO: 1207) |
| F9 | 2P_320 | GACTATTG CAAGCAGAAGACGGCATACGAGATGACTATTGGTGACTGGAGTTCAGACGTGTGCTCTTCCGATCT (SEQ ID NO: 1208) |
| F10 | 2P_509 | ACGCATAG CAAGCAGAAGACGGCATACGAGATACGCATAGGTGACTGGAGTTCAGACGTGTGCTCTTCCGATCT (SEQ ID NO: 1209) |
| F11 | 2P_544 | CGCCACAG CAAGCAGAAGACGGCATACGAGATCGCCACAGGTGACTGGAGTTCAGACGTGTGCTCTTCCGATCT (SEQ ID NO: 1210) |
| F12 | 2P_474 | ACATAGCG CAAGCAGAAGACGGCATACGAGATACATAGCGGTGACTGGAGTTCAGACGTGTGCTCTTCCGATCT (SEQ ID NO: 1211) |
| G1 | 2P_393 | CTAACTGG CAAGCAGAAGACGGCATACGAGATCTAACTGGGTGACTGGAGTTCAGACGTGTGCTCTTCCGATCT (SEQ ID NO: 1212) |

TABLE 10-continued 2P barcoded Primer for Library Amplification
The 2P barcoded primer in combination with the 2P universal primer will amplify from the terminal tag in the last library amplification stage. If dilution of complexes into multiple wells is performed prior to the library amplification stage, this 2P_barcoded primer adds an additional round of tagging to each complex. This barcode is read off during Illumina sequencing during the indexing step.

| 96 Well Position | Adaptor Name | Barcode Sequence |
|---|---|---|
| G2 | 2P_869 | CATTCCGA CAAGCAGAAGACGGCATACGAGATCATTCCGAGTGACTGGAGTTCAGACGTGTGCTCTTCCGATCT (SEQ ID NO: 1213) |
| G3 | 2P_422 | ATGGTAGG CAAGCAGAAGACGGCATACGAGATATGGTAGGGTGACTGGAGTTCAGACGTGTGCTCTTCCGATCT (SEQ ID NO: 1214) |
| G4 | 2P_564 | ACTTCTTC CAAGCAGAAGACGGCATACGAGATACTTCTTCGTGACTGGAGTTCAGACGTGTGCTCTTCCGATCT (SEQ ID NO: 1215) |
| G5 | 2P_851 | TTGCTGGA CAAGCAGAAGACGGCATACGAGATTTGCTGGAGTGACTGGAGTTCAGACGTGTGCTCTTCCGATCT (SEQ ID NO: 1216) |
| G6 | 2P_559 | CTAGGTTC CAAGCAGAAGACGGCATACGAGATCTAGGTTCGTGACTGGAGTTCAGACGTGTGCTCTTCCGATCT (SEQ ID NO: 1217) |
| G7 | 2P_581 | TCCTGGTC CAAGCAGAAGACGGCATACGAGATTCCTGGTCGTGACTGGAGTTCAGACGTGTGCTCTTCCGATCT (SEQ ID NO: 1218) |
| G8 | 2P_657 | GGCTAGGC CAAGCAGAAGACGGCATACGAGATGGCTAGGCGTGACTGGAGTTCAGACGTGTGCTCTTCCGATCT (SEQ ID NO: 1219) |
| G9 | 2P_747 | CTGTGGAC CAAGCAGAAGACGGCATACGAGATCTGTGGACGTGACTGGAGTTCAGACGTGTGCTCTTCCGATCT (SEQ ID NO: 1220) |
| G10 | 2P_583 | CAACGGTC CAAGCAGAAGACGGCATACGAGATCAACGGTCGTGACTGGAGTTCAGACGTGTGCTCTTCCGATCT (SEQ ID NO: 1221) |
| G11 | 2P_616 | TGGATATC CAAGCAGAAGACGGCATACGAGATTGGATATCGTGACTGGAGTTCAGACGTGTGCTCTTCCGATCT (SEQ ID NO: 1222) |
| G12 | 2P_652 | GTTGCGGC CAAGCAGAAGACGGCATACGAGATGTTGCGGCGTGACTGGAGTTCAGACGTGTGCTCTTCCGATCT (SEQ ID NO: 1223) |
| H1 | 2P_52 | ACATCCTT CAAGCAGAAGACGGCATACGAGATACATCCTTGTGACTGGAGTTCAGACGTGTGCTCTTCCGATCT (SEQ ID NO: 1224) |
| H2 | 2P_960 | AGGCTCAA CAAGCAGAAGACGGCATACGAGATAGGCTCAAGTGACTGGAGTTCAGACGTGTGCTCTTCCGATCT (SEQ ID NO: 1225) |
| H3 | 2P_293 | CCTAGAAT CAAGCAGAAGACGGCATACGAGATCCTAGAATGTGACTGGAGTTCAGACGTGTGCTCTTCCGATCT (SEQ ID NO: 1226) |
| H4 | 2P_800 | GCTAAGTA CAAGCAGAAGACGGCATACGAGATGCTAAGTAGTGACTGGAGTTCAGACGTGTGCTCTTCCGATCT (SEQ ID NO: 1227) |
| H5 | 2P_786 | GTTCATTA CAAGCAGAAGACGGCATACGAGATGTTCATTAGTGACTGGAGTTCAGACGTGTGCTCTTCCGATCT (SEQ ID NO: 1228) |
| H6 | 2P_388 | AGCTCTGG CAAGCAGAAGACGGCATACGAGATAGCTCTGGGTGACTGGAGTTCAGACGTGTGCTCTTCCGATCT (SEQ ID NO: 1229) |
| H7 | 2P_910 | CAGCAGCA CAAGCAGAAGACGGCATACGAGATCAGCAGCAGTGACTGGAGTTCAGACGTGTGCTCTTCCGATCT (SEQ ID NO: 1230) |
| H8 | 2P_818 | CCTGGATA CAAGCAGAAGACGGCATACGAGATCCTGGATAGTGACTGGAGTTCAGACGTGTGCTCTTCCGATCT (SEQ ID NO: 1231) |
| H9 | 2P_878 | CTTGCAGA CAAGCAGAAGACGGCATACGAGATCTTGCAGAGTGACTGGAGTTCAGACGTGTGCTCTTCCGATCT (SEQ ID NO: 1232) |
| H10 | 2P_968 | ATAGACAA CAAGCAGAAGACGGCATACGAGATATAGACAAGTGACTGGAGTTCAGACGTGTGCTCTTCCGATCT (SEQ ID NO: 1233) |
| H11 | 2P_944 | AGATATAA CAAGCAGAAGACGGCATACGAGATAGATATAAGTGACTGGAGTTCAGACGTGTGCTCTTCCGATCT (SEQ ID NO: 1234) |
| H12 | 2P_923 | GAGTTACA CAAGCAGAAGACGGCATACGAGATGAGTTACAGTGACTGGAGTTCAGACGTGTGCTCTTCCGATCT (SEQ ID NO: 1235) |

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method for identifying interactions of DNA, RNA, and/or protein molecules in a cell, comprising:
   (i) lysing the cell to form a cell lysate comprising DNA, RNA, and/or protein molecules;
   (ii) distributing the DNA, RNA, and/or protein molecules into a plurality of first suspensions;
   (iii) adding ligation adaptor molecules to each of the first suspensions, the ligation adaptor molecules configured to modify at least one end of each of the DNA, RNA, and/or protein molecules in the first suspensions and capable of ligating to a unique first nucleotide tag;
   (iv) adding the unique first nucleotide tag to each of the first suspensions to tag the DNA, RNA and/or protein molecules in the respective first suspension, thereby forming a plurality of tagged first suspensions;
   (v) pooling the plurality of tagged first suspensions to form a first tagged pool;
   (vi) distributing the DNA, RNA, and/or protein molecules of the first tagged pool into a plurality of second suspensions;
   (vii) adding a unique second nucleotide tag to each of the plurality of second suspensions to tag the DNA, RNA, and/or protein molecules in the respective second suspension, thereby forming a plurality of tagged second suspensions;
   (viii) pooling the plurality of tagged second suspensions to form a second tagged pool comprising the DNA, RNA, and/or protein molecules;
   repeating distributing the DNA, RNA, and/or protein molecules and steps (iv)-(viii) at least once, whereby the DNA, RNA, and/or protein molecules each comprises a set of unique nucleotide tags;
   obtaining sequence information for the DNA, RNA, and/or protein molecules and their respective set of unique nucleotide tags; and
   identifying the DNA, RNA, and/or protein molecules tagged with the same set of unique nucleotide tags as likely interacting molecules;
   wherein the ligation adaptor molecules configured to modify at least one end of the DNA molecules comprise a 3' spacer that allows the nucleotide tags to only ligate to the 5' end of each single-stranded DNA sequence and prevents formation of hairpins during the step of obtaining sequence information.

2. The method of claim 1, further comprising diluting the cell lysate prior to distributing the cell lysate into the plurality of first suspensions.

3. The method of claim 1, further comprising:
   adding an antibody modified with an oligonucleotide to the cell lysate.

4. The method of claim 1, further comprising adding a crosslinker to the cell prior to lysing the cell or after lysing the cell.

5. The method of claim 1, further comprising shearing chromatin in the cell lysate.

6. A method for identifying interactions of DNA, RNA, and/or protein molecules in a cell, comprising:
   (i) lysing the cell to form a cell lysate;
   (ii) distributing the cell lysate into a plurality of lysate suspensions;
   (iii) adding ligation adaptor molecules to each of the lysate suspensions, the ligation adaptor molecules configured to modify at least one end of each of the DNA, RNA, and/or protein molecules and capable of ligating to a unique nucleotide tag;
   (iv) adding the unique nucleotide tag to each of the lysate suspensions to tag the DNA, RNA, and/or protein molecules in the respective lysate suspension and thereby forming a plurality of tagged lysate suspensions, the unique nucleotide tag in each tagged lysate suspension being different from the unique nucleotide tags for the other tagged lysate suspensions;
   (v) pooling the plurality of tagged lysate suspensions to form a tagged pool;
   (vi) repeating distributing the tagged pool into a plurality of tagged suspensions and performing (iv) and (v) on the plurality of tagged suspensions, wherein the repeating is performed n number of times to form a final tagged pool comprising a plurality of tagged suspensions in which the DNA, RNA, and/or protein molecules have n+1 number of unique nucleotide tags;
   (vii) obtaining sequence information for the DNA, RNA, and/or protein molecules and their n+1 number of nucleotide tags; and
   (viii) identifying the DNA, RNA, and/or protein molecules having the same sequence and order of nucleotide tags as likely interacting molecules;
   wherein the ligation adaptor molecules configured to modify at least one end of the DNA molecules comprises a 3' spacer that allows the nucleotide tags to only ligate to the 5' end of each single-stranded DNA sequence and prevents formation of hairpins during step (vii).

7. A method for detecting interactions of molecules in a nucleus of a cell, comprising:
  (i) lysing the cell;
  (ii) isolating the nucleus from the cell lysate;
  (iii) shearing the chromatin in the nucleus forming a suspension of sheared chromatin;
  (iv) distributing the suspension into a plurality of suspensions;
  (v) modifying at least one end of each of the DNA, RNA, and/or protein molecules in the suspension of sheared chromatin with ligation adaptor molecules, the ligation adaptor molecules capable of ligating to a unique nucleotide tag;
  (vi) adding the unique nucleotide tag to DNA, RNA, and/or protein molecules of the sheared chromatin in each of the plurality of suspensions, each unique nucleotide tag being different for each suspension, thereby forming a plurality of tagged suspensions;
  (vii) pooling the plurality of tagged suspensions to form a tagged pool;
  repeating distributing the suspension of sheared chromatin and steps (vi)-(vii) at least once, whereby the DNA, RNA, and/or protein molecules each comprise a set of unique nucleotide tags;
  obtaining sequence information for the DNA, RNA, and/or protein molecules of the sheared chromatin and their respective set of unique nucleotide tags; and
  identifying the DNA, RNA, and/or protein molecules having the same set of unique nucleotide tags as likely interacting molecules;
  wherein the ligation adaptor molecules that modifies at least one end of the DNA molecules comprises a 3' spacer that allows the nucleotide tags to only ligate to the 5' end of each single-stranded DNA sequence and prevents formation of hairpins during the step of obtaining sequence information.

8. The method of claim 7, further comprising:
  adding an antibody modified with an oligonucleotide to the cell prior to isolating the nucleus.

9. The method of claim 7, further comprising adding a crosslinker to the cell prior to lysing the cell or after lysing the cell.

10. The method of claim 1, wherein the unique nucleotide tags anneal with a 7 nucleotide overhang.

11. The method of claim 6, wherein the unique nucleotide tags anneal with a 7 nucleotide overhang.

12. The method of claim 7, wherein the unique nucleotide tags anneal with a 7 nucleotide overhang.

* * * * *

UNITED STATES PATENT AND TRADEMARK OFFICE
CERTIFICATE OF CORRECTION

| | |
|---|---|
| PATENT NO. | : 10,900,974 B2 |
| APPLICATION NO. | : 15/466861 |
| DATED | : January 26, 2021 |
| INVENTOR(S) | : Quinodoz et al. |

It is certified that error appears in the above-identified patent and that said Letters Patent is hereby corrected as shown below:

On the Title Page

In Column 2, item (56), Other Publications, Lines 2-3, delete "ChemCommun." and insert --Chem. Commun.,--.

In Column 2, item (56), Other Publications, Line 7, delete "IncRNA" and insert --lncRNA--.

In Column 2, item (56), Other Publications, Line 18, delete "IncRNA" and insert --lncRNA--.

In the Drawings

Figure 3G:
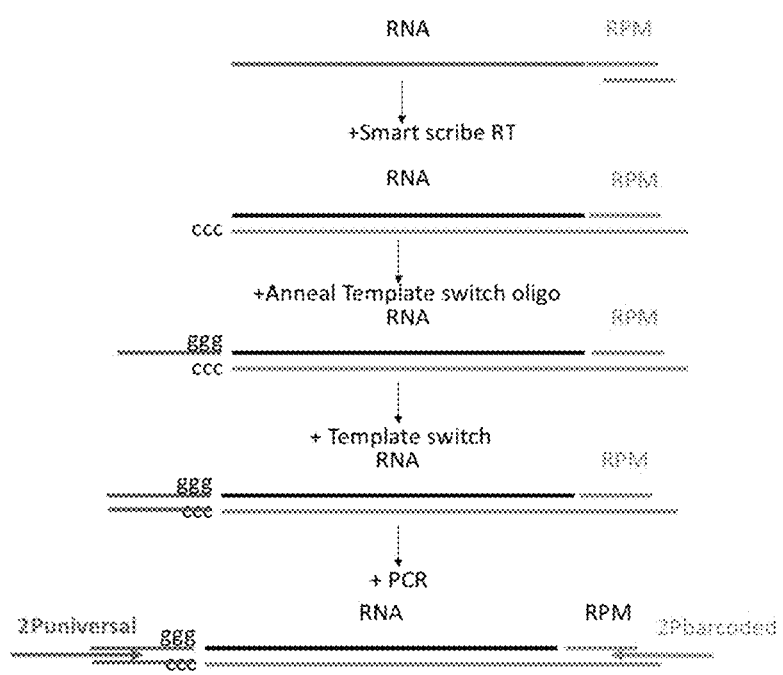
FIG. 3G is a schematic of template switching, according to embodiments of the present invention, in which 1) the reverse transcriptase synthesizes cDNA (shown in orange) and extends leaving 3 dCTP nucleotides (ccc) on the 3'end of the cDNA, 2) a complementary oligonucleotide with a GGG overhang is hybridized to the CCC sequence on the cDNA, this oligonucleotide also contains a 2P_universal priming sequence amplification, and 3) the cDNA is then extended (shown in blue) by the Reverse Transcriptase enzyme to extend the 3' end of the cDNA to contain the 2P_universal priming sequence.

In sheet 7 of 32, FIG. 3G, Line 15 (approx.), delete "2Puniversal" and insert --2P_universal--.

In sheet 7 of 32, FIG. 3G, Line 15 (approx.), delete "2Pbarcoded" and insert --2P_barcoded--.

In sheet 29 of 32, FIG. 10C, Line 10 (approx.), delete "Nucleoar" and insert --Nucleolar--.

In the Specification

In Column 1, Lines 16-18, delete "This invention was made with government support under Grant No. OD012190 and HL130007 awarded by the National Institutes of Health." and insert --This invention was made with government support under Grant Nos. OD012190, HL130007, and DA040612 awarded by the National Institutes of Health.--.

In Column 5, Line 46, delete "5A." and insert --5A--.

In Column 5, Line 59, delete "5D." and insert --5D--.

In Column 7, Line 33, delete "9B." and insert --9B--.

Signed and Sealed this
Twenty-first Day of June, 2022

Katherine Kelly Vidal
*Director of the United States Patent and Trademark Office*

CERTIFICATE OF CORRECTION (continued)
U.S. Pat. No. 10,900,974 B2

In Column 9, Line 42, delete "Labeing" and insert --Labeling--.

In Column 12, Line 50, delete "5B,)" and insert --5B)--.

In Column 17, Line 33, delete "IncRNA" and insert --lncRNA--.

In Column 17, Line 36, delete "IncRNA" and insert --lncRNA--.

In Column 17, Line 50, delete "IncRNA" and insert --lncRNA--.

In Column 19, Line 57, delete "Con" and insert --C on--.

In Column 20, Line 45, delete "DNAase" and insert --DNAse--.

In Column 20, Line 64, delete "Polynucleoide" and insert --Polynucleotide--.

In Column 20, Line 67, delete "(-exo)" and insert --(exo-)--.

In Column 21, Line 65, delete "Fast A P" and insert --FastAP--.

In Column 24, Line 3, delete "buffer" and insert --buffer.--.

In Column 25, Line 32, delete "depcit" and insert --depict--.

In Column 25, Line 60, delete "(RPM (Adaptor)." and insert --(RPM) Adaptor.--.

In Column 26, Line 45, delete "5'ligtag RNA" and insert --5'ligtagRNA--.

In Column 26, Line 52, delete "2Puniversal" and insert --2P_universal--.

In Column 27, Line 4, delete "molecules.\" and insert --molecules.--.

In Column 27, Line 7, delete "5th" and insert --5th,--.

In Column 27, Line 15 (approx.), delete "and and" and insert --and--.

In Column 27, Line 67, delete "Read1" and insert --Read 1--.

In Column 28, Line 28, delete "ie." and insert --i.e.--.

In Column 34, Line 32 (approx.), delete "wiki" and insert --wiki.--.

In Column 49, Line 53 (approx.), delete "TGATAATTAA" and insert --TGAGTAATTAA--.

In Column 63, Line 7 (approx.), delete "Polynucleoide" and insert --Polynucleotide--.

CERTIFICATE OF CORRECTION (continued)
U.S. Pat. No. 10,900,974 B2

In Column 65, Line 7 (approx.), delete "Polynucleoide" and insert --Polynucleotide--.

In Column 67, Line 7 (approx.), delete "Polynucleoide" and insert --Polynucleotide--.

In Column 69, Line 7 (approx.), delete "Polynucleoide" and insert --Polynucleotide--.

In Column 71, Line 7 (approx.), delete "Polynucleoide" and insert --Polynucleotide--.

In Column 71, Line 38 (approx.), delete "contstant" and insert --constant--.

In Column 73, Line 13 (approx.), delete "contstant" and insert --constant--.

In Column 75, Line 13 (approx.), delete "contstant" and insert --constant--.

In Column 77, Line 13 (approx.), delete "contstant" and insert --constant--.

In Column 79, Line 13 (approx.), delete "contstant" and insert --constant--.

In Column 81, Line 13 (approx.), delete "contstant" and insert --constant--.